United States Patent
Ubah et al.

(10) Patent No.: US 11,919,949 B2
(45) Date of Patent: Mar. 5, 2024

(54) SPECIFIC BINDING MOLECULES

(71) Applicant: ELASMOGEN LTD, Aberdeen (GB)

(72) Inventors: Obinna Ubah, Aberdeen (GB); Caroline Barelle, Aberdeen (GB); Andrew Porter, Aberdeen (GB)

(73) Assignee: ELASMOGEN LTD, Aberdeen (GB)

( * ) Notice: Subject to any disclaimer, the term of this patent is extended or adjusted under 35 U.S.C. 154(b) by 6 days.

(21) Appl. No.: 16/650,889

(22) PCT Filed: Sep. 27, 2018

(86) PCT No.: PCT/EP2018/076333
§ 371 (c)(1),
(2) Date: Mar. 26, 2020

(87) PCT Pub. No.: WO2019/063726
PCT Pub. Date: Apr. 4, 2019

(65) Prior Publication Data
US 2020/0407437 A1 Dec. 31, 2020

Related U.S. Application Data

(60) Provisional application No. 62/667,126, filed on May 4, 2018, provisional application No. 62/563,948, filed on Sep. 27, 2017.

(51) Int. Cl.
*C07K 16/24* (2006.01)
*C07K 16/46* (2006.01)

(52) U.S. Cl.
CPC .......... *C07K 16/241* (2013.01); *C07K 16/468* (2013.01); *C07K 2317/24* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| 6,180,370 B1* | 1/2001 | Queen ................ C07K 16/087 435/69.6 |
| 8,496,933 B2* | 7/2013 | Paniagua-Solis ....... A61P 29/00 424/130.1 |
| 9,399,677 B2 | 7/2016 | Paniagua-Solís et al. |
| 9,475,870 B2 | 10/2016 | Barelle et al. |
| 2014/0227259 A1 | 8/2014 | Ashman et al. |

FOREIGN PATENT DOCUMENTS

| WO | 2003/014161 A2 | 2/2003 |
| WO | 2005/118629 A1 | 12/2005 |
| WO | 2011/056056 A2 | 5/2011 |
| WO | 2013/167883 A1 | 11/2013 |
| WO | 2014/173959 A2 | 10/2014 |
| WO | 2014/173975 A1 | 10/2014 |
| WO | WO-2014173975 A1 * | 10/2014 ............. C07K 16/40 |
| WO | 2015/200883 A2 | 12/2015 |

OTHER PUBLICATIONS

Kovaleva, Marina et al. Expert opinion on biological therapy vol. 14, 10 (2014): 1527-39. doi:10.1517/14712598.2014.937701 (Year: 2014).*
Sela-Culang et al. Frontiers in immunology 4 (2013): 302 (Year: 2013).*
Janeway, Charles A. "Immunobiology: The Immune System in Health and Disease." 2001 (Year: 2001).*
Stryer, Biochemistry 4th, WH Freeman, New York. 1995 (Year: 1995).*
Colman, Peter M. Research in Immunology 145.1 (1994): 33-36 (Year: 1994).*
Kipriyanov, Sergey M., and Fabrice Le Gall. "Generation and production of engineered antibodies." Molecular biotechnology 26.1 (2004): 39-60. (Year: 2004).*
Stanfield, Robyn L et al. Journal of molecular biology vol. 367,2 (2007):358-72. doi:10.1016/j.jmb.2006.12.045 (Year: 2007).*
Altschul et al. Basic Local Alignment Search Tool. J Mol Biol (1990). 215, 403-410.
Bird et al. Single Chain Antigen Binding Proteins. Science. (1988). 242, 423-426.
Bojalil R et al. Anti-tumor necrosis factorVNAR single domainsreduce lethality and regulate underlyinginflammatory response in a murine model ofendotoxic shock. BMC Immunology (2013). 14(17), 1-7.
Camacho Villegas T et al. Human TNF cytokine neutralization with a vNAR from Heterodontus francisci sharkA potential therapeutic use. (2013). mAbs 5(1), 80-85.
Clayburgh D.R et al. A porous defense: the leaky epithelial barrier in intestinal disease. Laboratory Investigation (2004). 84(3), 282-291.
Coppieters et al. Formatted Anti-Tumor Necrosis FactorVHH ProteinsDerived From Camelids Show Superior Potency andTargeting to Inflamed Joints in a Murine Model ofCollagen-Induced Arthritis. Arthritis & Rheumatism. (2006). 54(6), 1856-1866.
Muller M.R et al. Improving the pharmacokinetic properties of biologics by fusion to an anti-HSA shark VNAR domain. mAbs, Landes Bioscience (2012). 4(6), 673-685.
Kovalenko Ov et al. Atypical Antigen Recognition Mode of a Shark Immunoglobulin New Antigen Receptor (IgNAR) Variable Domain Characterized by Humanization and Structural Analysis. J. Biol. Chem, (2013). 288 (24), 17408-17419.
Devereux, et al., A comprehensive set of sequene analysis programs for the VAX. Nucleic Acids Res (1984) 12, 387-395.
Dooley, H. and Flajnik, M. F., Shark immunity bites back: affinity maturation andmemory response in the nurse shark, Ginglymostomaciratum. Eur. J. Immunol., (2005), 35(3), 936-945.
Dooley, H., et al, Selection and characterization of naturally occurring single domain (IgNAR) antibody fragments from immunized sharks by phage display. Mol. Immunol, 2003. 40(1): p. 25-33.

(Continued)

Primary Examiner — Michael Szperka
Assistant Examiner — Lia E Taylor
(74) Attorney, Agent, or Firm — Arrigo, Lee, Guttman & Mouta-Bellum LLP

(57) ABSTRACT

The present invention relates to the formation of multi-domain specific binding molecules comprising VNARs. Specific binding domains that bind to Tumour Necrosis Factor alpha (TNFα) are also provided.

16 Claims, 39 Drawing Sheets
Specification includes a Sequence Listing.

(56) References Cited

OTHER PUBLICATIONS

Dooley, H., et al., First molecular and biochemical analysis of in vivo affinity maturation in an actothermic vertebrate. Proc Nat/ Acad Sci USA, 2006. 103(6), 1846-1851.
Els Conrath et al. Camel single-domain antibodies as molecular building units in biospecific and bivalent antibody constructs. J Biol Chem. 2001. 276(10), 7346-7350.
Assessment Report for Simponi. European Medicines Agency (2009). Doc Ref.: EMEA/446762/2009.
Assessment Report for Cimzia, European Medicines Agency (2009). Doc. Ref.: EMEA/664021/2009.
Flajnik M.F. et al. A Case Of Convergence: Why Did a Simple Alternative toCanonical Antibodies Arise in Sharks and Camels? PLoS Biol (2011), 9(8), 1-5, e1001120.
Greenberg A. S., et al. A new antigen receptor gene family that undergoes rearrangement and extensive somatic diversification in sharks. Nature, 1995, 374(6518), 168-173.
Haines et al. Immunohistochemistry: Forging the links between immunology and pathology. Veterinary Immunology and Immunopathology, 108 (2005) 151-156.
Hamers-Casterman, C. et al. Naturally occuring antibodies devoid of light chains. Nature, 1993. 363, 446-448.
Hidalgo, I.J., et al. Characterization of the Human Colon Carcinoma Cell Line (Caco-2) as a Model System for Intestinal Epithelial Permeability. Gastroenterology 1989. 96, 736-749.
Holliger P. et al., "Diabodies": Small bivalent and bispecific antibody fragments. Proc. tl. Acad. Sci. USA 1993. 90, 6444-6448.
Holliger P and Hudson P. Engineered antibody fragments and the rise of single domains. Nat. Biotechnology. (2005). 23(9), 1126-1136.
Huston et al. Protein engineering of antibody binding sites: Recovery of specific activity in an anti-digoxin single-chain Fv analogue produced in *Escherichia coli*. (1988) Proc Natl Acad Sci USA. 85, 5897-5883.
Irvine E.J. and Marshall J.K., Increased intestinal permeability precedes the onset of Crohn's disease in a subject with familial risk. Gastroenterology (2000). 119.6: 1740-1744.
Jahnichen S. et al. CXCR4 nanobodies (VHH-based single variabledomains) potently inhibit chemotaxis andHIV-1 replication and mobilize stem cells. Proc Nat/ Aced Sci USA. 2010. 107(47), 20565-20570.
Jost CR, et al. A single-chain bispecific Fv2 molecule produced in mammalian cells redirects lysis by activates CTL. MoL Immunol. 1996. 33(2), 211-219.
Jost C. and Pluckthun A. Engineered proteins with desired speci!city:DARPins, other alternative scaffolds and bispeci!c IgGs. Curr Opin Struct Biol. 2014. 27, 102-112.
Keffer et al. Transgenic mice expressing human turmour necrosis factor: a predictive genetic model of arthritis. EMBO J. (1991), 10(13), 4025-4031.
Kipriyanov S.M. et al., Bispecific Tandem Diabody for Tumor Therapy withImproved Antigen Binding and Pharmacokinetics. (1999). J. MoL Biol. 293, 41-56.
Kovaleva M. et al Shark variable new antigen receptor biologics—a novel tecnology platform for therapeutic drug development. Expert Opin. Biol. Ther. 2014. 14(10), 1527-1539.
Ward E.S. et al. Binding activities of a repertoire of single immunoglobulin variable domains secreted from *Escherichia coli*. Nature 1989, 341, 544-546.
Kontermann R. Dual targeting strategies with bispecific antibodies. mAbs 2012. 4(2), 182-197.
Liu, J.L., et al. Selection of cholera toxin specific IgNAR single-domain antibodies from a nave shark library. MoL Immunol. 2007. 44(7), 1775-1783.
Liu, J.L., et al. Isolation of anti-toxin single domain antibodies from a semi-synthetic spiny dogfish shark display library. BMC Biotechnol, 2007. 7(78), 1-10. doi:10.1186/1472-6750-7-78.

Mack M, et al. A small bispecific antibody construct expressed as a functional single-chain molecule with high tumor cell cytotoxicity. Proc. Natl. Acad. Sci. USA 1995. 92, 7021-7025.
McCormack E. et al. Bi-speci!c TCR-anti CD3 redirected redirected T-cell targetingof NY-ESO-1- and LAGE-1-positive tumors. Cancer Immunol Immunother. 2013. 62(4), 773-785.
Mould et al. VegfbGene Knockout Mice Display Reduced Pathology and Synovial Angiogenesis in Both Antigen-Induced and Collagen-Induced Models of Arthritis. 2003, Arthritis & Rheumatology, 48(9), 2660-2669.
Nuttall, S.D., et al. Isolation of the new antigen receptor from wobbegong sharks and use as a scaffold for the display of protein loop libraries. Mol Immunol, 2001. 38(4), 313-26.
Nuttall, S.D., et al. Isolation and characterization of an IgNAR variable domain specific for the human mitrochondrial translocase receptor Tom70. Eur J Biochem, 2003. 270(17), 3543-54.
Nuttall, S.D., et al. Selection and affinity maturation of IgNAR variable domains targeting plasmodium falciparum AMA1. Proteins, 2004. 55(1): p. 187-97.
Pettit, A.R., et al. TRANCE/RANKL Knockout Mice Are Protected from Bone Erosion in a Serum Transfer Model of Arthritis. The American journal of pathology, 2001, 159(5), 1689-1699.
Riechmann et al. Single domain antibodies: comparison of camel VH and camelised human VH domains J. Immunol. Methods, 1999. 231, 25-38.
Roovers R.C. et al. A bi-paratopic anti-EGFR nanobody efficiently inhibits solid tumour growth. Int J Cancer. 2011, 129 (8), 2013-2024.
Schmitz H. et al. Tumor necrosis factor-alpha (TNFa) regulates the epithelial barrier in the human intestinal cell line HT-29/B6. J. Cell Sci. 1999. 112(1), 137-146.
Schuerer-Maly C. et al. Colonic epithelial cell lines as a source of interleukin-8: stimulation by inflammatory cytokines and bacterial lipopolysaccharide. Immunology, 1994, 81(1), 85-91.
Schulzke J.D. et al., Epitehlial tight junctions in intestinal inflammation. Annals of the NY Academy of Sciences. 2009 1165, 294-300.
Scientific Discussion on Remicade, European Medicines Agency (2005) (http://www.ema.euroba.eu/docs/enGB/document library/EPAR—Scientific Discussion/human/000240/WC500050885.pdf).
Shao C.Y. et al. Rapid isolation of igNAR variable single-domain antibody fragments from a shark synthetic library. Mol Immunol. 2007. 44(4), 656-665.
Wang, F., et al. Interferon- and Tumor Necrosis Factor-Synergize to Induce Intestinal Epithelial Barrier Dysfunction by Up-Regulating Myosin Light Chain Kinase Expression. American Journal of Pathology. 2005, 166(2), 409-419.
Emerson et al., Enhancement of Polymeric Immunoglobulin Receptor Transcytosis by Biparatopic VHH, VHH. PLoS ONE 6(10): e26299, 1-10 (Oct. 14, 2011).
Konning et al. Semi-synthetic vNAR libraries screened against therapeutic antibodies primarily deliver anti-idiotypic binders. Nature: Scientific Reports. 7, 9676, 1-13.
Wesolowski, J., et al. Single domain antibodies: promising experimental and therapeutic tools in infection and immunity. Med Microbiol Immunol, 2009. 198(3), 157-174.
Wyatt et al., Intestinal permeability and the prediction of relapse in Crohn's disease. The Lancet 1993. 341(8858), 1437-1439.
Yoshinaga.S., K., et al., Characterization of a new human B7-related protein: B7RP-1 is the ligand to the co-stimulatory protein ICOS. Int. Immunol., 2000. 12(10), 1439-1447.
Zielonka S. et al. Structural insights and biomedical potential of IgNAR scaffolds from sharks. mAbs 2015. 7(1), 15-25.
Streltsov, V.A. et al. Structural evidence for evolution of shark Ig new antigen receptor variable domain antibodies from a cell-surface receptor (2004). Proc. Natl. Acad. Sci. U.S.A. 101(34), 12444-12449.
Streltsov, V.A., et al. Structure of a shark IgNAR antibody variabledomain and modeling of an early-developmentalisotype. Protein Sci., 2005. 14(11), 2901-2909.
Stanfield, R. L., et al. Crystal Structure of a Shark Single-Domain Antibody V Region in Complex with Lysozyme. Science, 2004. 305(5691),1770-1773.
Stanfield, R. L., et al., Maturation of Shark Single-domain (IgNAR) Antibodies: Evidence for Induced-fit Binding. J MoL Biol., 2007. 367(2), 358-372.

(56) References Cited

OTHER PUBLICATIONS

Traunecker A, et al. Bispecific single chain molecules (Janusins) target cytotoxic lymphocytes on HIV infected cells. MBO J. 1991. 10, 3655-36.
Traunecker A, et al. Janusin: New molecular design for bispecific reagents. Int J Cancer Supp. 1992. 7, 51-52.
Neri D et al. High-affinity antigen binding by chelating recombinant antibodies (CRAbs). J Mol Biol. 1995. 246(3), 367-73.
Spiess C. et al. Alternative molecular formats and therapeutic applications for bispecific antibodies. Mol Immunol 2015. 67(2), 95-106.
Simmons D.P. et al. Dimerisation strategies for shark IgNAR single domain antibody fragments. Immunol Methods. 2006, 315(1-2), 171-184.
Strohl W.R. and Strohl L.M., Therapeutic Antibody Engineering, Woodhead Publishing. 2012, pp. 322/323.
Wang et al., Overexpression of protein kinase C-a in the epidermis of transgenic mice results in striking alterations in phorbol ester-induced inflammation and COX-2, MIP-2 and TNF-a expression but not tumor promotion. J. Cell Science 1999. 112(1), 137-146.
Shealy et al., Characterization of golimumab, a human monoclonal antibody speci!c for human tumor necrosis factor a. MAbs. 2010, 2(4), 428-439.
Suenaert P. et al., Anti-Tumor Necrosis Factor Treatment Restores the Gut Barrier in Crohn's Disease. Am J Gastroenterol 2002. 97(8): 2000-2004.
Shealy et al., Anti-TNF-α antibody allows healing of joint damage in polyarthritic transgenic mice. Arthritis Research & Therapy. 2002, 4(5), p. R1-7.

\* cited by examiner

Figure 6

Anti-hICOSL or mICOSL binding ELISA data of four VNAR-Fc combinations, using 1/8 dilution of supernatant from transiently transfected cells

SEQUENCE LISTING

```
<160> NUMBER OF SEQ ID NOS: 96

<210> SEQ ID NO 1
<211> LENGTH: 11
<212> TYPE: PRT
<213> ORGANISM: Artificial Sequence
<220> FEATURE:
<223> OTHER INFORMATION: TNF VNAR D1 CDR3

<400> SEQUENCE: 1

Glu Cys Gln Tyr Gly Leu Ala Glu Tyr Asp Val
1               5                   10

<210> SEQ ID NO 2
<211> LENGTH: 106
<212> TYPE: PRT
<213> ORGANISM: Artificial Sequence
<220> FEATURE:
<223> OTHER INFORMATION: TNF VNAR D1 CDR3

<400> SEQUENCE: 2

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Ala Ser Glu Cys Gln Tyr Gly Leu Ala Glu Tyr Asp Val
                85                  90                  95

Tyr Gly Gly Gly Thr Val Val Thr Val Asn
            100                 105

<210> SEQ ID NO 3
<211> LENGTH: 128
<212> TYPE: PRT
<213> ORGANISM: Artificial Sequence
<220> FEATURE:
<223> OTHER INFORMATION: TNF VNAR D1

<400> SEQUENCE: 3

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
```

```
                50              55               60
Ser Phe Ser Leu Arg Ile Asn Asp Leu Thr Val Glu Asp Ser Gly Thr
 65                  70                  75                  80

Tyr Arg Cys Ala Ser Glu Cys Gln Tyr Gly Leu Ala Glu Tyr Asp Val
                 85                  90                  95

Tyr Gly Gly Gly Thr Val Val Thr Val Asn Ala Ala Ala His His
            100                 105                 110

His His His Gly Ala Ala Glu Ser Lys Leu Ile Ser Glu Glu Asp Leu
        115                 120                 125

<210> SEQ ID NO 4
<211> LENGTH: 318
<212> TYPE: DNA
<213> ORGANISM: Artificial Sequence
<220> FEATURE:
<223> OTHER INFORMATION: TNF VNAR D1

<400> SEQUENCE: 4
gctcgagtgg accaaacacc gcaaacaata acaaaggaga cgggcgaatc actgaccatc      60
aactgtgtcc tacgagatag ccactgtgca acctccagca cgtactggta tcgcaaaaaa     120
tcgggctcaa caaacgagga gagcatatcg aaaggtggac gatatgttga aacagttaac     180
agcggatcaa agtccttttc tttgagaatt aatgatctaa cagttgaaga cagtggcacg     240
tatcgatgcg cttccgagtg ccaatatgga ctggcagaat atgatgtata cggaggtggc     300
actgtcgtga ctgtgaat                                                   318

<210> SEQ ID NO 5
<211> LENGTH: 384
<212> TYPE: DNA
<213> ORGANISM: Artificial Sequence
<220> FEATURE:
<223> OTHER INFORMATION: TNF VNAR D1 WITH HIS AND MYC TAGS

<400> SEQUENCE: 5
gctcgagtgg accaaacacc gcaaacaata acaaaggaga cgggcgaatc actgaccatc      60
aactgtgtcc tacgagatag ccactgtgca acctccagca cgtactggta tcgcaaaaaa     120
tcgggctcaa caaacgagga gagcatatcg aaaggtggac gatatgttga aacagttaac     180
agcggatcaa agtccttttc tttgagaatt aatgatctaa cagttgaaga cagtggcacg     240
tatcgatgcg cttccgagtg ccaatatgga ctggcagaat atgatgtata cggaggtggc     300
actgtcgtga ctgtgaatgc ggccgcacat catcatcacc atcacggcgc cgcagaatca     360
aaactcatct cagaagagga tctg                                            384

<210> SEQ ID NO 6
<211> LENGTH: 14
<212> TYPE: PRT
<213> ORGANISM: Artificial Sequence
<220> FEATURE:
<223> OTHER INFORMATION: TNF VNAR C4 CDR3

<400> SEQUENCE: 6

Ser Trp Trp Thr Gln Asn Trp Arg Cys Ser Asn Ser Asp Val
 1               5                  10

<210> SEQ ID NO 7
<211> LENGTH: 108
<212> TYPE: PRT
<213> ORGANISM: Artificial Sequence
<220> FEATURE:
```

<223> OTHER INFORMATION: TNF VNAR C4

<400> SEQUENCE: 7

Arg Val Asp Gln Thr Pro Gln Thr Ile Thr Lys Glu Thr Gly Glu Ser
1               5                   10                  15

Leu Thr Ile Asn Cys Val Leu Arg Asp Ser Asn Cys Gly Leu Ser Ser
            20                  25                  30

Thr Tyr Trp Tyr Arg Lys Lys Ser Gly Ser Thr Asn Glu Glu Ser Ile
        35                  40                  45

Ser Lys Gly Gly Arg Tyr Val Glu Thr Ile Asn Glu Gly Ser Lys Ser
    50                  55                  60

Phe Ser Leu Arg Ile Asn Asp Leu Thr Val Glu Asp Ser Gly Thr Tyr
65                  70                  75                  80

Arg Cys Lys Leu Ser Trp Trp Thr Gln Asn Trp Arg Cys Ser Asn Ser
                85                  90                  95

Asp Val Tyr Gly Gly Gly Thr Val Val Thr Val Asn
            100                 105

<210> SEQ ID NO 8
<211> LENGTH: 131
<212> TYPE: PRT
<213> ORGANISM: Artificial Sequence
<220> FEATURE:
<223> OTHER INFORMATION: TNF VNAR C4 AMINO ACID SEQUENCE WITH HIS AND
      MYC TAGS

<400> SEQUENCE: 8

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Gly Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Ile Asn Glu Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Leu Ser Trp Trp Thr Gln Asn Trp Arg Cys Ser Asn
                85                  90                  95

Ser Asp Val Tyr Gly Gly Gly Thr Val Val Thr Val Asn Ala Ala Ala
            100                 105                 110

His His His His His His Gly Ala Ala Glu Ser Lys Leu Ile Ser Glu
        115                 120                 125

Glu Asp Leu
    130

<210> SEQ ID NO 9
<211> LENGTH: 327
<212> TYPE: DNA
<213> ORGANISM: Artificial Sequence
<220> FEATURE:
<223> OTHER INFORMATION: TNF VNAR C4

<400> SEQUENCE: 9
gctcgagtgg accaaacacc gcaaacaata caaaggaga cgggcgaatc actgaccatc        60
aactgtgtcc tacgagatag caactgtggg ttgtccagca cgtactggta tcgcaaaaaa      120
tcgggctcaa caaacgagga gagcatatcg aaaggtggac gatatgttga acaattaac      180

```
gaaggatcaa agtcctttc tttgagaatt aatgatctaa cagttgaaga cagtggcacg      240
tatcgatgca agttaagctg gtggacccag aactggagat gctcaaattc cgatgtatac      300
ggaggtggca ctgtcgtgac tgtgaat                                          327
```

<210> SEQ ID NO 10
<211> LENGTH: 393
<212> TYPE: DNA
<213> ORGANISM: Artificial Sequence
<220> FEATURE:
<223> OTHER INFORMATION: TNF VNAR D1 WITH HIS AND MYC TAGS

<400> SEQUENCE: 10

```
gctcgagtgg accaaacacc gcaaacaata caaaggaga cgggcgaatc actgaccatc       60
aactgtgtcc tacgagatag caactgtggg ttgtccagca cgtactgta tcgcaaaaaa      120 tcgggctcaa caaacgagga gagcatatcg aaaggtggac gatatgttga aacaattaac     180
gaaggatcaa agtcctttc tttgagaatt aatgatctaa cagttgaaga cagtggcacg     240
tatcgatgca agttaagctg gtggacccag aactggagat gctcaaattc cgatgtatac      300
ggaggtggca ctgtcgtgac tgtgaatgcg gccgcacatc atcatcacca tcacggcgcc      360
gcagaatcaa aactcatctc agaagaggat ctg                                   393
```

<210> SEQ ID NO 11
<211> LENGTH: 23
<212> TYPE: PRT
<213> ORGANISM: Artificial Sequence
<220> FEATURE:
<223> OTHER INFORMATION: TNF VNAR B4 CDR3

<400> SEQUENCE: 11

```
Tyr Ile Pro Cys Ile Asp Glu Leu Val Tyr Met Ile Ser Gly Gly Thr
1               5                   10                  15

Ser Gly Pro Ile His Asp Val
            20
```

<210> SEQ ID NO 12
<211> LENGTH: 118
<212> TYPE: PRT
<213> ORGANISM: Artificial Sequence
<220> FEATURE:
<223> OTHER INFORMATION: TNF VNAR B4

<400> SEQUENCE: 12

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Met Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Tyr Ile Pro Cys Ile Asp Glu Leu Val Tyr Met
                85                  90                  95

Ile Ser Gly Gly Thr Ser Gly Pro Ile His Asp Val Tyr Gly Gly Gly
            100                 105                 110

Thr Val Val Thr Val Asn
            115
```

<210> SEQ ID NO 13
<211> LENGTH: 140
<212> TYPE: PRT
<213> ORGANISM: Artificial Sequence
<220> FEATURE:
<223> OTHER INFORMATION: TNF VNAR B4 AMINO ACID SEQUENCE WITH HIS AND
      MYC TAGS

<400> SEQUENCE: 13

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Met Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Tyr Ile Pro Cys Ile Asp Glu Leu Val Tyr Met
                85                  90                  95

Ile Ser Gly Gly Thr Ser Gly Pro Ile His Asp Val Tyr Gly Gly Gly
            100                 105                 110

Thr Val Val Thr Val Asn Ala Ala Ala His His His His His His Gly
        115                 120                 125

Ala Ala Glu Ser Lys Leu Ile Ser Glu Glu Asp Leu
    130                 135                 140

<210> SEQ ID NO 14
<211> LENGTH: 354
<212> TYPE: DNA
<213> ORGANISM: Artificial Sequence
<220> FEATURE:
<223> OTHER INFORMATION: TNF VNAR B4

<400> SEQUENCE: 14
gctcgagtgg accaaacacc gcaaacaata acaaaggaga cgggcgaatc actgaccatc        60
aactgtgtcc tacgagatag taactgtgca ttgtccagca tgtactggta tcgcaaaaaa       120
tctggctcaa caaacgagga gagcatatcg aaaggtggac gatatgttga aacagttaac       180
agcggatcaa agtccttttc tttgagaatt aatgatctaa cagttgaaga cagtggcacg       240
tatcgatgca aggtatatat accttgcatc gatgaactgg tatatatgat cagtgggggt       300
acctctggcc cgattcatga tgtatacgga ggtggcactg tcgtgactgt gaat            354

<210> SEQ ID NO 15
<211> LENGTH: 71
<212> TYPE: DNA
<213> ORGANISM: Artificial Sequence
<220> FEATURE:
<223> OTHER INFORMATION: 15

<400> SEQUENCE: 15
gctaggctct agaaataatt ttgtttaact ttaagaagga gatataccat ggctcgagtg        60
gaccaaacac c                                                             71

<210> SEQ ID NO 16
<211> LENGTH: 87
<212> TYPE: DNA

```
<213> ORGANISM: Artificial Sequence
<220> FEATURE:
<223> OTHER INFORMATION: 16

<400> SEQUENCE: 16
cgcgccggat ccgccacctc cgctaccgcc acctccgcta ccgccacctc cgctaccgcc    60
acctccattc acagtcacga cagtgcc                                       87

<210> SEQ ID NO 17
<211> LENGTH: 46
<212> TYPE: DNA
<213> ORGANISM: Artificial Sequence
<220> FEATURE:
<223> OTHER INFORMATION: 17

<400> SEQUENCE: 17
ggtggcggat ccggcgcgca ctccgctcga gtggaccaaa caccgc                  46

<210> SEQ ID NO 18
<211> LENGTH: 53
<212> TYPE: DNA
<213> ORGANISM: Artificial Sequence
<220> FEATURE:
<223> OTHER INFORMATION: 18

<400> SEQUENCE: 18
gtccggaatt ctcacagatc ctcttctgag atgagttttt gttctgcggc ccc          53

<210> SEQ ID NO 19
<211> LENGTH: 48
<212> TYPE: DNA
<213> ORGANISM: Artificial Sequence
<220> FEATURE:
<223> OTHER INFORMATION: 19

<400> SEQUENCE: 19
aattcccctc tagaaggcgc gcactccgct cgagtggacc aaacaccg                48

<210> SEQ ID NO 20
<211> LENGTH: 420
<212> TYPE: DNA
<213> ORGANISM: Artificial Sequence
<220> FEATURE:
<223> OTHER INFORMATION: TNF VNAR B4 WITH HIS AND MYC TAGS

<400> SEQUENCE: 20
gctcgagtgg accaaacacc gcaaacaata acaaaggaga cgggcgaatc actgaccatc    60
aactgtgtcc tacgagatag taactgtgca ttgtccagca tgtactggta tcgcaaaaaa   120
tctggctcaa caaacgagga gagcatatcg aaaggtggac gatatgttga acagttaac   180 agcggatcaa agtcctttc tttgagaatt aatgatctaa cagttgaaga cagtggcacg    240
tatcgatgca aggtatatat accttgcatc gatgaactgg tatatatgat cagtggggt    300 acctctggcc cgattcatga tgtatacgga ggtggcactg tcgtgactgt gaatgcggcc    360
gcacatcatc atcaccatca cggcgccgca gaatcaaaac tcatctcaga agaggatctg    420

<210> SEQ ID NO 21
<211> LENGTH: 249
<212> TYPE: PRT
<213> ORGANISM: Artificial Sequence
<220> FEATURE:
<223> OTHER INFORMATION: TNF VNAR DIMER D1-D1 AMINO ACID SEQUENCE WITH
      HIS AND MYC TAGS
```

<400> SEQUENCE: 21

```
Ala Arg Val Asp Gln Thr Pro Gln Thr Ile Thr Lys Glu Thr Gly Glu
1               5                   10                  15
Ser Leu Thr Ile Asn Cys Val Leu Arg Asp Ser His Cys Ala Thr Ser
            20                  25                  30
Ser Thr Tyr Trp Tyr Arg Lys Lys Ser Gly Ser Thr Asn Glu Glu Ser
        35                  40                  45
Ile Ser Lys Gly Gly Arg Tyr Val Glu Thr Val Asn Ser Gly Ser Lys
50                  55                  60
Ser Phe Ser Leu Arg Ile Asn Asp Leu Thr Val Glu Asp Ser Gly Thr
65                  70                  75                  80
Tyr Arg Cys Ala Ser Glu Cys Gln Tyr Gly Leu Ala Glu Tyr Asp Val
                85                  90                  95
Tyr Gly Gly Gly Thr Val Val Thr Val Asn Gly Gly Gly Gly Ser Gly
            100                 105                 110
Gly Gly Gly Gly Ser Gly Ala His Ser Ala Arg Val Asp Gln Thr Pro
        115                 120                 125
Gln Thr Ile Thr Lys Glu Thr Gly Glu Ser Leu Thr Ile Asn Cys Val
    130                 135                 140
Leu Arg Asp Ser His Cys Ala Thr Ser Ser Thr Tyr Trp Tyr Arg Lys
145                 150                 155                 160
Lys Ser Gly Ser Thr Asn Glu Glu Ser Ile Ser Lys Gly Gly Arg Tyr
                165                 170                 175
Val Glu Thr Val Asn Ser Gly Ser Lys Ser Phe Ser Leu Arg Ile Asn
            180                 185                 190
Asp Leu Thr Val Glu Asp Ser Gly Thr Tyr Arg Cys Ala Ser Glu Cys
        195                 200                 205
Gln Tyr Gly Leu Ala Glu Tyr Asp Val Tyr Gly Gly Gly Thr Val Val
    210                 215                 220
Thr Val Asn Ala Ala Ala His His His His His Gly Ala Ala Glu
225                 230                 235                 240
Ser Lys Leu Ile Ser Glu Glu Asp Leu
                245
```

<210> SEQ ID NO 22
<211> LENGTH: 747
<212> TYPE: DNA
<213> ORGANISM: Artificial Sequence
<220> FEATURE:
<223> OTHER INFORMATION: TNF VNAR DIMER D1-D1 WITH HIS AND MYC TAGS

<400> SEQUENCE: 22

```
gctcgagtgg accaaacacc gcaaacaata acaaaggaga cgggcgaatc actgaccatc      60
aactgtgtcc tacgagatag ccactgtgca acctccagca cgtactggta tcgcaaaaaa     120
tcgggctcaa caaacgagga gagcatatcg aaaggtggac gatatgttga acagttaac      180
agcggatcaa agtcctttc tttgagaatt aatgatctaa cagttgaaga cagtggcacg      240
tatcgatgcg cttccgagtg ccaatatgga ctggcagaat atgatgtata cggaggtggc      300
actgtcgtga ctgtgaatgg aggtggcggt agcggaggtg gtggcggatc cggcgcgcac     360
tccgctcgag tggaccaaac accgcaaaca ataacaaagg agacgggcga atcactgacc     420
atcaactgtg tcctacgaga tagccactgt gcaacctcca gcacgtactg gtatcgcaaa     480
aaatcgggct caacaaacga ggagagcata tcgaaaggtg gacgatatgt tgaacagtt      540
aacagcggat caaagtcctt ttctttgaga attaatgatc taacagttga agacagtggc     600
```

```
acgtatcgat gcgcttccga gtgccaatat ggactggcag aatatgatgt atacggaggt      660
ggcactgtcg tgactgtgaa tgcggccgca catcatcatc accatcacgg ggccgcagaa      720
caaaaactca tctcagaaga ggatctg                                          747
```

<210> SEQ ID NO 23
<211> LENGTH: 255
<212> TYPE: PRT
<213> ORGANISM: Artificial Sequence
<220> FEATURE:
<223> OTHER INFORMATION: TNF VNAR DIMER C4-C4 AMINO ACID SEQUENCE WITH
      HIS AND MYC TAGS

<400> SEQUENCE: 23

```
Ala Arg Val Asp Gln Thr Pro Gln Thr Ile Thr Lys Glu Thr Gly Glu
1               5                  10                  15

Ser Leu Thr Ile Asn Cys Val Leu Arg Asp Ser Asn Cys Gly Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Ile Asn Glu Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Leu Ser Trp Trp Thr Gln Asn Trp Arg Cys Ser Asn
                85                  90                  95

Ser Asp Val Tyr Gly Gly Gly Thr Val Val Thr Val Asn Gly Gly Gly
            100                 105                 110

Gly Ser Gly Gly Gly Gly Ser Gly Ala His Ser Ala Arg Val Asp
        115                 120                 125

Gln Thr Pro Gln Thr Ile Thr Lys Glu Thr Gly Glu Ser Leu Thr Ile
130                 135                 140

Asn Cys Val Leu Arg Asp Ser Asn Cys Gly Leu Ser Ser Thr Tyr Trp
145                 150                 155                 160

Tyr Arg Lys Lys Ser Gly Ser Thr Asn Glu Glu Ser Ile Ser Lys Gly
                165                 170                 175

Gly Arg Tyr Val Glu Thr Ile Asn Glu Gly Ser Lys Ser Phe Ser Leu
            180                 185                 190

Arg Ile Asn Asp Leu Thr Val Glu Asp Ser Gly Thr Tyr Arg Cys Lys
        195                 200                 205

Leu Ser Trp Trp Thr Gln Asn Trp Arg Cys Ser Asn Ser Asp Val Tyr
    210                 215                 220

Gly Gly Gly Thr Val Val Thr Val Asn Ala Ala Ala His His His His
225                 230                 235                 240

His His Gly Ala Ala Glu Gln Lys Leu Ile Ser Glu Glu Asp Leu
                245                 250                 255
```

<210> SEQ ID NO 24
<211> LENGTH: 765
<212> TYPE: DNA
<213> ORGANISM: Artificial Sequence
<220> FEATURE:
<223> OTHER INFORMATION: TNF VNAR DIMER C4-C4 WITH HIS AND MYC TAGS

<400> SEQUENCE: 24

```
gctcgagtgg accaaacacc gcaaacaata acaaaggaga cgggcgaatc actgaccatc      60
aactgtgtcc tacgagatag caactgtggg ttgtccagca cgtactggta tcgcaaaaaa     120
tcgggctcaa caaacgagga gagcatatcg aaaggtggac gatatgttga acaattaac     180
```

-continued

```
gaaggatcaa agtcctttc tttgagaatt aatgatctaa cagttgaaga cagtggcacg      240
tatcgatgca agttaagctg gtggacccag aactggagat gctcaaattc cgatgtatac      300
ggaggtggca ctgtcgtgac tgtgaacgga ggtggcggta gcggaggtgg tggcggatcc      360
ggcgcgcact ccgctcgagt ggaccaaaca ccgcaaacaa taacaaagga cgggcgaa       420 tcactgacca tcaactgtgt cctacgagat agcaactgtg ggttgtccag cacgtactgg      480
tatcgcaaaa atcgggctc aacaaacgag gagagcatat cgaaaggtgg acgatatgtt      540
gaaacaatta cgaaggatc aaagtccttt tctttgagaa ttaatgatct aacagttgaa      600
gacagtggca cgtatcgatg caagttaagc tggtggaccc agaactggag atgctcaaat      660
tccgatgtat acggaggtgg cactgtcgtg actgtgaacg cggccgcaca tcatcatcac      720
catcacgggg ccgcagaaca aaaactcatc tcagaagagg atctg                    765
```

<210> SEQ ID NO 25
<211> LENGTH: 273
<212> TYPE: PRT
<213> ORGANISM: Artificial Sequence
<220> FEATURE:
<223> OTHER INFORMATION: TNF VNAR DIMER B4-B4 AMINO ACID SEQUENCE WITH
      HIS AND MYC TAGS <400> SEQUENCE: 25

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
            20                  25                  30

Ser Met Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Tyr Ile Pro Cys Ile Asp Glu Leu Val Tyr Met
                85                  90                  95

Ile Ser Gly Gly Thr Ser Gly Pro Ile His Asp Val Tyr Gly Gly Gly
            100                 105                 110

Thr Val Thr Val Asn Gly Gly Gly Ser Gly Gly Gly Gly
            115                 120                 125

Ser Gly Ala His Ser Ala Arg Val Asp Gln Thr Pro Gln Thr Ile Thr
        130                 135                 140

Lys Glu Thr Gly Glu Ser Leu Thr Ile Asn Cys Val Leu Arg Asp Ser
145                 150                 155                 160

Asn Cys Ala Leu Ser Ser Met Tyr Trp Tyr Arg Lys Lys Ser Gly Ser
                165                 170                 175

Thr Asn Glu Glu Ser Ile Ser Lys Gly Gly Arg Tyr Val Glu Thr Val
            180                 185                 190

Asn Ser Gly Ser Lys Ser Phe Ser Leu Arg Ile Asn Asp Leu Thr Val
        195                 200                 205

Glu Asp Ser Gly Thr Tyr Arg Cys Lys Val Tyr Ile Pro Cys Ile Asp
    210                 215                 220

Glu Leu Val Tyr Met Ile Ser Gly Gly Thr Ser Gly Pro Ile His Asp
225                 230                 235                 240

Val Tyr Gly Gly Gly Thr Val Thr Val Asn Ala Ala Ala His His
                245                 250                 255
```

His His His His Gly Ala Ala Glu Gln Lys Leu Ile Ser Glu Glu Asp
              260                 265                 270

Leu

<210> SEQ ID NO 26
<211> LENGTH: 819
<212> TYPE: DNA
<213> ORGANISM: Artificial Sequence
<220> FEATURE:
<223> OTHER INFORMATION: TNF VNAR DIMER B4-B4 WITH HIS AND MYC TAGS

<400> SEQUENCE: 26
gctcgagtgg accaaacacc gcaaacaata caaaggaga cgggcgaatc actgaccatc      60
aactgtgtcc tacgagatag taactgtgca ttgtccagca tgtactggta tcgcaaaaaa     120
tctggctcaa caaacgagga gagcatatcg aaaggtggac gatatgttga acagttaac     180 agcggatcaa agtccttttc tttgagaatt aatgatctaa cagttgaaga cagtggcacg     240
tatcgatgca aggtatatat accttgcatc gatgaactgg tatatatgat cagtgggggt     300
acctctggcc cgattcatga tgtatacgga ggtggcactg tcgtgactgt gaatggaggt     360
ggcggtagcg gaggtggtgg cggatccggc gcgcactccg ctcgagtgga ccaaacaccg     420
caaacaataa caaggagac gggcgaatca ctgaccatca actgtgtcct acgagatagt     480
aactgtgcat tgtccagcat gtactggtat cgcaaaaaat ctggctcaac aaacgaggag     540
agcatatcga aaggtggacg atatgttgaa acagttaaca gcggatcaaa gtccttttct     600
ttgagaatta atgatctaac agttgaagac agtggcacgt atcgatgcaa ggtatatata     660
ccttgcatcg atgaactggt atatatgatc agtgggggta cctctggccc gattcatgat     720
gtatacggag gtggcactgt cgtgactgtg aatgcggccg cacatcatca tcaccatcac     780
ggggccgcag aacaaaaact catctcagaa gaggatctg                            819

<210> SEQ ID NO 27
<211> LENGTH: 252
<212> TYPE: PRT
<213> ORGANISM: Artificial Sequence
<220> FEATURE:
<223> OTHER INFORMATION: TNF VNAR DIMER D1-C4 AMINO ACID SEQUENCE WITH
      HIS AND MYC TAGS

<400> SEQUENCE: 27

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser His Cys Ala Thr Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Ala Ser Glu Cys Gln Tyr Gly Leu Ala Glu Tyr Asp Val
                85                  90                  95

Tyr Gly Gly Gly Thr Val Val Thr Val Asn Gly Gly Gly Gly Ser Gly
            100                 105                 110

Gly Gly Gly Gly Ser Gly Ala His Ser Ala Arg Val Asp Gln Thr Pro
        115                 120                 125

```
Gln Thr Ile Thr Lys Glu Thr Gly Glu Ser Leu Thr Ile Asn Cys Val
            130                 135                 140

Leu Arg Asp Ser Asn Cys Gly Leu Ser Ser Thr Tyr Trp Tyr Arg Lys
145                 150                 155                 160

Lys Ser Gly Ser Thr Asn Glu Glu Ser Ile Ser Lys Gly Gly Arg Tyr
                165                 170                 175

Val Glu Thr Ile Asn Glu Gly Ser Lys Ser Phe Ser Leu Arg Ile Asn
            180                 185                 190

Asp Leu Thr Val Glu Asp Ser Gly Thr Tyr Arg Cys Lys Leu Ser Trp
                195                 200                 205

Trp Thr Gln Asn Trp Arg Cys Ser Asn Ser Asp Val Tyr Gly Gly Gly
210                 215                 220

Thr Val Thr Val Asn Ala Ala Ala His His His His His His Gly
225                 230                 235                 240

Ala Ala Glu Gln Lys Leu Ile Ser Glu Glu Asp Leu
                245                 250
```

<210> SEQ ID NO 28
<211> LENGTH: 756
<212> TYPE: DNA
<213> ORGANISM: Artificial Sequence
<220> FEATURE:
<223> OTHER INFORMATION: TNF VNAR DIMER D1-C4 WITH HIS AND MYC TAGS

<400> SEQUENCE: 28

```
gctcgagtgg accaaacacc gcaaacaata caaaggaga cgggcgaatc actgaccatc      60
aactgtgtcc tacgagatag ccactgtgca acctccagca cgtactggta tcgcaaaaaa    120
tcgggctcaa caaacgagga gagcatatcg aaaggtggac gatatgttga acagttaac     180
agcggatcaa agtccttttc tttgagaatt aatgatctaa cagttgaaga cagtggcacg    240
tatcgatgcg cttccgagtg ccaatatgga ctggcagaat atgatgtata cggaggtggc    300
actgtcgtga ctgtgaatgg aggtggcggt agcggaggtg gtggcggatc cggcgcgcac    360
tccgctcgag tggaccaaac accgcaaaca ataacaaagg agacgggcga atcactgacc    420
atcaactgtg tcctacgaga tagcaactgt gggttgtcca gcacgtactg gtatcgcaaa    480
aaatcgggct caacaaacga ggagagcata tcgaaaggtg gacgatatgt tgaaacaatt    540
aacgaaggat caagtccctt ttctttgaga attaatgatc taacagttga agacagtggc    600
acgtatcgat gcaagttaag ctggtggacc cagaactgga gatgctcaaa ttccgatgta    660
tacggaggtg gcactgtcgt gactgtgaac gcggccgcac atcatcatca ccatcacggg    720
gccgcagaac aaaaactcat ctcagaagag gatctg                              756
```

<210> SEQ ID NO 29
<211> LENGTH: 261
<212> TYPE: PRT
<213> ORGANISM: Artificial Sequence
<220> FEATURE:
<223> OTHER INFORMATION: TNF VNAR DIMER D1-B4 AMINO ACID SEQUENCE WITH HIS AND MYC TAGS

<400> SEQUENCE: 29

```
Ala Arg Val Asp Gln Thr Pro Gln Thr Ile Thr Lys Glu Thr Gly Glu
1               5                   10                  15

Ser Leu Pro Ile Asn Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45
```

```
Ile Ser Lys Gly Gly Arg Tyr Val Glu Thr Val Asn Ser Gly Ser Lys
 50                  55                  60
Ser Phe Ser Leu Arg Ile Asn Asp Leu Thr Val Glu Asp Ser Gly Thr
 65                  70                  75                  80
Tyr Arg Cys Ala Ser Glu Cys Gln Tyr Gly Leu Ala Glu Tyr Asp Val
                 85                  90                  95
Tyr Gly Gly Gly Thr Val Val Thr Val Asn Gly Gly Gly Gly Ser Gly
                100                 105                 110
Gly Gly Gly Gly Ser Gly Ala His Ser Ala Arg Val Asp Gln Thr Pro
                115                 120                 125
Gln Thr Ile Thr Lys Glu Thr Gly Glu Ser Leu Thr Ile Asn Cys Val
130                 135                 140
Leu Arg Asp Ser Asn Cys Ala Leu Ser Ser Met Tyr Trp Tyr Arg Lys
145                 150                 155                 160
Lys Ser Gly Ser Thr Asn Glu Glu Ser Ile Ser Lys Gly Gly Arg Tyr
                165                 170                 175
Val Glu Thr Val Asn Ser Gly Ser Lys Ser Phe Ser Leu Arg Ile Asn
                180                 185                 190
Asp Leu Thr Val Glu Asp Ser Gly Thr Tyr Arg Cys Lys Val Tyr Ile
                195                 200                 205
Pro Cys Ile Asp Glu Leu Val Tyr Met Ile Ser Gly Gly Thr Ser Gly
210                 215                 220
Pro Ile His Asp Val Tyr Gly Gly Gly Thr Val Val Thr Val Asn Ala
225                 230                 235                 240
Ala Ala His His His His His His Gly Ala Ala Glu Gln Lys Leu Ile
                245                 250                 255
Ser Glu Glu Asp Leu
                260

<210> SEQ ID NO 30
<211> LENGTH: 783
<212> TYPE: DNA
<213> ORGANISM: Artificial Sequence
<220> FEATURE:
<223> OTHER INFORMATION: NUCLEOTIDE SEQUENCE CODIGN FOR THE TNF VNAR
      DIMER D1-B4 NUCLEOTIDE SEQUENCE WITH HIS AND MYC TAGS

<400> SEQUENCE: 30
gctcgagtgg accaaacacc gcaaacaata caaaggaga cgggcgaatc actgaccatc      60
aactgtgtcc tacgagatag ccactgtgca acctccagca cgtactgta tcgcaaaaaa    120
tcgggctcaa caaacgagga gagcatatcg aaaggtggac gatatgttga acagttaac    180
agcggatcaa agtccttttc tttgagaatt aatgatctaa cagttgaaga cagtggcacg    240
tatcgatgcg cttccgagtg ccaatatgga ctggcagaat atgatgtata cggaggtggc    300
actgtcgtga ctgtgaatgg aggtggcggt agcggaggtg gtggcggatc cggcgcgcac    360
tccgctcgag tggaccaaac accgcaaaca ataacaaagg agacgggcga atcactgacc    420
atcaactgtg tcctacgaga tagtaactgt gcattgtcca gcatgtactg gtatcgcaaa    480
aaatctggct caacaaacga ggagagcata tcgaaaggtg gacgatatgt tgaaacagtt    540
aacagcggat caaagtcctt ttctttgaga attaatgatc taacagttga agacagtggc    600
acgtatcgat gcaaggtata tatccttgc atcgatgaac tggtatatat gatcagtggg    660
ggtacctctg gccgattca tgatgtatac ggaggtggca ctgtcgtgac tgtgaatgcg    720
gccgcacatc atcatcacca tcacggggcc gcagaacaaa aactcatctc agaagaggat    780
``` ctg                                                                        783

<210> SEQ ID NO 31
<211> LENGTH: 261
<212> TYPE: PRT
<213> ORGANISM: Artificial Sequence
<220> FEATURE:
<223> OTHER INFORMATION: TNF VNAR DIMER B4-D1 AMINO ACID SEQUENCE

<400> SEQUENCE: 31

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Met Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Tyr Ile Pro Cys Ile Asp Glu Leu Val Tyr Met
                85                  90                  95

Ile Ser Gly Gly Thr Ser Gly Pro Ile His Asp Val Tyr Gly Gly Gly
            100                 105                 110

Thr Val Val Thr Val Asn Gly Gly Gly Ser Gly Gly Gly Gly
        115                 120                 125

Ser Gly Ala His Ser Ala Arg Val Asp Gln Thr Pro Gln Thr Ile Thr
    130                 135                 140

Lys Glu Thr Gly Glu Ser Leu Pro Ile Asn Cys Val Leu Arg Asp Ser
145                 150                 155                 160

His Cys Ala Thr Ser Ser Thr Tyr Trp Tyr Arg Lys Lys Ser Gly Ser
                165                 170                 175

Thr Asn Glu Glu Ser Ile Ser Lys Gly Gly Arg Tyr Val Glu Thr Val
            180                 185                 190

Asn Ser Gly Ser Lys Ser Phe Ser Leu Arg Ile Asn Asp Leu Thr Val
        195                 200                 205

Glu Asp Ser Gly Thr Tyr Arg Cys Ala Ser Glu Cys Gln Tyr Gly Leu
    210                 215                 220

Ala Glu Tyr Asp Val Tyr Gly Gly Thr Val Val Thr Val Asn Ala
225                 230                 235                 240

Ala Ala His His His His His Gly Ala Ala Glu Gln Lys Leu Ile
                245                 250                 255

Ser Glu Glu Asp Leu
            260

<210> SEQ ID NO 32
<211> LENGTH: 783
<212> TYPE: DNA
<213> ORGANISM: Artificial Sequence
<220> FEATURE:
<223> OTHER INFORMATION: TNF VNAR DIMER B4-D1 NUCLEOTIDE SEQUENCE

<400> SEQUENCE: 32
gctcgagtgg accaaacacc gcaaacaata acaaaggaga cgggcgaatc actgaccatc      60
aactgtgtcc tacgagatag taactgtgca ttgtccagca tgtactggta tcgcaaaaaa    120
tctggctcaa caaacgagga gagcatatcg aaaggtggac gatatgttga aacagttaac    180

```
agcggatcaa agtccttttc tttgagaatt aatgatctaa cagttgaaga cagtggcacg    240
tatcgatgca aggtatatat accttgcatc gatgaactgg tatatatgat cagtgggggt    300
acctctggcc cgattcatga tgtatacgga ggtggcactg tcgtgactgt gaatggaggt    360
ggcggtagcg gaggtggtgg cggatccggc gcgcactccg ctcgagtgga ccaaacaccg    420
caaacaataa caaaggagac gggcgaatca ctgaccatca actgtgtcct acgagatagc    480
cactgtgcaa cctccagcac gtactggtat cgcaaaaaat cgggctcaac aaacgaggag    540
agcatatcga aggtggacg atatgttgaa acagttaaca gcggatcaaa gtccttttct    600
ttgagaatta atgatctaac agttgaagac agtggcacgt atcgatgcgc ttccgagtgc    660
caatatggac tggcagaata tgatgtatac ggaggtggca ctgtcgtgac tgtgaatgcg    720
gccgcacatc atcatcacca tcacggggcc gcagaacaaa aactcatctc agaagaggat    780
ctg                                                                  783
```

```
<210> SEQ ID NO 33
<211> LENGTH: 263
<212> TYPE: PRT
<213> ORGANISM: Artificial Sequence
<220> FEATURE:
<223> OTHER INFORMATION: TNF VNAR DIMER C4-B4 AMINO ACID SEQUENCE

<400> SEQUENCE: 33
```

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Gly Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Ile Asn Glu Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Leu Ser Trp Trp Thr Gln Asn Trp Arg Cys Ser Asn
                85                  90                  95

Ser Asp Val Tyr Gly Gly Gly Thr Val Val Thr Val Asn Gly Gly Gly
                100                 105                 110

Gly Ser Gly Gly Gly Gly Ser Gly Ala His Ser Ala Arg Val Asp
            115                 120                 125

Gln Thr Pro Gln Thr Ile Thr Lys Glu Thr Gly Glu Ser Leu Thr Ile
    130                 135                 140

Asn Cys Val Leu Arg Asp Ser Asn Cys Ala Leu Ser Ser Met Tyr Trp
145                 150                 155                 160

Tyr Arg Lys Lys Ser Gly Ser Thr Asn Glu Glu Ser Ile Ser Lys Gly
                165                 170                 175

Gly Arg Tyr Val Glu Thr Val Asn Ser Gly Ser Lys Ser Phe Ser Leu
            180                 185                 190

Arg Ile Asn Asp Leu Thr Val Glu Asp Ser Gly Thr Tyr Arg Cys Lys
        195                 200                 205

Val Tyr Ile Pro Cys Ile Asp Glu Leu Val Tyr Met Ile Ser Gly Gly
    210                 215                 220

Thr Ser Gly Pro Ile His Asp Val Tyr Gly Gly Gly Thr Val Val Thr
225                 230                 235                 240

Val Asn Ala Ala Ala His His His His His His Gly Ala Ala Glu Gln

```
                    245                 250                 255
Lys Leu Ile Ser Glu Glu Asp
                260

<210> SEQ ID NO 34
<211> LENGTH: 792
<212> TYPE: DNA
<213> ORGANISM: Artificial Sequence
<220> FEATURE:
<223> OTHER INFORMATION: TNF VNAR DIMER C4-B4 NUCLEOTIDE SEQUENCE

<400> SEQUENCE: 34
gctcgagtgg accaaacacc gcaaacaata acaaaggaga cgggcgaatc actgaccatc        60
aactgtgtcc tacgagatag caactgtggg ttgtccagca cgtactggta tcgcaaaaaa       120
tcgggctcaa caaacgagga gagcatatcg aaaggtggac gatatgttga acaattaac        180 gaaggatcaa agtccttttc tttgagaatt aatgatctaa cagttgaaga cagtggcacg       240
tatcgatgca gttaagctg gtggacccag aactggagat gctcaaattc cgatgtatac        300
ggaggtggca ctgtcgtgac tgtgaacgga ggtggcggta gcggaggtgg tggcggatcc       360
ggcgcgcact ccgctcgagt ggaccaaaca ccgcaaacaa taacaaagga cgggcgaa         420 tcactgacca tcaactgtgt cctacgagat agtaactgtg cattgtccag catgtactgg       480
tatcgcaaaa aatctggctc aacaaacgag gagagcatat cgaaaggtgg acgatatgtt       540
gaaacagtta acagcggatc aaagtccttt tctttgagaa ttaatgatct aacagttgaa       600
gacagtggca cgtatcgatg caaggtatat ataccttgca tcgatgaact ggtatatatg       660
atcagtgggg gtacctctgg cccgattcat gatgtatacg gaggtggcac tgtcgtgact       720
gtgaatgcgg ccgcacatca tcatcaccat cacggggccg cagaacaaaa actcatctca       780
gaagaggatc tg                                                           792

<210> SEQ ID NO 35
<211> LENGTH: 263
<212> TYPE: PRT
<213> ORGANISM: Artificial Sequence
<220> FEATURE:
<223> OTHER INFORMATION: TNF VNAR DIMER B4-C4 AMINO ACID SEQUENCE

<400> SEQUENCE: 35

Ala Arg Val Asp Gln Thr Pro Gln Thr Ile Thr Lys Glu Thr Gly Glu
1               5                  10                  15

Ser Leu Thr Ile Asn Cys Val Leu Arg Asp Ser Asn Cys Ala Leu Ser
            20                  25                  30

Ser Met Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Tyr Ile Pro Cys Ile Asp Glu Leu Val Tyr Met
                85                  90                  95

Ile Ser Gly Gly Thr Ser Gly Pro Ile His Asp Val Tyr Gly Gly Gly
            100                 105                 110

Thr Val Val Thr Val Asn Gly Gly Gly Ser Gly Gly Gly Gly Gly
        115                 120                 125

Ser Gly Ala His Ser Ala Arg Val Asp Gln Thr Pro Gln Thr Ile Thr
    130                 135                 140
```

-continued

Lys Glu Thr Gly Glu Ser Leu Thr Ile Asn Cys Val Leu Arg Asp Ser
145                 150                 155                 160

Asn Cys Gly Leu Ser Ser Thr Tyr Trp Tyr Arg Lys Lys Ser Gly Ser
                165                 170                 175

Thr Asn Glu Glu Ser Ile Ser Lys Gly Gly Arg Tyr Val Glu Thr Ile
            180                 185                 190

Asn Glu Gly Ser Lys Ser Phe Ser Leu Arg Ile Asn Asp Leu Thr Val
        195                 200                 205

Glu Asp Ser Gly Thr Tyr Arg Cys Lys Leu Ser Trp Trp Thr Gln Asn
    210                 215                 220

Trp Arg Cys Ser Asn Ser Asp Val Tyr Gly Gly Thr Val Val Thr
225                 230                 235                 240

Val Asn Ala Ala Ala His His His His His Gly Ala Ala Glu Gln
                245                 250                 255

Lys Leu Ile Ser Glu Glu Asp
            260

<210> SEQ ID NO 36
<211> LENGTH: 792
<212> TYPE: DNA
<213> ORGANISM: Artificial Sequence
<220> FEATURE:
<223> OTHER INFORMATION: TNF VNAR DIMER B4-C4 NUCLEOTIDE SEQUENCE

<400> SEQUENCE: 36
gctcgagtgg accaaacacc gcaaacaata acaaaggaga cgggcgaatc actgaccatc      60
aactgtgtcc tacgagatag taactgtgca ttgtccagca tgtactggta tcgcaaaaaa    120
tctggctcaa caaacgagga gagcatatcg aaaggtggac gatatgttga acagttaac    180 agcggatcaa agtccttttc tttgagaatt aatgatctaa cagttgaaga cagtggcacg    240
tatcgatgca aggtatatat accttgcatc gatgaactgg tatatatgat cagtgggggt    300
acctctggcc cgattcatga tgtatacgga ggtggcactg tcgtgactgt gaatggaggt    360
ggcggtagcg gaggtggtgg cggatccggc gcgcactccg ctcgagtgga ccaaacaccg    420
caaacaataa caaaggagac gggcgaatca ctgaccatca actgtgtcct acgagatagc    480
aactgtgggt tgtccagcac gtactggtat cgcaaaaaat cgggctcaac aaacgaggag    540
agcatatcga aaggtggacg atatgttgaa acaattaacg aaggatcaaa gtccttttct    600
ttgagaatta atgatctaac agttgaagac agtggcacgt atcgatgcaa gttaagctgg    660
tggacccaga actggagatg ctcaaattcc gatgtatacg gaggtggcac tgtcgtgact    720
gtgaacgcgg ccgcacatca tcatcaccat cacggggccg cagaacaaaa actcatctca    780
gaagaggatc tg                                                       792

<210> SEQ ID NO 37
<211> LENGTH: 383
<212> TYPE: PRT
<213> ORGANISM: Artificial Sequence
<220> FEATURE:
<223> OTHER INFORMATION: TNF VNAR D1-BA11-C4 AMINO ACID SEQUENCE WITH
      HIS AND MYC TAGS

<400> SEQUENCE: 37

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
    35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Ala Ser Glu Cys Gln Tyr Gly Leu Ala Glu Tyr Asp Val
                85                  90                  95

Tyr Gly Gly Gly Thr Val Val Thr Val Asn Gly Gly Gly Ser Gly
                100                 105                 110

Gly Gly Gly Ser Gly Gly Gly Ser Gly Gly Gly Ser Gly Ala
            115                 120                 125

His Ser Thr Arg Val Asp Gln Ser Pro Ser Ser Leu Ser Ala Ser Val
    130                 135                 140

Gly Asp Arg Val Thr Ile Thr Cys Val Leu Thr Asp Thr Ser Tyr Pro
145                 150                 155                 160

Leu Tyr Ser Thr Tyr Trp Tyr Arg Lys Asn Pro Gly Ser Ser Asn Lys
                165                 170                 175

Glu Gln Ile Ser Ile Ser Gly Arg Tyr Ser Glu Ser Val Asn Lys Gly
            180                 185                 190

Thr Lys Ser Phe Thr Leu Thr Ile Ser Ser Leu Gln Pro Glu Asp Ser
        195                 200                 205

Ala Thr Tyr Tyr Cys Arg Ala Met Ser Thr Asn Ile Trp Thr Gly Asp
    210                 215                 220

Gly Ala Gly Thr Lys Val Glu Ile Lys Gly Gly Gly Gly Ser Gly Gly
225                 230                 235                 240

Gly Gly Ser Gly Gly Gly Gly Ser Gly Gly Gly Gly Ser Gly Ala His
                245                 250                 255

Ser Ala Arg Val Asp Gln Thr Pro Gln Thr Ile Thr Lys Glu Thr Gly
            260                 265                 270

Glu Ser Leu Thr Ile Asn Cys Val Leu Arg Asp Ser Asn Cys Gly Leu
        275                 280                 285

Ser Ser Thr Tyr Trp Tyr Arg Lys Lys Ser Gly Ser Thr Asn Glu Glu
    290                 295                 300

Ser Ile Ser Lys Gly Gly Arg Tyr Val Glu Thr Ile Asn Glu Gly Ser
305                 310                 315                 320

Lys Ser Phe Ser Leu Arg Ile Asn Asp Leu Thr Val Glu Asp Ser Gly
                325                 330                 335

Thr Tyr Arg Cys Lys Leu Ser Trp Trp Thr Gln Asn Trp Arg Cys Ser
            340                 345                 350

Asn Ser Asp Val Tyr Gly Gly Gly Thr Val Val Thr Val Asn His His
        355                 360                 365

His His His His Glu Gln Lys Leu Ile Ser Glu Glu Asp Leu
370                 375                 380

<210> SEQ ID NO 38
<211> LENGTH: 1149
<212> TYPE: DNA
<213> ORGANISM: Artificial Sequence
<220> FEATURE:
<223> OTHER INFORMATION: NUCLEOTIDE SEQUENCE CODING FOR THE TNF VNAR
      D1-BA11-C4 WITH HIS AND MYC TAGS

<400> SEQUENCE: 38
gctcgagtgg accaaacacc gcaaacaata caaaggaga cgggcgaatc actgaccatc    60

```
aactgtgtcc tacgagatag ccactgtgca acctccagca cgtactggta tcgcaaaaaa    120
tcgggctcaa caaacgagga gagcatatcg aaaggtggac gatatgttga aacagttaac    180
agcggatcaa agtccttttc tttgagaatt aatgatctaa cagttgaaga cagtggcacg    240
tatcgatgcg cttccgagtg ccaatatgga ctggcagaat atgatgtata cggaggtggc    300
actgtcgtga ctgtgaatgg aggtggcgga tccggggggtg gcggtagcgg aggtggcggt    360
agcggaggtg gcggtagtgg agctcattca acaagagtgg accaaagtcc aagctctctg    420
tccgccagtg tgggcgaccg cgtgaccatc acctgcgtcc tgactgatac cagctatcct    480
ctgtacagca catactggta tcggaagaat cccggttcca gcaacaagga gcagatttcc    540
atctccggcc gctatagtga atcagtcaac aagggcacta agtcctttac cctgacaatc    600
agttccctgc agcccgagga ctccgccacc tattactgca gagctatgag tacaaatatc    660
tggaccgggg acggagctgg taccaaggtg gagatcaagg gaggtggcgg ttccggaggt    720
ggcggtagcg gaggtggcgg tagcggaggt ggcggtagcg gggcccattc tgctcgagtg    780
gaccaaacac cgcaaacaat aacaaaggag acgggcgaat cactgaccat caactgtgtc    840
ctacgagata gcaactgtgg gttgtccagc acgtactggt atcgcaaaaa atcgggctca    900
acaaacgagg agagcatatc gaaaggtgga cgatatgttg aaacaattaa cgaaggatca    960
aagtcctttt ctttgagaat taatgatcta acagttgaag acagtggcac gtatcgatgc    1020
aagttaagct ggtggaccca gaactggaga tgctcaaatt ccgatgtata cggaggtggc    1080
actgtcgtga ctgtgaatca tcaccatcac catcaccatg aacaaaaact catctcagaa    1140
gaggatctg                                                             1149
```

<210> SEQ ID NO 39  
<211> LENGTH: 380  
<212> TYPE: PRT  
<213> ORGANISM: Artificial Sequence  
<220> FEATURE:  
<223> OTHER INFORMATION: TNF VNAR D1-BA11-D1 AMINO ACID SEQUENCE WITH
HIS AND MYC TAGS

<400> SEQUENCE: 39

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Ala Ser Glu Cys Gln Tyr Gly Leu Ala Glu Tyr Asp Val
                85                  90                  95

Tyr Gly Gly Gly Thr Val Val Thr Val Asn Gly Gly Gly Gly Ser Gly
            100                 105                 110

Gly Gly Gly Ser Gly Gly Gly Gly Ser Gly Gly Gly Gly Ser Gly Ala
        115                 120                 125

His Ser Thr Arg Val Asp Gln Ser Pro Ser Ser Leu Ser Ala Ser Val
    130                 135                 140

Gly Asp Arg Val Thr Ile Thr Cys Val Leu Thr Asp Thr Ser Tyr Pro
145                 150                 155                 160
```

Leu Tyr Ser Thr Tyr Trp Tyr Arg Lys Asn Pro Gly Ser Asn Lys
            165                 170                 175

Glu Gln Ile Ser Ile Ser Gly Arg Tyr Ser Glu Ser Val Asn Lys Gly
        180                 185                 190

Thr Lys Ser Phe Thr Leu Thr Ile Ser Ser Leu Gln Pro Glu Asp Ser
        195                 200                 205

Ala Thr Tyr Tyr Cys Arg Ala Met Ser Thr Asn Ile Trp Thr Gly Asp
    210                 215                 220

Gly Ala Gly Thr Lys Val Glu Ile Lys Gly Gly Gly Ser Gly Gly
225                 230                 235                 240

Gly Gly Ser Gly Gly Gly Gly Ser Gly Gly Gly Gly Ser Gly Ala His
            245                 250                 255

Ser Ala Arg Val Asp Gln Thr Pro Gln Thr Ile Thr Lys Glu Thr Gly
            260                 265                 270

Glu Ser Leu Thr Ile Asn Cys Val Leu Arg Asp Ser His Cys Ala Thr
        275                 280                 285

Ser Ser Thr Tyr Trp Tyr Arg Lys Lys Ser Gly Ser Thr Asn Glu Glu
    290                 295                 300

Ser Ile Ser Lys Gly Gly Arg Tyr Val Glu Thr Val Asn Ser Gly Ser
305                 310                 315                 320

Lys Ser Phe Ser Leu Arg Ile Asn Asp Leu Thr Val Glu Asp Ser Gly
            325                 330                 335

Thr Tyr Arg Cys Ala Ser Glu Cys Gln Tyr Gly Leu Ala Glu Tyr Asp
            340                 345                 350

Val Tyr Gly Gly Gly Thr Val Val Thr Val Asn His His His His
        355                 360                 365

His His Glu Gln Lys Leu Ile Ser Glu Glu Asp Leu
    370                 375                 380

<210> SEQ ID NO 40
<211> LENGTH: 1140
<212> TYPE: DNA
<213> ORGANISM: Artificial Sequence
<220> FEATURE:
<223> OTHER INFORMATION: NUCLEOTIDE SEQUENCE CODING FOR THE TNF VNAR
      D1-BA11-D1 WITH HIS AND MYC TAGS

<400> SEQUENCE: 40
gctcgagtgg accaaacacc gcaaacaata caaaggaga cgggcgaatc actgaccatc        60
aactgtgtcc tacgagatag ccactgtgca acctccagca cgtactggta tcgcaaaaaa      120
tcgggctcaa caaacgagga gagcatatcg aaaggtggac gatatgttga acagttaac      180 agcggatcaa agtcctttc tttgagaatt aatgatctaa cagttgaaga cagtggcacg      240
tatcgatgcg cttccgagtg ccaatatgga ctggcagaat atgatgtata cggaggtggc      300
actgtcgtga ctgtgaatgg aggtggcgga tccggggggtg gcggtagcgg aggtggcggt      360
agcggaggtg gcggtagtgg agctcattca acaagagtgg accaaagtcc aagctctctg      420
tccgccagtg tgggcgaccg cgtgaccatc acctgcgtcc tgactgatac cagctatcct      480
ctgtacagca catactggta tcggaagaat cccggttcca gcaacaagga gcagatttcc      540
atctccggcc gctatagtga atcagtcaac aagggcacta gtcctttac cctgacaatc      600 agttccctgc agcccgagga ctccgccacc tattactgca gagctatgag tacaaatatc      660
tggaccgggg acggagctgg taccaaggtg agatcaagg gaggtggcgg ttccggaggt      720
ggcggtagcg gaggtggcgg tagcggaggt ggcggtagcg gggcccattc tgctcgagtg      780

```
gaccaaacac cgcaaacaat aacaaaggag acgggcgaat cactgaccat caactgtgtc    840
ctacgagata gccactgtgc aacctccagc acgtactggt atcgcaaaaa atcgggctca    900
acaaacgagg agagcatatc gaaaggtgga cgatatgttg aaacagttaa cagcggatca    960
aagtcctttt ctttgagaat taatgatcta acagttgaag acagtggcac gtatcgatgc   1020
gcttccgagt gccaatatgg actggcagaa tatgatgtat acggaggtgg cactgtcgtg   1080
actgtgaatc atcaccatca ccatcaccat gaacaaaaac tcatctcaga agaggatctg   1140
```

<210> SEQ ID NO 41
<211> LENGTH: 392
<212> TYPE: PRT
<213> ORGANISM: Artificial Sequence
<220> FEATURE:
<223> OTHER INFORMATION: TNF VNAR D1-BA11-B4 AMINO ACID SEQUENCE WITH
      HIS AND MYC TAGS

<400> SEQUENCE: 41

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Ala Ser Glu Cys Gln Tyr Gly Leu Ala Glu Tyr Asp Val
                85                  90                  95

Tyr Gly Gly Gly Thr Val Val Thr Val Asn Gly Gly Gly Ser Gly
            100                 105                 110

Gly Gly Gly Ser Gly Gly Gly Gly Ser Gly Gly Gly Ser Gly Ala
        115                 120                 125

His Ser Thr Arg Val Asp Gln Ser Pro Ser Ser Leu Ser Ala Ser Val
    130                 135                 140

Gly Asp Arg Val Thr Ile Thr Cys Val Leu Thr Asp Thr Ser Tyr Pro
145                 150                 155                 160

Leu Tyr Ser Thr Tyr Trp Tyr Arg Lys Asn Pro Gly Ser Ser Asn Lys
                165                 170                 175

Glu Gln Ile Ser Ile Ser Gly Arg Tyr Ser Glu Ser Val Asn Lys Gly
            180                 185                 190

Thr Lys Ser Phe Thr Leu Thr Ile Ser Ser Leu Gln Pro Glu Asp Ser
        195                 200                 205

Ala Thr Tyr Tyr Cys Arg Ala Met Ser Thr Asn Ile Trp Thr Gly Asp
    210                 215                 220

Gly Ala Gly Thr Lys Val Glu Ile Lys Gly Gly Gly Ser Gly Gly
225                 230                 235                 240

Gly Gly Ser Gly Gly Gly Gly Ser Gly Gly Gly Gly Ser Gly Ala His
                245                 250                 255

Ser Ala Arg Val Asp Gln Thr Pro Gln Thr Ile Thr Lys Glu Thr Gly
            260                 265                 270

Glu Ser Leu Thr Ile Asn Cys Val Leu Arg Asp Ser Asn Cys Ala Leu
        275                 280                 285

Ser Ser Met Tyr Trp Tyr Arg Lys Lys Ser Gly Ser Thr Asn Glu Glu

```
            290                 295                 300
Ser Ile Ser Lys Gly Gly Arg Tyr Val Glu Thr Val Asn Gly Ser
305                 310                 315                 320

Lys Ser Phe Ser Leu Arg Ile Asn Asp Leu Thr Val Glu Asp Ser Gly
                325                 330                 335

Thr Tyr Arg Cys Lys Val Tyr Ile Pro Cys Ile Asp Glu Leu Val Tyr
            340                 345                 350

Met Ile Ser Gly Gly Thr Ser Gly Pro Ile His Asp Val Tyr Gly Gly
        355                 360                 365

Gly Thr Val Val Thr Val Asn His His His His His His Glu Gln
    370                 375                 380

Lys Leu Ile Ser Glu Glu Asp Leu
385                 390

<210> SEQ ID NO 42
<211> LENGTH: 1176
<212> TYPE: DNA
<213> ORGANISM: Artificial Sequence
<220> FEATURE:
<223> OTHER INFORMATION: NUCLEOTIDE SEQUENCE CODING FOR THE TNF VNAR
      D1-BA11-B4 WITH HIS AND MYC TAGS

<400> SEQUENCE: 42
gctcgagtgg accaaacacc gcaaacaata acaaaggaga cgggcgaatc actgaccatc      60
aactgtgtcc tacgagatag ccactgtgca acctccagca cgtactggta tcgcaaaaaa     120
tcgggctcaa caaacgagga gagcatatcg aaaggtggac gatatgttga aacagttaac     180
agcggatcaa agtccttttc tttgagaatt aatgatctaa cagttgaaga cagtggcacg     240
tatcgatgcg cttccgagtg ccaatatgga ctggcagaat atgatgtata cggaggtggc     300
actgtcgtga ctgtgaatgg aggtggcgga tccggggggtg gcggtagcgg aggtggcggt     360
agcggaggtg gcggtagtgg agctcattca acaagagtgg accaaagtcc aagctctctg     420
tccgccagtg tgggcgaccg cgtgaccatc acctgcgtcc tgactgatac cagctatcct     480
ctgtacagca catactggta tcggaagaat cccggttcca gcaacaagga gcagatttcc     540
atctccggcc gctatagtga atcagtcaac aagggcacta gtcctttac cctgacaatc     600 agttccctgc agcccgagga ctccgccacc tattactgca gagctatgag tacaaatatc     660
tggaccgggg acggagctgg taccaaggtg gagatcaagg gaggtggcgg ttccggaggt     720
ggcggtagcg gaggtggcgg tagcggaggt ggcggtagcg ggccattc tgctcgagtg     780 gaccaaacac cgcaaacaat aacaaaggag acgggcgaat cactgaccat caactgtgtc     840
ctacgagata gtaactgtgc attgtccagc atgtactggt atcgcaaaaa atctggctca     900
acaaacgagg agagcatatc gaaaggtgga cgatatgttg aaacagttaa cagcggatca     960
aagtcctttt ctttgagaat taatgatcta acagttgaag acagtggcac gtatcgatgc    1020
aaggtatata taccttgcat cgatgaactg gtatatatga tcagtggggg tacctctggc    1080
ccgattcatg atgtatacgg aggtggcact gtcgtgactg tgaatcatca ccatcaccat    1140
caccatgaac aaaaactcat ctcagaagag gatctg                              1176

<210> SEQ ID NO 43
<211> LENGTH: 485
<212> TYPE: PRT
<213> ORGANISM: Artificial Sequence
<220> FEATURE:
<223> OTHER INFORMATION: ICOS VNAR 2D4-Fc-2D4 AMINO ACID SEQUENCE
```

```
<400> SEQUENCE: 43

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asp Tyr Gly Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Phe Thr Trp Pro Trp Glu Trp Pro Asp Arg Trp
                85                  90                  95

Phe Arg Pro Trp Tyr Asp Gly Ala Gly Thr Val Leu Thr Val Asn Gly
            100                 105                 110

Gly Gly Gly Ser Gly Gly Gly Ala Asp Gln Glu Pro Lys Ser Ser Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys Thr Ala Ala Ala Thr Ala Ala Ala Thr Ala Ala Ala
        355                 360                 365

Ala Thr Ala Ala Ala Thr Arg Val Asp Gln Thr Pro Arg Thr Ala
    370                 375                 380

Thr Lys Glu Thr Gly Glu Ser Leu Thr Ile Asn Cys Val Leu Thr Asp
385                 390                 395                 400

Thr Asp Tyr Gly Leu Phe Ser Thr Ser Trp Phe Arg Lys Asn Pro Gly
                405                 410                 415
```

```
Thr Thr Asp Trp Glu Arg Met Ser Ile Gly Gly Arg Tyr Val Glu Ser
            420                 425                 430

Val Asn Lys Gly Ala Lys Ser Phe Ser Leu Arg Ile Lys Asp Leu Thr
        435                 440                 445

Val Ala Asp Ser Ala Thr Tyr Tyr Cys Lys Ala Phe Thr Trp Pro Trp
    450                 455                 460

Glu Trp Pro Asp Arg Trp Phe Arg Pro Trp Tyr Asp Gly Ala Gly Thr
465                 470                 475                 480

Val Leu Thr Val Asn
            485

<210> SEQ ID NO 44
<211> LENGTH: 1455
<212> TYPE: DNA
<213> ORGANISM: Artificial Sequence
<220> FEATURE:
<223> OTHER INFORMATION: ICOS VNAR 2D4-Fc-2D4

<400> SEQUENCE: 44
acacgtgttg accagacacc gcgtaccgca accaaagaaa ccggtgaaag cctgaccatt        60
aattgtgttc tgaccgatac cgattatggt ttgttctcca ccagctggtt tcgtaaaaat       120
ccgggtacaa ccgattggga acgtatgagc attggtggtc gttatgttga agcgtgaat        180 aaaggtgcca aaagctttag cctgcgcatt aaagatctga ccgttgcaga tagcgcaacc       240
tattactgta aagcattcac ttggccgtgg gaatggccgg accgttggtt ccgtccgtgg       300
tatgatggtg caggcaccgt tctgaccgtt aatggcggtg gtggttctgg tggtggtgct       360
gatcaggagc ccaaatcttc tgacaaaact cacacatgtc caccgtgccc agcacctgaa       420
ctcctgggtg accgtcagt cttcctcttc cccccaaaac ccaaggacac cctcatgatc        480
tcccggaccc ctgaggtcac atgcgtggtg gtggacgtga gccacgaaga ccctgaggtc       540
aagttcaact ggtacgtgga cggcgtggag gtgcataatg ccaagacaaa gccgcgggag       600
gagcagtaca acagcacgta ccgtgtggtc agcgtcctca ccgtcctgca ccaggactgg       660
ctgaatggca aggagtacaa gtgcaaggtc tccaacaaag ccctcccagc ccccatcgag       720
aaaaccatct ccaaagccaa agggcagccc cgagaaccac aggtgtacac cctgccccca       780
tcccgggagg agatgaccaa gaaccaggtc agcctgacct gcctggtcaa aggcttctat       840
cccagcgaca tcgccgtgga gtgggagagc aatgggcagc cggagaacaa ctacaagacc       900
acgcctcccg tgctggactc cgacggctcc ttcttcctct atagcaagct caccgtggac       960
aagagcaggt ggcagcaggg gaacgtcttc tcatgctccg tgatgcatga ggctctgcac      1020
aaccactaca cgcagaagag cctctccctg tccccgggta aaaccgccgc cgccgccacc      1080
gccgccgccg ccaccgccgc cgccgccacc gccgcggccg ccacacgtgt tgatcagaca      1140
ccgcgtaccg caaccaaaga aaccggtgaa agcctgacca ttaattgtgt tctgaccgat      1200
accgattatg gtttgttctc caccagctgg tttcgtaaaa atccgggtac aaccgattgg      1260
gaacgtatga gcattggtgg tcgttatgtt gaaagcgtga ataaaggtgc caaaagcttt      1320
agcctgcgca ttaaagatct gaccgttgca gatagcgcaa cctattactg taaagcattc      1380
acttggccgt gggaatggcc ggaccgttgg ttccgtccgt ggtatgatgg tgcaggcacc      1440
gttctgaccg ttaat                                                       1455

<210> SEQ ID NO 45
<211> LENGTH: 481
```

```
<212> TYPE: PRT
<213> ORGANISM: Artificial Sequence
<220> FEATURE:
<223> OTHER INFORMATION: ICOS VNAR 2D4-Fc-CC3 AMINO ACID SEQUENCE

<400> SEQUENCE: 45

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asp Tyr Gly Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Phe Thr Trp Pro Trp Glu Trp Pro Asp Arg Trp
                85                  90                  95

Phe Arg Pro Trp Tyr Asp Gly Ala Gly Thr Val Leu Thr Val Asn Gly
            100                 105                 110

Gly Gly Gly Ser Gly Gly Gly Ala Asp Gln Glu Pro Lys Ser Ser Asp
        115                 120                 125

Lys Thr His Thr Cys Pro Pro Cys Pro Ala Pro Glu Leu Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys Thr Ala Ala Ala Ala Thr Ala Ala Ala Thr Ala Ala Ala
        355                 360                 365

Ala Thr Ala Ala Ala Ala Thr Arg Val Asp Gln Thr Pro Arg Thr Ala
370                 375                 380
```

```
Thr Lys Glu Thr Gly Glu Ser Leu Thr Ile Asn Cys Val Leu Thr Asp
385                 390                 395                 400

Thr Glu Tyr Gly Leu Phe Ser Thr Ser Trp Phe Arg Lys Asn Pro Gly
            405                 410                 415

Thr Thr Asp Trp Glu Arg Met Ser Ile Gly Gly Arg Tyr Val Glu Ser
            420                 425                 430

Val Asn Lys Gly Ala Lys Ser Phe Ser Leu Arg Ile Lys Asp Leu Thr
            435                 440                 445

Val Ala Asp Ser Ala Thr Tyr Tyr Cys Lys Ala Leu Gly Trp Trp Pro
            450                 455                 460

Pro Ala Phe Pro His Trp Tyr Asp Gly Ala Gly Thr Val Leu Thr Val
465                 470                 475                 480

Asn
```

<210> SEQ ID NO 46
<211> LENGTH: 1443
<212> TYPE: DNA
<213> ORGANISM: Artificial Sequence
<220> FEATURE:
<223> OTHER INFORMATION: ICOS VNAR 2D4-Fc-CC3

<400> SEQUENCE: 46

```
acacgtgttg accagacacc gcgtaccgca accaaagaaa ccggtgaaag cctgaccatt      60
aattgtgttc tgaccgatac cgattatggt ttgttctcca ccagctggtt tcgtaaaaat     120
ccgggtacaa ccgattggga acgtatgagc attggtggtc gttatgttga agcgtgaat     180
aaaggtgcca aaagctttag cctgcgcatt aaagatctga ccgttgcaga tagcgcaacc     240
tattactgta aagcattcac ttggccgtgg gaatggccgg accgttggtt ccgtccgtgg     300
tatgatggtg caggcaccgt tctgaccgtt aatggcggtg gtggttctgg tggtggtgct     360
gatcaggagc ccaaatcttc tgacaaaact cacacatgtc caccgtgccc agcacctgaa     420
ctcctgggtg accgtcagt cttcctcttc cccccaaaac ccaaggacac cctcatgatc     480
tcccggaccc ctgaggtcac atgcgtggtg gtggacgtga gccacgaaga ccctgaggtc     540
aagttcaact ggtacgtgga cggcgtggag gtgcataatg ccaagacaaa gccgcgggag     600
gagcagtaca acagcacgta ccgtgtggtc agcgtcctca ccgtcctgca ccaggactgg     660
ctgaatggca aggagtacaa gtgcaaggtc tccaacaaag ccctcccagc ccccatcgag     720
aaaaccatct ccaaagccaa agggcagccc cgagaaccac aggtgtacac cctgccccca     780
tcccgggagg agatgaccaa gaaccaggtc agcctgacct gcctggtcaa aggcttctat     840
cccagcgaca tcgccgtgga gtgggagagc aatgggcagc cggagaacaa ctacaagacc     900
acgcctcccg tgctggactc cgacggctcc ttcttcctct atagcaagct caccgtggac     960
aagagcaggt ggcagcaggg gaacgtcttc tcatgctccg tgatgcatga ggctctgcac    1020
aaccactaca cgcagaagag cctctccctg tccccgggta aaaccgccgc cgccgccacc    1080
gccgccgccg ccaccgccgc cgccgccacc gccgcggccg ccacacgtgt tgatcagaca    1140
ccgcgtaccg caaccaaaga aaccggtgaa agcctgacca ttaattgtgt tctgaccgat    1200
accgagtatg gtttgttctc caccagctgg tttcgtaaaa atccgggtac aaccgattgg    1260
gaacgtatga gcattggtgg tcgttatgtt gaaagcgtga ataaaggtgc caaaagcttt    1320
agcctgcgca ttaaagatct gaccgttgca gatagcgcaa cctattactg taaagcactg    1380
ggttggtggc cgccggcttt cccgcattgg tatgatggtg caggcaccgt tctgaccgtt    1440
aat                                                                 1443
```

```
<210> SEQ ID NO 47
<211> LENGTH: 481
<212> TYPE: PRT
<213> ORGANISM: Artificial Sequence
<220> FEATURE:
<223> OTHER INFORMATION: ICOS VNAR CC3-Fc-2D4 AMINO ACID SEQUENCE

<400> SEQUENCE: 47
```

| | | | | | | | | | | | | | | | |
|---|---|---|---|---|---|---|---|---|---|---|---|---|---|---|---|
| Thr | Arg | Val | Asp | Gln | Thr | Pro | Arg | Thr | Ala | Thr | Lys | Glu | Thr | Gly | Glu |
| 1 | | | | 5 | | | | | 10 | | | | | 15 | |
| Ser | Leu | Thr | Ile | Asn | Cys | Val | Leu | Thr | Asp | Thr | Glu | Tyr | Gly | Leu | Phe |
| | | | 20 | | | | | 25 | | | | | 30 | | |
| Ser | Thr | Ser | Trp | Phe | Arg | Lys | Asn | Pro | Gly | Thr | Thr | Asp | Trp | Glu | Arg |
| | | 35 | | | | | 40 | | | | | 45 | | | |
| Met | Ser | Ile | Gly | Gly | Arg | Tyr | Val | Glu | Ser | Val | Asn | Lys | Gly | Ala | Lys |
| | 50 | | | | | 55 | | | | | 60 | | | | |
| Ser | Phe | Ser | Leu | Arg | Ile | Lys | Asp | Leu | Thr | Val | Ala | Asp | Ser | Ala | Thr |
| 65 | | | | | 70 | | | | | 75 | | | | | 80 |
| Tyr | Tyr | Cys | Lys | Ala | Leu | Gly | Trp | Trp | Pro | Ala | Phe | Pro | His | Trp | |
| | | | | 85 | | | | | 90 | | | | | 95 | |
| Tyr | Asp | Gly | Ala | Gly | Thr | Val | Leu | Thr | Val | Asn | Gly | Gly | Gly | Ser | |
| | | | 100 | | | | | 105 | | | | | 110 | | |
| Gly | Gly | Gly | Gly | Arg | Thr | Glu | Pro | Lys | Ser | Ser | Asp | Lys | Thr | His | Thr |
| | | 115 | | | | | 120 | | | | | 125 | | | |
| Cys | Pro | Pro | Cys | Pro | Ala | Pro | Glu | Ala | Ala | Gly | Ala | Pro | Ser | Val | Phe |
| | 130 | | | | | 135 | | | | | 140 | | | | |
| Leu | Phe | Pro | Pro | Lys | Pro | Lys | Asp | Thr | Leu | Met | Ile | Ser | Arg | Thr | Pro |
| 145 | | | | | 150 | | | | | 155 | | | | | 160 |
| Glu | Val | Thr | Cys | Val | Val | Val | Asp | Val | Ser | His | Glu | Asp | Pro | Glu | Val |
| | | | | 165 | | | | | 170 | | | | | 175 | |
| Lys | Phe | Asn | Trp | Tyr | Val | Asp | Gly | Val | Glu | Val | His | Asn | Ala | Lys | Thr |
| | | | 180 | | | | | 185 | | | | | 190 | | |
| Lys | Pro | Arg | Glu | Glu | Gln | Tyr | Asn | Ser | Thr | Tyr | Arg | Val | Val | Ser | Val |
| | | 195 | | | | | 200 | | | | | 205 | | | |
| Leu | Thr | Val | Leu | His | Gln | Asp | Trp | Leu | Asn | Gly | Lys | Glu | Tyr | Lys | Cys |
| | 210 | | | | | 215 | | | | | 220 | | | | |
| Lys | Val | Ser | Asn | Lys | Ala | Leu | Pro | Ala | Pro | Ile | Glu | Lys | Thr | Ile | Ser |
| 225 | | | | | 230 | | | | | 235 | | | | | 240 |
| Lys | Ala | Lys | Gly | Gln | Pro | Arg | Glu | Pro | Gln | Val | Tyr | Thr | Leu | Pro | Pro |
| | | | | 245 | | | | | 250 | | | | | 255 | |
| Ser | Arg | Glu | Glu | Met | Thr | Lys | Asn | Gln | Val | Ser | Leu | Thr | Cys | Leu | Val |
| | | | 260 | | | | | 265 | | | | | 270 | | |
| Lys | Gly | Phe | Tyr | Pro | Ser | Asp | Ile | Ala | Val | Glu | Trp | Glu | Ser | Asn | Gly |
| | | 275 | | | | | 280 | | | | | 285 | | | |
| Gln | Pro | Glu | Asn | Asn | Tyr | Lys | Thr | Thr | Pro | Pro | Val | Leu | Asp | Ser | Asp |
| | 290 | | | | | 295 | | | | | 300 | | | | |
| Gly | Ser | Phe | Phe | Leu | Tyr | Ser | Lys | Leu | Thr | Val | Asp | Lys | Ser | Arg | Trp |
| 305 | | | | | 310 | | | | | 315 | | | | | 320 |
| Gln | Gln | Gly | Asn | Val | Phe | Ser | Cys | Ser | Val | Met | His | Glu | Ala | Leu | His |
| | | | | 325 | | | | | 330 | | | | | 335 | |
| Asn | His | Tyr | Thr | Gln | Lys | Ser | Leu | Ser | Leu | Ser | Pro | Gly | Lys | Thr | Ala |
| | | | 340 | | | | | 345 | | | | | 350 | | |
| Ala | Ala | Ala | Thr | Ala | Ala | Ala | Ala | Thr | Ala | Ala | Ala | Thr | Ala | Ala | |
| | | 355 | | | | | 360 | | | | | 365 | | | |

```
Ala Ala Thr Arg Val Asp Gln Thr Pro Arg Thr Ala Thr Lys Glu Thr
        370                 375                 380

Gly Glu Ser Leu Thr Ile Asn Cys Val Leu Thr Asp Thr Asp Tyr Gly
385                 390                 395                 400

Leu Phe Ser Thr Ser Trp Phe Arg Lys Asn Pro Gly Thr Thr Asp Trp
            405                 410                 415

Glu Arg Met Ser Ile Gly Gly Arg Tyr Val Glu Ser Val Asn Lys Gly
            420                 425                 430

Ala Lys Ser Phe Ser Leu Arg Ile Lys Asp Leu Thr Val Ala Asp Ser
        435                 440                 445

Ala Thr Tyr Tyr Cys Lys Ala Phe Thr Trp Pro Trp Glu Trp Pro Asp
        450                 455                 460

Arg Trp Phe Arg Pro Trp Tyr Asp Gly Ala Gly Thr Val Leu Thr Val
465                 470                 475                 480

Asn

<210> SEQ ID NO 48
<211> LENGTH: 1443
<212> TYPE: DNA
<213> ORGANISM: Artificial Sequence
<220> FEATURE:
<223> OTHER INFORMATION: ICOS VNAR CC3-Fc-2D4

<400> SEQUENCE: 48
acacgtgttg atcagacacc gcgtaccgca accaaagaaa ccggtgaaag cctgaccatt      60
aattgtgttc tgaccgatac cgagtatggt ttgttctcca ccagctggtt tcgtaaaaat     120
ccgggtacaa ccgattggga acgtatgagc attggtggtc gttatgttga agcgtgaat      180 aaaggtgcca aaagctttag cctgcgcatt aaagatctga ccgttgcaga tagcgcaacc     240
tattactgta aagcactggg ttggtggccg ccggctttcc cgcattggta tgatggtgca     300
ggcaccgttc tgaccgttaa tggcggtggt ggttctggtg gtggtggtcg tacggagccc     360
aaatcttctg acaaaactca cacatgccca ccgtgcccag cacctgaagc cgctggggca     420
ccgtcagtct tcctcttccc cccaaaaccc aaggacaccc tcatgatctc ccggacccct     480
gaggtcacat gcgtggtggt ggacgtgagc cacgaagacc ctgaggtcaa gttcaactgg     540
tacgtggacg gcgtggaggt gcataatgcc aagacaaagc cgcggagga gcagtacaac     600 agcacgtacc gtgtggtcag cgtcctcacc gtcctgcacc aggactggct gaatggcaag     660
gagtacaagt gcaaggtctc caacaaagcc ctcccagccc ccatcgagaa aaccatctcc     720
aaagccaaag ggcagccccg agaaccacag gtgtacaccc tgcccccatc ccgggaggag     780
atgaccaaga accaggtcag cctgacctgc ctggtcaaag gcttctatcc cagcgacatc     840
gccgtggagt gggagagcaa tgggcagccg gagaacaact acaagaccac gcctcccgtg     900
ctggactccg acggctcctt cttcctctat agcaagctca ccgtggacaa gagcaggtgg     960
cagcagggga acgtcttctc atgctccgtg atgcatgagg ctctgcacaa ccactacacg    1020
cagaagagcc tctccctgtc cccgggtaaa ccgccgccg ccgccaccgc cgccgccgcc    1080
accgccgccg ccgccaccgc cgcggccgcc acacgtgttg atcagacacc gcgtaccgca    1140
accaaagaaa ccggtgaaag cctgaccatt aattgtgttc tgaccgatac cgattatggt    1200
ttgttctcca ccagctggtt tcgtaaaaat ccgggtacaa ccgattggga acgtatgagc    1260
attggtggtc gttatgttga agcgtgaat aaaggtgcca aaagctttag cctgcgcatt    1320
aaagatctga ccgttgcaga tagcgcaacc tattactgta aagcattcac ttggccgtgg    1380
```

```
gaatggccgg accgttggtt ccgtccgtgg tatgatggtg caggcaccgt tctgaccgtt    1440
aat                                                                  1443
```

<210> SEQ ID NO 49
<211> LENGTH: 477
<212> TYPE: PRT
<213> ORGANISM: Artificial Sequence
<220> FEATURE:
<223> OTHER INFORMATION: ICOS VNAR CC3-Fc-CC3 AMINO ACID SEQUENCE

<400> SEQUENCE: 49

```
Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Glu Tyr Gly Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Leu Gly Trp Trp Pro Pro Ala Phe Pro His Trp
                85                  90                  95

Tyr Asp Gly Ala Gly Thr Val Leu Thr Val Asn Gly Gly Gly Gly Ser
            100                 105                 110

Gly Gly Gly Gly Arg Thr Glu Pro Lys Ser Ser Asp Lys Thr His Thr
        115                 120                 125

Cys Pro Pro Cys Pro Ala Pro Glu Ala Ala Gly Ala Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys Thr Ala
```

```
                340             345             350
Ala Ala Thr Ala Ala Ala Ala Thr Ala Ala Ala Thr Ala Ala
            355             360             365

Ala Ala Thr Arg Val Asp Gln Thr Pro Arg Thr Ala Thr Lys Glu Thr
        370             375             380

Gly Glu Ser Leu Thr Ile Asn Cys Val Leu Thr Asp Thr Glu Tyr Gly
385             390             395                         400

Leu Phe Ser Thr Ser Trp Phe Arg Lys Asn Pro Gly Thr Thr Asp Trp
                405             410             415

Glu Arg Met Ser Ile Gly Gly Arg Tyr Val Glu Ser Val Asn Lys Gly
            420             425             430

Ala Lys Ser Phe Ser Leu Arg Ile Lys Asp Leu Thr Val Ala Asp Ser
            435             440             445

Ala Thr Tyr Tyr Cys Lys Ala Leu Gly Trp Trp Pro Pro Ala Phe Pro
        450             455             460

His Trp Tyr Asp Gly Ala Gly Thr Val Leu Thr Val Asn
465             470             475

<210> SEQ ID NO 50
<211> LENGTH: 1431
<212> TYPE: DNA
<213> ORGANISM: Artificial Sequence
<220> FEATURE:
<223> OTHER INFORMATION: ICOS VNAR CC3-Fc-CC3

<400> SEQUENCE: 50
acacgtgttg atcagacacc gcgtaccgca accaaagaaa ccggtgaaag cctgaccatt      60
aattgtgttc tgaccgatac cgagtatggt ttgttctcca ccagctggtt tcgtaaaaat     120
ccgggtacaa ccgattggga acgtatgagc attggtggtc gttatgttga aagcgtgaat     180
aaaggtgcca aaagctttag cctgcgcatt aaagatctga ccgttgcaga tagcgcaacc     240
tattactgta aagcactggg ttggtggccg ccggcttttc cgcattggta tgatggtgca     300
ggcaccgttc tgaccgttaa tggcggtggt ggttctggtg gtggtggtcg tacggagccc     360
aaatcttctg acaaaactca cacatgccca ccgtgcccag cacctgaagc cgctgggcga     420
ccgtcagtct tcctcttccc cccaaaaccc aaggacaccc tcatgatctc ccggacccct     480
gaggtcacat gcgtggtggt ggacgtgagc cacgaagacc ctgaggtcaa gttcaactgg     540
tacgtggacg gcgtggaggt gcataatgcc aagacaaagc cgcgggagga gcagtacaac     600
agcacgtacc gtgtggtcag cgtcctcacc gtcctgcacc aggactggct gaatggcaag     660
gagtacaagt gcaaggtctc caacaaagcc ctcccagccc ccatcgagaa aaccatctcc     720
aaagccaaag gcagccccg agaaccacag gtgtacaccc tgcccccatc ccgggaggag     780
atgaccaaga accaggtcag cctgacctgc ctggtcaaag gcttctatcc cagcgacatc     840
gccgtggagt gggagagcaa tgggcagccg gagaacaact acaagaccac gcctcccgtg     900
ctggactccg acggctcctt cttcctctat agcaagctca ccgtggacaa gagcaggtgg     960
cagcagggga acgtcttctc atgctccgtg atgcatgagg ctctgcacaa ccactacacg    1020
cagaagagcc tctccctgtc cccgggtaaa accgccgccg ccgccaccgc cgccgccgcc    1080
accgccgccg ccgccaccgc cgcggccgcc acacgtgttg atcagacacc gcgtaccgca    1140
accaaagaaa ccggtgaaag cctgaccatt aattgtgttc tgaccgatac cgagtatggt    1200
ttgttctcca ccagctggtt tcgtaaaaat ccgggtacaa ccgattggga acgtatgagc    1260
attggtggtc gttatgttga aagcgtgaat aaaggtgcca aaagctttag cctgcgcatt    1320
```

-continued

```
aaagatctga ccgttgcaga tagcgcaacc tattactgta aagcactggg ttggtggccg    1380
ccggctttcc cgcattggta tgatggtgca ggcaccgttc tgaccgttaa t             1431
```

<210> SEQ ID NO 51
<211> LENGTH: 112
<212> TYPE: PRT
<213> ORGANISM: Artificial Sequence
<220> FEATURE:
<223> OTHER INFORMATION: SoloMER™ VNAR D1-v1 AMINO ACID SEQUENCE WITH
      HIS TAG

<400> SEQUENCE: 51

```
Ala Arg Val Asp Gln Ser Pro Ser Ser Leu Ser Ala Ser Val Gly Asp
1               5                   10                  15

Arg Val Thr Ile Thr Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Ala Ser Glu Cys Gln Tyr Gly Leu Ala Glu Tyr Asp Val
                85                  90                  95

Tyr Gly Gly Gly Thr Lys Val Glu Ile Lys His His His His His His
            100                 105                 110
```

<210> SEQ ID NO 52
<211> LENGTH: 336
<212> TYPE: DNA
<213> ORGANISM: Artificial Sequence
<220> FEATURE:
<223> OTHER INFORMATION: NUCLEOTIDE SEQUENCE CODING FOR THE SoloMER™
      VNAR D1-v1 WITH HIS TAG

<400> SEQUENCE: 52

```
gcccgcgtgg accagtcccc ctcctccctg tccgcctccg tgggcgaccg cgtgaccatc    60
acctgcgtgc tgcgcgactc ccactgcgcc acctcctcca cctactggta ccgcaagaag    120
tccggctcca ccaacgagga gtccatctcc aagggggggcc gctacgtgga gaccgtgaac    180
tccggctcca gtccttctc cctgcgcatc aacgacctga ccgtggagga ctccggcacc    240
taccgctgcg cctccgagtg ccagtacggc ctggccgagt acgacgtgta cggcggcggc    300
accaaggtgg agatcaagca ccaccaccac caccac                              336
```

<210> SEQ ID NO 53
<211> LENGTH: 112
<212> TYPE: PRT
<213> ORGANISM: Artificial Sequence
<220> FEATURE:
<223> OTHER INFORMATION: SoloMER™ VNAR D1-v2 AMINO ACID SEQUENCE WITH
      HIS TAG

<400> SEQUENCE: 53

```
Ala Arg Val Asp Gln Ser Pro Ser Ser Leu Ser Ala Ser Val Gly Asp
1               5                   10                  15

Arg Val Thr Ile Thr Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45
```

```
Ile Ser Lys Gly Gly Arg Tyr Val Glu Thr Val Asn Ser Gly Ser Lys
 50                  55                  60

Ser Phe Thr Leu Thr Ile Ser Ser Leu Gln Pro Glu Asp Phe Ala Thr
 65                  70                  75                  80

Tyr Tyr Cys Ala Ser Glu Cys Gln Tyr Gly Leu Ala Glu Tyr Asp Val
                 85                  90                  95

Tyr Gly Gly Gly Thr Lys Val Glu Ile Lys His His His His His His
            100                 105                 110
```

<210> SEQ ID NO 54
<211> LENGTH: 336
<212> TYPE: DNA
<213> ORGANISM: Artificial Sequence
<220> FEATURE:
<223> OTHER INFORMATION: NUCLEOTIDE SEQUENCE CODING FOR THE SoloMER™
      VNAR D1-v2 WITH HIS TAG

<400> SEQUENCE: 54

```
gcccgcgtgg accagtcccc ctcctccctg tccgcctccg tgggcgaccg cgtgaccatc     60
acctgcgtgc tgcgcgactc ccactgcgcc acctcctcca cctactggta ccgcaagaag    120
tccggctcca ccaacgagga gtccatctcc aagggggggcc gctacgtgga gaccgtgaac    180
tccggctcca gtccttcac cctgaccatc tcctccctgc agcccgagga cttcgccacc     240
tactactgcg cctccgagtg ccagtacggc ctggccgagt acgacgtgta cggcggcggc    300
accaaggtgg agatcaagca ccaccaccac caccac                              336
```

<210> SEQ ID NO 55
<211> LENGTH: 112
<212> TYPE: PRT
<213> ORGANISM: Artificial Sequence
<220> FEATURE:
<223> OTHER INFORMATION: SoloMER™ VNAR D1-v3 AMINO ACID SEQUENCE WITH
      HIS TAG

<400> SEQUENCE: 55

```
Ala Arg Val Asp Gln Ser Pro Ser Ser Leu Ser Ala Ser Val Gly Asp
 1               5                  10                  15

Arg Val Thr Ile Thr Cys Val Leu Arg Asp Ser His Cys Ala Thr Ser
             20                  25                  30

Ser Thr Tyr Trp Tyr Gln Gln Lys Pro Gly Lys Thr Asn Glu Glu Ser
             35                  40                  45

Ile Ser Lys Gly Gly Arg Tyr Val Glu Thr Val Asn Ser Gly Ser Lys
 50                  55                  60

Ser Phe Thr Leu Thr Ile Ser Ser Leu Gln Pro Glu Asp Phe Ala Thr
 65                  70                  75                  80

Tyr Tyr Cys Ala Ser Glu Cys Gln Tyr Gly Leu Ala Glu Tyr Asp Val
                 85                  90                  95

Tyr Gly Gly Gly Thr Lys Val Glu Ile Lys His His His His His His
            100                 105                 110
```

<210> SEQ ID NO 56
<211> LENGTH: 336
<212> TYPE: DNA
<213> ORGANISM: Artificial Sequence
<220> FEATURE:
<223> OTHER INFORMATION: NUCLEOTIDE SEQUENCE CODING FOR THE SoloMER™
      VNAR D1-v3 WITH HIS TAG

<400> SEQUENCE: 56

```
gcccgcgtgg accagtcccc ctcctccctg tccgcctccg tgggcgaccg cgtgaccatc    60
acctgcgtgc tgcgcgactc ccactgcgcc acctcctcca cctactggta ccagcagaag   120
cccggcaaga ccaacgagga gtccatctcc aagggggggcc gctacgtgga gaccgtgaac   180
tccggctcca gtccttcac cctgaccatc tcctccctgc agcccgagga cttcgccacc   240
tactactgcg cctccgagtg ccagtacggc ctggccgagt acgacgtgta cggcggcggc   300
accaaggtgg agatcaagca ccaccaccac caccac                              336
```

<210> SEQ ID NO 57
<211> LENGTH: 112
<212> TYPE: PRT
<213> ORGANISM: Artificial Sequence
<220> FEATURE:
<223> OTHER INFORMATION: SoloMER™ VNAR D1-v4 AMINO ACID SEQUENCE WITH HIS TAG

<400> SEQUENCE: 57

```
Ala Arg Val Asp Gln Ser Pro Ser Ser Leu Ser Ala Ser Val Gly Asp
1               5                   10                  15

Arg Val Thr Ile Thr Cys Val Leu Arg Asp Ser His Cys Ala Thr Ser
            20                  25                  30

Ser Thr Tyr Trp Tyr Arg Lys Lys Pro Gly Ser Thr Asn Glu Glu Ser
        35                  40                  45

Ile Ser Lys Gly Gly Arg Phe Ser Gly Ser Gly Ser Gly Ser Lys
    50                  55                  60

Ser Phe Thr Leu Thr Ile Ser Ser Leu Gln Pro Glu Asp Phe Ala Thr
65                  70                  75                  80

Tyr Tyr Cys Ala Ser Glu Cys Gln Tyr Gly Leu Ala Glu Tyr Asp Val
                85                  90                  95

Phe Gly Gln Gly Thr Lys Val Glu Ile Lys His His His His His
            100                 105                 110
```

<210> SEQ ID NO 58
<211> LENGTH: 336
<212> TYPE: DNA
<213> ORGANISM: Artificial Sequence
<220> FEATURE:
<223> OTHER INFORMATION: NUCLEOTIDE SEQUENCE CODING FOR THE SoloMER™ VNAR D1-v4 WITH HIS TAG

<400> SEQUENCE: 58

```
gcccgcgtgg accagtcccc ctcctccctg tccgcctccg tgggcgaccg cgtgaccatc    60
acctgcgtgc tgcgcgactc ccactgcgcc acctcctcca cctactggta ccgcaagaag   120
cccggctcca ccaacgagga gtccatctcc aagggggggcc gcttctccgg ctccggctcc   180
tccggctcca gtccttcac cctgaccatc tcctccctgc agcccgagga cttcgccacc   240
tactactgcg cctccgagtg ccagtacggc ctggccgagt acgacgtgtt cggccagggc   300
accaaggtgg agatcaagca ccaccaccac caccac                              336
```

<210> SEQ ID NO 59
<211> LENGTH: 483
<212> TYPE: PRT
<213> ORGANISM: Artificial Sequence
<220> FEATURE:
<223> OTHER INFORMATION: Quad-X™ D1-Fc-C4 AMINO ACID SEQUENCE

<400> SEQUENCE: 59

```
Ala Arg Val Asp Gln Thr Pro Gln Thr Ile Thr Lys Glu Thr Gly Glu
1               5                   10                  15
```

Ser Leu Thr Ile Asn Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Ala Ser Glu Cys Gln Tyr Gly Leu Ala Glu Tyr Asp Val
                85                  90                  95

Tyr Gly Gly Gly Thr Val Val Thr Val Asn Gly Ser Gly Gly Gly Ser
            100                 105                 110

Gly Gly Gly Gly Ser Gly Glu Pro Lys Ser Ser Asp Lys Thr His Thr
            115                 120                 125

Cys Pro Pro Cys Pro Ala Pro Glu Leu Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
            195                 200                 205

Leu Thr Val Leu His Gln Asp Trp Leu Asn Gly Lys Glu Tyr Lys Cys
            210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
            290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys Gly Gly
            340                 345                 350

Gly Gly Ser Gly Gly Gly Gly Ser Gly Gly Gly Gly Ser Gly Gly Gly
            355                 360                 365

Gly Ser Gly Ala His Ser Ala Arg Val Asp Gln Thr Pro Gln Thr Ile
            370                 375                 380

Thr Lys Glu Thr Gly Glu Ser Leu Thr Ile Asn Cys Val Leu Arg Asp
385                 390                 395                 400

Ser Asn Cys Gly Leu Ser Ser Thr Tyr Trp Tyr Arg Lys Lys Ser Gly
                405                 410                 415

Ser Thr Asn Glu Glu Ser Ile Ser Lys Gly Gly Arg Tyr Val Glu Thr
            420                 425                 430

Ile Asn Glu Gly Ser Lys Ser Phe Ser Leu Arg Ile Asn Asp Leu Thr
435                 440                 445

Val Glu Asp Ser Gly Thr Tyr Arg Cys Lys Leu Ser Trp Trp Thr Gln
    450                 455                 460

Asn Trp Arg Cys Ser Asn Ser Asp Val Tyr Gly Gly Thr Val Val
465                 470                 475                 480

Thr Val Asn

<210> SEQ ID NO 60
<211> LENGTH: 1449
<212> TYPE: DNA
<213> ORGANISM: Artificial Sequence
<220> FEATURE:
<223> OTHER INFORMATION: NUCLEOTIDE SEQUENCE CODING FOR THE Quad-X™ D1-Fc-C4

<400> SEQUENCE: 60

| | | | | |
|---|---|---|---|---|
| gctcgagtgg | accaaacacc | gcaaacaata | acaaaggaga | cgggcgaatc | actgaccatc | 60 |
| aactgtgtcc | tacgagatag | ccactgtgca | acctccagca | cgtactggta | tcgcaaaaaa | 120 |
| tcgggctcaa | caaacgagga | gagcatatcg | aaaggtggac | gatatgttga | aacagttaac | 180 |
| agcggatcaa | agtcctttc | tttgagaatt | aatgatctaa | cagttgaaga | cagtggcacg | 240 |
| tatcgatgcg | cttccgagtg | ccaatatgga | ctggcagaat | atgatgtata | cggaggtggc | 300 |
| actgtcgtga | ctgtgaatgg | atccggtggt | gggtccggag | gaggtggctc | aggagagccc | 360 |
| aaatctagcg | acaaaactca | cacatgccca | ccgtgcccag | cacctgaact | cctggggga | 420 |
| ccgtcagtct | tcctcttccc | cccaaaaccc | aaggacaccc | tcatgatctc | ccggaccct | 480 |
| gaggtcacat | gcgtggtggt | ggacgtgagc | cacgaagacc | ctgaggtcaa | gttcaactgg | 540 |
| tacgtggacg | gcgtggaggt | gcataatgcc | aagacaaagc | cgcgggagga | gcagtacaac | 600 |
| agcacgtacc | gggtggtcag | cgtcctcacc | gtcctgcacc | aggactggct | gaatggcaag | 660 |
| gagtacaagt | gcaaggtctc | caacaaagcc | ctcccagccc | ccatcgagaa | aaccatctcc | 720 |
| aaagccaaag | ggcagccccg | agaaccacag | gtgtacaccc | tgcccccatc | ccgggatgag | 780 |
| ctgaccaaga | accaggtcag | cctgacctgc | ctggtcaaag | gcttctatcc | cagcgacatc | 840 |
| gccgtggagt | gggagagcaa | tgggcagccg | gagaacaact | acaagaccac | gcctcccgtg | 900 |
| ctggactccg | acggctcctt | cttcctctac | agcaagctca | ccgtggacaa | gagcaggtgg | 960 |
| cagcagggga | acgtcttctc | atgctccgtg | atgcatgagg | ctctgcacaa | ccactacacg | 1020 |
| cagaagagcc | tctccctgtc | tccggggaaa | ggaggtggcg | gttccggagg | tggcggtagc | 1080 |
| ggaggtggcg | gtagcggagg | tggcggtagc | ggggcccatt | ctgctcgagt | ggaccaaaca | 1140 |
| ccgcaaacaa | taacaaagga | gacgggcgaa | tcactgacca | tcaactgtgt | cctacgagat | 1200 |
| agcaactgtg | ggttgtccag | cacgtactgg | tatcgcaaaa | aatcgggctc | aacaaacgag | 1260 |
| gagagcatat | cgaaaggtgg | acgatatgtt | gaaacaatta | cgaaggatc | aaagtccttt | 1320 |
| tctttgagaa | ttaatgatct | aacagttgaa | gacagtggca | cgtatcgatg | caagttaagc | 1380 |
| tggtggaccc | agaactggag | atgctcaaat | tccgatgtat | acggaggtgg | cactgtcgtg | 1440 |
| actgtgaat | | | | | 1449 |

<210> SEQ ID NO 61
<211> LENGTH: 472
<212> TYPE: PRT
<213> ORGANISM: Artificial Sequence
<220> FEATURE:
<223> OTHER INFORMATION: Quad-Y-D1C4™ D1-C4-Fc AMINO ACID SEQUENCE

<400> SEQUENCE: 61

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Ala Ser Glu Cys Gln Tyr Gly Leu Ala Glu Tyr Asp Val
                85                  90                  95

Tyr Gly Gly Gly Thr Val Thr Val Asn Gly Gly Gly Ser Gly
            100                 105                 110

Gly Gly Gly Gly Ser Gly Ala His Ser Ala Arg Val Asp Gln Thr Pro
        115                 120                 125

Gln Thr Ile Thr Lys Glu Thr Gly Glu Ser Leu Thr Ile Asn Cys Val
    130                 135                 140

Leu Arg Asp Ser Asn Cys Gly Leu Ser Ser Thr Tyr Trp Tyr Arg Lys
145                 150                 155                 160

Lys Ser Gly Ser Thr Asn Glu Glu Ser Ile Ser Lys Gly Gly Arg Tyr
                165                 170                 175

Val Glu Thr Ile Asn Glu Gly Ser Lys Ser Phe Ser Leu Arg Ile Asn
            180                 185                 190

Asp Leu Thr Val Glu Asp Ser Gly Thr Tyr Arg Cys Lys Leu Ser Trp
        195                 200                 205

Trp Thr Gln Asn Trp Arg Cys Ser Asn Ser Asp Val Tyr Gly Gly Gly
    210                 215                 220

Thr Val Thr Val Asn Gly Gly Gly Ser Gly Gly Gly Gly Ser Gly
225                 230                 235                 240

Glu Pro Lys Ser Ser Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
```

```
                405                 410                 415
Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

<210> SEQ ID NO 62
<211> LENGTH: 1416
<212> TYPE: DNA
<213> ORGANISM: Artificial Sequence
<220> FEATURE:
<223> OTHER INFORMATION: NUCLEOTIDE SEQUENCE CODING FOR THE Quad-Y-D1C4™
      AMINO ACID SEQUENCE

<400> SEQUENCE: 62

| | | |
|---|---|---|
| gctcgagtgg accaaacacc gcaaacaata caaaggaga cgggcgaatc actgaccatc | 60 |
| aactgtgtcc tacgagatag ccactgtgca acctccagca cgtactgta tcgcaaaaaa | 120 |
| tcgggctcaa caaacgagga gagcatatcg aaaggtggac gatatgttga aacagttaac | 180 |
| agcggatcaa agtcctttc tttgagaatt aatgatctaa cagttgaaga cagtggcacg | 240 |
| tatcgatgcg cttccgagtg ccaatatgga ctggcagaat atgatgtata cggaggtggc | 300 |
| actgtcgtga ctgtgaatgg aggtggcggt agcggaggtg gtggcggatc cggggcgcac | 360 |
| tccgctcgag tggaccaaac accgcaaaca ataacaaagg agacgggcga atcactgacc | 420 |
| atcaactgtg tcctacgaga tagcaactgt gggttgtcca gcacgtactg gtatcgcaaa | 480 |
| aaatcgggct caacaaacga ggagagcata tcgaaaggtg gacgatatgt tgaaacaatt | 540 |
| aacgaaggat caagtccttt tctttgaga attaatgatc taacagttga agacagtggc | 600 |
| acgtatcgat gcaagttaag ctggtggacc cagaactgga gatgctcaaa ttccgatgta | 660 |
| tacgaggtg gcactgtcgt gactgtgaac ggtggtgggt ccggaggagg tggctcagga | 720 |
| gagcccaaat ctagcgacaa aactcacaca tgcccaccgt gcccagcacc tgaactcctg | 780 |
| gggggaccgt cagtcttcct cttcccccca aaacccaagg acaccctcat gatctcccgg | 840 |
| acccctgagg tcacatgcgt ggtggtggac gtgagccacg aagaccctga ggtcaagttc | 900 |
| aactggtacg tggacggcgt ggaggtgcat aatgccaaga caaagccgcg ggaggagcag | 960 |
| tacaacagca cgtaccgtgt ggtcagcgtc ctcaccgtcc tgcaccagga ctggctgaat | 1020 |
| ggcaaggagt acaagtgcaa ggtctccaac aaagccctcc cagcccccat cgagaaaacc | 1080 |
| atctccaaag ccaaagggca gccccgagaa ccacaggtgt acaccctgcc cccatcccgg | 1140 |
| gatgagctga ccaagaacca ggtcagcctg acctgcctgg tcaaaggctt ctatcccagc | 1200 |
| gacatcgccg tggagtggga gagcaatggg cagccggaga caactacaa gaccacgcct | 1260 |
| cccgtgctgg actccgacgg ctccttcttc ctctacagca agctcaccgt ggacaagagc | 1320 |
| aggtggcagc aggggaacgt cttctcatgc tccgtgatgc atgaggctct gcacaaccac | 1380 |
| tacacgcaga gagcctctc cctgtctccg gggaaa | 1416 |

<210> SEQ ID NO 63
<211> LENGTH: 472
<212> TYPE: PRT
<213> ORGANISM: Artificial Sequence
<220> FEATURE:

<223> OTHER INFORMATION: Quad-Y-C4D1™ C4-D1-Fc AMINO ACID SEQUENCE

<400> SEQUENCE: 63

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Gly Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Ile Asn Glu Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Leu Ser Trp Trp Thr Gln Asn Trp Arg Cys Ser Asn
                85                  90                  95

Ser Asp Val Tyr Gly Gly Gly Thr Val Val Thr Val Asn Gly Gly Gly
            100                 105                 110

Gly Ser Gly Gly Gly Gly Ser Gly Ala His Ser Ala Arg Val Asp
        115                 120                 125

Gln Thr Pro Gln Thr Ile Thr Lys Glu Thr Gly Glu Ser Leu Thr Ile
    130                 135                 140

Asn Cys Val Leu Arg Asp Ser His Cys Ala Thr Ser Ser Thr Tyr Trp
145                 150                 155                 160

Tyr Arg Lys Lys Ser Gly Ser Thr Asn Glu Glu Ser Ile Ser Lys Gly
                165                 170                 175

Gly Arg Tyr Val Glu Thr Val Asn Gly Ser Lys Ser Phe Ser Leu
            180                 185                 190

Arg Ile Asn Asp Leu Thr Val Glu Asp Ser Gly Thr Tyr Arg Cys Ala
        195                 200                 205

Ser Glu Cys Gln Tyr Gly Leu Ala Glu Tyr Asp Val Tyr Gly Gly Gly
    210                 215                 220

Thr Val Val Thr Val Asn Gly Gly Gly Ser Gly Gly Gly Gly Ser Gly
225                 230                 235                 240

Glu Pro Lys Ser Ser Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400
```

-continued

```
Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 64
<211> LENGTH: 1416
<212> TYPE: PRT
<213> ORGANISM: Artificial Sequence
<220> FEATURE:
<223> OTHER INFORMATION: NUCLEOTIDE SEQUENCE CODING FOR THE Quad-Y-C4D1™
      AMINO ACID SEQUENCE

<400> SEQUENCE: 64

Gly Cys Thr Cys Gly Ala Gly Thr Gly Gly Ala Cys Cys Ala Ala Ala
1               5                   10                  15

Cys Ala Cys Cys Gly Cys Ala Ala Cys Ala Ala Thr Ala Ala Cys
            20                  25                  30

Ala Ala Ala Gly Gly Ala Gly Ala Cys Gly Gly Cys Gly Ala Ala
        35                  40                  45

Thr Cys Ala Cys Thr Gly Ala Cys Cys Ala Thr Cys Ala Ala Cys Thr
    50                  55                  60

Gly Thr Gly Thr Cys Cys Thr Ala Cys Gly Ala Gly Ala Thr Ala Gly
65                  70                  75                  80

Cys Ala Ala Cys Thr Gly Thr Gly Gly Gly Thr Gly Thr Cys Cys
            85                  90                  95

Ala Gly Cys Ala Cys Gly Thr Ala Cys Thr Gly Gly Thr Ala Thr Cys
        100                 105                 110

Gly Cys Ala Ala Ala Ala Ala Thr Cys Gly Gly Gly Cys Thr Cys
    115                 120                 125

Ala Ala Cys Ala Ala Cys Gly Ala Gly Gly Ala Gly Ala Gly Cys
130                 135                 140

Ala Thr Ala Thr Cys Gly Ala Ala Gly Gly Thr Gly Gly Ala Cys
145                 150                 155                 160

Gly Ala Thr Ala Thr Gly Thr Thr Gly Ala Ala Ala Cys Ala Ala Thr
            165                 170                 175

Thr Ala Ala Cys Gly Ala Ala Gly Gly Ala Thr Cys Ala Ala Ala Gly
        180                 185                 190

Thr Cys Cys Thr Thr Thr Thr Cys Thr Thr Gly Ala Gly Ala Ala
    195                 200                 205

Thr Thr Ala Ala Thr Gly Ala Thr Cys Thr Ala Ala Cys Ala Gly Thr
210                 215                 220

Thr Gly Ala Ala Gly Ala Cys Ala Gly Thr Gly Gly Cys Ala Cys Gly
225                 230                 235                 240

Thr Ala Thr Cys Gly Ala Thr Gly Cys Ala Ala Gly Thr Thr Ala Ala
            245                 250                 255

Gly Cys Thr Gly Gly Thr Gly Gly Ala Cys Cys Cys Ala Gly Ala Ala
        260                 265                 270

Cys Thr Gly Gly Ala Gly Ala Thr Gly Cys Thr Cys Ala Ala Ala Thr
    275                 280                 285
```

```
Thr Cys Cys Gly Ala Thr Gly Thr Ala Thr Ala Cys Gly Gly Ala Gly
    290                 295                 300

Gly Thr Gly Gly Cys Ala Cys Thr Gly Thr Cys Gly Thr Gly Ala Cys
305                 310                 315                 320

Thr Gly Thr Gly Ala Ala Cys Gly Gly Ala Gly Gly Thr Gly Gly Cys
                325                 330                 335

Gly Gly Thr Ala Gly Cys Gly Gly Ala Gly Gly Thr Gly Gly Thr Gly
            340                 345                 350

Gly Cys Gly Gly Ala Thr Cys Cys Gly Gly Gly Gly Cys Gly Cys Ala
        355                 360                 365

Cys Thr Cys Cys Gly Cys Thr Cys Gly Ala Gly Thr Gly Gly Ala Cys
    370                 375                 380

Cys Ala Ala Ala Cys Ala Cys Cys Gly Cys Ala Ala Ala Cys Ala Ala
385                 390                 395                 400

Thr Ala Ala Cys Ala Ala Ala Gly Gly Ala Gly Ala Cys Gly Gly Gly
                405                 410                 415

Cys Gly Ala Ala Thr Cys Ala Cys Thr Gly Ala Cys Cys Ala Thr Cys
            420                 425                 430

Ala Ala Cys Thr Gly Thr Gly Thr Cys Cys Thr Ala Cys Gly Ala Gly
        435                 440                 445

Ala Thr Ala Gly Cys Cys Ala Cys Thr Gly Thr Gly Cys Ala Ala Cys
    450                 455                 460

Cys Thr Cys Cys Ala Gly Cys Ala Cys Gly Thr Ala Cys Thr Gly Gly
465                 470                 475                 480

Thr Ala Thr Cys Gly Cys Ala Ala Ala Ala Ala Ala Thr Cys Gly Gly
                485                 490                 495

Gly Cys Thr Cys Ala Ala Cys Ala Ala Ala Cys Gly Ala Gly Gly Ala
            500                 505                 510

Gly Ala Gly Cys Ala Thr Ala Thr Cys Gly Ala Ala Ala Gly Gly Thr
        515                 520                 525

Gly Gly Ala Cys Gly Ala Thr Ala Thr Gly Thr Thr Gly Ala Ala Ala
    530                 535                 540

Cys Ala Gly Thr Thr Ala Ala Cys Ala Gly Cys Gly Gly Ala Thr Cys
545                 550                 555                 560

Ala Ala Ala Gly Thr Cys Cys Thr Thr Thr Thr Cys Thr Thr Thr Gly
                565                 570                 575

Ala Gly Ala Ala Thr Thr Ala Ala Thr Gly Ala Thr Cys Thr Ala Ala
            580                 585                 590

Cys Ala Gly Thr Thr Gly Ala Ala Gly Ala Cys Ala Gly Thr Gly Gly
        595                 600                 605

Cys Ala Cys Gly Thr Ala Thr Cys Gly Ala Thr Gly Cys Gly Cys Thr
    610                 615                 620

Thr Cys Cys Gly Ala Gly Thr Gly Cys Cys Ala Ala Thr Ala Thr Gly
625                 630                 635                 640

Gly Ala Cys Thr Gly Gly Cys Ala Gly Ala Ala Thr Ala Thr Gly Ala
                645                 650                 655

Thr Gly Thr Ala Thr Ala Cys Gly Gly Ala Gly Gly Thr Gly Gly Cys
            660                 665                 670

Ala Cys Thr Gly Thr Cys Gly Thr Gly Ala Cys Thr Gly Thr Gly Ala
        675                 680                 685

Ala Thr Gly Gly Thr Gly Gly Thr Gly Gly Gly Thr Cys Cys Gly Gly
    690                 695                 700
```

Ala Gly Gly Ala Gly Thr Gly Gly Cys Thr Cys Ala Gly Gly Ala
705                 710                 715                 720

Gly Ala Gly Cys Cys Ala Ala Thr Cys Thr Ala Gly Cys Gly
            725                 730                 735

Ala Cys Ala Ala Ala Ala Cys Thr Cys Ala Cys Ala Cys Thr Gly
            740                 745                 750

Cys Cys Cys Ala Cys Cys Gly Thr Gly Cys Cys Ala Gly Cys Ala
            755                 760                 765

Cys Cys Thr Gly Ala Ala Cys Thr Cys Thr Gly Gly Gly Gly
    770                 775                 780

Gly Ala Cys Cys Gly Thr Cys Ala Gly Thr Cys Thr Thr Cys Thr
785                 790                 795                 800

Cys Thr Thr Cys Cys Cys Cys Cys Ala Ala Ala Cys Cys Cys
            805                 810                 815

Ala Ala Gly Gly Ala Cys Ala Cys Cys Cys Thr Cys Ala Thr Gly
            820                 825                 830

Thr Cys Thr Cys Cys Gly Gly Ala Cys Cys Cys Thr Gly Ala
    835                 840                 845

Gly Gly Thr Cys Ala Cys Ala Thr Gly Cys Gly Thr Gly Thr Gly
850                 855                 860

Gly Thr Gly Gly Ala Cys Gly Thr Gly Ala Gly Cys Cys Ala Cys Gly
865                 870                 875                 880

Ala Ala Gly Ala Cys Cys Cys Thr Gly Ala Gly Gly Thr Cys Ala Ala
            885                 890                 895

Gly Thr Thr Cys Ala Ala Cys Thr Gly Gly Thr Ala Cys Gly Thr Gly
    900                 905                 910

Gly Ala Cys Gly Gly Cys Gly Thr Gly Gly Ala Gly Gly Thr Gly Cys
    915                 920                 925

Ala Thr Ala Ala Thr Gly Cys Cys Ala Ala Gly Ala Cys Ala Ala Ala
930                 935                 940

Gly Cys Cys Gly Cys Gly Gly Gly Ala Gly Gly Ala Gly Cys Ala Gly
945                 950                 955                 960

Thr Ala Cys Ala Ala Cys Ala Gly Cys Ala Cys Gly Thr Ala Cys Cys
            965                 970                 975

Gly Thr Gly Thr Gly Gly Thr Cys Ala Gly Cys Gly Thr Cys Cys Thr
    980                 985                 990

Cys Ala Cys Cys Gly Thr Cys Cys Thr Gly Cys Ala Cys Cys Ala Gly
        995                 1000                1005

Gly Ala Cys Thr Gly Gly Cys Thr Gly Ala Ala Thr Gly Gly Cys
    1010                1015                1020

Ala Ala Gly Gly Ala Gly Thr Ala Cys Ala Ala Gly Thr Gly Cys
    1025                1030                1035

Ala Ala Gly Gly Thr Cys Thr Cys Cys Ala Ala Cys Ala Ala Ala
    1040                1045                1050

Gly Cys Cys Cys Thr Cys Cys Cys Ala Gly Cys Cys Cys Cys Cys
    1055                1060                1065

Ala Thr Cys Gly Ala Gly Ala Ala Ala Ala Cys Cys Ala Thr Cys
    1070                1075                1080

Thr Cys Cys Ala Ala Ala Gly Cys Cys Ala Ala Ala Gly Gly Gly
    1085                1090                1095

Cys Ala Gly Cys Cys Cys Cys Gly Ala Gly Ala Ala Cys Cys Ala
    1100                1105                1110

Cys Ala Gly Gly Thr Gly Thr Ala Cys Ala Cys Cys Cys Thr Gly

```
            1115                1120                1125

Cys Cys Cys Cys Cys Ala Thr Cys Cys Cys Gly Gly Gly Ala Thr
        1130                1135                1140

Gly Ala Gly Cys Thr Gly Ala Cys Cys Ala Ala Gly Ala Ala Cys
        1145                1150                1155

Cys Ala Gly Gly Thr Cys Ala Gly Cys Cys Thr Gly Ala Cys Cys
        1160                1165                1170

Thr Gly Cys Cys Thr Gly Gly Thr Cys Ala Ala Gly Gly Gly Cys
        1175                1180                1185

Thr Thr Cys Thr Ala Thr Cys Cys Cys Ala Gly Cys Gly Ala Cys
        1190                1195                1200

Ala Thr Cys Gly Cys Cys Gly Thr Gly Ala Gly Thr Gly Gly Gly
        1205                1210                1215

Gly Ala Gly Ala Gly Cys Ala Ala Thr Gly Gly Gly Cys Ala Gly
        1220                1225                1230

Cys Cys Gly Gly Ala Gly Ala Ala Cys Ala Ala Cys Thr Ala Cys
        1235                1240                1245

Ala Ala Gly Ala Cys Cys Ala Cys Gly Cys Cys Thr Cys Cys Cys
        1250                1255                1260

Gly Thr Gly Cys Thr Gly Gly Ala Cys Thr Cys Cys Gly Ala Cys
        1265                1270                1275

Gly Gly Cys Thr Cys Cys Thr Thr Cys Thr Thr Cys Cys Thr Cys
        1280                1285                1290

Thr Ala Cys Ala Gly Cys Ala Ala Gly Cys Thr Cys Ala Cys Cys
        1295                1300                1305

Gly Thr Gly Gly Ala Cys Ala Ala Gly Ala Gly Cys Ala Gly Gly
        1310                1315                1320

Thr Gly Gly Cys Ala Gly Cys Ala Gly Gly Gly Gly Ala Ala Cys
        1325                1330                1335

Gly Thr Cys Thr Thr Cys Thr Cys Ala Thr Gly Cys Thr Cys Cys
        1340                1345                1350

Gly Thr Gly Ala Thr Gly Cys Ala Thr Gly Ala Gly Gly Cys Thr
        1355                1360                1365

Cys Thr Gly Cys Ala Cys Ala Ala Cys Cys Ala Cys Thr Ala Cys
        1370                1375                1380

Ala Cys Gly Cys Ala Gly Ala Ala Gly Ala Gly Cys Cys Thr Cys
        1385                1390                1395

Thr Cys Cys Cys Thr Gly Thr Cys Thr Cys Cys Gly Gly Gly Gly
        1400                1405                1410

Ala Ala Ala
        1415

<210> SEQ ID NO 65
<211> LENGTH: 111
<212> TYPE: PRT
<213> ORGANISM: Artificial Sequence
<220> FEATURE:
<223> OTHER INFORMATION: 2D4

<400> SEQUENCE: 65

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Asp Tyr Gly Leu Phe
            20                  25                  30

Ser Thr Ser Trp Phe Arg Lys Asn Pro Gly Thr Thr Asp Trp Glu Arg
```

```
                35                  40                  45
Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
65                  70                  75                  80

Tyr Tyr Cys Lys Ala Phe Thr Trp Pro Trp Glu Trp Pro Asp Arg Trp
                 85                  90                  95

Phe Arg Pro Trp Tyr Asp Gly Ala Gly Thr Val Leu Thr Val Asn
            100                 105                 110

<210> SEQ ID NO 66
<211> LENGTH: 107
<212> TYPE: PRT
<213> ORGANISM: Artificial Sequence
<220> FEATURE:
<223> OTHER INFORMATION: CC3

<400> SEQUENCE: 66

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Glu Tyr Gly Leu Phe
                20                  25                  30

Ser Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
65                  70                  75                  80

Tyr Tyr Cys Lys Ala Leu Gly Trp Trp Pro Pro Ala Phe Pro His Trp
                 85                  90                  95

Tyr Asp Gly Ala Gly Thr Val Leu Thr Val Asn
            100                 105

<210> SEQ ID NO 67
<211> LENGTH: 103
<212> TYPE: PRT
<213> ORGANISM: Artificial Sequence
<220> FEATURE:
<223> OTHER INFORMATION: BA11

<400> SEQUENCE: 67

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
 50                  55                  60

Ser Phe Thr Leu Thr Ile Ser Ser Leu Gln Pro Glu Asp Ser Ala Thr
65                  70                  75                  80

Tyr Tyr Cys Arg Ala Met Ser Thr Asn Ile Trp Thr Gly Asp Gly Ala
                 85                  90                  95

Gly Thr Lys Val Glu Ile Lys
            100

<210> SEQ ID NO 68
<211> LENGTH: 6
```

```
<212> TYPE: PRT
<213> ORGANISM: Artificial Sequence
<220> FEATURE:
<223> OTHER INFORMATION: TNF-alpha specific VNAR binding domain CDR1

<400> SEQUENCE: 68

His Cys Ala Thr Ser Ser
1               5

<210> SEQ ID NO 69
<211> LENGTH: 6
<212> TYPE: PRT
<213> ORGANISM: Artificial Sequence
<220> FEATURE:
<223> OTHER INFORMATION: TNF-alpha spcific VNAR binding domain CDR1

<400> SEQUENCE: 69

Asn Cys Gly Leu Ser Ser
1               5

<210> SEQ ID NO 70
<211> LENGTH: 6
<212> TYPE: PRT
<213> ORGANISM: Artificial Sequence
<220> FEATURE:
<223> OTHER INFORMATION: TNF-alpha specific VNAR binding domain CDR1

<400> SEQUENCE: 70

Asn Cys Ala Leu Ser Ser
1               5

<210> SEQ ID NO 71
<211> LENGTH: 9
<212> TYPE: PRT
<213> ORGANISM: Artificial Sequence
<220> FEATURE:
<223> OTHER INFORMATION: TNF-alpha specific VNAR binding domain hyper-
      variable region 2

<400> SEQUENCE: 71

Thr Asn Glu Glu Ser Ile Ser Lys Gly
1               5

<210> SEQ ID NO 72
<211> LENGTH: 5
<212> TYPE: PRT
<213> ORGANISM: Artificial Sequence
<220> FEATURE:
<223> OTHER INFORMATION: TNF-alpha specific VNAR binding domain hyper-
      variable region 4

<400> SEQUENCE: 72

Ser Gly Ser Lys Ser
1               5

<210> SEQ ID NO 73
<211> LENGTH: 5
<212> TYPE: PRT
<213> ORGANISM: Artificial Sequence
<220> FEATURE:
<223> OTHER INFORMATION: TNF-alpha specific VNAR binding domain hyper-
      variable region 4

<400> SEQUENCE: 73

Glu Gly Ser Lys Ser
1               5
```

```
<210> SEQ ID NO 74
<211> LENGTH: 46
<212> TYPE: DNA
<213> ORGANISM: Artificial Sequence
<220> FEATURE:
<223> OTHER INFORMATION: NARF4For1 primer

<400> SEQUENCE: 74
ataatcaagc ttgcggccgc attcacagtc acgacagtgc cacctc         46

<210> SEQ ID NO 75
<211> LENGTH: 46
<212> TYPE: DNA
<213> ORGANISM: Artificial Sequence
<220> FEATURE:
<223> OTHER INFORMATION: NARF4For2 primer

<400> SEQUENCE: 75
ataatcaagc ttgcggccgc attcacagtc acggcagtgc catctc         46

<210> SEQ ID NO 76
<211> LENGTH: 39
<212> TYPE: DNA
<213> ORGANISM: Artificial Sequence
<220> FEATURE:
<223> OTHER INFORMATION: NARF1Rev primer

<400> SEQUENCE: 76
ataataagga attccatggc tcgagtggac caaacaccg              39

<210> SEQ ID NO 77
<211> LENGTH: 103
<212> TYPE: PRT
<213> ORGANISM: Artificial Sequence
<220> FEATURE:
<223> OTHER INFORMATION: E06

<400> SEQUENCE: 77

Thr Arg Val Asp Gln Thr Pro Arg Thr Ala Thr Arg Glu Thr Gly Glu
1               5                   10                  15

Ser Leu Thr Ile Asn Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
        35                  40                  45

Ile Ser Ile Ser Gly Arg Tyr Val Glu Ser Val Asn Lys Gly Thr Lys
    50                  55                  60

Ser Phe Ser Leu Arg Ile Lys Asp Leu Thr Val Ala Asp Ser Ala Thr
65                  70                  75                  80

Tyr Ile Cys Arg Ala Met Gly Thr Asn Ile Trp Thr Gly Asp Gly Ala
                85                  90                  95

Gly Thr Val Leu Thr Val Asn
            100

<210> SEQ ID NO 78
<211> LENGTH: 103
<212> TYPE: PRT
<213> ORGANISM: Artificial Sequence
<220> FEATURE:
<223> OTHER INFORMATION: hE06v1.10

<400> SEQUENCE: 78

Thr Arg Val Asp Gln Ser Pro Ser Ser Leu Ser Ala Ser Val Gly Asp
1               5                   10                  15
```

```
Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
            50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 79
<211> LENGTH: 103
<212> TYPE: PRT
<213> ORGANISM: Artificial Sequence
<220> FEATURE:
<223> OTHER INFORMATION: AC9

<400> SEQUENCE: 79

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
            50                  55                  60

Ser Ser Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 80
<211> LENGTH: 103
<212> TYPE: PRT
<213> ORGANISM: Artificial Sequence
<220> FEATURE:
<223> OTHER INFORMATION: AD4

<400> SEQUENCE: 80

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
            35                  40                  45

Ile Ser Met Ser Gly Arg Tyr Ser Glu Ser Val Asn Lys Ser Thr Lys
            50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100
```

<210> SEQ ID NO 81
<211> LENGTH: 103
<212> TYPE: PRT
<213> ORGANISM: Artificial Sequence
<220> FEATURE:
<223> OTHER INFORMATION: AG11

<400> SEQUENCE: 81

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Thr Lys
            100

<210> SEQ ID NO 82
<211> LENGTH: 103
<212> TYPE: PRT
<213> ORGANISM: Artificial Sequence
<220> FEATURE:
<223> OTHER INFORMATION: AH7

<400> SEQUENCE: 82

Thr Arg Val Asp Gln Thr Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Ser Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 83
<211> LENGTH: 103
<212> TYPE: PRT
<213> ORGANISM: Artificial Sequence
<220> FEATURE:
<223> OTHER INFORMATION: BB10

<400> SEQUENCE: 83

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Phe Trp Thr Gly Asp Gly Ala
                85                  90                  95

Gly Thr Lys Val Glu Ile Lys
            100

<210> SEQ ID NO 84
<211> LENGTH: 103
<212> TYPE: PRT
<213> ORGANISM: Artificial Sequence
<220> FEATURE:
<223> OTHER INFORMATION: BB11

<400> SEQUENCE: 84

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Ala Thr Asn Ile Trp Thr Gly Asp Gly Ala
                85                  90                  95

Gly Thr Lys Val Glu Ile Lys
            100

<210> SEQ ID NO 85
<211> LENGTH: 103
<212> TYPE: PRT
<213> ORGANISM: Artificial Sequence
<220> FEATURE:
<223> OTHER INFORMATION: BC3

<400> SEQUENCE: 85

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
            20                  25                  30

Ser Thr Tyr Trp Tyr Arg Lys Asn Pro Gly Ser Asn Asn Lys Glu Gln
            35                  40                  45

Ile Ser Ile Ser Gly Arg Tyr Ser Glu Ser Val Asn Lys Gly Thr Lys
    50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 86

```
<211> LENGTH: 103
<212> TYPE: PRT
<213> ORGANISM: Artificial Sequence
<220> FEATURE:
<223> OTHER INFORMATION: BD12

<400> SEQUENCE: 86

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Asn
        50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 87
<211> LENGTH: 103
<212> TYPE: PRT
<213> ORGANISM: Artificial Sequence
<220> FEATURE:
<223> OTHER INFORMATION: BE4

<400> SEQUENCE: 87

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Ser Leu Tyr
                20                  25                  30

Ser Thr Tyr Trp Tyr Arg Lys Asn Pro Gly Ser Ser Asn Lys Glu Gln
            35                  40                  45

Ile Ser Ile Ser Gly Arg Tyr Ser Glu Ser Val Asn Lys Gly Thr Lys
        50                  55                  60

Ser Phe Thr Leu Thr Ile Ser Ser Leu Gln Pro Glu Asp Phe Ala Thr
65                  70                  75                  80

Tyr Tyr Cys Arg Ala Met Gly Thr Asn Ile Trp Thr Gly Asp Gly Ala
                85                  90                  95

Gly Thr Lys Val Glu Ile Lys
            100

<210> SEQ ID NO 88
<211> LENGTH: 103
<212> TYPE: PRT
<213> ORGANISM: Artificial Sequence
<220> FEATURE:
<223> OTHER INFORMATION: BH4

<400> SEQUENCE: 88

Thr Arg Val Asp Gln Ser Pro Ser Ser Leu Ser Ala Ser Val Gly Asp
1               5                   10                  15

Arg Val Thr Ile Thr Cys Val Leu Thr Asp Thr Ser Tyr Pro Leu Tyr
                20                  25                  30

Ser Thr Tyr Trp Tyr Arg Lys Asn Pro Gly Ser Ser Asn Lys Glu Gln
            35                  40                  45
```

```
Ile Ser Ile Ser Gly Arg Tyr Ser Glu Ser Val Asn Lys Gly Thr Lys
 50                  55                  60

Ser Phe Thr Leu Thr Ile Ser Ser Leu Gln Pro Glu Asp Phe Ala Thr
 65                  70                  75                  80

Tyr Tyr Cys Arg Ala Met Gly Thr Asn Leu Trp Thr Gly Asp Gly Ala
                 85                  90                  95

Gly Thr Lys Val Glu Ile Lys
            100

<210> SEQ ID NO 89
<211> LENGTH: 239
<212> TYPE: PRT
<213> ORGANISM: Artificial Sequence
<220> FEATURE:
<223> OTHER INFORMATION: Artificial Sequence

<400> SEQUENCE: 89

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser His Cys Ala Thr Ser
                20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Ala Ser Glu Cys Gln Tyr Gly Leu Ala Glu Tyr Asp Val
                 85                  90                  95

Tyr Gly Gly Thr Val Val Thr Val Asn Gly Gly Gly Ser Gly
            100                 105                 110

Gly Gly Gly Gly Ser Gly Gly Ser Ala Arg Val Asp Gln Thr Pro
            115                 120                 125

Gln Thr Ile Thr Lys Glu Thr Gly Glu Ser Leu Thr Ile Asn Cys Val
    130                 135                 140

Leu Arg Asp Ser Asn Cys Gly Leu Ser Ser Thr Tyr Trp Tyr Arg Lys
145                 150                 155                 160

Lys Ser Gly Ser Thr Asn Glu Glu Ser Ile Ser Lys Gly Gly Arg Tyr
                165                 170                 175

Val Glu Thr Ile Asn Glu Gly Ser Lys Ser Phe Ser Leu Arg Ile Asn
                180                 185                 190

Asp Leu Thr Val Glu Asp Ser Gly Thr Tyr Arg Cys Lys Leu Ser Trp
            195                 200                 205

Trp Thr Gln Asn Trp Arg Cys Ser Asn Ser Asp Val Tyr Gly Gly Gly
        210                 215                 220

Thr Val Thr Val Asn Ala Ala Ala His His His His His His
225                 230                 235

<210> SEQ ID NO 90
<211> LENGTH: 717
<212> TYPE: DNA
<213> ORGANISM: Artificial Sequence
<220> FEATURE:
<223> OTHER INFORMATION: Artificial Sequence

<400> SEQUENCE: 90
gctcgagtgg accaaacacc gcaaacaata acaaaggaga cgggcgaatc actgaccatc    60
```

```
aactgtgtcc tacgagatag ccactgtgca acctccagca cgtactggta tcgcaaaaaa    120
tcgggctcaa caaacgagga gagcatatcg aaaggtggac gatatgttga aacagttaac    180
agcggatcaa agtcctttc tttgagaatt aatgatctaa cagttgaaga cagtggcacg    240
tatcgatgcg cttccgagtg ccaatatgga ctggcagaat atgatgtata cggaggtggc    300
actgtcgtga ctgtgaatgg aggtggcggt agcggaggtg gtggcggatc cggcggtggt    360
tccgctcgag tggaccaaac accgcaaaca ataacaaagg agacgggcga atcactgacc    420
atcaactgtg tcctacgaga tagcaactgt gggttgtcca gcacgtactg gtatcgcaaa    480
aaatcgggct caacaaacga ggagagcata tcgaaaggtg gacgatatgt tgaaacaatt    540
aacgaaggat caaagtcctt ttctttgaga attaatgatc taacagttga agacagtggc    600
acgtatcgat gcaagttaag ctggtggacc cagaactgga gatgctcaaa ttccgatgta    660
tacgaggtg gcactgtcgt gactgtgaac gcggccgcac atcatcatca ccatcac       717
```

<210> SEQ ID NO 91
<211> LENGTH: 239
<212> TYPE: PRT
<213> ORGANISM: Artificial Sequence
<220> FEATURE:
<223> OTHER INFORMATION: Artificial Sequence

<400> SEQUENCE: 91

Ala Arg Val Asp Gln Ser Pro Ser Ser Leu Ser Ala Ser Val Gly Asp
1               5                   10                  15

Arg Val Thr Ile Thr Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Thr Leu Thr Ile Ser Ser Leu Gln Pro Glu Asp Phe Ala Thr
65                  70                  75                  80

Tyr Tyr Cys Ala Ser Glu Cys Gln Tyr Gly Leu Ala Glu Tyr Asp Val
                85                  90                  95

Tyr Gly Gly Gly Thr Lys Val Glu Ile Lys Gly Gly Gly Gly Ser Gly
            100                 105                 110

Gly Gly Gly Ser Gly Gly Gly Ser Ala Arg Val Asp Gln Ser Pro
        115                 120                 125

Ser Ser Leu Ser Ala Ser Val Gly Asp Arg Val Thr Ile Thr Cys Val
    130                 135                 140

Leu Arg Asp Ser Asn Cys Gly Leu Ser Ser Thr Tyr Trp Tyr Arg Lys
145                 150                 155                 160

Lys Ser Gly Ser Thr Asn Glu Glu Ser Ile Ser Lys Gly Gly Arg Tyr
                165                 170                 175

Val Glu Thr Ile Asn Glu Gly Ser Lys Ser Phe Ser Leu Arg Ile Asn
            180                 185                 190

Asp Leu Thr Val Glu Asp Ser Gly Thr Tyr Arg Cys Lys Leu Ser Trp
        195                 200                 205

Trp Thr Gln Asn Trp Arg Cys Ser Asn Ser Asp Val Tyr Gly Gly Gly
    210                 215                 220

Thr Lys Val Glu Ile Lys Ala Ala Ala His His His His His His
225                 230                 235

<210> SEQ ID NO 92

```
<211> LENGTH: 717
<212> TYPE: DNA
<213> ORGANISM: Artificial Sequence
<220> FEATURE:
<223> OTHER INFORMATION: Artificial Sequence

<400> SEQUENCE: 92
gcccgcgtgg accagtcccc ctcctccctg tccgcctccg tgggcgaccg cgtgaccatc      60
acctgcgtgc tgcgcgactc ccactgcgcc acctcctcca cctactggta ccgcaagaag     120
tccggctcca ccaacgagga gtccatctcc aagggggggcc gctacgtgga gaccgtgaac    180
tccggctcca agtccttcac cctgaccatc tcctccctgc agcccgagga cttcgccacc     240
tactactgcg cctccgagtg ccagtacggc ctggccgagt acgacgtgta cggcggcggc     300
accaaggtgg agatcaaggg aggtggcggt agcggaggtg gtggcggatc cggcggtggt     360
tccgcccgcg tggaccagtc cccctcctcc ctgtccgcct ccgtgggcga ccgcgtgacc     420
atcacctgcg tgctgcgcga ctccaactgc ggcctgtcct ccacctactg gtaccgcaag     480
aagtccggct ccaccaacga ggagtccatc tccaagggcg gccgctacgt ggagaccatc     540
aacgagggct ccaagtcctt ctccctgcgc atcaacgacc tgaccgtgga ggactccggc     600
acctaccgct gcaagctgtc ctggtggacc cagaactggg ctgctccaa ctccgacgtg      660 tacggcggcg gcaccaaggt ggagatcaag gcggccgcac atcatcatca ccatcac       717
```

```
<210> SEQ ID NO 93
<211> LENGTH: 249
<212> TYPE: PRT
<213> ORGANISM: Artificial Sequence
<220> FEATURE:
<223> OTHER INFORMATION: Artificial Sequence

<400> SEQUENCE: 93

Ala Arg Val Asp Gln Ser Pro Ser Ser Leu Ser Ala Ser Val Gly Asp
1               5                   10                  15

Arg Val Thr Ile Thr Cys Val Leu Arg Asp Ser His Cys Ala Thr Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Thr Leu Thr Ile Ser Ser Leu Gln Pro Glu Asp Phe Ala Thr
65                  70                  75                  80

Tyr Tyr Cys Ala Ser Glu Cys Gln Tyr Gly Leu Ala Glu Tyr Asp Val
                85                  90                  95

Tyr Gly Gly Gly Thr Lys Val Glu Ile Lys Gly Gly Gly Gly Ser Gly
                100                 105                 110

Gly Gly Gly Ser Gly Gly Gly Gly Ser Gly Gly Gly Gly Ser Gly Gly
            115                 120                 125

Gly Gly Ser Ala Arg Val Asp Gln Ser Pro Ser Ser Leu Ser Ala Ser
        130                 135                 140

Val Gly Asp Arg Val Thr Ile Thr Cys Val Leu Arg Asp Ser Asn Cys
145                 150                 155                 160

Gly Leu Ser Ser Thr Tyr Trp Tyr Arg Lys Lys Ser Gly Ser Thr Asn
                165                 170                 175

Glu Glu Ser Ile Ser Lys Gly Gly Arg Tyr Val Glu Thr Ile Asn Glu
                180                 185                 190

Gly Ser Lys Ser Phe Ser Leu Arg Ile Asn Asp Leu Thr Val Glu Asp
```

```
                195                 200                 205
Ser Gly Thr Tyr Arg Cys Lys Leu Ser Trp Trp Thr Gln Asn Trp Arg
            210                 215                 220

Cys Ser Asn Ser Asp Val Tyr Gly Gly Gly Thr Lys Val Glu Ile Lys
225                 230                 235                 240

Ala Ala Ala His His His His His
                245

<210> SEQ ID NO 94
<211> LENGTH: 747
<212> TYPE: DNA
<213> ORGANISM: Artificial Sequence
<220> FEATURE:
<223> OTHER INFORMATION: Artificial Sequence

<400> SEQUENCE: 94
gcccgcgtgg accagtcccc ctcctccctg tccgcctccg tgggcgaccg cgtgaccatc      60
acctgcgtgc tgcgcgactc ccactgcgcc acctcctcca cctactggta ccgcaagaag    120
tccggctcca ccaacgagga gtccatctcc aagggggggcc gctacgtgga gaccgtgaac   180
tccggctcca gtccttcac cctgaccatc tcctccctgc agcccgagga cttcgccacc     240
tactactgcg cctccgagtg ccagtacggc ctggccgagt acgacgtgta cggcggcggc    300
accaaggtgg agatcaaggg tggtggtggt agcggtggtg gcggttcagg tggcggtggt    360
tctggcggtg gcggtagtgg cggaggtggt agtgcccgcg tggaccagtc ccctcctcc    420
ctgtccgcct ccgtgggcga ccgcgtgacc atcacctgcg tgctgcgcga ctccaactgc    480
ggcctgtcct ccacctactg gtaccgcaag aagtccggct ccaccaacga ggagtccatc   540
tccaagggcg gccgctacgt ggagaccatc aacgagggct ccaagtcctt ctccctgcgc   600
atcaacgacc tgaccgtgga ggactccggc acctaccgct gcaagctgtc ctggtggacc   660
cagaactggc gctgctccaa ctccgacgtg tacggcggcg gcaccaaggt ggagatcaag   720
gcggccgcac atcatcatca ccatcac                                       747

<210> SEQ ID NO 95
<211> LENGTH: 484
<212> TYPE: PRT
<213> ORGANISM: Artificial Sequence
<220> FEATURE:
<223> OTHER INFORMATION: Artificial Sequence

<400> SEQUENCE: 95

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr His Ala Lys Val Phe
            20                  25                  30

Thr Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gly Gly Tyr Leu Ser Gln Pro Arg Val Tyr Trp
                85                  90                  95

Asp Val Tyr Gly Ala Gly Thr Val Leu Thr Val Asn Gly Gly Gly Gly
            100                 105                 110

Ser Gly Gly Gly Gly Arg Thr Glu Pro Arg Gly Pro Thr Ile Lys Pro
```

```
            115                 120                 125
Cys Pro Pro Cys Lys Cys Pro Ala Pro Asn Leu Leu Gly Pro Ser
130                 135                 140

Val Phe Ile Phe Pro Lys Ile Lys Asp Val Leu Met Ile Ser Leu
145                 150                 155                 160

Ser Pro Ile Val Thr Cys Val Val Val Asp Val Ser Glu Asp Asp Pro
                165                 170                 175

Asp Val Gln Ile Ser Trp Phe Val Asn Asn Val Glu Val His Thr Ala
            180                 185                 190

Gln Thr Gln Thr His Arg Glu Asp Tyr Asn Ser Thr Leu Arg Val Val
        195                 200                 205

Ser Ala Leu Pro Ile Gln His Gln Asp Trp Met Ser Gly Lys Glu Phe
210                 215                 220

Lys Cys Lys Val Asn Asn Lys Asp Leu Pro Ala Pro Ile Glu Arg Thr
225                 230                 235                 240

Ile Ser Lys Pro Lys Gly Ser Val Arg Ala Pro Gln Val Tyr Val Leu
                245                 250                 255

Pro Pro Pro Glu Glu Glu Met Thr Lys Lys Gln Val Thr Leu Thr Cys
            260                 265                 270

Met Val Thr Asp Phe Met Pro Glu Asp Ile Tyr Val Glu Trp Thr Asn
        275                 280                 285

Asn Gly Lys Thr Glu Leu Asn Tyr Lys Asn Thr Glu Pro Val Leu Asp
290                 295                 300

Ser Asp Gly Ser Tyr Phe Met Tyr Ser Lys Leu Arg Val Glu Lys Lys
305                 310                 315                 320

Asn Trp Val Glu Arg Asn Ser Tyr Ser Cys Ser Val Val His Glu Gly
                325                 330                 335

Leu His Asn His His Thr Thr Lys Ser Phe Ser Arg Thr Pro Gly Lys
            340                 345                 350

Gly Gly Gly Gly Ser Gly Gly Gly Ser Gly Gly Gly Ser Gly
        355                 360                 365

Gly Gly Gly Ser Gly Ala His Ser Ala Ser Val Asn Gln Thr Pro Arg
370                 375                 380

Thr Ala Thr Lys Glu Thr Gly Glu Ser Leu Thr Ile Asn Cys Val Leu
385                 390                 395                 400

Thr Asp Thr His Ala Lys Val Phe Thr Thr Ser Trp Phe Arg Lys Asn
                405                 410                 415

Pro Gly Thr Thr Asp Trp Glu Arg Met Ser Ile Gly Gly Arg Tyr Val
            420                 425                 430

Glu Ser Val Asn Lys Gly Ala Lys Ser Phe Ser Leu Arg Ile Lys Asp
        435                 440                 445

Leu Thr Val Ala Asp Ser Ala Thr Tyr Ile Cys Arg Ala Gly Gly Tyr
450                 455                 460

Leu Ser Gln Pro Arg Val Tyr Trp Asp Val Tyr Gly Ala Gly Thr Val
465                 470                 475                 480

Leu Thr Val Asn
```

<210> SEQ ID NO 96
<211> LENGTH: 1452
<212> TYPE: DNA
<213> ORGANISM: Artificial Sequence
<220> FEATURE:
<223> OTHER INFORMATION: Artificial Sequence

<400> SEQUENCE: 96

-continued

```
gcaagcgtta atcagacacc gcgtaccgca accaaagaaa ccggtgaaag cctgaccatt      60
aattgtgttc tgaccgatac ccatgctaaa gttttcacta ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tatatctgtc gtgccggtgg ttacctgtct cagccgcgtg tttactggga tgtttatggt    300
gcaggcaccg ttctgaccgt taatggcggt ggtggttctg gtggtggtgg tcgtacggag    360
cctcgaggcc ccacaatcaa gccctgtcct ccatgcaaat gcccagcacc taacctcttg    420
ggtggaccat ccgtcttcat cttccctcca aagatcaagg atgtactcat gatctccctg    480
agccccatag tcacatgtgt ggtggtggat gtgagcgagg atgacccaga tgtccagatc    540
agctggtttg tgaacaacgt ggaagtacac acagctcaga cacaaaccca tagagaggat    600
tacaacagta ctctccgggt ggtcagtgcc ctccccatcc agcaccagga ctggatgagt    660
ggcaaggagt tcaaatgcaa ggtcaacaac aaagacctcc cagcgcccat cgagagaacc    720
atctcaaaac ccaaagggtc agtaagagct ccacaggtat atgtcttgcc tccaccagaa    780
gaagagatga ctaagaaaca ggtcactctg acctgcatgg tcacagactt catgcctgaa    840
gacatttacg tggagtggac caacaacggg aaaacagagc taaactacaa gaacactgaa    900
ccagtcctgg actctgatgg ttcttacttc atgtacagca agctgagagt ggaaaagaag    960
aactgggtgg aaagaaatag ctactcctgt tcagtggtcc acgagggtct gcacaatcac   1020
cacacgacta agagcttctc ccggactccg ggtaaaggag gtggcggttc cggaggtggc   1080
ggtagcggag gtggcggtag cggaggtggc ggtagcgggg cccattctgc aagcgttaat   1140
cagacaccgc gtaccgcaac caaagaaacc ggtgaaagcc tgaccattaa ttgtgttctg   1200
accgataccc atgctaaagt tttcactacc agctggtttc gtaaaaatcc gggtacaacc   1260
gattgggaac gtatgagcat tggtggtcgt tatgttgaaa gcgtgaataa aggtgccaaa   1320
agctttagcc tgcgcattaa agatctgacc gttgcagata gcgcaaccta tatctgtcgt   1380
gccggtggtt acctgtctca gccgcgtgtt tactgggatg tttatggtgc aggcaccgtt   1440
ctgaccgtta at                                                       1452
```

SPECIFIC BINDING MOLECULES

FIELD OF INVENTION

The present invention relates to the formation of multi-domain specific binding molecules comprising VNARs. Specific binding domains that bind to Tumour Necrosis Factor alpha (TNFα) are also provided.

BACKGROUND

The search for specific, increasingly efficacious, and diversified therapeutic weapons to combat diseases has utilised a myriad of distinct modalities. From the traditional small molecule to incrementally larger biologic pharmaceuticals, for example single binding domains (10-15 kDa) to full IgG (~150 kDa). Single domains currently under investigation as potential therapeutics include a wide variety of distinct protein scaffolds, all with their associated advantages and disadvantages.

Such single domain scaffolds can be derived from an array of proteins from distinct species. The Novel or New antigen receptor (IgNAR) is an approximately 160 kDa homodimeric protein found in the sera of cartilaginous fish (Greenberg A. S., et al., Nature, 1995. 374(6518): p. 168-173, Dooley, H., et al, Mol. Immunol, 2003. 40(1): p. 25-33; Müller, M.R., et al., mAbs, 2012. 4(6): p. 673-685)). Each molecule consists of a single N-terminal variable domain (VNAR) and five constant domains (CNAR). The IgNAR domains are members of the immunoglobulin-superfamily. The VNAR is a tightly folded domain with structural and some sequence similarities to the immunoglobulin and T-cell receptor Variable domains and to cell adhesion molecules and is termed the VNAR by analogy to the N Variable terminal domain of the classical immunoglobulins and T Cell receptors. The VNAR shares limited sequence homology to immunoglobulins, for example 25-30% similarity between VNAR and human light chain sequences (Dooley, H. and Flajnik, M. F., Eur. J. Immunol., 2005. 35(3): p. 936-945).

Kovaleva M. et al Expert Opin. Biol. Ther. 2014. 14(10): p. 1527-1539 and Zielonka S. et al mAbs 2015. 7(1): p. 15-25 have recently provided summaries of the structural characterization and generation of the VNARs which are hereby incorporated by reference.

The VNAR does not appear to have evolved from a classical immunoglobulin antibody ancestor. The distinct structural features of VNARs are the truncation of the sequences equivalent to the CDR2 loop present in conventional immunoglobulin variable domains and the lack of the hydrophobic VH/VL interface residues which would normally allow association with a light chain domain, which is not present in the IgNAR structure and the presence in some of the VNAR subtypes of additional Cysteine residues in the CDR regions that are observed to form additional disulphide bridges in addition to the canonical Immunoglobulin superfamily bridge between the Cysteines in the Framework 1 and 3 regions N terminally adjacent to CDRs 1 and 3.

To date, there are three defined types of shark IgNAR known as I, II and III (FIG. 1). These have been categorized based on the position of non-canonical cysteine residues which are under strong selective pressure and are therefore rarely replaced.

All three types have the classical immunoglobulin canonical cysteines at positions 35 and 107 (numbering as in Kabat, E. A. et al. *Sequences of proteins of immunological interest.* 5th ed. 1991, Bethesda: US Dept. of Health and Human Services, PHS, NIH) that stabilize the standard immunoglobulin fold, together with an invariant tryptophan at position 36. There is no defined CDR2 as such, but regions of sequence variation that compare more closely to TCR HV2 and HV4 have been defined in framework 2 and 3 respectively. Type I has germline encoded cysteine residues in framework 2 and framework 4 and an even number of additional cysteines within CDR3. Crystal structure studies of a Type I IgNAR isolated against and in complex with lysozyme enabled the contribution of these cysteine residues to be determined. Both the framework 2 and 4 cysteines form disulphide bridges with those in CDR3 forming a tightly packed structure within which the CDR3 loop is held tightly down towards the HV2 region. To date Type I IgNARs have only been identified in nurse sharks—all other elasmobranchs, including members of the same order have only Type II or variations of this type.

Type II IgNAR are defined as having a cysteine residue in CDR1 and CDR3 which form intramolecular disulphide bonds that hold these two regions in close proximity, resulting in a protruding CDR3 (FIG. 2) that is conducive to binding pockets or grooves. Type I sequences typically have longer CDR3s than type II with an average of 21 and 15 residues respectively. This is believed to be due to a strong selective pressure for two or more cysteine residues in Type I CDR3 to associate with their framework 2 and 4 counterparts. Studies into the accumulation of somatic mutations show that there are a greater number of mutations in CDR1 of type II than type I, whereas HV2 regions of Type I show greater sequence variation than Type II. This evidence correlates well with the determined positioning of these regions within the antigen binding sites.

A third IgNAR type known as Type III has been identified in neonates. This member of the IgNAR family lacks diversity within CDR3 due to the germline fusion of the D1 and D2 regions (which form CDR3) with the V-gene. Almost all known clones have a CDR3 length of 15 residues with little or no sequence diversity.

Another structural type of VNAR, termed type (IIIb or IV), has only two canonical cysteine residues. So far, this type has been found primarily in dogfish sharks (Liu, J. L., et al. *Mol. Immunol.* 2007. 44(7): p. 1775-1783; Kovalenko O. V., et al. *J Biol Chem.* 2013. 288(24): p. 17408-19) and was also isolated from semisynthetic V-NAR libraries derived from wobbegong sharks (Streltsov, V. A. et al. (2004) *Proc. Nat. Acad. Sci. U.S.A.* 101(34): p. 12444-12449).

It has been shown however specific VNARs isolated from synthetic libraries formed from the VNAR sequences can bind with high affinity to other proteins (Shao C. Y. et al. *Mol Immunol.* 2007. 44(4): p. 656-65; WO2014/173959) and that the IgNAR is part of the adaptive immune system as cartilaginous fish can be immunized with antigen and responsive IgNARs obtained that bind to the antigen (Dooley, H., et al, *Mol. Immunol,* 2003. 40(1): p. 25-33; WO2003/014161). It has been shown that the IgNAR has a mechanism for combinatorial joining of V like sequences with D and J sequences similar to that of immunoglobulins and the T cell receptor (summarized by Zielonka S. et al mAbs 2015. 7(1): p. 15-25).

The VNAR binding surface, unlike the variable domains in other natural immunoglobulins, derives from four regions of diversity: CDR1, HV2, HV4 and CDR3 (see also Stanfield, R. L., et al, *Science,* 2004. 305(5691): p. 1770-1773; Streltsov, V. A., et al, *Protein Sci.,* 2005. 14(11): p. 2901-2909; Stanfield, R. L., et al., *J Mol. Biol.,* 2007. 367(2): p. 358-372), joined by intervening framework sequences in the order: FW1-CDR1-FW2-HV2-FW3a-HV4-FW3b-CDR3-FW4. The combination of a lack of a natural light chain partner and lack of CDR2 make VNARs the smallest naturally occurring binding domains in the vertebrate kingdom.

The IgNAR shares some incidental features with the heavy chain only immunoglobulin (HCAb) found in camelidae (camels, dromedaries and llamas, Hamers-Casterman, C. et al. *Nature,* 1993. 363, 446-448; Wesolowski, J., et al., *Med Microbiol Immunol,* 2009. 198(3): p. 157-74) Unlike the IgNAR the HCAb is clearly derived from the immunoglobulin family and shares significant sequence homology to standard immunoglobulins. Importantly one key distinction of VNARs is that the molecule has not had at any point in its evolution a partner light chain, unlike classical immunoglobulins or the HCAbs. Flajnik M. F. et al *PLoS Biol* 2011. 9(8): e1001120 and Zielonka S. et al *mAbs* 2015. 7(1): p. 15-25 have commented on the similarities and differences between, and the distinct evolutionary origins of, the VNAR and the immunoglobulin-derived $V_{HH}$ single binding domain from the camelids.

The binding domains derived from light and heavy chains (VL and VH respectively) of classical immunoglobulins, have been shown to be able to be linked together to form bivalent or multivalent and bispecific binding entities whether in the scFv format (Bird et al., 1988; Huston et al., 1988), in which the immunoglobulin VL and VH domains are joined by a short peptide linker Traunecker et al. (Traunecker A, et al. *EMBO J.* 1991. 10, p. 3655-36, Traunecker A, et al. *Int J Cancer Suppl.* 7, 51-52; Neri D. *J Mol Biol.* 1995. 246(3): p. 367-73 or as diabodies (Holliger P. et al., *Proc. Nat. Acad. Sci. USA* 1993. 90, 6444-6448; Holliger P. et al. *Nat. Biotechnol.* 15, 632-636. See Mack M, et al *Proc. Nat. Acad. Sci. USA* 1995. 92, p. 7021-7025, Jost CR, et al *Mol. Immunol.* 1996. 33, p. 211-219 for other early examples). Tandabs comprise two pairs of VL and VH domains connected in a single polypeptide chain (Kipriyanov S. M. et al., *J. Mol. Biol.* 293, 41-56 to form bispecific and bivalent for molecules).

Additionally $V_{HH}$s have been shown to be able to be linked together to form bivalent or multivalent and bispecific binding entities (Els Conrath et al. *J Biol Chem.* 2001. 276(10) p. 7346-7350). Similarly the variable domains from T cell receptors can be linked to immunoglobulin scFv to form bispecific formats (McCormack E. et al. *Cancer Immunol Immunother.* 2013. 62(4): p. 773-85). Single antibody variable domains from classical immunoglobulins (dABs: Ward E. S. et al. *Nature* 1989, 341, p. 544-546) can also be dimerized. The overall concept of bispecific binding molecules and current progress in their development has recently been reviewed by, for example, Kontermann R. *mAbs* 2012. 4(2): 185-197; Jost C. and Pluckthun A. *Curr Opin Struct Biol.* 2014. 27: p. 102-112; Spiess C. et al. *Mol Immunol* 2015. 67(2): 95-106.

In addition to bispecific molecules that recognize epitopes on separate molecules, the concept of linking two antibody binding domains that recognize adjacent epitopes on the same protein (biparatopic) has a long history (see Neri D. *J Mol Biol.* 1995. 246(3): p. 367-73). Biparatopic $V_{HH}$ molecules have been disclosed (for example, Jahnichen S. et al *Proc Natl Acad Sci USA.* 2010. 107(47): p. 20565-70; Roovers R. C. et al *Int J Cancer.* 2011 129(8): p. 2013-24).

However, it has been suggested that, unlike $V_{HH}$s, VNARs might not be able efficiently to form dimeric fusion molecules (Simmons D. P. et al. *Immunol Methods.* 2006 315(1-2): p. 171-84). (See also comments in *Bispecific Antibodies* Konterman R. E. Springer Publishing 2011; 6.6; also see comments in p322/323 of Strohl W. R. and Strohl L. M., *Therapeutic Antibody Engineering,* Woodhead Publishing 2012).

SUMMARY OF INVENTION

The present invention relates to the provision of multi-domain specific binding molecules comprising two or more VNAR domains. More particularly, the invention relates to the provision of bi- and multi-valent VNARs. The current inventors have recently shown that, contrary to the general understanding in the art, in fact dimeric, trimeric and bispecific fusions of VNARs can be formed.

Recently Muller M.R. et al *mAbs* 2012. 4(6): p. 673-685; WO2013/167883) disclosed a bispecific VNAR that comprises a VNAR in which one domain has specificity for human serum albumin (HSA), which allows the bivalent structure to bind in serum to HSA and so extend the biological half-life of the partner domain. Fusion of VNARs at both the N and C terminus of the HSA-binding VNAR was demonstrated with retention of function of the HSA binding domain. More recently, WO/2014/173975 discloses VNARS that can bind to ICOSL (CD275), a cell surface antigen expressed constitutively on antigen presenting cells (APCs) such as B cells, activated monocytes and dendritic cells and is the ligand for the B7 family member, ICOS (CD278) (Yoshinaga. S., K., et al., *Int. Immunol.,* 2000. 12(10): p. 1439-1447). Certain of these ICOSL VNARs can be linked to HSA-binding VNARS and it was shown that both domains retain functionality. Trimeric forms each recognizing different antigens (hICOSL, mICOSL and HSA) could be prepared and each domain shown to retain function.

However it has not been previously shown that bi- or multispecific VNARs could be formed that recognize the same or different epitopes on the same antigen. Additionally, and unexpectedly, bispecific molecules of this form show improved properties over bivalent molecules formed from the constituent monomers, or the monomer forms themselves, or the monomer joined to a VNAR recognizing HSA.

The present invention relates to specific VNAR domain sequences that have the capability of being combined into multivalent or multispecific entities and within which multidomain entity each domain retains binding function.

Therefore, in a first aspect of the present invention there is provided a multi-domain specific binding molecule comprising two or more VNAR domains which bind to the same or different epitopes of one or more specific antigens.

In certain preferred embodiments the VNARs in the multi-domain specific binding molecule of the first aspect of the invention bind the same antigen on a specific antigen.

In further preferred embodiments, the VNARs of multi-domain specific binding molecule bind different epitopes on a specific antigen. Multi-domain specific binding molecules in accordance with these embodiments may be termed bi-paratopic molecules, as further described herein.

In one embodiment specific VNAR binding domain sequences are combined into multivalent or multispecific entities and, within which multidomain entity each domain retains binding function, wherein the binding domains recognize distinct epitopes on a single antigen.

A preferred embodiment of the invention is a bi- or multi-specific binding molecule comprising two (or more) different VNAR binding domains wherein the binding specificity is for distinct epitopes on a single specific antigen and in which the resultant entity shows improved properties compared to the individual VNAR binding domains. An example of an improved property includes increased agonistic or antagonistic effect compared to the monomer VNARs.

Preferably the VNAR domains of the multi-domain specific binding molecule of the present invention are separated by a spacer sequence. More preferably, the spacer sequence has independent functionality which is exhibited in the binding molecule. In one embodiment, the spacer sequence is a VNAR domain or functional fragment thereof. In a specific example the spacer may be a VNAR or functional fragment thereof that binds serum albumin, including human serum albumin or ICOSL. In certain embodiments the spacer sequence comprises the amino acid sequence of any one of SEQ ID NO: 67, 77, 78, 79, 80, 81, 82, 83, 84, 85, 86, 87 or 88, or a functional fragment having at least 60% sequence identity thereto. In a further embodiment the spacer sequence may be the Fc portion of an immunoglobulin, including but not limited to a human immunoglobulin Fc region. The improved properties may partially or completely derive from the properties of the spacer, for example by passively separating the VNAR domains in space or by the inherent properties of the spacer such as serum albumin binding which may lead to a longer in vivo half-life for the resultant entity, or by the recognition of a second therapeutic auto-immune target such as ICOSL or by introduction of a capacity for engagement with cells of the immune system or complement, in the case of immunoglobulin Fc regions.

Embodiments of the multi-domain specific binding molecule of the invention comprising two or more VNAR domains separated by a spacer sequence may be referred to herein as a Quad-X format.

In other preferred embodiments, the multi-domain specific binding molecule may further comprise one or more non-VNAR domains. The one or more non-VNAR domains may be placed in any position relative to the VNAR domains. Typically, and in preferred embodiments, the non-VNAR domain will be C-terminal or N-terminal to the VNAR domains.

Embodiments of the multi-domain specific binding molecule of the invention comprising two or more VNAR domains and a non-VNAR domain that is C-terminal or N-terminal to the VNAR domains may be referred to herein as a Quad-Y format.

Exemplary non-VNAR domains include, but are not limited to, TNF R1 and immunoglobulin Fc.

The specific antigen can be from a group comprising a cytokine, a growth factor, an enzyme, a cell surface associated molecule, a cell-surface membrane component, an intracellular molecule, an extracellular matrix component, a stromal antigen, a serum protein, a skeletal antigen, a microbial antigen or an antigen from a normally immune-privileged location.

A further aspect of the invention is the specific combination of VNAR binding domains that recognize cytokines Also provided by the present invention are specific domains that recognize human TNF and bind to an epitope that is different from all other well characterized anti-TNF antibody and VHH binders that are currently used to treat disease.

Accordingly, in a second aspect the present invention provides a TNF-alpha specific VNAR binding domain comprising the following CDRs and hyper-variable regions (HV):

CDR1:
HCATSS (SEQ ID NO. 68)
or
NCGLSS (SEQ ID NO. 69)
or
NCALSS (SEQ ID NO. 70)

HV2:
TNEESISKG (SEQ ID NO. 71)

HV4:
SGSKS (SEQ ID NO. 72)
or
EGSKS (SEQ ID NO. 73)

CDR3:
ECQYGLAEYDV (SEQ ID NO. 1)
or
SWWTQNWRCSNSDV (SEQ ID NO. 6)
or
YIPCIDELVYMISGGTSGPIHDV (SEQ ID NO. 11)

or a functional variant thereof with a sequence identity of at least 60%.

In particularly preferred embodiments, the TNF-alpha specific VNAR binding domain comprising the amino acid sequence of SEQ ID 2, 7 or 12, or a functional variant thereof with a sequence identity of at least 60%.

In preferred embodiments the TNF-alpha specific VNAR domain of the invention is modified at one or more amino acid sequence position to reduce the potential for immunogenicity in vivo, by for example humanization, deimmunization or similar technologies, while retaining functional binding activity for the specific epitopes on the specific antigen.

One embodiment of the invention is the specific combination of VNAR binding domains into a resultant multidomain binding molecule that recognize TNFα and which, in the forms outlined in this invention, provide improved functional properties over the individual binding domains. It is known that VNARs can be raised that are claimed to recognize TNFα (Camacho-Villegas T, et al MAbs. 2013. 5(1): P. 80-85; Bojalil R, et al BMC Immunol. 2013. 14:17; WO2011/056056; US20110129473; US20140044716). These VNARs have not however been linked to form dimeric or bispecific forms. In addition these domains in a monomeric format are 70 to 200 times less potent than the monomeric anti-TNF VNAR domains described here.

Accordingly, the TNF-alpha specific VNAR binding domain of the second aspect of the invention may be used as one or both VNAR domains in the multi-domain specific binding molecule of the first aspect. Therefore, in a preferred embodiment there is provided a multi-domain specific binding molecule of the first aspect, wherein one or more of the VNAR domains have an amino acid sequence selected from the group comprising SEQ ID 2, 7 or 12, or a functional variant thereof with a sequence identity of at least 60%. In other preferred embodiments, there is provided a multi-domain specific binding molecule of the first aspect, wherein two or more of the VNAR domains have an amino acid sequence selected from the group comprising SEQ ID 2, 7 or 12, or a functional variant thereof with a sequence identity of at least 60%.

Other preferred embodiments of the first aspect of the invention include the multi-domain specific binding molecule of the first aspect comprising one or more of the VNAR domains having an amino acid sequence selected from the group comprising SEQ ID 65 or 66, or a functional variant thereof with a sequence identity of at least 60%. Yet further embodiments of the first aspect include the multi-domain specific binding molecule of the first aspect comprising two or more of the VNAR domains having an amino acid sequence selected from the group comprising SEQ ID 65 or 66, or a functional variant thereof with a sequence identity of at least 60%.

The VNAR domain or domains used in the first aspect of the invention may be modified at one or more amino acid sequence position to reduce the potential for immunogenicity in vivo, by for example humanization, deimmunization or similar technologies, while retaining functional binding activity for the specific epitopes on the specific antigen.

The present invention also provides an isolated nucleic acid comprising a polynucleotide sequence that encodes a binding molecule according to any aspect or embodiment described herein. Furthermore, there is provided herein a method for preparing a binding molecule according to the invention, comprising cultivating or maintaining a host cell comprising the polynucleotide under conditions such that said host cell produces the binding molecule, optionally further comprising isolating the binding molecule.

According to a further aspect of the invention, there is provided a pharmaceutical composition of a specific antigen binding molecule and/or the multi-domain specific binding molecule of the previous aspects of the invention.

Pharmaceutical compositions of the invention may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg, 10 mg/kg or up to 100 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention. The present invention also provides a kit comprising a pharmaceutical composition as defined herein with instructions for use.

According to a further aspect of the invention, there is provided a pharmaceutical composition of the previous aspect for use in medicine. Such uses include methods for the treatment of a disease associated with the interaction between the target antigen of the binding domain of the invention and its ligand partner(s) through administration of a therapeutically effective dose of a pharmaceutical composition of the invention as defined above. The composition may comprise at least one specific antigen binding molecule (VNAR domain) or multi-domain specific binding molecule of the invention, or a combination of such molecules and/or a humanized variant thereof.

In accordance with this aspect of the invention, there is provided a composition for use in the manufacture of a medicament for the treatment of a disease associated with the interaction between target antigen of the binding domain of the invention and its ligand partner(s).

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

According to the invention, there is provided an antigen specific antigen binding molecule or multi-domain specific binding molecule of the invention for use in medicine. This aspect of the invention therefore extends to the use of such of an antigen specific antigen binding molecule or multi-domain binding molecule of the invention in the manufacture of a medicament for the treatment of a disease in a patient in need thereof. An antigen specific antigen binding molecule of the invention can also be used to prepare a fusion protein comprising such a specific binding molecule or multi-domain binding molecule as defined above in relation to pharmaceutical compositions of the invention. Such uses also embrace methods of treatment of diseases in patients in need of treatment comprising administration to the patient of a therapeutically effective dosage of a pharmaceutical composition as defined herein comprising an antigen specific antigen binding molecule or multi-domain binding molecule of the invention.

As used herein, the term "treatment" includes any regime that can benefit a human or a non-human animal. The treatment of "non-human animals" in veterinary medicine extends to the treatment of domestic animals, including horses and companion animals (e.g. cats and dogs) and farm/agricultural animals including members of the ovine, caprine, porcine, bovine and equine families. The treatment may be a therapeutic treatment in respect of any existing condition or disorder, or may be prophylactic (preventive treatment). The treatment may be of an inherited or an acquired disease. The treatment may be of an acute or chronic condition. The treatment may be of a condition/disorder associated with inflammation and/or cancer. The antigen specific antigen binding molecules or multi-domain specific binding molecules of the invention may be used in the treatment of a disorder, including, but not limited to osteoarthritis, scleroderma, renal disease, rheumatoid arthritis, inflammatory bowel disease, multiple sclerosis, atherosclerosis, or any inflammatory disease.

In a further aspect the present invention provides a method for treating a condition mediated by TNFα, the method comprising the administration of a therapeutically effective amount of a composition of the invention that specifically binds to TNFα.

In yet a further aspect the present invention provides a method for treating at least one condition mediated by ICOSL, comprising the administration of an effective amount of a composition of the invention that specifically binds to ICOSL.

A further aspect of the invention is the specific combination of VNAR binding domains that recognize cell-surface molecules. In certain embodiments, the VNARs of the multi-domain binding molecule bind different classes of ligand or target. One non-limiting example contemplated herein is a multi-domain specific binding molecule of the first aspect of the invention in which at least one VNAR domain binds a target associated with auto-immune disease and at least one VNAR domain binds to a target associated with the inflammatory response.

A particularly preferred multi-domain specific antigen binding molecule of the invention includes a TNF-specific VNAR and an ICOSL specific VNAR. Preferably, the TNF-specific VNAR is the VNAR of the second aspect of the invention.

One embodiment of the invention is the specific combination of VNAR binding domains into a resultant multidomain binding molecule that recognize ICOSL and which, in the forms outlined in this invention, provide improved functional properties over the individual binding domains.

In the present application reference is made to a number of drawings in which:

FIG. 1 Anti-hTNF-alpha IgNAR titration of immunized nurse shark plasma using anti-Nurse shark IgNAR hybridoma antibody ELISA titration of serum from immunized animals, pre-immunization and after bleed 5 Binding ELISA measurement of anti-rhTNF-α IgNAR titer in immunized nurse shark. Detection was carried out with GA8 monoclonal anti-nurse IgNAR antibody, and anti-mouse IgG-HRP conjugated antibody was used as secondary antibody.

FIG. 2 Neutralisation of hTNF-alpha induced cytotoxicity in L929 cells

In this assay, the ability of the anti-TNF domains (D1 and C4) and control anti-human serum albumin domain (BA11) to neutralize the activity of hTNF-α in a cell bio-assay was determined. Both the D1 and C4 domains demonstrated a similar level of concentration dependent neutralization (for calculated values see Table 2). The BA11 control does not recognize hTNF and so no neutralization was observed even at the highest concentrations. The hTNF-α +Actinomycin-D acted as control demonstrating classical cytotoxicity in the absence of a neutralizing domain.

FIG. 3 In vitro rhTNFα neutralization assay in L929 fibrosarcoma cell line.

Neutralisation of 10×LD80 [3 ng/ml rhTNFα], n=2 with duplicates per experiment, SD.

TNF30-Fc is a fusion of an anti-rhTNFα VHH nanobody isolated from immunized camelid fused to IgG Fc (Coppieters et al., Arthritis and Rheumatism, 2006, 54 (6): 1856-1866; Riechmann et al., J. Immunol. Methods, 1999. 231: 25-38)

Alb8-Fc is a $V_{HH}$ domain which recognizes HSA, fused to IgG Fc. 2V is a negative control VNAR which recognizes no known target. 2V-Fc is a fusion of 2V to IgG Fc.

Only those binders that were specific for hTNF (D1, C4 and TNF-30) were able to demonstrate neutralization of the activity of the free hTNF and in a concentration dependent manner. The neutralization potency was enhanced by conversion from a monomer to a bivalent Fc format. The combination of D1-Fc and C4-Fc together delivered a neutralization potency that was better than D1-Fc alone or C4-Fc alone. (see Table 2 for all calculated neutralization values). Both the controls, Alb-8 and 2V, were unable to neutralize even in this bivalent Fc format.

FIG. 4 Diagram of format of bivalent and bispecific constructs FIG. 5 ELISA binding of dimeric VNARs together with a TNF-30 VHH control (TNF30-TNF30).

All the tested VNAR domains D1, C4, B4 were either paired with themselves (eg D1-D1, C4-C4 etc) or paired with each other (eg D1-C4, D1-B4) in both possible orientations (eg C4-D1, B4-D1). The ELISA ranking placed the D1-D1 dimer pair as the best (lowest concentration of VNAR required to reach a saturating signal) and B4-C4 and B4-B4 as the worst performing in this ELSA format. A number of the VNAR pairings were better than the VHH dimer control.

Figure 6:
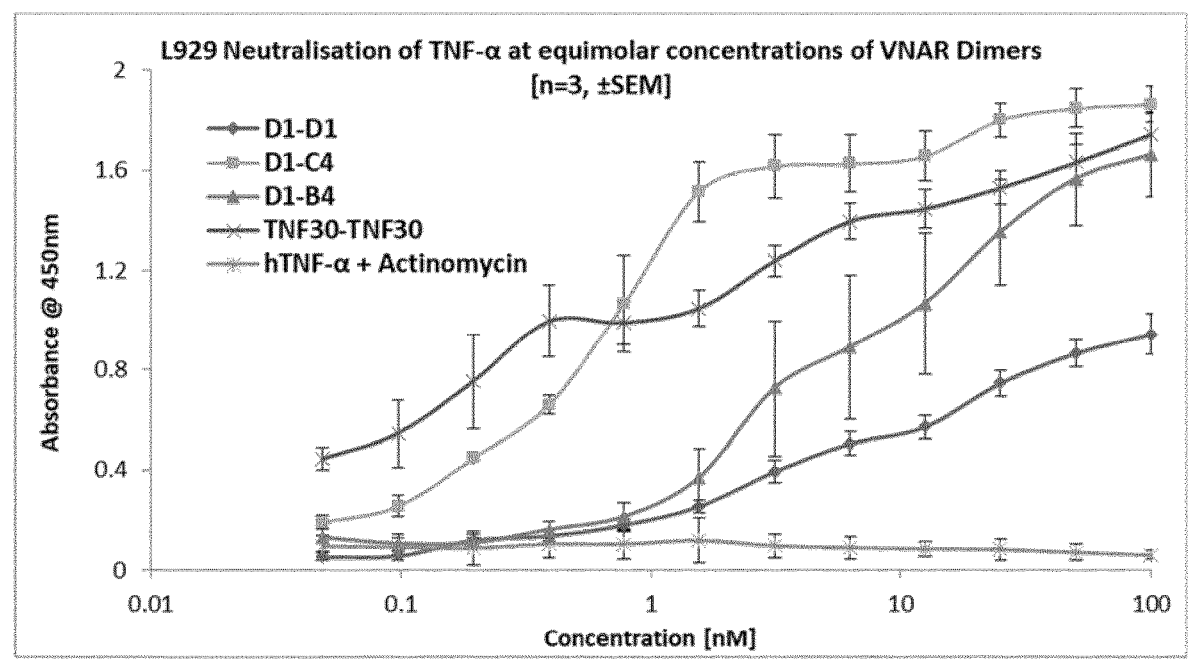

FIG. 6 L929 assay to measure TNF neutralization by VNAR dimer pairs

The neutralizing ability of the anti-TNF α VNAR dimer pairs D1-D1, D1-C4, D1-B4 and the positive control anti-TNF VHH dimer (TNF30-TNF30) were assessed using an appropriate bioassay. The domain pairing showing the most potent neutralizing activity in this assay format was the VNAR pair D1-C4 (for calculated values of neutralisation see Table 2). hTNFα+ actinomycin-D treated cells without any neutralizing domain provided an appropriate classical uninhibited cytotoxicity control.

FIG. 7 Neutralisation of hTNFαinduced cytotoxicity in L929 cells using trimeric anti-hTNF-α VNARs The lead anti-hTNFαVNAR dimers (D1-D1 and D1-C4) were reformatting into multivalent trimeric constructs by incorporating an anti-HSA humanised VNAR (soloMER™ BA11) in the middle of both dimeric constructs to achieve D1-BA11-D1 and D1-BA11-C4 respectively. The ability of these multivalent trimeric constructs and humira (Adalimumab) and TNF30-BA11-TNF30 to neutralize hTNFα was assessed in a classical L929 assay. The D1-BA11-C4 construct demonstrated comparable neutralizing potency as Adalimumab, and significantly improved potency than the VHH trimeric construct, and also the anti-hTNFαdimeric (D1-C4 and D1-D1) VNARs (see Table 2 for calculated $ND_{50}$ values).

FIG. 8 Caco2 Epithelial Permeability in Polarized Caco2 cells Caco-2 cells were treated and incubated for 18 h with 10 ng/mL TNFα, LPS and IFNγ+/− anti-TNFα protein. 5 µl of 10 mg/ml FITC-Dextran [3000-5000 kDa] was added to the apical chamber and transport across the membrane to the basolateral chamber was measured 24 h later.

Treatment with VNAR/VHH monomers and VNAR control proteins was at 50 nM concentration, while Treatment with VNAR dimers (2C and 2D) and Adalimumab was at 25 nM.

BA11 and 2V are non-TNFα binding VNAR control, while B4 is a non-neutralising TNF-binding VNAR The ability of the anti-hTNFαVNAR constructs (monomers D1, C4, B4; dimers D1-D1, D1-C4; trimers, D1-BA11-D1, D1-BA11-C4), VHH constructs TNF30, TNF30-TNF30, TNF30-BA11-TNF30, and Adalimumab to prevent intestinal barrier dysfunction in cytokine treated Caco-2 cells was assessed using this classical assay. The VNAR domains D1-C4 and D1-BA11-C4 demonstrated comparable efficacy to Adalimumab. Negative controls BA11 and 2V were unable to prevent intestinal barrier dysfunction.

FIG. 9 Epithelial Resistance in Polarized Caco-2 cells Differentiated Caco-2 cells were treated and incubated for 24 h with 10 ng/mL TNFα and IFNγ +/− anti-TNFα. Effect of cytokine treatment on Trans-epithelial resistance was determined using a volt-ohm meter. Resistance was normalised to the surface area under treatment (ohm.cm$^2$).

Treatment with VNAR/VHH monomers and VNAR control proteins was at 50 nM concentration, while Treatment with VNAR dimers (2C and 2D) and Adalimumab was at 25 nM.

BA11 and 2V are non-TNFα binding VNAR control, while B4 is a non-neutralising TNF-binding VNAR

[n=1±SD with 8 replicates per treatment, one-way ANOVA and Dunnett's post-hoc test using GraphPad Prism 5)

The efficacy of the anti-hTNFαVNAR domains to restore epithelial resistance in cytokine treated Caco-2 cells were investigated in comparison with the efficacy of the VHH TNF30 and the clinically available Adalimumab at equimolar dosing range. The anti-hTNFαdimeric and trimeric VNAR domains demonstrated significant capacity in restoring epithelial resistance in a comparable fashion to the effect observed with Adalimumab. The negative controls BA11 and 2V did not restore epithelial resistance.

FIG. 10 Format of ICOSL VNAR-Fc fusions

FIG. 11 ICOSL ELISA binding data

Binding ELISA of the different anti-ICOSL Quad-X™ constructs to both human and mouse ICOS ligands.

FIG. 12 Formats for multivalent and multispecific VNARs of the invention incorporating the TNF R1 domain, ICOSL VNARs and human IgG Fc FIG. 13 Efficacy data for multivalent and multispecific VNARs incorporating the TNF R1 domain, ICOSL. VNARs and human IgG Fc, which provides additional improved functional characteristics.

VNAR-TNFR1 Fc bi-functional constructs demonstrate specific and potent efficacy in cell based neutralisation assays Format 1: anti-TNFα scFv
Format 2: anti-mICOSL VNAR (CC3)
Format 3: anti-hICOSL scFv
Format 4: anti-hICOSL VNAR (2D4)

FIG. 14 hTNF-alpha Binding profile between VNAR T43 horn shark clone and VNAR Nurse shark D1 and C4.

Binding ELISA of the VNAR T43 from the Horn shark and VNAR D1 and C4 to 1 µg/ml hTNFαcoated wells. The binding profile of T43 clone could not be determined at experimental concentration used.

FIG. 15 hTNF-alpha Neutralisation efficacy in L929 cells of VNAR T43 horn shark clone and VNAR Nurse shark D1 and C4

Comparison of the neutralising efficacy of anti-hTNFαVNAR monomers D1 and C4 compared to the Horn Shark T43 VNAR at equimolar dosing range. The T43 domain did not demonstrate any dose-dependent neutralising effect, and has similar profile as the unprotected cells treated with hTNFα and Actinomycin-D (See table 2)

FIG. 16 Binding profile of a successfully humanised anti-hTNF-alpha D1 (also known as D1 soloMER™)

Binding profile of a number of progressively improved framework humanised versions of VNAR D1 domain. D1-v1, D1-v2, D1-v3 and D1-v4 represents varying extents of humanisation, while VNAR D1 (wt) is the parental VNAR D1 domain. Substituting nurse shark framework amino acid residues with those of DPK-9, human germline kappa did not disrupt the ability of the humanised D1 versions to recognise hTNFα.

FIG. 17 Neutralisation efficacy in L929 cells of a D1 soloMER™

The capacity to neutralize hTNFαmediated cytotoxicity in L929 cells was assessed in a humanised VNAR D1 variant. The soloMER D1-v2 retained neutralizing potency for hTNFαinduced cytotoxicity.

FIG. 18 Formats for multivalent and multispecific VNARs of the invention incorporating the human IgG Fc FIG. 19 hTNF-alpha Binding profile of multivalent/multispecific VNAR-Fc constructs Demonstrating the binding profile of biparatopic/bispecific D1-Fc-C4 (Quad-X™) vs biparatopic VNAR Fc constructs D1-Fc and C4-Fc. The anti-hTNF-α VNAR Quad-X™ D1-Fc-C4 retained binding to hTNFα, with binding profile comparable and slightly improved comparable to D1-Fc and C4-Fc.

FIG. 20 Assessing the hTNF-alpha Neutralising activity of the multivalent/multispecific VNAR-Fc constructs in L929

Assessing Neutralising potency of VNAR Quad-X™ D1-Fc-C4 vs Humira (Adalimumab) in an L929 cell based assay of hTNFαmediated cytotoxicity. VNAR Quad-X™ D1-Fc-C4 retained neutralising capacity and demonstrated a superior neutralising activity compared to Humira (see Table 2 for $ND_{50}$ values).

FIG. 21 Formats for multivalent, bi-paratopic VNARs of the invention incorporating anti-mouse TNF-alpha VNAR; and anti-HSA soloMER™ BA11 or ICOSL VNAR domain, A5 or mouse IgG2a Fc FIG. 22A Mouse TNF-alpha binding profile of the bi-paratopic anti-mouse TNF-alpha VNAR constructs.

Reformatting a VNAR anti-mouse TNFα S17 domain as multivalent/multispecific trimer incorporating either an anti-ICOS ligand VNAR A5 or anti-HSA humanised VNAR, soloMER™ BA11. Both constructs retained recognition to mouse TNF-alpha.

FIG. 22B HSA binding profile of the bi-paratopic anti-mouseTNF-alpha VNAR constructs. Reformatting a VNAR anti-mouse TNFα S17 domain as multivalent/multispecific trimer incorporating either an anti-ICOS ligand VNAR A5 or anti-HSA humanised VNAR, soloMER™ BA11. S17-BA11-S17 retained binding to HSA, and the negative control, S17-A5-S17 did not recognise HSA.

FIG. 22C Mouse ICOS Ligand binding profile of the bi-paratopic dimeric/trimeric anti-ICOSL VNAR construct.

Binding profile of the reformatted S17-A5-S17 and A5-A5 homodimer to mouse ICOS ligand demonstrated that the reformatted trimeric construct incorporating an anti-mouse ICOS ligand VNAR A5 in the middle as S17-A5-S17 retained binding to mouse ICOS Ligand.

FIG. 23A & B Mouse TNF-alpha Neutralisation in L929 profile of the bi-paratopic and IgG2a Fc fusion anti-mouse TNF-alpha VNAR S17 constructs respectively.

The Neutralising efficacy of the anti-mouse TNFα constructs (S17-A5-S17, S17-BA11-S17, S17-Fc) were assessed in a mouse TNFα mediated cytotoxicity L929 assay. Both trimeric S17 and the bi-paratopic S17-Fc constructs demonstrated neutralising activities against mouse TNFα mediated cytotoxicity in L929 cells. The S17-A5-S17 demonstrated the highest potency amongst the three constructs. BA11 was a negative control in the assay, also hTNFα+ Actinomycin D represented a classical cytotoxicity effect observed in the absence of an anti-mouse TNFα inhibitor/neutraliser. Cells alone indicate healthy untreated cells.

FIG. 24 CHO-based huICOS/recombinant mouse ICOS Ligand-Fc (ICOSL-Fc) Neutralisation (blocking) Assay-ELISA based.

In this blocking assay, the multivalent VNAR constructs demonstrated significant capacity to block the mouse ICOSL-Fc from interacting with its cognate binding partner, ICOS on CHO cells. This leads to reduced/compromised detection of the Fc portion of the mouse ICOSL-Fc using an anti-human Fc-HRP antibody in a cell based ELISA format. A5-A5 dimer is the most potent blocker, followed by the S17-A5-S17, while S17 monomer is a negative control in this assay.

FIG. 25 Binding Cross-reactivity differences between the anti-hTNF-alpha VNAR vs VHH TNF30 and Humira®.

This figure illustrates the binding crossreactivity profile of the VNAR D1-C4 compared to the VHH TNF30 and Humira. The VNAR D1-C4 binds to only human, Dog and Cynomolgus TNFα; the VHH TNF30 including binding to human, dog and cynomolgus TNFα, binds weakly to pig TNFα and also human TNFβ. Humira binds to human, dog, cynomolgus and mouse TNFα. Also see tables table 3A and 3B for detailed binding and neutralisation profiles of these anti-TNFα domains.

FIG. 26 BIAcore™ T200 epitope binning analysis of anti-hTNF-alpha VNAR heterodimer vs VHH TNF30 dimer.

This epitope binning data demonstrates that VNAR D1-C4 recognizes and interacts with distinct epitope on the hTNFαmolecule from those recognised by VHH TNF30 domain. This assay involves reaching available epitope saturation with the first binding domain (in this instance, VNAR D1-C4 using saturating concentration determined as 100 times its KD value), and then followed with the second binding domain (TNF30).

FIG. 27 Functional binding to hTNF-alpha by Quad-X™ and Quad-Y™ constructs in an ELISA format.

FIG. 28 Assessing the hTNF-alpha Neutralising activity of the multivalent/multispecific VNAR-Fc constructs in L929

Assessing Neutralising potency of VNAR Quad-X™ D1-Fc-C4, Quad-Y™ D1-C4-Fc and C4-D1-Fc vs Humira (Adalimumab) in an L929 cell based assay of hTNFαmediated cytotoxicity. VNAR Quad-Y™ constructs retained neutralising capacity, with D1-C4-Fc construct demonstrating comparable neutralising activity as Quad-X™ in the presence of either 0.3 ng/ml or 3 ng/ml hTNF-alpha (see Table 2 for $ND_{50}$ values).

FIG. 29 The effect of D1-Fc-C4 (Quad-X™) and Humira® on the body weight gain of experimental Tg197 mice. By the end of the study (10 weeks of age), the mean body weights of all groups treated twice weekly from week 3 were as follows: G1-Vehicle=19.3±1.4 g, G4-Humira® 10 mg/kg=24.4±1.5 g, G2-D1-Fc-C4 3 mg/kg=24.1±1.5 g, G5-D1-Fc-C4 10 mg/kg=24.1±1.7 g and G3-D1-Fc-D4 30 mg/kg=23.4±1.4 g. Control mice at week 3 had a mean body weight of 9.8±0.2 g. Error bars indicate standard error of the mean FIG. 30 The effect of D1-Fc-C4 (Quad-X™) and Humira® on in vivo arthritis scores of experimental Tg197 mice. By the end of the study (10 weeks of age), the mean in vivo disease severity scores of all groups treated twice weekly from week 3, were as follows: G1-Vehicle=1.36±0.07, G4-Humira® 10 mg/kg=0.25+0.05, G2-D1-Fc-C4 3 mg/kg=0.17±0.04, G5-D1-Fc-C4 10 mg/kg=0.17±0.04 and G3-D1-Fc-D4 30 mg/kg=0.17±0.04. Control mice at week 3 had an in vivo arthritic score=0.13±0.05. Error bars indicate standard error of the mean.

FIG. 31 The effect of D1-Fc-C4 (Quad-X™) and Humira® on arthritis histopathology scores of experimental Tg197 mice. By the end of the study (10 weeks of age), the mean arthritis histopathology scores of all groups treated twice weekly from week 3, were as follows: G1-Vehicle=2.94±0.12, G4-Humira® 10 mg/kg=0.42+0.07, G2-D1-Fc-C4 3 mg/kg=0.41±0.03, G5-D1-Fc-C4 10 mg/kg=0.50±0.05 and G3-D1-Fc-D4 30 mg/kg=0.42±0.07. Control mice at week 3 had a histopathology score=1.22±0.10. Error bars indicate standard error of the mean.

FIG. 32 Comparison of the effect of D1-Fc-C4 (Quad-X™) and Humira® on the in vivo arthritis scores versus the ankle histopathological scores of experimental Tg197 mice. By the end of study (10 weeks of age), the mean disease severity scores of all groups treated twice weekly from week 3, were as follows: G1-Vehicle=2.94±0.12 (HS) and 1.36±0.07 (AS), G4-Humira® 10 mg/kg=0.42±0.07 (HS) and 0.25±0.05 (AS), G2-D1-Fc-C4 3 mg/kg=0.41±0.03 (HS) and 0.17±0.04 (AS), G5-D1-Fc-C4 10 mg/kg=0.50±0.05 (HS) and 0.17±0.04 (AS) and G3-D1-Fc-D4 30 mg/kg=0.42±0.07 (HS) and 0.17±0.04 (AS). Error bars indicate standard error of the mean.

FIG. 33 Efficacy evaluation of D1-Fc-C4 (Quad-X™) at 0.5, 1 and 3 mg/kg and D1-BA11-C4 at 30 mg/kg vs Humira® at 1 mg/kg and 3 mg/kg in ameliorating arthritis pathology in the Tg197 model of arthritis.

FIG. 34 The effect of D1-Fc-C4 (Quad-X™) at 0.5, 1 and 3 mg/kg and D1-BA11-C4 at 30 mg/kg vs Humira® at 1 mg/kg and 3 mg/kg on the mean group weight of Tg197 model of arthritis.

FIG. 35 The effect of different Humira® dosing regimen on in vivo arthritic and histology scores. This was performed as a separate experiment but using identical methods to those described for FIGS. 29-32.

FIG. 36 Twelve rats were immunized with Interphotoreceptor Retinal Binding Protein (IRBP) to induce Experimental Auto-Immune Uveitis (EAU). Four animals each were treated via intraperitoneal injections with a (rodent protein specific) anti TNFα VNAR-Fc at 20 mg/kg on day 8, day 10 and day 12; four animals were treated with dexamethasone intraperitoneal on same days and four animals were treated with vehicle identically. The Optical Coherence Tomography (OCT) of both the anterior and posterior segment of the rats' eyes was performed on days 0, 7, 10, 12, 13, and 14. To minimize any scientific bias of the outcomes, OCT images were scored by an "experimentally blinded observer" for total inflammation using a validated scoring system. The experiment also included a vehicle control and a positive control using a standard dose of Dexamethazone steroid.

FIG. 37A & B Assessing the hTNF-alpha Neutralizing activity of soloMER VNAR dimer constructs in L929 cells FIG. 38: Assessing the hTNF-alpha Neutralizing activity of S17-Fc vs S17-Fc-S17 (Quad-X™) constructs in L929 cells. The Fc used in the S17 constructs is derived from mouse IgG2a.

FIG. 39A, B & C: Cross-reactivity binding profile of S17-Quad-X™ and D1-C4 Quad-X™ against human and mouse TNF-alpha Various nucleotide and amino acid sequences are provided herein as follows:

SEQ ID NO 1
TNF VNAR D1 CDR3 AMINO ACID SEQUENCE
ECQYGLAEYDV

SEQ ID NO 2
TNF VNAR D1 AMINO ACID SEQUENCE (CDR1 and CDR3 single underlined)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVN SEQ ID NO 3
TNF VNAR D1 AMINO ACID SEQUENCE WITH HIS AND MYC TAGS (double underlining) (CDR1
and CDR3 single underlined)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVNAAAHHHHHHGAAESKLISEEDL SEQ ID NO 4
NUCLEOTIDE SEQUENCE CODING FOR TNF VNAR D1
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAAT SEQ ID NO 5
NUCLEOTIDE SEQUENCE CODING FOR TNF VNAR D1 WITH HIS AND MYC TAGS
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGCGGCC
GCACATCATCATCACCATCACGGCGCCGCAGAATCAAAACTCATCTCAGAAGAGGATCTG

SEQ ID NO 6
TNF VNAR C4 CDR3 AMINO ACID SEQUENCE
SWWTQNWRCSNSDV

SEQ ID NO 7
TNF VNAR C4 AMINO ACID SEQUENCE (CDR1 and CDR3 underlined)
RVDQTPQTITKETGESLTINCVLRDSNCGLSSTYWYRKKSGSTNEESISKGGRYVETINEGSKSFSLRI
NDLTVEDSGTYRCKLSWWTQNWRCSNSDVYGGGTVVTVN SEQ ID NO 8
TNF VNAR C4 AMINO ACID SEQUENCE WITH HIS AND MYC TAGS (double underlining) (CDR1
and CDR3 single underlined)
ARVDQTPQTITKETGESLTINCVLRDSNCGLSSTYWYRKKSGSTNEESISKGGRYVETINEGSKSFSL
RINDLTVEDSGTYRCKLSWWTQNWRCSNSDVYGGGTVVTVNAAAHHHHHHGAAESKLISEEDL SEQ ID NO 9
NUCLEOTIDE SEQUENCE CODING FOR TNF VNAR C4
GCTCGAGTGGACCAAACACCGCAAACAATAACAAAGGAGACGGGCGAATCACTGACCATCAACT
GTGTCCTACGAGATAGCAACTGTGGGTTGTCCAGCACGTACTGGTATCGCAAAAAATCGGGCTCA
ACAAACGAGGAGAGCATATCGAAAGGTGGACGATATGTTGAAACAATTAACGAAGGATCAAAGTC
CTTTTCTTTGAGAATTAATGATCTAACAGTTGAAGACAGTGGCACGTATCGATGCAAGTTAAGCTG
GTGGACCCAGAACTGGAGATGCTCAAATTCCGATGTATACGGAGGTGGCACTGTCGTGACTGTG
AAT SEQ ID NO 10
NUCLEOTIDE SEQUENCE CODING FOR TNF VNAR D1 WITH HIS AND MYC TAGS
GCTCGAGTGGACCAAACACCGCAAACAATAACAAAGGAGACGGGCGAATCACTGACCATCAACT
GTGTCCTACGAGATAGCAACTGTGGGTTGTCCAGCACGTACTGGTATCGCAAAAAATCGGGCTCA
ACAAACGAGGAGAGCATATCGAAAGGTGGACGATATGTTGAAACAATTAACGAAGGATCAAAGTC
CTTTTCTTTGAGAATTAATGATCTAACAGTTGAAGACAGTGGCACGTATCGATGCAAGTTAAGCTG
GTGGACCCAGAACTGGAGATGCTCAAATTCCGATGTATACGGAGGTGGCACTGTCGTGACTGTG
AATGCGGCCGCACATCATCATCACCATCACGGCGCCGCAGAATCAAAACTCATCTCAGAAGAGG
ATCTG

SEQ ID NO 11
TNF VNAR B4 CDR3 AMINO ACID SEQUENCE
YIPCIDELVYMISGGTSGPIHDV

SEQ ID NO 12
TNF VNAR B4 AMINO ACID SEQUENCE (CDR1 and CDR3 single underlined)
ARVDQTPQTITKETGESLTINCVLRDSNCALSSMYWYRKKSGSTNEESISKGGRYVETVNSGSKSFSL
RINDLTVEDSGTYRCKVYIPCIDELVYMISGGTSGPIHDVYGGGTVVTVN SEQ ID NO 13
TNF VNAR B4 AMINO ACID SEQUENCE WITH HIS AND MYC TAGS (double underlining) (CDR1
and CDR3 single underlined)
ARVDQTPQTITKETGESLTINCVLRDSNCALSSMYWYRKKSGSTNEESISKGGRYVETVNSGSKSFSL
RINDLTVEDSGTYRCKVYIPCIDELVYMISGGTSGPIHDVYGGGTVVTVNAAAHHHHHHGAAESKLISE
EDL SEQ ID NO 14
NUCLEOTIDE SEQUENCE CODING FOR TNF VNAR B4
*GCTCGAGTGGACCAAACACCGCAAACAATAACAAAGGAGACGGGCGAATCACTGACCATCAACT*
*GTGTCCTACGAGATAGTAACTGTGCATTGTCCAGCATGTACTGGTATCGCAAAAAATCTGGCTCA*
*ACAAACGAGGAGAGCATATCGAAAGGTGGACGATATGTTGAAACAGTTAACAGCGGATCAAAGTC*
*CTTTTCTTTGAGAATTAATGATCTAACAGTTGAAGACAGTGGCACGTATCGATGCAAGGTATATAT*
*ACCTTGCATCGATGAACTGGTATATATGATCAGTGGGGGTACCTCTGGCCCGATTCATGATGTAT*
*ACGGAGGTGGCACTGTCGTGACTGTGAAT*

SEQ ID NO 15
GCTAGGCTCTAGAAATAATTTTGTTTAACTTTAAGAAGGAGATATACCATGGCTCGAGTGGACCAA
ACACC

SEQ ID NO 16
CGCGCCGGATCCGCCACCTCCGCTACCGCCACCTCCGCTACCGCCACCTCCGCTACCGCCACC
TCCATTCACAGTCACGACAGTGCC

SEQ ID NO 17
GGTGGCGGATCCGGCGCGCACTCCGCTCGAGTGGACCAAACACCGC

SEQ ID NO 18
GTCCGGAATTCTCACAGATCCTCTTCTGAGATGAGTTTTTGTTCTGCGGCCCC

SEQ ID NO 19
AATTCCCCTCTAGAAGGCGCGCACTCCGCTCGAGTGGACCAAACACCG

SEQ ID NO 20
NUCLEOTIDE SEQUENCE CODING FOR TNF VNAR B4 WITH HIS AND MYC TAGS
*GCTCGAGTGGACCAAACACCGCAAACAATAACAAAGGAGACGGGCGAATCACTGACCATCAACT*
*GTGTCCTACGAGATAGTAACTGTGCATTGTCCAGCATGTACTGGTATCGCAAAAAATCTGGCTCA*
*ACAAACGAGGAGAGCATATCGAAAGGTGGACGATATGTTGAAACAGTTAACAGCGGATCAAAGTC*
*CTTTTCTTTGAGAATTAATGATCTAACAGTTGAAGACAGTGGCACGTATCGATGCAAGGTATATAT*
*ACCTTGCATCGATGAACTGGTATATATGATCAGTGGGGGTACCTCTGGCCCGATTCATGATGTAT*
*ACGGAGGTGGCACTGTCGTGACTGTGAATGCGGCCGCACATCATCATCACCATCACGGCGCCGC*
*AGAATCAAAACTCATCTCAGAAGAGGATCTG*

SEQ ID NO 21
TNF VNAR DIMER D1-D1 AMINO ACID SEQUENCE WITH HIS AND MYC TAGS (double
underlining) (CDR1 and CDR3 single underlined, linker shown in italics)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVN*GGGGSGGGGGSGAHS*ARVDQTPQTITKE
TGESLTINCVLRDSHCATSSTYWYRKKSGSTNEESISKGGRYVETVNSGSKSFSLRINDLTVEDSGTY
RCASECQYGLAEYDVYGGGTVVTVNAAAHHHHHHGAAESKLISEEDL SEQ ID NO 22
NUCLEOTIDE SEQUENCE CODING FOR TNF VNAR DIMER D1-D1 WITH HIS AND MYC TAGS
*GCTCGAGTGGACCAAACACCGCAAACAATAACAAAGGAGACGGGCGAATCACTGACCATCAACT*
*GTGTCCTACGAGATAGCCACTGTGCAACCTCCAGCACGTACTGGTATCGCAAAAAATCGGGCTCA*
*ACAAACGAGGAGAGCATATCGAAAGGTGGACGATATGTTGAAACAGTTAACAGCGGATCAAAGTC*
*CTTTTCTTTGAGAATTAATGATCTAACAGTTGAAGACAGTGGCACGTATCGATGCGCTTCCGAGTG*
*CCAATATGGACTGGCAGAATATGATGTATACGGAGGTGGCACTGTCGTGACTGTGAATGGAGGT*
*GGCGGTAGCGGAGGTGGTGGCGGATCCGGCGCGCACTCCGCTCGAGTGGACCAAACACCGCA*
*AACAATAACAAAGGAGACGGGCGAATCACTGACCATCAACTGTGTCCTACGAGATAGCCACTGTG*
*CAACCTCCAGCACGTACTGGTATCGCAAAAAATCGGGCTCAACAAACGAGGAGAGCATATCGAAA*
*GGTGGACGATATGTTGAAACAGTTAACAGCGGATCAAAGTCCTTTTCTTTGAGAATTAATGATCTA*
*ACAGTTGAAGACAGTGGCACGTATCGATGCGCTTCCGAGTGCCAATATGGACTGGCAGAATATG*
*ATGTATACGGAGGTGGCACTGTCGTGACTGTGAATGCGGCCGCACATCATCATCACCATCACGG*
*GGCCGCAGAACAAAAACTCATCTCAGAAGAGGATCTG*

SEQ ID NO 23
TNF VNAR DIMER C4-C4 AMINO ACID SEQUENCE WITH HIS AND MYC TAGS (double
underlining) (CDR1 and CDR3 single underlined, linker shown in italics)
ARVDQTPQTITKETGESLTINCVLRDSNCGLSSTYWYRKKSGSTNEESISKGGRYVETINEGSKSFSL
RINDLTVEDSGTYRCKLSWWTQNWRCSNSDVYGGGTVVTVN*GGGGSGGGGGSGAHS*ARVDQTPQ
TITKETGESLTINCVLRDSNCGLSSTYWYRKKSGSTNEESISKGGRYVETINEGSKSFSLRINDLTVED
SGTYRCKLSWWTQNWRCSNSDVYGGGTVVTVNAAAHHHHHHGAAEQKLISEEDL SEQ ID NO 24
NUCLEOTIDE SEQUENCE CODING FOR TNF VNAR DIMER C4-C4 WITH HIS AND MYC TAGS
*GCTCGAGTGGACCAAACACCGCAAACAATAACAAAGGAGACGGGCGAATCACTGACCATCAACT*
*GTGTCCTACGAGATAGCAACTGTGGGTTGTCCAGCACGTACTGGTATCGCAAAAAATCGGGCTCA*
*ACAAACGAGGAGAGCATATCGAAAGGTGGACGATATGTTGAAACAATTAACGAAGGATCAAAGTC*
*CTTTTCTTTGAGAATTAATGATCTAACAGTTGAAGACAGTGGCACGTATCGATGCAAGTTAAGCTG*
*GTGGACCCAGAACTGGAGATGCTCAAATTCCGATGTATACGGAGGTGGCACTGTCGTGACTGTG*
*AACGGAGGTGGCGGTAGCGGAGGTGGTGGCGGATCCGGCGCGCACTCCGCTCGAGTGGACCA*
*AACACCGCAAACAATAACAAAGGAGACGGGCGAATCACTGACCATCAACTGTGTCCTACGAGATA*
*GCAACTGTGGGTTGTCCAGCACGTACTGGTATCGCAAAAAATCGGGCTCAACAAACGAGGAGAG*
*CATATCGAAAGGTGGACGATATGTTGAAACAATTAACGAAGGATCAAAGTCCTTTTCTTTGAGAAT*

-continued

TAATGATCTAACAGTTGAAGACAGTGGCACGTATCGATGCAAGTTAAGCTGGTGGACCCAGAACT
GGAGATGCTCAAATTCCGATGTATACGGAGGTGGCACTGTCGTGACTGTGAACGCGGCCGCACA
TCATCATCACCATCACGGGGCCGCAGAACAAAAACTCATCTCAGAAGAGGATCTG

SEQ ID NO 25
TNF VNAR DIMER B4-B4 AMINO ACID SEQUENCE WITH HIS AND MYC TAGS (double
underlining) (CDR1 and CDR3 single underlined, linker shown in italics)
ARVDQTPQTITKETGESLTINCVLRDSNCALSSMYWYRKKSGSTNEESISKGGRYVETVNSGSKSFSL
RINDLTVEDSGTYRCKVYIPCIDELVYMISGGTSGPIHDVYGGGTVVTVN*GGGGSGGGGGSGAHS*AR
VDQTPQTITKETGESLTINCVLRDSNCALSSMYWYRKKSGSTNEESISKGGRYVETVNSGSKSFSLRI
NDLTVEDSGTYRCKVYIPCIDELVYMISGGTSGPIHDVYGGGTVVTVNAAAHHHHHHGAAEQKLISEE
DL SEQ ID NO 26
NUCLEOTIDE SEQUENCE CODING FOR TNF VNAR DIMER B4-B4 WITH HIS AND MYC TAGS
*GCTCGAGTGGACCAAACACCGCAAACAATAACAAAGGAGACGGGCGAATCACTGACCATCAACT
GTGTCCTACGAGATAGTAACTGTGCATTGTCCAGCATGTACTGGTATCGCAAAAAATCTGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCAAGGTATATAT
ACCTTGCATCGATGAACTGGTATATATGATCAGTGGGGGTACCTCTGGCCCGATTCATGATGTAT
ACGGAGGTGGCACTGTCGTGACTGTGAATGGAGGTGGCGGTAGCGGAGGTGGTGGCGGATCCG
GCGCGCACTCCGCTCGAGTGGACCAAACACCGCAAACAATAACAAAGGAGACGGGCGAATCACT
GACCATCAACTGTGTCCTACGAGATAGTAACTGTGCATTGTCCAGCATGTACTGGTATCGCAAAA
AATCTGGCTCAACAAACGAGGAGAGCATATCGAAAGGTGGACGATATGTTGAAACAGTTAACAGC
GGATCAAAGTCCTTTTCTTTGAGAATTAATGATCTAACAGTTGAAGACAGTGGCACGTATCGATGC
AAGGTATATATACCTTGCATCGATGAACTGGTATATATGATCAGTGGGGGTACCTCTGGCCCGAT
TCATGATGTATACGGAGGTGGCACTGTCGTGACTGTGAATGCGGCCGCACATCATCATCACCATC
ACGGGGCCGCAGAACAAAAACTCATCTCAGAAGAGGATCTG*

SEQ ID NO 27
TNF VNAR DIMER D1-C4 AMINO ACID SEQUENCE WITH HIS AND MYC TAGS (double
underlining) (CDR1 and CDR3 single underlined, linker shown in italics)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVN*GGGGSGGGGGSGAHS*ARVDQTPQTITKE
TGESLTINCVLRDSNCGLSSTYWYRKKSGSTNEESISKGGRYVETINEGSKSFSLRINDLTVEDSGTYR
CKLSWWVTQNWRCSNSDVYGGGTVVTVNAAAHHHHHHGAAEQKLISEEDL SEQ ID NO 28
NUCLEOTIDE SEQUENCE CODING FOR THE TNF VNAR DIMER D1-C4 WITH HIS AND MYC
TAGS
*GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGGAGGT
GGCGGTAGCGGAGGTGGTGGCGGATCCGGCGCGCACTCCGCTCGAGTGGACCAAACACCGCA
AACAATAACAAAGGAGACGGGCGAATCACTGACCATCAACTGTGTCCTACGAGATAGCAACTGTG
GGTTGTCCAGCACGTACTGGTATCGCAAAAAATCGGGCTCAACAAACGAGGAGAGCATATCGAA
AGGTGGACGATATGTTGAAACAATTAACGAAGGATCAAAGTCCTTTTCTTTGAGAATTAATGATCT
AACAGTTGAAGACAGTGGCACGTATCGATGCAAGTTAAGCTGGTGGACCCAGAACTGGAGATGC
TCAAATTCCGATGTATACGGAGGTGGCACTGTCGTGACTGTGAACGCGGCCGCACATCATCATCA
CCATCACGGGGCCGCAGAACAAAAACTCATCTCAGAAGAGGATCTG*

SEQ ID NO 29
TNF VNAR DIMER D1-B4 AMINO ACID SEQUENCE WITH HIS AND MYC TAGS (double
underlining) (CDR1 and CDR3 single underlined, linker shown in italics)
ARVDQTPQTITKETGESLPINCVLRDSHCATSSTYWYRKKSGSTNEESISKGGRYVETVNSGSKSFSL
RINDLTVEDSGTYRCASECQYGLAEYDVYGGGTVVTVN*GGGGSGGGGGSGAHS*ARVDQTPQTITKE
TGESLTINCVLRDSNCALSSMYWYRKKSGSTNEESISKGGRYVETVNSGSKSFSLRINDLTVEDSGTY
RCKVYIPCIDELVYMISGGTSGPIHDVYGGGTVVTVNAAAHHHHHHGAAEQKLISEEDL.

SEQ ID NO 30
NUCLEOTIDE SEQUENCE CODIGN FOR THE TNF VNAR DIMER D1-B4 NUCLEOTIDE
SEQUENCE WITH HIS AND MYC TAGS
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGGAGGT
GGCGGTAGCGGAGGTGGTGGCGGATCCGGCGCGCACTCCGCTCGAGTGGACCAAACACCGCA
AACAATAACAAAGGAGACGGGCGAATCACTGACCATCAACTGTGTCCTACGAGATAGTAACTGTG
CATTGTCCAGCATGTACTGGTATCGCAAAAAATCTGGCTCAACAAACGAGGAGAGCATATCGAAA
GGTGGACGATATGTTGAAACAGTTAACAGCGGATCAAAGTCCTTTTCTTTGAGAATTAATGATCTA
ACAGTTGAAGACAGTGGCACGTATCGATGCAAGGTATATATACCTTGCATCGATGAACTGGTATA
TATGATCAGTGGGGGTACCTCTGGCCCGATTCATGATGTATACGGAGGTGGCACTGTCGTGACT
GTGAATGCGGCCGCACATCATCATCACCATCACGGGGCCGCAGAACAAAAACTCATCTCAGAAG
AGGATCTG

SEQ ID NO 31
TNF VNAR DIMER B4-D1 AMINO ACID SEQUENCE (His and Myc Tags-double underlining, CDR1
and CDR3 single underlined, linker shown in italics)
ARVDQTPQTITKETGESLTINCVLRDSNCALSSMYWYRKKSGSTNEESISKGGRYVETVNSGSKSFSL
RINDLTVEDSGTYRCKVYIPCIDELVYMISGGTSGPIHDVYGGGTVVTVNGGGGSGGGGGSGAHSAR
VDQTPQTITKETGESLPINCVLRDSHCATSSTYWYRKKSGSTNEESISKGGRYVETVNSGSKSFSLRI
NDLTVEDSGTYRCASECQYGLAEYDVYGGGTVVTVNAAAHHHHHHGAAEQKLISEEDL SEQ ID NO 32
TNF VNAR DIMER B4-D1 NUCLEOTIDE SEQUENCE
*GCTCGAGTGGACCAAACACCGCAAACAATAACAAAGGAGACGGGCGAATCACTGACCATCAACT*
*GTGTCCTACGAGATAGTAACTGTGCATTGTCCAGCATGTACTGGTATCGCAAAAAATCTGGCTCA*
*ACAAACGAGGAGAGCATATCGAAAGGTGGACGATATGTTGAAACAGTTAACAGCGGATCAAAGTC*
*CTTTTCTTTGAGAATTAATGATCTAACAGTTGAAGACAGTGGCACGTATCGATGCAAGGTATATAT*
*ACCTTGCATCGATGAACTGGTATATATGATCAGTGGGGGTACCTCTGGCCCGATTCATGATGTAT*
*ACGGAGGTGGCACTGTCGTGACTGTGAATGGAGGTGGCGGTAGCGGAGGTGGTGGCGGATCCG*
*GCGCGCACTCCGCTCGAGTGGACCAAACACCGCAAACAATAACAAAGGAGACGGGCGAATCACT*
*GACCATCAACTGTGTCCTACGAGATAGCCACTGTGCAACCTCCAGCACGTACTGGTATCGCAAAA*
*AATCGGGCTCAACAAACGAGGAGAGCATATCGAAAGGTGGACGATATGTTGAAACAGTTAACAGC*
*GGATCAAAGTCCTTTTCTTTGAGAATTAATGATCTAACAGTTGAAGACAGTGGCACGTATCGATGC*
*GCTTCCGAGTGCCAATATGGACTGGCAGAATATGATGTATACGGAGGTGGCACTGTCGTGACTG*
*TGAATGCGGCCGCACATCATCATCACCATCACGGGGCCGCAGAACAAAAACTCATCTC*
*AGAAGAGGATCTG*

SEQ ID NO 33
TNF VNAR DIMER C4-B4 AMINO ACID SEQUENCE (His and Myc Tags-double underlining, CDR1
and CDR3 single underlined, linker shown in italics)
ARVDQTPQTITKETGESLTINCVLRDSNCGLSSTYWYRKKSGSTNEESISKGGRYVETINEGSKSFSL
RINDLTVEDSGTYRCKLSWWTQNWRCSNSDVYGGGTVVTVNGGGGSGGGGGSGAHSARVDQTPQ
TITKETGESLTINCVLRDSNCALSSMYWYRKKSGSTNEESISKGGRYVETVNSGSKSFSLRINDLTVED
SGTYRCKVYIPCIDELVYMISGGTSGPIHDVYGGGTVVTVNAAAHHHHHHGAAEQKLISEED SEQ ID NO 34
TNF VNAR DIMER C4-B4 NUCLEOTIDE SEQUENCE
*GCTCGAGTGGACCAAACACCGCAAACAATAACAAAGGAGACGGGCGAATCACTGACCATCAACT*
*GTGTCCTACGAGATAGCAACTGTGGGTTGTCCAGCACGTACTGGTATCGCAAAAAATCGGGCTCA*
*ACAAACGAGGAGAGCATATCGAAAGGTGGACGATATGTTGAAACAATTAACGAAGGATCAAAGTC*
*CTTTTCTTTGAGAATTAATGATCTAACAGTTGAAGACAGTGGCACGTATCGATGCAAGTTAAGCTG*
*GTGGACCCAGAACTGGAGATGCTCAAATTCCGATGTATACGGAGGTGGCACTGTCGTGACTGTG*
*AACGGAGGTGGCGGTAGCGGAGGTGGTGGCGGATCCGGCGCGCACTCCGCTCGAGTGGACCA*
*AACACCGCAAACAATAACAAAGGAGACGGGCGAATCACTGACCATCAACTGTGTCCTACGAGATA*
*GTAACTGTGCATTGTCCAGCATGTACTGGTATCGCAAAAAATCTGGCTCAACAAACGAGGAGAGC*
*ATATCGAAAGGTGGACGATATGTTGAAACAGTTAACAGCGGATCAAAGTCCTTTTCTTTGAGAATT*
*AATGATCTAACAGTTGAAGACAGTGGCACGTATCGATGCAAGGTATATACCTTGCATCGATGAA*
*CTGGTATATATGATCAGTGGGGGTACCTCTGGCCCGATTCATGATGTATACGGAGGTGGCACTGT*
*CGTGACTGTGAATGCGGCCGCACATCATCATCACCATCACGGGGCCGCAGAACAAAAACTCATC*
*TCAGAAGAGGATCTG*

SEQ ID NO 35
TNF VNAR DIMER B4-C4 AMINO ACID SEQUENCE (His and Myc Tags-double underlining, CDR1
and CDR3 single underlined, linker shown in italics)
ARVDQTPQTITKETGESLTINCVLRDSNCALSSMYWYRKKSGSTNEESISKGGRYVETVNSGSKSFSL
RINDLTVEDSGTYRCKVYIPCIDELVYMISGGTSGPIHDVYGGGTVVTVNGGGGSGGGGGSGAHSAR
VDQTPQTITKETGESLTINCVLRDSNCGLSSTYWYRKKSGSTNEESISKGGRYVETINEGSKSFSLRIN
DLTVEDSGTYRCKLSWWTQNWRCSNSDVYGGGTVVTVNAAAHHHHHHGAAEQKLISEED SEQ ID NO 36
TNF VNAR DIMER B4-C4 NUCLEOTIDE SEQUENCE
*GCTCGAGTGGACCAAACACCGCAAACAATAACAAAGGAGACGGGCGAATCACTGACCATCAACT*
*GTGTCCTACGAGATAGTAACTGTGCATTGTCCAGCATGTACTGGTATCGCAAAAAATCTGGCTCA*
*ACAAACGAGGAGAGCATATCGAAAGGTGGACGATATGTTGAAACAGTTAACAGCGGATCAAAGTC*
*CTTTTCTTTGAGAATTAATGATCTAACAGTTGAAGACAGTGGCACGTATCGATGCAAGGTATATAT*
*ACCTTGCATCGATGAACTGGTATATATGATCAGTGGGGGTACCTCTGGCCCGATTCATGATGTAT*
*ACGGAGGTGGCACTGTCGTGACTGTGAATGGAGGTGGCGGTAGCGGAGGTGGTGGCGGATCCG*
*GCGCGCACTCCGCTCGAGTGGACCAAACACCGCAAACAATAACAAAGGAGACGGGCGAATCACT*
*GACCATCAACTGTGTCCTACGAGATAGCAACTGTGGGTTGTCCAGCACGTACTGGTATCGCAAAA*
*AATCGGGCTCAACAAACGAGGAGAGCATATCGAAAGGTGGACGATATGTTGAAACAATTAACGAA*
*GGATCAAAGTCCTTTTCTTTGAGAATTAATGATCTAACAGTTGAAGACAGTGGCACGTATCGATGC*
*AAGTTAAGCTGGTGGACCCAGAACTGGAGATGCTCAAATTCCGATGTATACGGAGGTGGCACTG*
*TCGTGACTGTGAACGCGGCCGCACATCATCATCACCATCACGGGGCCGCAGAACAAAA*
*ACTCATCTCAGAAGAGGATCTG*

SEQ ID NO 37
TNF VNAR D1-BA11-C4 AMINO ACID SEQUENCE WITH HIS AND MYC TAGS (His and Myc Tags-
double underlining, CDR1 and CDR3 single underlined, linker shown in italics)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVNGGGGSGGGGSGGGGSGGGGSGAHSTR
VDQSPSSLSASVGDRVTITCVLTDTSYPLYSTYWYRKNPGSSNKEQISISGRYSESVNKGTKSFTLTIS

```
SLQPEDSATYYCRAMSTNIVVTGDGAGTKVEIKGGGGSGGGGSGGGGSGGGGSGAHSARVDQTPQ
TITKETGESLTINCVLRDSNCGLSSTYWYRKKSGSTNEESISKGGRYVETINEGSKSFSLRINDLTVED
SGTYRCKLSWWTQNWRCSNSDVYGGGTVVTVNHHHHHHHEQKLISEEDL

SEQ ID NO 38
NUCLEOTIDE SEQUENCE CODING FOR THE TNF VNAR D1-BA11-C4 WITH HIS AND MYC TAGS
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGGAGGT
GGCGGATCCGGGGGTGGCGGTAGCGGAGGTGGCGGTAGCGGAGGTGGCGGTAGTGGAGCTCA
TTCAACAAGAGTGGACCAAAGTCCAAGCTCTCTGTCCGCCAGTGTGGGCGACCGCGTGACCATC
ACCTGCGTCCTGACTGATACCAGCTATCCTCTGTACAGCACATACTGGTATCGGAAGAATCCCGG
TTCCAGCAACAAGGAGCAGATTTCCATCTCCGGCCGCTATAGTGAATCAGTCAACAAGGGCACTA
AGTCCTTTACCCTGACAATCAGTTCCCTGCAGCCCGAGGACTCCGCCACCTATTACTGCAGAGCT
ATGAGTACAAATATCTGGACCGGGGACGGAGCTGGTACCAAGGTGGAGATCAAGGGAGGTGGC
GGTTCCGGAGGTGGCGGTAGCGGAGGTGGCGGTAGCGGAGGTGGCGGTAGCGGGGCCCATTC
TGCTCGAGTGGACCAAACACCGCAAACAATAACAAAGGAGACGGGCGAATCACTGACCATCAAC
TGTGTCCTACGAGATAGCAACTGTGGGTTGTCCAGCACGTACTGGTATCGCAAAAAATCGGGCTC
AACAAACGAGGAGAGCATATCGAAAGGTGGACGATATGTTGAAACAATTAACGAAGGATCAAAGT
CCTTTTCTTTGAGAATTAATGATCTAACAGTTGAAGACAGTGGCACGTATCGATGCAAGTTAAGCT
GGTGGACCCAGAACTGGAGATGCTCAAATTCCGATGTATACGGAGGTGGCACTGTCGTGACTGT
GAATCATCACCATCACCATCACCATGAACAAAAACTCATCTCAGAAGAGGATCTG

SEQ ID NO 39
TNF VNAR D1-BA11-D1 AMINO ACID SEQUENCE WITH HIS AND MYC TAGS (His and Myc Tags-
double underlining, CDR1 and CDR3 single underlined, linker shown in italics)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVNGGGGSGGGGSGGGGSGGGGSGAHSTR
VDQSPSSLSASVGDRVTITCVLTDTSYPLYSTYWYRKNPGSSNKEQISISGRYSESVNKGTKSFTLTIS
SLQPEDSATYYCRAMSTNIVVTGDGAGTKVEIKGGGGSGGGGSGGGGSGGGGSGAHSARVDQTPQ
TITKETGESLTINCVLRDSHCATSSTYWYRKKSGSTNEESISKGGRYVETVNSGSKSFSLRINDLTVED
SGTYRCASECQYGLAEYDVYGGGTVVTVNHHHHHHHEQKLISEEDL SEQ ID NO 40
NUCLEOTIDE SEQUENCE CODING FOR THE TNF VNAR D1-BA11-D1 WITH HIS AND MYC TAGS
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGGAGGT
GGCGGATCCGGGGGTGGCGGTAGCGGAGGTGGCGGTAGCGGAGGTGGCGGTAGTGGAGCTCA
TTCAACAAGAGTGGACCAAAGTCCAAGCTCTCTGTCCGCCAGTGTGGGCGACCGCGTGACCATC
ACCTGCGTCCTGACTGATACCAGCTATCCTCTGTACAGCACATACTGGTATCGGAAGAATCCCGG
TTCCAGCAACAAGGAGCAGATTTCCATCTCCGGCCGCTATAGTGAATCAGTCAACAAGGGCACTA
AGTCCTTTACCCTGACAATCAGTTCCCTGCAGCCCGAGGACTCCGCCACCTATTACTGCAGAGCT
ATGAGTACAAATATCTGGACCGGGGACGGAGCTGGTACCAAGGTGGAGATCAAGGGAGGTGGC
GGTTCCGGAGGTGGCGGTAGCGGAGGTGGCGGTAGCGGAGGTGGCGGTAGCGGGGCCCATTC
TGCTCGAGTGGACCAAACACCGCAAACAATAACAAAGGAGACGGGCGAATCACTGACCATCAAC
TGTGTCCTACGAGATAGCCACTGTGCAACCTCCAGCACGTACTGGTATCGCAAAAAATCGGGCTC
AACAAACGAGGAGAGCATATCGAAAGGTGGACGATATGTTGAAACAGTTAACAGCGGATCAAAGT
CCTTTTCTTTGAGAATTAATGATCTAACAGTTGAAGACAGTGGCACGTATCGATGCGCTTCCGAGT
GCCAATATGGACTGGCAGAATATGATGTATACGGAGGTGGCACTGTCGTGACTGTGAATCATCAC
CATCACCATCACCATGAACAAAAACTCATCTCAGAAGAGGATCTG SEQ ID NO 41
TNF VNAR D1-BA11-B4 AMINO ACID SEQUENCE WITH HIS AND MYC TAGS (His and Myc Tags -
double underlining, CDR1 and CDR3 single underlined, linker shown in italics)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVNGGGGSGGGGSGGGGSGGGGSGAHSTR
VDQSPSSLSASVGDRVTITCVLTDTSYPLYSTYWYRKNPGSSNKEQISISGRYSESVNKGTKSFTLTIS
SLQPEDSATYYCRAMSTNIWTGDGAGTKVEIKGGGGSGGGGSGGGGSGGGGSGAHSARVDQTPQ
TITKETGESLTINCVLRDSNCALSSMYWYRKKSGSTNEESISKGGRYVETVNSGSKSFSLRINDLTVED
SGTYRCKVYIPCIDELVYMISGGTSGPIHDVYGGGTVVTVNHHHHHHHEQKLISEEDL SEQ ID NO 42
NUCLEOTIDE SEQUENCE CODING FOR THE TNF VNAR D1-BA11-B4 WITH HIS AND MYC TAGS
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGGAGGT
GGCGGATCCGGGGGTGGCGGTAGCGGAGGTGGCGGTAGCGGAGGTGGCGGTAGTGGAGCTCA
TTCAACAAGAGTGGACCAAAGTCCAAGCTCTCTGTCCGCCAGTGTGGGCGACCGCGTGACCATC
ACCTGCGTCCTGACTGATACCAGCTATCCTCTGTACAGCACATACTGGTATCGGAAGAATCCCGG
TTCCAGCAACAAGGAGCAGATTTCCATCTCCGGCCGCTATAGTGAATCAGTCAACAAGGGCACTA
AGTCCTTTACCCTGACAATCAGTTCCCTGCAGCCCGAGGACTCCGCCACCTATTACTGCAGAGCT
ATGAGTACAAATATCTGGACCGGGGACGGAGCTGGTACCAAGGTGGAGATCAAGGGAGGTGGC
```

```
GGTTCCGGAGGTGGCGGTAGCGGAGGTGGCGGTAGCGGAGGTGGCGGTAGCGGGCCCATTC
TGCTCGAGTGGACCAAACACCGCAAACAATAACAAAGGAGACGGGCGAATCACTGACCATCAAC
TGTGTCCTACGAGATAGTAACTGTGCATTGTCCAGCATGTACTGGTATCGCAAAAAATCTGGCTC
AACAAACGAGGAGAGCATATCGAAAGGTGGACGATATGTTGAAACAGTTAACAGCGGATCAAAGT
CCTTTTCTTTGAGAATTAATGATCTAACAGTTGAAGACAGTGGCACGTATCGATGCAAGGTATATA
TACCTTGCATCGATGAACTGGTATATATGATCAGTGGGGGTACCTCTGGCCCGATTCATGATGTA
TACGGAGGTGGCACTGTCGTGACTGTGAATCATCACCATCACCATCACCATGAACAAAAACTCAT
CTCAGAAGAGGATCTG
```

SEQ ID NO 43
ICOS VNAR 2D4-Fc-2D4 AMINO ACID SEQUENCE (linkers shown in italics, Fc
portion underlined)
TRVDQTPRTATKETGESLTINCVLTDTDYGLFSTSWFRKNPGTTDWERMSIGGRYVESVNKGAKSFS
LRIKDLTVADSATYYCKAFTWPWEWPDRWFRPWYDGAGTVLTVN*GGGGSGGGGAD*QEPKSSDKTHT
<u>CPPCPAPELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQGNVFSCS
VMHEALHNHYTQKSLSLSPGK</u>*TAAAATAAAATAAAATAAAA*TRVDQTPRTATKETGESLTINCVLTDT
DYGLFSTSWFRKNPGTTDWERMSIGGRYVESVNKGAKSFSLRIKDLTVADSATYYCKAFTWPWEWP
DRWFRPWYDGAGTVLTVN SEQ ID NO 44
ICOS VNAR 2D4-Fc-2D4 NUCELOTIDE SEQUENCE
```
ACACGTGTTGACCAGACACCGCGTACCGCAACCAAAGAAACCGGTGAAAGCCTGACCATT
AATTGTGTTC TGACCGATAC CGATTATGGT TTGTTCTCCA CCAGCTGGTT TCGTAAAAAT
CCGGGTACAA CCGATTGGGA ACGTATGAGC ATTGGTGGTC GTTATGTTGA AAGCGTGAAT
AAAGGTGCCA AAAGCTTTAG CCTGCGCATT AAAGATCTGA CCGTTGCAGA TAGCGCAACC
TATTACTGTA AAGCATTCAC TTGGCCGTGG AATGGCCGG ACCGTTGTT CCGTCCGTGG
TATGATGGTG CAGGCACCGT TCTGACCGTT AATGGCGGTG GTGGTTCTGG TGGTGGTGCT
GATCAGGAGC CCAAATCTTC TGACAAAACT CACACATGTC CACCGTGCCC AGCACCTGAA
CTCCTGGGTG GACCGTCAGT CTTCCTCTTC CCCCCAAAAC CCAAGGACAC CCTCATGATC
TCCCGGACCC CTGAGGTCAC ATGCGTGGTG GTGGACGTGA GCCACGAAGA CCCTGAGGTC
AAGTTCAACT GGTACGTGGA CGGCGTGGAG GTGCATAATG CCAAGACAAA GCCGCGGGAG
GAGCAGTACA ACAGCACGTA CCGTGTGGTC AGCGTCCTCA CCGTCCTGCA CCAGGACTGG
CTGAATGGCA AGGAGTACAA GTGCAAGGTC TCCAACAAAG CCCTCCCAGC CCCCATCGAG
AAAACCATCT CCAAAGCCAA AGGGCAGCCC CGAGAACCAC AGGTGTACAC CCTGCCCCCA
TCCCGGGAGG AGATGACCAA GAACCAGGTC AGCCTGACCT GCCTGGTCAA AGGCTTCTAT
CCCAGCGACA TCGCCGTGGA GTGGGAGAGC AATGGGCAGC CGGAGAACAA CTACAAGACC
ACGCCTCCCG TGCTGGACTC CGACGGCTCC TTCTTCCTCT ATAGCAAGCT CACCGTGGAC
AAGAGCAGGT GGCAGCAGGG GAACGTCTTC TCATGCTCCG TGATGCATGA GGCTCTGCAC
AACCACTACA CGCAGAAGAG CCTCTCCCTG TCCCCGGGTA AACCGCCGC CGCCGCCACC
GCCGCCGCCG CCACCGCCGC CGCCGCCACC GCCGCGGCC CCACACGTGT TGATCAGACA
CCGCGTACCG CAACCAAAGA AACCGGTGAA AGCCTGACCA TTAATTGTGT TCTGACCGAT
ACCGATTATG GTTTGTTCTC CACCAGCTGG TTTCGTAAAA ATCCGGGTAC AACCGATTGG
GAACGTATGA GCATTGGTGG TCGTTATGTT GAAAGCGTGA ATAAAGGTGC CAAAAGCTTT
AGCCTGCGCA TTAAAGATCT GACCGTTGCA GATAGCGCAA CCTATTACTG TAAAGCATTC
ACTTGGCCGT GGGAATGGCC GGACCGTTGG TTCCGTCCGT GGTATGA TGG TGCAGGCACC
GTTCTGACCG TTAAT
```

SEQ ID NO 45
ICOS VNAR 2D4-Fc-CC3 AMINO ACID SEQUENCE (linkers shown in italics, Fc
portion underlined)
TRVDQTPRTATKETGESLTINCVLTDTDYGLFSTSWFRKNPGTTDWERMSIGGRYVESVNKGAKSFS
LRIKDLTVADSATYYCKAFTWPWEWPDRWFRPWYDGAGTVLTVN*GGGGSGGGGAD*QEPKSSDKTHT
<u>CPPCPAPELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQGNVFSCS
VMHEALHNHYTQKSLSLSPGK</u>*TAAAATAAAATAAAATAAAA*TRVDQTPRTATKETGESLTINCVLTDT
EYGLFSTSWFRKNPGTTDWERMSIGGRYVESVNKGAKSFSLRIKDLTVADSATYYCKALGWWPPAF
PHWYDGAGTVLTVN SEQ ID NO 46
ICOS VNAR 2D4-Fc-CC3 NUCELOTIDE SEQUENCE
```
ACACGTGTTG ACCAGACACC GCGTACCGCA ACCAAAGAAA CCGGTGAAAG CCTGACCATT
AATTGTGTTC TGACCGATAC CGATTATGGT TTGTTCTCCA CCAGCTGGTT TCGTAAAAAT
CCGGGTACAA CCGATTGGGA ACGTATGAGC ATTGGTGGTC GTTATGTTGA AAGCGTGAAT
AAAGGTGCCA AAAGCTTTAG CCTGCGCATT AAAGATCTGA CCGTTGCAGA TAGCGCAACC
TATTACTGTA AAGCATTCAC TTGGCCGTGG AATGGCCGG ACCGTTGTT CCGTCCGTGG
TATGATGGTG CAGGCACCGT TCTGACCGTT AATGGCGGTG GTGGTTCTGG TGGTGGTGCT
GATCAGGAGC CCAAATCTTC TGACAAAACT CACACATGTC CACCGTGCCC AGCACCTGAA
CTCCTGGGTG GACCGTCAGT CTTCCTCTTC CCCCCAAAAC CCAAGGACAC CCTCATGATC
TCCCGGACCC CTGAGGTCAC ATGCGTGGTG GTGGACGTGA GCCACGAAGA CCCTGAGGTC
AAGTTCAACT GGTACGTGGA CGGCGTGGAG GTGCATAATG CCAAGACAAA GCCGCGGGAG
GAGCAGTACA ACAGCACGTA CCGTGTGGTC AGCGTCCTCA CCGTCCTGCA CCAGGACTGG
CTGAATGGCA AGGAGTACAA GTGCAAGGTC TCCAACAAAG CCCTCCCAGC CCCCATCGAG
AAAACCATCT CCAAAGCCAA AGGGCAGCCC CGAGAACCAC AGGTGTACAC CCTGCCCCCA
TCCCGGGAGG AGATGACCAA GAACCAGGTC AGCCTGACCT GCCTGGTCAA AGGCTTCTAT
CCCAGCGACA TCGCCGTGGA GTGGGAGAGC AATGGGCAGC CGGAGAACAA CTACAAGACC
ACGCCTCCCG TGCTGGACTC CGACGGCTCC TTCTTCCTCT ATAGCAAGCT CACCGTGGAC
```

```
AAGAGCAGGT GGCAGCAGGG GAACGTCTTC TCATGCTCCG TGATGCATGA GGCTCTGCAC
AACCACTACA CGCAGAAGAG CCTCTCCCTG TCCCCGGGTA AAACCGCCGC CGCCGCCACC
GCCGCCGCCG CCACCGCCGC CGCCGCCACC GCCGCGGCCG CCACACGTGT TGATCAGACA
CCGCGTACCG CAACCAAAGA AACCGGTGAA AGCCTGACCA TTAATTGTGT TCTGACCGAT
ACCGAGTATG GTTTGTTCTC CACCAGCTGG TTTCGTAAAA ATCCGGGTAC AACCGATTGG
GAACGTATGA GCATTGGTGG TCGTTATGTT GAAAGCGTGA ATAAAGGTGC CAAAAGCTTT
AGCCTGCGCA TTAAAGATCT GACCGTTGCA GATAGCGCAA CCTATTACTG TAAAGCACTG
GGTTGGTGGC CGCCGGCTTT CCCGCATTGG TATGATGGTG CAGGCACCGT TCTGACCGTT
AAT

SEQ ID NO 47
ICOS VNAR CC3-Fc-2D4 AMINO ACID SEQUENCE (linkers shown in italics, Fc portion
underlined)
TRVDQTPRTATKETGESLTINCVLTDTEYGLFSTSWFRKNPGTTDWERMSIGGRYVESVNKGAKSFS
LRIKDLTVADSATYYCKALGWWPPAFPHWYDGAGTVLTVNGGGGSGGGGRTEPKSSDKTHTCPPC
PAPEAAGAPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMH
EALHNHYTQKSLSLSPGKTAAAATAAAATAAAATAAAATRVDQTPRTATKETGESLTINCVLTDTDYGL
FSTSWFRKNPGTTDWERMSIGGRYVESVNKGAKSFSLRIKDLTVADSATYYCKAFTWPWEWPDRWF
RPWYDGAGTVLTVN SEQ ID NO 48
ICOS VNAR CC3-Fc-2D4 NUCLEOTIDE SEQUENCE
ACACGTGTTG ATCAGACACC GCGTACCGCA ACCAAAGAAA CCGGTGAAAG CCTGACCATT
AATTGTGTTC TGACCGATAC CGAGTATGGT TTGTTCTCCA CCAGCTGGTT TCGTAAAAAT
CCGGGTACAA CCGATTGGGA ACGTATGAGC ATTGGTGGTC GTTATGTTGA AAGCGTGAAT
AAAGGTGCCA AAAGCTTTAG CCTGCGCATT AAAGATCTGA CCGTTGCAGA TAGCGCAACC
TATTACTGTA AAGCACTGGG TTGGTGGCCG CCGGCTTTCC CGCATTGGTA TGATGGTGCA
GGCACCGTTC TGACCGTTAA TGGCGGTGGT GGTTCTGGTG GTGGTGGTCG TACGGAGCCC
AAATCTTCTG ACAAAACTCA CACATGCCCA CCGTGCCCAG CACCTGAAGC CGCTGGGGCA
CCGTCAGTCT TCCTCTTCCC CCCAAAACCC AAGGACACCC TCATGATCTC CCGGACCCCT
GAGGTCACAT GCGTGGTGGT GGACGTGAGC CACGAAGACC CTGAGGTCAA GTTCAACTGG
TACGTGGACG GCGTGGAGGT GCATAATGCC AAGACAAAGC CGCGGGAGGA GCAGTACAAC
AGCACGTACC GTGTGGTCAG CGTCCTCACC GTCCTGCACC AGGACTGGCT GAATGGCAAG
GAGTACAAGT GCAAGGTCTC CAACAAAGCC CTCCCAGCCC CATCGAGAA AACCATCTCC
AAAGCCAAAG GCAGCCCCG AGAACCACAG GTGTACACCC TGCCCCCATC CCGGGAGGAG
ATGACCAAGA ACCAGGTCAG CCTGACCTGC CTGGTCAAAG GCTTCTATCC CAGCGACATC
GCCGTGGAGT GGGAGAGCAA TGGGCAGCCG GAGAACAACT ACAAGACCAC GCCTCCCGTG
CTGGACTCCG ACGGCTCCTT CTTCCTCTAT AGCAAGCTCA CCGTGGACAA GAGCAGGTGG
CAGCAGGGGA ACGTCTTCTC ATGCTCCGTG ATGCATGAGG CTCTGCACAA CCACTACACG
CAGAAGAGCC TCTCCCTGTC CCCGGGTAAA ACCGCCGCCG CCGCCACCGC CGCCGCCGCC
ACCGCCGCCG CCGCCACCGC CGCGGCCGCC ACACGTGTTG ATCAGACACC GCGTACCGCA
ACCAAAGAAA CCGGTGAAAG CCTGACCATT AATTGTGTTC TGACCGATAC CGATTATGGT
TTGTTCTCCA CCAGCTGGTT TCGTAAAAAT CCGGGTACAA CCGATTGGGA ACGTATGAGC
ATTGGTGGTC GTTATGTTGA AAGCGTGAAT AAAGGTGCCA AAAGCTTTAG CCTGCGCATT
AAAGATCTGA CCGTTGCAGA TAGCGCAACC TATTACTGTA AAGCATTCAC TTGGCCGTGG
GAATGGCCGG ACCGTTGGTT CCGTCCGTGG TATGATGGTG CAGGCACCGT TCTGACCGTT
AAT SEQ ID NO 49
ICOS VNAR CC3-Fc-CC3 AMINO ACID SEQUENCE (linkers shown in italics, Fc portion
underlined)
TRVDQTPRTATKETGESLTINCVLTDTEYGLFSTSWFRKNPGTTDWERMSIGGRYVESVNKGAKSFS
LRIKDLTVADSATYYCKALGWWPPAFPHWYDGAGTVLTVNGGGGSGGGGRTEPKSSDKTHTCPPC
PAPEAAGAPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMH
EALHNHYTQKSLSLSPGKTAAAATAAAATAAAATAAAATRVDQTPRTATKETGESLTINCVLTDTEYGL
FSTSWFRKNPGTTDWERMSIGGRYVESVNKGAKSFSLRIKDLTVADSATYYCKALGWWPPAFPHWY
DGAGTVLTVN SEQ ID NO 50
ICOS VNAR CC3-Fc-CC3 NUCLEOTIDE SEQUENCE
ACACGTGTTG ATCAGACACC GCGTACCGCA ACCAAAGAAA CCGGTGAAAG CCTGACCATT
AATTGTGTTC TGACCGATAC CGAGTATGGT TTGTTCTCCA CCAGCTGGTT TCGTAAAAAT
CCGGGTACAA CCGATTGGGA ACGTATGAGC ATTGGTGGTC GTTATGTTGA AAGCGTGAAT
AAAGGTGCCA AAAGCTTTAG CCTGCGCATT AAAGATCTGA CCGTTGCAGA TAGCGCAACC
TATTACTGTA AAGCACTGGG TTGGTGGCCG CCGGCTTTCC CGCATTGGTA TGATGGTGCA
GGCACCGTTC TGACCGTTAA TGGCGGTGGT GGTTCTGGTG GTGGTGGTCG TACGGAGCCC
AAATCTTCTG ACAAAACTCA CACATGCCCA CCGTGCCCAG CACCTGAAGC CGCTGGGGCA
CCGTCAGTCT TCCTCTTCCC CCCAAAACCC AAGGACACCC TCATGATCTC CCGGACCCCT
GAGGTCACAT GCGTGGTGGT GGACGTGAGC CACGAAGACC CTGAGGTCAA GTTCAACTGG
TACGTGGACG GCGTGGAGGT GCATAATGCC AAGACAAAGC CGCGGGAGGA GCAGTACAAC
AGCACGTACC GTGTGGTCAG CGTCCTCACC GTCCTGCACC AGGACTGGCT GAATGGCAAG
GAGTACAAGT GCAAGGTCTC CAACAAAGCC CTCCCAGCCC CATCGAGAA AACCATCTCC
AAAGCCAAAG GCAGCCCCG AGAACCACAG GTGTACACCC TGCCCCCATC CCGGGAGGAG
ATGACCAAGA ACCAGGTCAG CCTGACCTGC CTGGTCAAAG GCTTCTATCC CAGCGACATC
GCCGTGGAGT GGGAGAGCAA TGGGCAGCCG GAGAACAACT ACAAGACCAC GCCTCCCGTG
```

-continued

```
CTGGACTCCG ACGGCTCCTT CTTCCTCTAT AGCAAGCTCA CCGTGGACAA GAGCAGGTGG
CAGCAGGGGA ACGTCTTCTC ATGCTCCGTG ATGCATGAGG CTCTGCACAA CCACTACACG
CAGAAGAGCC TCTCCCTGTC CCCGGGTAAA ACCGCCGCCG CCGCCACCGC CGCCGCCGCC
ACCGCCGCCG CCGCCACCGC CGCGGCCGCC ACACGTGTTG ATCAGACACC GCGTACCGCA
ACCAAAGAAA CCGGTGAAAG CCTGACCATT AATTGTGTTC TGACCGATAC CGAGTATGGT
TTGTTCTCCA CCAGCTGGTT TCGTAAAAAT CCGGGTACAA CCGATTGGGA ACGTATGAGC
ATTGGTGGTC GTTATGTTGA AAGCGTGAAT AAAGGTGCCA AAAGCTTTAG CCTGCGCATT
AAAGATCTGA CCGTTGCAGA TAGCGCAACC TATTACTGTA AAGCACTGGG TTGGTGGCCG
CCGGCTTTCC CGCATTGGTA TGATGGTGCA GGCACCGTTC TGACCGTTAA T
```

SEQ ID NO 51
SoloMER ™ VNAR D1-v1 AMINO ACID SEQUENCE WITH HIS TAG
ARVDQSPSSLSASVGDRVTITCVLRDSHCATSSTYWYRKKSGSTNEESISKGGRYVETVNSGSKSFS
LRINDLTVEDSGTYRCASECQYGLAEYDVYGGGTKVEIKHHHHHH SEQ ID NO 52
NUCLEOTIDE SEQUENCE CODING FOR THE SoloMER ™ VNAR D1-v1 WITH HIS TAG
```
GCCCGCGTGGACCAGTCCCCCTCCTCCCTGTCCGCCTCCGTGGGCGACCGCGTGACCATCACC
TGCGTGCTGCGCGACTCCCACTGCGCCACCTCCTCCACCTACTGGTACCGCAAGAAG
TCCGGCTCCACCAACGAGGAGTCCATCTCCAAGGGGGGCCGCTACGTGGAGACCGTGAACTCC
GGCTCCAAGTCCTTCTCCCTGCGCATCAACGACCTGACCGTGGAGGACTCCGGCACC
TACCGCTGCGCCTCCGAGTGCCAGTACGGCCTGGCCGAGTACGACGTGTACGGCGGCGGCACC
AAGGTGGAGATCAAGCACCACCACCACCACCAC
```

SEQ ID NO 53
SoloMER ™ VNAR D1-v2 AMINO ACID SEQUENCE WITH HIS TAG
ARVDQSPSSLSASVGDRVTITCVLRDSHCATSSTYWYRKKSGSTNEESISKGGRYVETVNSGSKSFT
LTISSLQPEDFATYYCASECQYGLAEYDVYGGGTKVEIKHHHHHH SEQ ID NO 54
NUCLEOTIDE SEQUENCE CODING FOR THE SoloMER ™ VNAR D1-v2 WITH HIS TAG
```
GCCCGCGTGGACCAGTCCCCCTCCTCCCTGTCCGCCTCCGTGGGCGACCGCGTGACCATCACC
TGCGTGCTGCGCGACTCCCACTGCGCCACCTCCTCCACCTACTGGTACCGCAAGAAG
TCCGGCTCCACCAACGAGGAGTCCATCTCCAAGGGGGGCCGCTACGTGGAGACCGTGAACTCC
GGCTCCAAGTCCTTCACCCTGACCATCTCCTCCCTGCAGCCCGAGGACTTCGCCACC
TACTACTGCGCCTCCGAGTGCCAGTACGGCCTGGCCGAGTACGACGTGTACGGCGGCGGCACC
AAGGTGGAGATCAAGCACCACCACCACCACCAC
```

SEQ ID NO 55
SoloMER ™ VNAR D1-v3 AMINO ACID SEQUENCE WITH HIS TAG
ARVDQSPSSLSASVGDRVTITCVLRDSHCATSSTYWYQQKPGKTNEESISKGGRYVETVNSGSKSFT
LTISSLQPEDFATYYCASECQYGLAEYDVYGGGTKVEIKHHHHHH SEQ ID NO 56
NUCLEOTIDE SEQUENCE CODING FOR THE SoloMER ™ VNAR D1-v3 WITH HIS TAG
```
GCCCGCGTGGACCAGTCCCCCTCCTCCCTGTCCGCCTCCGTGGGCGACCGCGTGACCATCACC
TGCGTGCTGCGCGACTCCCACTGCGCCACCTCCTCCACCTACTGGTACCAGCAGAAG
CCCGGCAAGACCAACGAGGAGTCCATCTCCAAGGGGGGCCGCTACGTGGAGACCGTGAACTCC
GGCTCCAAGTCCTTCACCCTGACCATCTCCTCCCTGCAGCCCGAGGACTTCGCCACC
TACTACTGCGCCTCCGAGTGCCAGTACGGCCTGGCCGAGTACGACGTGTACGGCGGCGGCACC
AAGGTGGAGATCAAGCACCACCACCACCACCAC
```

SEQ ID NO 57
SoloMER ™ VNAR D1-v4 AMINO ACID SEQUENCE WITH HIS TAG
ARVDQSPSSLSASVGDRVTITCVLRDSHCATSSTYWYRKKPGSTNEESISKGGRFSGSGSSGSKSFT
LTISSLQPEDFATYYCASECQYGLAEYDVFGQGTKVEIKHHHHHH SEQ ID NO 58
NUCLEOTIDE SEQUENCE CODING FOR THE SoloMER ™ VNAR D1-v4 WITH HIS TAG
```
GCCCGCGTGGACCAGTCCCCCTCCTCCCTGTCCGCCTCCGTGGGCGACCGCGTGACCATCACC
TGCGTGCTGCGCGACTCCCACTGCGCCACCTCCTCCACCTACTGGTACCGCAAGAAG
CCCGGCTCCACCAACGAGGAGTCCATCTCCAAGGGGGGCCGCTTCTCCGGCTCCGGCTCCTCC
GGCTCCAAGTCCTTCACCCTGACCATCTCCTCCCTGCAGCCCGAGGACTTCGCCACC
TACTACTGCGCCTCCGAGTGCCAGTACGGCCTGGCCGAGTACGACGTGTTCGGCCAGGGCACC
AAGGTGGAGATCAAGCACCACCACCACCACCAC
```

SEQ ID NO 59
Quad-X ™ D1-Fc-C4 AMINO ACID SEQUENCE (Fc portion underlined)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTNGSGGGSGGGGSGEPKSSDKTHTCPPCP
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEA
LHNHYTQKSLSLSPGKGGGGSGGGGSGGGGSGGGGSGAHSARVDQTPQTITKETGESLTINCVLRD
SNCGLSSTYWYRKKSGSTNEESISKGGRYVETINEGSKSFSLRINDLTVEDSGTYRCKLSWWTQNWR
CSNSDVYGGGTVVTVN SEQ ID NO 60
NUCLEOTIDE SEQUENCE CODING FOR THE Quad-X ™ D1-Fc-C4
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGGATCC
GGTGGTGGGTCCGGAGGAGGTGGCTCAGGAGAGCCCAAATCTAGCGACAAAACTCACACATGC
CCACCGTGCCCAGCACCTGAACTCCTGGGGGGACCGTCAGTCTTCCTCTTCCCCCCAAAACCCA
AGGACACCCTCATGATCTCCCGGACCCCTGAGGTCACATGCGTGGTGGTGGACGTGAGCCACG
AAGACCCTGAGGTCAAGTTCAACTGGTACGTGGACGGCGTGGAGGTGCATAATGCCAAGACAAA
GCCGCGGGAGGAGCAGTACAACAGCACGTACCGGGTGGTCAGCGTCCTCACCGTCCTGCACCA
GGACTGGCTGAATGGCAAGGAGTACAAGTGCAAGGTCTCCAACAAAGCCCTCCCAGCCCCCATC
GAGAAAACCATCTCCAAAGCCAAAGGGCAGCCCCGAGAACCACAGGTGTACACCCTGCCCCCAT
CCCGGGATGAGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACCACGCCTCC
CGTGCTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACGCAGA
AGAGCCTCTCCCTGTCTCCGGGGAAAGGAGGTGGCGGTTCCGGAGGTGGCGGTAGCGGAGGT
GGCGGTAGCGGAGGTGGCGGTAGCGGGCCCATTCTGCTCGAGTGGACCAAACACCGCAAACA
ATAACAAAGGAGACGGGCGAATCACTGACCATCAACTGTGTCCTACGAGATAGCAACTGTGGTT
GTCCAGCACGTACTGGTATCGCAAAAAATCGGGCTCAACAAACGAGGAGAGCATATCGAAAGGT
GGACGATATGTTGAAACAATTAACGAAGGATCAAAGTCCTTTTCTTTGAGAATTAATGATCTAACA
GTTGAAGACAGTGGCACGTATCGATGCAAGTTAAGCTGGTGGACCCAGAACTGGAGATGCTCAA
ATTCCGATGTATACGGAGGTGGCACTGTCGTGACTGTGAAT SEQ ID NO 61
Quad-Y-D1C4 ™ D1-C4-Fc AMINO ACID SEQUENCE (Fc portion underlined)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVNGGGGSGGGGGSGAHSARVDQTPQTITKE
TGESLTINCVLRDSNCGLSSTYWYRKKSGSTNEESISKGGRYVETINEGSKSFSLRINDLTVEDSGTYR
CKLSWWTQNWRCSNSDVYGGGTVVTVNGGGSGGGGGSGEPKSSDKTHTCPPCPAPELLGGPSVFL
FPPKPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHYTQKSLSL
SPGK SEQ ID NO 62
NUCLEOTIDE SEQUENCE CODING FOR THE Quad-Y-D1C4 ™ AMINO ACID SEQUENCE
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGGAGGT
GGCGGTAGCGGAGGTGGTGGCGGATCCGGGGCGCACTCCGCTCGAGTGGACCAAACACCGCA
AACAATAACAAAGGAGACGGGCGAATCACTGACCATCAACTGTGTCCTACGAGATAGCAACTGTG
GGTTGTCCAGCACGTACTGGTATCGCAAAAAATCGGGCTCAACAAACGAGGAGAGCATATCGAA
AGGTGGACGATATGTTGAAACAATTAACGAAGGATCAAAGTCCTTTTCTTTGAGAATTAATGATCT
AACAGTTGAAGACAGTGGCACGTATCGATGCAAGTTAAGCTGGTGGACCCAGAACTGGAGATGC
TCAAATTCCGATGTATACGGAGGTGGCACTGTCGTGACTGTGAATGGTGGGTCCGGAGGAG
GTGGCTCAGGAGAGCCCAAATCTAGCGACAAAACTCACACATGCCCACCGTGCCCAGCACCTGA
ACTCCTGGGGGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGGATGAGCTGACCAA
GAACCAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTCTTCT
CATGCTCCGTGATGCATGAGGCTCTGCACAACCACTACACGCAGAAGAGCCTCTCCCTGTCTCC
GGGGAAA SEQ ID NO 63
Quad-Y-C4D1 ™ C4-D1-Fc AMINO ACID SEQUENCE (Fc portion underlined)
ARVDQTPQTITKETGESLTINCVLRDSNCGLSSTYWYRKKSGSTNEESISKGGRYVETINEGSKSFSL
RINDLTVEDSGTYRCKLSWWTQNWRCSNSDVYGGGTVVTVNGGGSGGGGGSGAHSARVDQTPQ
TITKETGESLTINCVLRDSHCATSSTYWYRKKSGSTNEESISKGGRYVETVNSGSKSFSLRINDLTVED
SGTYRCASECQYGLAEYDVYGGGTVVTVNGGGSGGGGGSGEPKSSDKTHTCPPCPAPELLGGPSVF
LFPPKPKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEALHNHYTQKSLS
LSPGK SEQ ID NO 64
NUCLEOTIDE SEQUENCE CODING FOR THE Quad-Y-C4D1 ™ AMINO ACID SEQUENCE
GCTCGAGTGGACCAAACACCGCAAACAATAACAAAGGAGACGGGCGAATCACTGACCATCAACT
GTGTCCTACGAGATAGCAACTGTGGGTTGTCCAGCACGTACTGGTATCGCAAAAAATCGGGCTCA -continued

```
ACAAACGAGGAGAGCATATCGAAAGGTGGACGATATGTTGAAACAATTAACGAAGGATCAAAGTC
CTTTTCTTTGAGAATTAATGATCTAACAGTTGAAGACAGTGGCACGTATCGATGCAAGTTAAGCTG
GTGGACCCAGAACTGGAGATGCTCAAATTCCGATGTATACGGAGGTGGCACTGTCGTGACTGTG
AACGGAGGTGGCGGTAGCGGAGGTGGTGGCGGATCCGGGGCGCACTCCGCTCGAGTGGACCA
AACACCGCAAACAATAACAAAGGAGACGGGCGAATCACTGACCATCAACTGTGTCCTACGAGATA
GCCACTGTGCAACCTCCAGCACGTACTGGTATCGCAAAAAATCGGGCTCAACAAACGAGGAGAG
CATATCGAAAGGTGGACGATATGTTGAAACAGTTAACAGCGGATCAAAGTCCTTTTCTTTGAGAAT
TAATGATCTAACAGTTGAAGACAGTGGCACGTATCGATGCGCTTCCGAGTGCCAATATGGACTGG
CAGAATATGATGTATACGGAGGTGGCACTGTCGTGACTGTGAATGGTGGTGGGTCCGGAGGAGG
TGGCTCAGGAGAGCCCAAATCTAGCGACAAAACTCACACATGCCCACCGTGCCCAGCACCTGAA
CTCCTGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCA
ACTGGTACGTGGACGGCGTGGAGGTGCATAATGCCAAGACAAAGCCGCGGGAGGAGCAGTACA
ACAGCACGTACCGTGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGATGAGCTGACCAAG
AACCAGGTCAGCCTGACCTGCCTGGTCAAAGGCTTCTATCCCAGCGACATCGCCGTGGAGTGGG
AGAGCAATGGGCAGCCGGAGAACAACTACAAGACCACGCCTCCCGTGCTGGACTCCGACGGCT
CCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGCCTCTCCCTGTCTCCG
GGGAAA
```

SEQ ID NO 65-2D4
TRVDQTPRTATKETGESLTINCVLTDTDYGLFSTSWFRKNPGTTDWERMSIGGRYVESVNKGAKSFS
LRIKDLTVADSATYYCKAFTWPWEWPDRWFRPWYDGAGTVLTVN

SEQ ID NO 66-CC3
TRVDQTPRTATKETGESLTINCVLTDTEYGLFSTSWFRKNPGTTDWERMSIGGRYVESVNKGAKSFS
LRIKDLTVADSATYYCKALGWWPPAFPHWYDGAGTVLTVN

SEQ ID NO 67-BA11
TRVDQSPSSLSASVGDRVTITCVLTDTSYPLYSTYWYRKNPGSSNKEQISISGRYSESVNKGTKSFTL
TISSLQPEDSATYYCRAMSTNIWTGDGAGTKVEIK

SEQ ID NO 68-CDR1
HCATSS

SEQ ID NO 69-CDR1
NCGLSS

SEQ ID NO 70-CDR1
NCALSS

SEQ ID NO 71-HV2
TNEESISKG

SEQ ID NO 72-HV4
SGSKS

SEQ ID NO 73-HV4
EGSKS

SEQ ID NO 74-NARF4For1
ATA ATC AAG CTT GCG GCC GCA TTC ACA GTC ACG ACA GTG CCA CCT C

SEQ ID NO 75-NARF4For2
ATA ATC AAG CTT GCG GCC GCA TTC ACA GTC ACG GCA GTG CCA TCT C

SEQ ID NO 76-NARF1Rev
ATA ATA AGG AAT TCC ATG GCT CGA GTG GAC CAA ACA CCG

SEQ ID NO 77-E06
TRVDQTPRTATRETGESLTINCVLTDTSYPLYSTYWYRKNPGSSNKEQISISGRYVESVNKGTKSFSL
RIKDLTVADSATYICRAMGTNIWTGDGAGTVLTVN

SEQ ID NO 78-hE06v1.10
TRVDQSPSSLSASVGDRVTITCVLTDTSYPLYSTYWYRKNPGSSNKEQISISGRYSESVNKGTKSFTL
TISSLQPEDFATYYCRAMGTNIWTGDGAGTKVEIK

SEQ ID NO 79-AC9
TRVDQSPSSLSASVGDRVTITCVLTDTSYPLYSTYWYRKNPGSSNKEQISISGRYSESVNKGTKSSTL
TISSLQPEDFATYYCRAMGTNIWTGDGAGTKVEIK

SEQ ID NO 80-AD4
TRVDQSPSSLSASVGDRVTITCVLTDTSYPLYSTYWYRKNPGSSNKEQISMSGRYSESVNKSTKSFTL
TISSLQPEDFATYYCRAMGTNIWTGDGAGTKVEIK

-continued

SEQ ID NO 81-AG11
TRVDQSPSSLSASVGDRVTITCVLTDTSYPLYSTYWYRKNPGSSNKEQISISGRYSESVNKGTKSFTL
TISSLQPEDFATYYCRAMGTNIWTGDGAGTKVETK

SEQ ID NO 82-AH7
TRVDQTPSSLSASVGDRVTITCVLTDTSYPLYSTYWYRKNPGSSNKEQISISGRYSESVNKGTKSSTL
TISSLQPEDFATYYCRAMGTNIWTGDGAGTKVEIK

SEQ ID NO 83-BB10
TRVDQSPSSLSASVGDRVTITCVLTDTSYPLYSTYWYRKNPGSSNKEQISISGRYSESVNKGTKSFTL
TISSLQPEDFATYYCRAMGTNFWTGDGAGTKVEIK

SEQ ID NO 84-BB11
TRVDQSPSSLSASVGDRVTITCVLTDTSYPLYSTYWYRKNPGSSNKEQISISGRYSESVNKGTKSFTL
TISSLQPEDFATYYCRAMATNIWTGDGAGTKVEIK

SEQ ID NO 85-BC3
TRVDQSPSSLSASVGDRVTITCVLTDTSYPLYSTYWYRKNPGSNNKEQISISGRYSESVNKGTKSFTL
TISSLQPEDFATYYCRAMGTNIWTGDGAGTKVEIK

SEQ ID NO 86-BD12
TRVDQSPSSLSASVGDRVTITCVLTDTSYPLYSTYWYRKNPGSSNKEQISISGRYSESVNKGTNSFTL

TISSLQPEDFATYYCRAMGTNIWTGDGAGTKVEIK
SEQ ID NO 87-BE4

TRVDQSPSSLSASVGDRVTITCVLTDTSYSLYSTYWYRKNPGSSNKEQISISGRYSESVNKGTKSFTL
TISSLQPEDFATYYCRAMGTNIWTGDGAGTKVEIK

SEQ ID NO 88-BH4
TRVDQSPSSLSASVGDRVTITCVLTDTSYPLYSTYWYRKNPGSSNKEQISISGRYSESVNKGTKSFTL
TISSLQPEDFATYYCRAMGTNLWTGDGAGTKVEIK

SEQ ID NO 89-TNF VNAR DIMER D1-C4 with (Gly4Ser)3 AMINO ACID SEQUENCE WITH HIS TAG
(linker shown in italics and tag double underlined)
ARVDQTPQTITKETGESLTINCVLRDSHCATSSTYWYRKKSGSTNEESISKGGRYVETVNSGSKSFSL
RINDLTVEDSGTYRCASECQYGLAEYDVYGGGTVVTVN*GGGGSGGGGSGGGGS*ARVDQTPQTITK
ETGESLTINCVLRDSNCGLSSTYWYRKKSGSTNEESISKGGRYVETINEGSKSFSLRINDLTVEDSGTY
RCKLSWWTQNWRCSNSDVYGGGTVVTVNAAA<u>HHHHHH</u>

SEQ ID NO 90-TNF VNAR DIMER D1-C4 with (Gly4Ser)3 NEUCLEOTIDE SEQUENCE WITH HIS
TAG
GCTCGAGTGGACCAAACACCGCAAACAATAACAAAGGAGACGGGCGAATCACTGACCATCAACT
GTGTCCTACGAGATAGCCACTGTGCAACCTCCAGCACGTACTGGTATCGCAAAAAATCGGGCTCA
ACAAACGAGGAGAGCATATCGAAAGGTGGACGATATGTTGAAACAGTTAACAGCGGATCAAAGTC
CTTTTCTTTGAGAATTAATGATCTAACAGTTGAAGACAGTGGCACGTATCGATGCGCTTCCGAGTG
CCAATATGGACTGGCAGAATATGATGTATACGGAGGTGGCACTGTCGTGACTGTGAATGGAGGT
GGCGGTAGCGGAGGTGGTGGCGGATCCGGCGGTGGTTCCGCTCGAGTGGACCAAACACCGCA
AACAATAACAAAGGAGACGGGCGAATCACTGACCATCAACTGTGTCCTACGAGATAGCAACTGTG
GGTTGTCCAGCACGTACTGGTATCGCAAAAAATCGGGCTCAACAAACGAGGAGAGCATATCGAA
AGGTGGACGATATGTTGAAACAATTAACGAAGGATCAAAGTCCTTTTCTTTGAGAATTAATGATCT
AACAGTTGAAGACAGTGGCACGTATCGATGCAAGTTAAGCTGGTGGACCCAGAACTGGAGATGC
TCAAATTCCGATGTATACGGAGGTGGCACTGTCGTGACTGTGAACGCGGCCGCACATCATCATCA
CCATCAC SEQ ID NO 91-TNF soloMER™ DIMER D1v2-C4v1 with (Gly4Ser)3 AMINO ACID SEQUENCE WITH
HIS TAG (linker shown in italics and tag double underlined)
ARVDQSPSSLSASVGD RVTITCVLRDSHCATSSTYWYRKKSGSTNEESISKGGRYVETVNSGSKSFT
LTISSLQPEDFATYYCASECQYGLAEYDVYGGGTKVEIK*GGGGSGGGGSGGGGS*ARVDQSPSSLSA
SVGDRVTITCVLRDSNCGLSSTYWYRKKSGSTNEESISKGGRYVETINEGSKSFSLRINDLTVEDSGT
YRCKLSWWTQNWRCSNSDVYGGGTKVEIKAAA<u>HHHHHH</u>

SEQ ID NO 92-TNF soloMER™ DIMER D1v2-C4v1 with (Gly4Ser)3 NUCLEOTIDE SEQUENCE
WITH HIS TAG
GCCCGCGTGGACCAGTCCCCCTCCTCCCTGTCCGCCTCCGTGGGCGACCGCGTGACCATCACC
TGCGTGCTGCGCGACTCCCACTGCGCCACCTCCTCCACCTACTGGTACCGCAAGAAGTCCGGCT
CCACCAACGAGGAGTCCATCTCCAAGGGGGGCCGCTACGTGGAGACCGTGAACTCCGGCTCCA
AGTCCTTCACCCTGACCATCTCCTCCCTGCAGCCCGAGGACTTCGCCACCTACTACTGCGCCTC
CGAGTGCCAGTACGGCCTGGCCGAGTACGACGTGTACGGCGGCGGCACCAAGGTGGAGATCAA
GGGAGGTGGCGGTAGCGGAGGTGGTGGCGGATCCGGCGGTGGTTCCGCCCGCGTGGACCAGT
CCCCCTCCTCCCTGTCCGCCTCCGTGGGCGACCGCGTGACCATCACCTGCGTGCTGCGCGACT
CCAACTGCGGCCTGTCCTCCACCTACTGGTACCGCAAGAAGTCCGGCTCCACCAACGAGGAGTC
CATCTCCAAGGGCGGCCGCTACGTGGAGACCATCAACGAGGGCTCCAAGTCCTTCTCCCTGCGC
ATCAACGACCTGACCGTGGAGGACTCCGGCACCTACCGCTGCAAGCTGTCCTGGTGGACCCAGA
ACTGGCGCTGCTCCAACTCCGACGTGTACGGCGGCGGCACCAAGGTGGAGATCAAGGCGGCCG
CACATCATCATCACCATCAC

```
SEQ ID NO 93-TNF soloMER ™ DIMER D1v2-C4v1 with (Gly4Ser)5 AMINO ACID SEQUENCE WITH
HIS TAG (linker shown in italics and tag double underlined)
ARVDQSPSSLSASVGD RVTITCVLRDSHCATSSTYWYRKKSGSTNEESISKGGRYVETVNSGSKSFT
LTISSLQPEDFATYYCASECQYGLAEYDVYGGGTKVEIKGGGGSGGGGSGGGGSGGGGSGGGGSA
RVDQSPSSLSASVGDRVTITCVLRDSNCGLSSTYWYRKKSGSTNEESISKGGRYVETINEGSKSFSLR
INDLTVEDSGTYRCKLSWWTQNWRCSNSDVYGGGTKVEIKAAAHHHHHH SEQ ID NO 94-TNF soloMER ™ DIMER D1v2-C4v1 with (Gly4Ser)5 NUCLEOTIDE SEQUENCE
WITH HIS TAG
GCCCGCGTGGACCAGTCCCCCTCCTCCCTGTCCGCCTCCGTGGGCGACCGCGTGACCATCACC
TGCGTGCTGCGCGACTCCCACTGCGCCACCTCCTCCACCTACTGGTACCGCAAGAAGTCCGGCT
CCACCAACGAGGAGTCCATCTCCAAGGGGGGCCGCTACGTGGAGACCGTGAACTCCGGCTCCA
AGTCCTTCACCCTGACCATCTCCTCCCTGCAGCCCGAGGACTTCGCCACCTACTACTGCGCCTC
CGAGTGCCAGTACGGCCTGGCCGAGTACGACGTGTACGGCGGCGGCACCAAGGTGGAGATCAA
GGGTGGTGGTGGTAGCGGTGGTGGCGGTTCAGGTGGCGGTGGTTCTGGCGGTGGCGGTAGTG
GCGGAGGTGGTAGTGCCCGCGTGGACCAGTCCCCCTCCTCCCTGTCCGCCTCCGTGGGCGACC
GCGTGACCATCACCTGCGTGCTGCGCGACTCCAACTGCGGCCTGTCCTCCACCTACTGGTACCG
CAAGAAGTCCGGCTCCACCAACGAGGAGTCCATCTCCAAGGGCGGCCGCTACGTGGAGACCAT
CAACGAGGGCTCCAAGTCCTTCTCCCTGCGCATCAACGACCTGACCGTGGAGGACTCCGGCACC
TACCGCTGCAAGCTGTCCTGGTGGACCCAGAACTGGCGCTGCTCCAACTCCGACGTGTACGGCG
GCGGCACCAAGGTGGAGATCAAGGCGGCCGCACATCATCATCACCATCAC SEQ ID NO 95-TNF S17-Quad-X ™ with (Gly4Ser)5 AMINO ACID SEQUENCE (Fc portion
underlined)
ASVNQTPRTATKETGESLTINCVLTDTHAKVFTTSWFRKNPGTTDWERMSIGGRYVESVNKGAKSFS
LRIKDLTVADSATYICRAGGYLSQPRVYWDVYGAGTVLTVNGGGGSGGGGRTEPRGPTIKPCPPCKC
PAPNLLGGPSVFIFPPKIKDVLMISLSPIVTCVVVDVSEDDPDVQISWFVNNVEVHTAQTQTHREDYNS
TLRVVSALPIQHQDWMSGKEFKCKVNNKDLPAPIERTISKPKGSVRAPQVYVLPPPEEEMTKKQVTLT
CMVTDFMPEDIYVEVVTNNGKTELNYKNTEPVLDSDGSYFMYSKLRVEKKNWVERNSYSCSVVHEGL
HNHHTTKSFSRTPGKGGGGSGGGGSGGGGSGGGGSGAHSASVNQTPRTATKETGESLTINCVLTD
THAKVFTTSWFRKNPGTTDWERMSIGGRYVESVNKGAKSFSLRIKDLTVADSATYICRAGGYLSQPR
VYWDVYGAGTVLTVN SEQ ID NO 96-TNF S17-Quad-X ™ with (Gly4Ser)5 NUCLEOTIDE SEQUENCE
GCAAGCGTTAATCAGACACCGCGTACCGCAACCAAAGAAACCGGTGAAAGCCTGACCATTAATTG
TGTTCTGACCGATACCCATGCTAAAGTTTTCACTACCAGCTGGTTTCGTAAAAATCCGGGTACAAC
CGATTGGGAACGTATGAGCATTGGTGGTCGTTATGTTGAAAGCGTGAATAAAGGTGCCAAAAGCT
TTAGCCTGCGCATTAAAGATCTGACCGTTGCAGATAGCGCAACCTATATCTGTCGTGCCGGTGGT
TACCTGTCTCAGCCGCGTGTTTACTGGGATGTTTATGGTGCAGGCACCGTTCTGACCGTTAATGG
CGGTGGTGGTTCTGGTGGTGGTGGTCGTACGGAGCCTCGAGGCCCCACAATCAAGCCCTGTCC
TCCATGCAAATGCCCAGCACCTAACCTCTTGGGTGGACCATCCGTCTTCATCTTCCCTCCAAAGA
TCAAGGATGTACTCATGATCTCCCTGAGCCCCATAGTCACATGTGTGGTGGTGGATGTGAGCGA
GGATGACCCAGATGTCCAGATCAGCTGGTTTGTGAACAACGTGGAAGTACACACAGCTCAGACA
CAAACCCATAGAGAGGATTACAACAGTACTCTCCGGGTGGTCAGTGCCCTCCCCATCCAGCACC
AGGACTGGATGAGTGGCAAGGAGTTCAAATGCAAGGTCAACAACAAAGACCTCCCAGCGCCCAT
CGAGAGAACCATCTCAAAACCCAAAGGGTCAGTAAGAGCTCCACAGTATATGTCTTGCCTCCAC
CAGAAGAAGAGATGACTAAGAAACAGGTCACTCTGACCTGCATGGTCACAGACTTCATGCCTGAA
GACATTTACGTGGAGTGGACCAACAACGGGAAAACAGAGCTAAACTACAAGAACACTGAACCAGT
CCTGGACTCTGATGGTTCTTACTTCATGTACAGCAAGCTGAGAGTGGAAAAGAAGAACTGGGTGG
AAAGAAATAGCTACTCCTGTTCAGTGGTCCACGAGGGTCTGCACAATCACCACACGACTAAGAGC
TTCTCCCGGACTCCGGGTAAAGGAGGTGGCGGTTCCGGAGGTGGCGGTAGCGGAGGTGGCGG
TAGCGGAGGTGGCGGTAGCGGGGCCCATTCTGCAAGCGTTAATCAGACACCGCGTACCGCAAC
CAAAGAAACCGGTGAAAGCCTGACCATTAATTGTGTTCTGACCGATACCCATGCTAAAGTTTTCAC
TACCAGCTGGTTTCGTAAAAATCCGGGTACAACCGATTGGGAACGTATGAGCATTGGTGGTCGTT
ATGTTGAAAGCGTGAATAAAGGTGCCAAAAGCTTTAGCCTGCGCATTAAAGATCTGACCGTTGCA
GATAGCGCAACCTATATCTGTCGTGCCGGTGGTTACCTGTCTCAGCCGCGTGTTTACTGGGATGT
TTATGGTGCAGGCACCGTTCTGACCGTTAAT
```

DETAILED DESCRIPTION OF THE INVENTION

Definitions

Amino acids are represented herein as either a single letter code or as the three-letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "Complementarity Determining Regions" or CDRs (i.e., CDR1 and CDR3) refers to the amino acid residues of a VNAR domain the presence of which are necessary for antigen binding. Each VNAR typically has CDR regions identified as CDR1 and CDR3. Each complementarity determining region may comprise amino acid residues from a "complementarity determining region" and/or those residues from a "hypervariable loop" (HV). In some instances, a complementarity determining region can include amino acids from both a CDR region and a hypervariable loop. According to the generally accepted nomenclature for VNAR molecules, a CDR2 region is not present.

"Framework regions" (FW) are those VNAR residues other than the CDR residues. Each VNAR typically has five framework regions identified as FW1, FW2, FW3a, FW3b and FW4. VNAR domains therefore typically have the structure FW1-CDR1-FW2-HV2-FW3a-HV4-FW3b-CDR3-FW4 in the N- to C-terminal direction.

"Cell", "cell line", and "cell culture" are used interchangeably (unless the context indicates otherwise) and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, etc. Eukaryotic cells use control sequences such as promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

The term "fusion protein" in this text means, in general terms, one or more proteins joined together by chemical means, including hydrogen bonds or salt bridges, or by peptide bonds through protein synthesis or both.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from an allogenic or xenogenic source. The DNA may, optionally, include marker or selection genes, for example, antibiotic resistance genes, temperature resistance genes, etc.

A "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR regions.

"Identity" describes the relationship between two or more polypeptide sequences or two or more polynucleotide sequences, as determined by comparing the sequences. Identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., *Nucleic Acids Res*, 1984, 12, 387 BLASTP, BLASTN, and FASTA (Atschul et al., *J. Molec. Biol*. (1990) 215, 403).

Preferably, the amino acid sequence of the protein has at least 60% identity, using the default parameters of the BLAST computer program (Atschul et al., *J. Mol. Biol*. 1990 215, 403-410) provided by HGMP (Human Genome Mapping Project), at the amino acid level, to the amino acid sequences disclosed herein.

More preferably, the protein sequence may have at least 65%, 66%, 67%, 68%, 69%, 70%, 75%, 80%, 85%, 90% and still more preferably 95% (still more preferably at least 96%, 97%, 98% or 99%) identity, at the nucleic acid or amino acid level, to the amino acid sequences as shown herein.

The protein may also comprise a sequence which has at least 60%, 65%, 66%, 67%, 68%, 69%, 70%, 75%, 80%, 85%, 90%, 95%, 96%, 97%, 98%, or 99% identity with a sequence disclosed herein, using the default parameters of the BLAST computer program provided by HGMP, thereto.

A "library" refers to a plurality of VNARs or VNAR fragment sequences or the nucleic acids that encode these sequences. The origin of the library can be from non-natural sources or synthetic in nature where diversity has been engineered into a natural or combination of natural frameworks or can be from a natural source as exemplified from VNAR domains isolated from RNA extracted from an immunized animal.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 \ig of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

"Natural" or "naturally occurring" VNARs, refers to VNARs identified from a non-synthetic source, for example, from a tissue source obtained ex vivo, or from the serum of an animal of the Elasmobranchii subclass. These VNARs can include VNARs generated in any type of immune response, either natural or otherwise induced. Natural VNARs include the amino acid sequences, and the nucleotide sequences that constitute or encode these antibodies. As used herein, natural VNARs are different than "synthetic VNARs", synthetic VNARs referring to VNAR sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promotor or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of coat protein on the surface of phage, e.g., filamentous phage, particles. Phage display technology allows for the preparation of large libraries of randomized protein variants which can be rapidly and efficiently sorted for those sequences that bind to a target antigen with high affinity. The display of peptide and protein libraries on phage can be used for screening millions of polypeptides for ones with specific binding properties. Polyvalent phage display methods have been used for displaying small random peptides and small proteins through fusions to the genes encoding coat proteins pIII, pV III, pVI, pVII or pIX of filamentous phage.

A "phagemid" is a plasmid vector having a bacterial origin of replication, e.g., ColEI, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle. An example of a phagemid display vector is pWRIL-1.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, or a derivative thereof.

The term "protein" means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues, variants and derivatives of a protein wherein the fragment, analogue, variant or derivative retains essentially the same biological activity or function as a reference protein. Examples of protein analogues and derivatives include peptide nucleic acids, and DARPins (Designed Ankyrin Repeat Proteins). A "polypeptide of the invention" is TNFα specific antigen binding molecule as defined herein.

A fragment, analogue, variant or derivative of the protein may be at least 25 preferably 30 or 40, or up to 50 or 100, or 60 to 120 amino acids long, depending on the length of the original protein sequence from which it is derived. A length of 90 to 120, 100 to 1 10 amino acids may be convenient in some instances.

The fragment, derivative, variant or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the additional amino acids are fused to the mature polypeptide, such as a leader or auxiliary sequence which is employed for purification of the polypeptide. Such fragments, derivatives, variants and analogues are deemed to be within the scope of those skilled in the art from the teachings herein.

"Oligonucleotides" are short-length, single-or double-stranded polydeoxynucleotides that are chemically synthesized by known methods (such as phosphotriester, phosphite, or phosphoramidite chemistry, using solid-phase techniques). Further methods include the polymerase chain reaction (PCR) used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation. DNA is "purified" when the DNA is separated from non-nucleic acid impurities (which may be polar, non-polar, ionic, etc.).

A "source" or "template" VNAR", as used herein, refers to a VNAR or VNAR antigen binding fragment whose antigen binding sequence serves as the template sequence upon which diversification according to the criteria described herein is performed. An antigen binding sequence generally includes within a VNAR preferably at least one CDR, preferably including framework regions.

A "transcription regulatory element" will contain one or more of the following components: an enhancer element, a promoter, an operator sequence, a repressor gene, and a transcription termination sequence.

"Transformation" means a process whereby a cell takes up DNA and becomes a "transformant". The DNA uptake may be permanent or transient. A "transformant" is a cell which has taken up and maintained DNA as evidenced by the expression of a phenotype associated with the DNA (e.g., antibiotic resistance conferred by a protein encoded by the DNA).

A "variant" or "mutant" of a starting or reference polypeptide (for example, a source VNAR or a CDR thereof), such as a fusion protein (polypeptide) or a heterologous polypeptide (heterologous to a phage), is a polypeptide that (1) has an amino acid sequence different from that of the starting or reference polypeptide and (2) was derived from the starting or reference polypeptide through either natural or artificial mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a non-random codon set that encodes a sequence with a variant amino acid (with respect to the amino acid found at the corresponding position in a source VNAR or antigen binding fragment) would be a variant polypeptide with respect to a source VNAR or antigen binding fragment. Thus, a variant CDR refers to a CDR comprising a variant sequence with respect to a starting or reference polypeptide sequence (such as that of a source VNAR or antigen binding fragment). A variant amino acid, in this context, refers to an amino acid different from the amino acid at the corresponding position in a starting or reference polypeptide sequence (such as that of a source VNAR or antigen binding fragment). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type" or "reference" sequence or the sequence of a "wild-type" or "reference" protein/polypeptide, such as a coat protein, or a CDR of a source VNAR, may be the reference sequence from which variant polypeptides are derived through the introduction of mutations. In general, the "wild-type" sequence for a given protein is the sequence that is most common in nature.

Similarly, a "wild-type" gene sequence is the sequence for that gene which is most commonly found in nature. Mutations may be introduced into a "wild-type" gene (and thus the protein it encodes) either through natural processes or through man induced means. The products of such processes are "variant" or "mutant" forms of the original "wild-type" protein or gene.

General methods for DNA manipulation, transfection methods and culture methods are well known to those skilled in the art. In this respect, reference is made to Molecular Cloning: A Laboratory Manual (Fourth Edition) Cold Spring Harbor Publishing.

Isolation of VNARs

VNAR domains may be obtained from phage-displayed libraries constructed using tissues from target-immunized sharks (Dooley, H., et al. *Mol Immunol*, 2003. 40(1): p. 25-33; Nuttall, S. D., et al, Proteins, 2004. 55(1): p. 187-97; and Dooley, H., et al., *Proc Natl Acad Sci USA*, 2006. 103(6): p. 1846-51), WO2003/014161, incorporated by reference describes a useful method for immunizing a shark and obtaining binding domains.

VNAR binding domains may also be obtained from synthetic libraries comprising VNAR sequences. WO2014/173959, incorporated by reference, describes a useful method for developing VNAR libraries and obtaining binding domains.

Additionally it has been shown that libraries with synthetic diversity targeted to CDR3 can be used to obtain binding domains based on VNAR structures (Nuttall, S. D., et al. *Mol Immunol*, 2001. 38(4): p. 313-26; Nuttall, S. D., et al. *Eur J Biochem*, 2003. 270(17): p. 3543-54; Shao, C. Y., et al. *Mol Immunol*, 2007. 44(4): p. 656-65 and Liu, J. L., et al. *BMC Biotechnol*, 2007. 7: p. 78; WO2005/118629.

VNARS of the invention may be further adapted to reduce potential immunogenicity when administered to man (humanization).

Humanization of antibody variable domains is a technique well-known in the art to modify an antibody which has been raised, in a species other than humans, against a therapeutically useful target so that the humanized form may avoid unwanted immunological reaction when administered to a human subject. The methods involved in humanization are summarized in Almagro J. C and William Strohl W. *Antibody Engineering: Humanization, Affinity Maturation, and Selection Techniques in Therapeutic Monoclonal Antibodies: From Bench to Clinic*. Edited by An J. 2009 John Wiley & Sons, Inc and in Strohl W. R. and Strohl L. M., *Therapeutic Antibody Engineering*, Woodhead Publishing 2012.

Although IgNARs have distinct origins compared to immunoglobulins and have very little sequence homology compared to immunoglobulin variable domains there are some structural similarities between immunoglobulin and IgNAR variable domains, so that similar processes can be applied to the VNAR domain. For example, WO2013/167883, incorporated by reference, provides a description of the humanization of VNARs, see also Kovalenko O. V., et al. *J Biol Chem*. 2013. 288(24): p. 17408-19.

Protein Expression

Nucleic acid sequences encoding antigen specific antigen binding molecules or multi-domain specific binding molecules of the invention may be present in a nucleic acid construct. Such nucleic acid constructs may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

The nucleic acid construct may suitably include a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence. Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidine kinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA element, optionally without enhancer element) for example, the minimum sequence of the CMV promoter. Preferably, the promoter is contiguous to the nucleic acid sequence.

As stated herein, the nucleic acid construct may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

The vector may be any suitable expression vector, such as pET. The vector may include such additional control sequences as desired, for example selectable markers (e.g. antibiotic resistance, fluorescence, etc.), transcriptional control sequences and promoters, including initiation and termination sequences.

The promoter may be any suitable promoter for causing expression of the protein encoded by a nucleic acid sequence of the invention, e.g. a CMV promoter, human phosphoglycerate kinase (hPGK) promoter.

Such vectors may be present in a host cell. Representative examples of appropriate host cells for expression of the nucleic acid construct of the invention include virus packaging cells which allow encapsulation of the nucleic acid into a viral vector; bacterial cells, such as *Streptococci, Staphylococci, E. coli, Streptomyces* and *Bacillus subtilis*; single cells, such as yeast cells, for example, *Saccharomyces cerevisiae*, and *Aspergillus* cells; insect cells such as *Drosophila* S2 and *Spodoptera* Sf9 cells, animal cells such as CHO, COS, C127, 3T3, PHK.293, and Bowes Melanoma cells and other suitable human cells; and plant cells e.g. *Arabidopsis thaliana*. Suitably, the host cell is a eukaryotic cell, such as a CHO cell or a HEK293 cell.

Introduction of an expression vector into the host cell can be achieved by calcium phosphate transfection, DEAE-dextran mediated transfection, microinjection, cationic-lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Cold Spring Harbor Laboratory Press, Cold Spring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the third aspect of the present invention. Appropriate cloning and expression vectors for use with prokaryotic and eukaryotic hosts are described by Sambrook et al, Molecular Cloning, a Laboratory Manual, Second Edition, Cold Spring Harbor Laboratory Press, Cold Spring Harbor, N.Y. (1989).

The invention also provides a host cell comprising any of the polynucleotides and/or vectors of the invention described herein. According to the invention, there is provided a process for the production of an antigen specific antigen binding molecule or multi-domain specific binding molecule of the invention, comprising the step of expressing a nucleic acid sequence encoding said molecule in a suitable host cell as defined herein.

Proteins can be recovered and purified from recombinant cell cultures by standard methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin and/or heparin chromatography. For therapy, the nucleic acid construct, e.g. in the form of a recombinant vector, may be purified by techniques known in the art, such as by means of column chromatography as described in Sambrook et al, Molecular Cloning, a Laboratory Manual, Second Edition, Cold Spring Harbor Laboratory Press, Cold Spring Harbor, N.Y. (1989).

This aspect of the invention therefore extends to processes for preparing a fusion protein of the invention comprising production of the fusion protein recombinantly by expression in a host cell, purification of the expressed fusion protein by means of peptide bond linkage, hydrogen or salt bond or chemical cross linking. In some embodiments of this aspect of the invention, the fusion protein could be prepared using hydrogen or salt bonds where the peptide is capable or multimerisation, for example dimerisation or trimerisation.

The antigen specific antigen binding molecule or multi-domain specific binding molecule may comprise additional N-terminal or C-terminal sequences which are cleaved off prior to use which may assist in purification and/or isolation during processes for the production of the molecule as described herein. For example, $(Ala)_3(His)_6$ at the C-terminal end of the molecule.

Also included within the invention are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions where the properties of a protein of the present invention are preserved in the variant form compared to the original form. Variants also include fusion proteins comprising an antigen specific antigen binding molecule according to the invention.

As discussed above, an example of a variant of the present invention includes a protein in which there is a substitution of one or more amino acids with one or more other amino acids. The skilled person is aware that various amino acids have similar properties. One or more such amino acids of a substance can often be substituted by one or more other such amino acids without interfering with or eliminating a desired activity of that substance. Such substitutions may be referred to as "non-conservative" amino acid substitutions.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced-for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

A fusion protein may comprise an antigen specific antigen binding molecule of the present invention fused to a heterologous peptide or protein sequence providing a structural element to the fusion protein. In other embodiments, the fusion protein may comprise an antigen specific antigen binding molecule of the present invention fused with a molecule having biological activity. The molecule may be a peptide or protein sequence, or another biologically active molecule.

For example, the antigen specific antigen binding molecule may be fused to a heterologous peptide sequence which may be a poly-amino acid sequence, for example a plurality of histidine residues or a plurality of lysine residues (suitably 2, 3, 4, 5, or 6 residues), or an immunoglobulin domain (for example an Fc domain).

References to heterologous peptides sequences include sequences from other mammalian species, such as murine and human and any heterologous peptides sequences originated from other VNAR domains.

Where the fusion protein comprises an antigen specific antigen binding molecule of the present invention fused with a molecule having biological activity, a biologically active moiety may be a peptide or protein having biological activity such as an enzyme, immunoglobulin, cytokine or a fragment thereof. Alternatively, the biologically active molecule may be an antibiotic, an anti-cancer drug, an NSAID, a steroid, an analgesic, a toxin or other pharmaceutically active agent. Anti-cancer drugs may include cytotoxic or cytostatic drugs.

In some embodiments, the fusion protein may comprise an antigen specific antigen binding molecule of the invention fused to another immunoglobulin variable or constant region, or another antigen specific antigen binding molecule of the invention. In other words, fusions of antigen specific antigen binding molecules of the invention of variable length, e.g. dimers, trimers, tetramers, or higher multimer (i.e. pentamers, hexamers, heptamers octamers, nonamers, or decamers, or greater). In specific embodiments this can be represented as a multimer of monomer VNAR subunits.

In fusion proteins of the present invention, the antigen specific antigen binding molecule may be directly fused or linked via a linker moiety to the other elements of the fusion protein. The linker may be a peptide, peptide nucleic acid, or polyamide linkage. Suitable peptide linkers may include a plurality of amino acid residues, for example, 4, 5, 6, 7, 8, 9, 10, 15, 20 or 25 amino acids., such as (Gly)4, (Gly)s, (Gly)$_4$Ser, (Gly)4(Ser)(Gly)4, or combinations thereof or a multimer thereof (for example a dimer, a trimer, or a tetramer, or greater). For example, a suitable linker may be (GGGGS)$_3$. Alternative linkers include (Ala)$_3$(His)$_6$ or multimers thereof. Also included is a sequence which has at least 50%, 60%, 70%, 80%, 90%, 95% or 99% identity, using the default parameters of the BLAST computer program provided by HGMP, thereto.

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using: Cells are grown in culture in standard culture broth, optionally for about 6-48 hours (or to OD600=0.6-0.8) at about 37° C., and then the broth is centrifuged and the supernatant removed (e.g. decanted). Initial purification is preferably by resuspending the cell pellet in a buffer solution (e.g. 1.0 mM HEPES pH 7.4) followed by recentrifugation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

The use of higher DNA concentrations during electroporation (about 10×) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

Pharmaceutical Compositions and Uses

According to the invention, there is provided a pharmaceutical composition of antigen specific antigen binding molecule or multi-domain specific binding molecule of the invention. Such compositions include fusion proteins comprising said antigen specific antigen binding molecules.

The pharmaceutical composition may also comprise an antigen specific antigen binding molecule of the present invention fused to a therapeutic protein, or a fragment thereof. The therapeutic protein may be a hormone, a growth factor (e.g. TGFβ, epidermal growth factor (EGF), platelet derived growth factor (PDGF), nerve growth factor (NGF), colony stimulating factor (CSF), hepatocyte growth factor, insulin-like growth factor, placenta growth factor); a differentiation factor; a blood clotting factor (for example, Factor VIIa, Factor VIII, Factor IX, VonWillebrand Factor or Protein C) or another protein from the blood coagulation cascade (for example, antithrombin); a cytokine e.g. an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 or IL-33 or an interferon (e.g. IFN-α, IFN-β and IFN-γ), tumour necrosis factor (TNF), IFN-γ inducing factor (IGIF), a bone morphogenetic protein (BMP, e.g. BMP-1, BMP-2, BMP-3, BMP-4, BMP-4, BMP-5, BMP-6, BMP-7, BMP-8, BMP-9, BMP10, BMP-11, BMP-12, BMP-13); an interleukin receptor antagonist (e.g. IL-1ra, IL-1 RII); a chemokine (e.g. MIPs (Macrophage Inflammatory Proteins) e.g. MIP1α and MIP1β; MCPs (Monocyte Chemotactic Proteins) e.g. MCP1, 2 or 3; RANTES (regulated upon activation normal T-cell expressed and secreted)); a trophic factor; a cytokine inhibitor; a cytokine receptor; an enzyme, for example a free-radical scavenging enzyme e.g. superoxide dismutase or catalase or a pro-drug converting enzyme (e.g. angiotensin converting enzyme, deaminases, dehydrogenases, reductases, kinases and phosphatases); a peptide mimetic; a protease inhibitor; a tissue inhibitor of metalloproteinases (TIMPs e.g. TIMP1, TIMP2, TIMP3 or TIMP4) or a serpin (inhibitors of serine proteases).

In other embodiments of the invention, the therapeutic protein in the fusion protein may be an antibody, or a engineered fragment thereof, including Fab, Fc, F(ab')$_2$ (including chemically linked F(ab')$_2$ chains), Fab', scFv (including multimer forms thereof, i.e. di-scFv, or tri-scFv), sdAb, or BiTE (bi-specific T-cell engager). Antibody fragments also include variable domains and fragments thereof, as well as other VNAR type fragments (IgNAR molecules).

The pharmaceutical composition may be composed of a number of antigen specific antigen binding molecules of the invention, for example dimers, trimers, or higher order multimers, i.e. 2, 3, 4, 5, 6, 7, or 8-mers, fused to the therapeutic protein.

The fusion of the antigen specific antigen binding molecules of the invention to the therapeutic protein may at any convenient site on the protein and may be N-, C- and/or N-/C-terminal fusion(s). In one embodiment of the invention, the fusion of the antigen specific antigen binding molecules of the invention is to both the N- and C-terminals of a therapeutic protein.

Pharmaceutical compositions of the invention may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg or up to 4 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

According to the invention, there is provided an antigen specific antigen binding molecule or multi-domain specific binding molecule of the invention for use in medicine. This aspect of the invention therefore extends to the use of such of an antigen specific antigen binding molecule or multi-domain specific binding molecule of the invention in the manufacture of a medicament for the treatment of a disease in a patient in need thereof. An antigen specific antigen binding molecule of the invention can also be used to prepare a fusion protein comprising such a specific binding molecule as defined above in relation to pharmaceutical compositions of the invention.

Such uses also embrace methods of treatment of diseases in patients in need of treatment comprising administration to the patient of a therapeutically effective dosage of a pharmaceutical composition as defined herein comprising an antigen specific antigen binding molecule or multi-domain specific binding molecule of the invention.

As used herein, the term "treatment" includes any regime that can benefit a human or a non-human animal. The treatment of "non-human animals" in veterinary medicine extends to the treatment of domestic animals, including horses and companion animals (e.g. cats and dogs) and farm/agricultural animals including members of the ovine, caprine, porcine, bovine and equine families. The treatment may be a therapeutic treatment in respect of any existing condition or disorder, or may be prophylactic (preventive treatment). The treatment may be of an inherited or an acquired disease. The treatment may be of an acute or chronic condition. The treatment may be of a condition/disorder associated with inflammation and/or cancer. The antigen specific antigen binding molecules or multi-domain specific binding molecules of the invention may be used in the treatment of a disorder, including, but not limited to osteoarthritis, scleroderma, renal disease, rheumatoid arthritis, inflammatory bowel disease, multiple sclerosis, atherosclerosis, or any inflammatory disease.

The antigen specific antigen binding molecules or multi-domain specific binding molecules of the present invention may also be used to investigate the nature of a disease condition in a patient. The antigen specific antigen binding molecules or multi-domain specific binding molecules may be used to prepare images of sites of disease in the body of a subject using imaging techniques such as X-ray, gamma-ray, or PET scanning, or similar. The invention may therefore extend to a method of imaging a site of disease in a subject, comprising administration of a suitably detectably labeled antigen specific antigen binding molecule or multi-domain specific binding molecules to a subject and scanning the subject's body subsequently. Alternatively, administration of said molecules to a subject may provide for a test result by analysing a sample from the subject following administration of the molecule. Such embodiments may include a method of diagnosis of a disease or medical condition in a subject comprising administration of an antigen specific antigen binding molecule or multi-domain specific binding molecule of the invention. The multi-domain specific binding molecules of the invention may be especially useful with regard to diagnostic sensitivity, in particular when multiple VNARs that target different epitopes on the same antigen are used.

Measurement of Binding

Detection and measurement of binding of a VNAR to a target can be measured in a number of ways well known in the art including ELISA and surface plasmon resonance.

Functional Activity

VNARs of the invention may function in a number of ways including binding to and neutralizing the biological effects of a molecule such as a cytokine, binding to a receptor preventing ligand binding or causing a biological effect post-binding.

Methods of measuring the functional activity of a binding domain are known in the art.

The present invention is illustrated in further details by the following non-limiting examples.

EXAMPLE 1: Isolation of Specific Antigen Binding VNARs

A. TNF Binding VNARs

Immunization and Selection

Nurse sharks [Ginglymostoma cirratum] were placed in containers containing artificial sea water containing 0.1% (w/v) tricaine methanesulfonate [MS-222]. Following attainment of desired level of narcosis, they were removed for immunisation or bleeding. hTNFα[250 µg] emulsified in complete Freund's adjuvant [CFA] was injected using a 20 gauge needle into the lateral fin of the shark. Boosts were given at 4 week intervals intravenously into the caudal vein as soluble antigen in Phosphate buffered saline (PBS) [sample 0.45 µM sterile filtered]. Blood samples were collected from the caudal vein into a 30 ml syringe containing 200 µl porcine heparin [1000 U/ml in PBS]. Blood samples were spun at 2000 rpm for 10 min to separate blood cells from plasma. The plasma supernatant fraction was carefully removed into a sterile tube with RNA stabilisation buffer, stored at −80° C.

Detection of hTNFαSpecific IgNAR in Shark Serum

An ELISA plate was coated with 1 µg/ml rhTNFα, incubated at 37° C. for 1 h followed by blocking in 4% (w/v) MPBS for 1 h at 37° C. Shark sera [pre-bleed, bleed 4 and 5] were added to designated wells in a 1:2 dilution series and incubated for 1 h at 37° C. The plate was incubated with 100 µl/well of purified anti-Nurse shark IgNAR monoclonal antibody [GA8] at a dilution of 1:200 in PBS. Binding signal was generated by the addition of anti-mouse IgG-HRP at a dilution of 1:2000 in 0.1% (v/v) Tween-20 PBS (PBST), incubated at room temperature for 1 h. The plate was washed 3×with PBST after every step, and a further 3×PBS after incubation with anti-mouse IgG-horseradish peroxidase (HRP) conjugated antibody [Sigma]. The plate developed by adding SureBlue TMB Microwell Peroxidase Substrate [Thermo Scientific], the reaction stopped with 1 M $H_2SO_4$ and absorbance measured at 450 nm wavelength using a microplate reader.

rhTNFαspecific IgNAR response following each immunisation boost was measured by binding ELISA using sera obtained after each boost. GA8, a mouse monoclonal anti-Nurse shark IgNAR antibody, diluted as hybridoma tissue culture supernatant in PBS was used as the detection antibody (Haines et al., 2005; Müller, et al. 2012). Result showed a convincing trend of IgNAR increase overtime following immunisation as shown in bleeds 4 and 5, also a background response seen in the pre-bleed sample suggest no significant rhTNFα-specific IgNAR response prior to immunisation [FIG. 1].

Total RNA Isolation from PBLs and PCR Amplification

Peripheral blood lymphocytes [PBLs] were harvested from the plasma of the bleed with the best IgNAR response [Bleed 5] and total RNA prepared. Total RNA from the harvested PBLs was used at approximately 2 µg/µl as template for cDNA synthesis using Superscript III First strand synthesis supermix [Invitrogen]. cDNA was generated with the framework specific primers NARF4For1
(SEQ ID NO. 74)
[5'-ATA ATC AAG CTT <u>GCG GCC GCA</u> TTC ACA GTC ACG ACA GTG CCA CCT C-3']
and NARF4For2
(SEQ ID NO. 75)
[5'-ATA ATC AAG CTT <u>GCG GCC GCA</u> TTC ACA GTC ACG GCA GTG CCA TCT C-3']

(see Dooley, H., et al, *Mol. Immunol*, 2003. 40(1): p. 25-33). Following cDNA synthesis, the common framework one specific primer NARF1 Rev [5'-ATA ATA AGG AAT TCC ATG GCT CGA GTG GAC CAA ACA CCG-3'] (SEQ ID NO. 76) was introduced and IgNAR V region DNA amplified using a 3-step polymerase chain reaction (PCR) amplification protocol. The resultant PCR product of approximately 400 base pairs was ran on 1.5% agarose gel, and NAR V region cut out and purified [QIAquick purification kit, QIAGEN]. Purified DNA was digested at the primer-encoded restriction sites [underlined] with the restriction enzymes NcoI and NotI [New England Biolabs], and re-purified.

Library Construction

The Phagemid vector pHEN2 was digested with the restriction enzymes NcoI and NotI, PCR purified [QIAquick PCR purification] and ligated to similarly prepared PCR product. Ligated material was transformed into Electroporation-competent *E. coli* TG1 cells [Lucigen]. Transformed cells were plated on TYE agar plates containing 2% glucose [w/v], 100 µg/ml ampicillin and grown overnight at 37° C. Library size was calculated and colonies scraped from plates and aliquots of the library stock stored at −80° C.

Phage Display Selection

A single aliquot of library stock equivalent to $OD_{600}$ of 0.1 was added to 2×TY growth media containing 2% glucose [w/v], 100 µg/ml ampicillin, and grown at 37° C. to mid-log phase [$OD_{600}$ of 0.4 to 0.6] prior to infection with M13K07 helper phage [New England Biolabs]. Library expression was conducted overnight in 2×TY media, 0.2% glucose, 100 µg/ml ampicillin and 50 µg/ml kanamycin at 30° C. Phage were precipitated from the culture supernatant with polyethylene glycol (PEG) and used for bio-panning. The library was panned against biotinylated rhTNFαcaptured on Dynabeads® M-280 streptavidin beads [Dynabeads, Invitrogen]. Library phage and Dynabeads® M-280 streptavidin were separately pre-blocked with block solution [3% (w/v) milk, 1% (w/v) BSA in PBS] for 1 h, rotating at room temperature. Biotinylated-rhTNFα[400 nM] was added to blocked beads and incubated for 1 h, rotating at room temperature. In a different tube, library phage was incubated with previously blocked streptavidin beads for 1 h rotating at room temperature. Unbound phage was recovered using the Dynabeads magnetic rack and recovered phage is here-in referred to as deselected phage. Phage were deselected by incubating with blocked beads, 1 h rotating at room temperature. Biotin-rhTNFαdecorated beads were incubated with deselected phage for 1 h, rotating at room temperature. Beads were washed 5×PBST and 5×PBS prior to a strict 8 min elution with 400 µl of 100 mM Triethylamine (TEA), and neutralised by adding 200 µl of 1 M Tris-HCl pH 7.5. Mid-log phase *E. coli* TG1 cells [10 ml] were infected with 400 µl eluted phage for 30 min, at 37 0C. Then grown overnight at 37° C. on TYE agar plates containing 2% glucose (w/v), 100 µg/ml ampicillin. Three further rounds of selection were conducted and stringency was increased in round 3 and 4 by reducing the concentration of biotin-rhTNFα to 200 nM.

Screening and Selection of Clones

Enrichment of antigen binding monoclonal phage was evaluated using ELISA plates coated with 1 µg/ml rhTNFα, blocked with 4% [w/v] Milk-PBS. Binding was detected with anti-M13-HRP conjugated monoclonal antibody [GE Healthcare]. Also monoclonal phage was analysed for selectivity and specificity against Streptavidin and HSA coated ELISA plates respectively.

The library was subjected to four iterative rounds of panning against rhTNFα. The biopanning antigen concentration was kept constant for rounds 1 and 2 but was reduced by half for subsequent rounds of panning in a bid to favour high-affinity binders. Enrichment of positive monoclonal phage binders were evaluated at the end of each round of biopanning for rhTNFαbinding by ELISA. A steady increase in antigen binding was observed from pre-selected clones through round 2, with a drop in the number of monoclonal phage binders after rounds 3 and 4. rhTNFαmonoclonal binders increased from about 6% [11/184] in round 0 [pre-selected library] to 99.46% [183/184] following round 2.

A number of unique sequences were identified from the library panning. These include VNARs named D1, C4 and B4.

top_myc_#129 (SEQ ID 29) introducing cloning sites Xbal and EcoRI respectively, while primer SEQ ID 29 incorporated c-myc, 6×Histidine tags and a stop codon into the VNAR gene sequence. Purified VNAR DNA PCR product and pET28b (+) plasmid DNA were digested at 37° C., 2 h with 50 U Xbal and 10 U EcoRI-HF. Digested samples were purified, ligated and transformed into electrocompetent *E. coli* SHuffle® T7 Express cells [New England Biolabs], and selected on TYE agar plates containing 50 µg/ml kanamycin. The VNAR anti-hTNFα-D1, C4 and B4 fusion proteins were expressed in the cytoplasm of SHuffle® cells upon induction with IPTG at 30° C. Cells were harvested by centrifugation, and the cell pellet treated with Bugbuster™ protein extraction reagent [Novagen] to lyse cells and release soluble protein. The VNAR soluble protein was purified by immobilised metal affinity chromatography [IMAC] via the hexa-histidine tail, and eluted from IMAC resin with 500 mM Imidazole, pH 8. Protein samples were dialysed against PBS, pH 7.4 before use. Protein concentration was determined using Ultraspec 6300 pro UV/Visible spectrophotometer [Amersham, Biosciences]. Total purified protein was visualised on Coomassie blue stained SDS-PAGE. The purified VNAR monomeric protein migrated as a single band of approximately 14 kDa [including hexa-histidine and c-myc tags] with no evidence of protein aggregation. Purity was estimated to be about 90% based on an SDS-PAGE gel Determination of Protein Integrity and Purity Denaturing sodium dodecyl sulphate-polyacrylamide gel electrophoresis [SDS-PAGE] was used to assess purified protein purity and size. Protein samples were prepared in NuPAGE® LDS sample buffer [Life Technologies] containing 5% β-mercaptoethanol and heated to 95° C. for 5 min. Denatured protein samples were loaded onto NuPAGE® 4-12% Bis-Tris Gel [Life Technologies] immersed in a MES SDS running buffer, and electrophoresis carried out at 160 volts, for 55 min. A Full Range recombinant protein molecu-

```
     FW1                          CDR1    FW2       HV2
D1   ARVDQTPQTITKETGESLTINCVLRDS  HCATSS  TYWYRKKSGS TNEESISKG
C4   ARVDQTPQTITKETGESLTINCVLRDS  NCGLSS  TYWYRKKSGS TNEESISKG
B4   ARVDQTPQTITKETGESLTINCVLRDS  NCALSS  MYWYRKKSGS TNEESISKG

FW3a      HV4    FW3b
D1   GRYVETVN  SGSKS  FSLRINDLTVEDSGTYRCAS
C4   GRYVETIN  EGSKS  FSLRINDLTVEDSGTYRCKL
B4   GRYVETVN  SGSKS  FSLRINDLTVEDSGTYRCKV

CDR3                   FW4
D1   ECQYGLAEY_____DV  YGGGTVVTVN  SEQ ID NO 2
C4   SWWTQNWRCSNS_____DV  YGGGTVVTVN  SEQ ID NO 7
B4   YIPCIDELVYMISGGTSGPIH_DV YGGGTVVTVN SEQ ID NO 12
```

The Cysteine (C) residues in CDR1 and CDR3 (double underlined) are typical of Type II VNARs and are observed to form a second disulphide bridge in addition to the canonical Immunoglobulin superfamily bridge between the Cysteines in FW1 and FW3b (single underlined).

Expression of VNARs that Bind to TNFα

Preparation of soluble VNAR protein in cytoplasm of SHuffle cells

The IgNAR V region inserts of interest identified from the monoclonal phage screening were cloned into the expression vector pET28b (+) (Novagen) via the Xbal and EcoRI restriction enzyme sites. VNAR DNA was prepared from *E. coli* TG1 culture (using QIAprep miniprep kit, QIAGEN) and PCR amplified using in-house designed primer pair Xbal_NARFW1_#127 (SEQ ID 26) and EcoRI_s- lar weight marker [GE Healthcare] was used as molecular weight ladder standard. The gel was washed in distilled water, and stained with Coomassie blue for 1 h followed by an overnight de-staining process in distilled water.

Determination of Selectivity and Specificity

Specificity and selectivity of binding was determined on ELISA plates coated with either 1 µg/ml Biotin-TNF and rhTNFα, or 10 µg/ml HSA, BSA, streptavidin, single stranded DNA, thyroglobulin or lysozyme. ELISA plates were suitably blocked in 4% [w/v] Milk-PBS, and protein samples loaded at a top concentration of 1 µg/ml and serial dilution performed. Binding was detected with an anti-c-myc-HRP conjugated monoclonal antibody [Roche].

To obtain more accurate binding data certain molecules were also measured using surface plasmon resonance with BIACore T200 or Octet RED96 instruments.

BIACore™ T200 (GE Healthcare)

Amine coupling is a very common approach for immobilising the ligand to the chip surface. The chip surface has a dextran matrix derivatised with carboxyl groups, which after activation with N-hydroxysuccinimide (NHS) and 1-ethyl-3-(3-dimethylaminopropyl)carbodiimide (EDC), form reactive succinimide esters which allows the covalent capturing of the ligand via any available primary amine groups (e.g. Lysine) on the ligand.

TNFα was diluted 1/10 in 10 mM Sodium acetate buffer pH 5.5 and injected unto the activated chip. An "aim for" software immobilisation wizard or a specific time period may be used to aim-for 200 RU of immobilised TNFα. In addition the run buffer was changed to PBS in absence of 0.05% Tween20 as it was thought perhaps the detergent may affect ligand activity. A final ligand immobilised level of 202 RU was obtained.

Start-up cycles were composed of a 60s buffer injection at a flow rate of 30 μl/min followed by a 30s dissociation period. The anti-TNFα sample cycles included a 120s injection of sample at 30 μl/min followed by a regeneration step of a 60s injection of 10 mM glycine pH2 at 30p/min. Finally, a 120s stabilisation period was included at the end of each cycle to allow for baseline equilibration prior to beginning the next cycle.

The concentration series screened and the dissociation periods were variable and were as follows: All samples were assayed at a top start concentration of 100 nM and a 1200s dissociation time, with the exception of all monomeric domains D1, C4, B4, TNF43 and TNF30 where the dissociation time was 600s. B4 and TNF43 VNAR were assayed at top start concentrations of 500 nM and 5 μM respectively. 5 blank sample cycles were included to be used to generate double referenced datasets.

Binding responses for domain were analysed using the BIACore™ T200 evaluation software and double referenced data was fitted to a 1:1 Langmuir model to obtain kinetic and affinity characterisation.

OCTET® RED96 [ForteBio™]

Biolayer interferometry (BLI) was used to determine the equilibrium dissociation constant ($K_D$). Dip and read streptavidin biosensors were rehydrated for at least 30 min in PBS, pH 7.4. Sensors were loaded with 20 μg/ml biotinylated hTNF-α and anti-TNF-α VNAR proteins were serially diluted with top concentration of 100 nM while TNF43 and VNAR negative controls were assayed at top concentration of 1 μM. Binding association was monitored for 10 min followed by a 5 min dissociation time. For all anti-TNF-α VNAR measurements, kinetic data sets were fitted using a two-site model since the curve fit data showed complex multiphasic curves, however for the control anti-TNF-α nanobody, TNF30 a 1:1 Langmuir binding with Mass Transport model was used.

The data obtained is shown in TABLE 1. TABLE 1 indicates that the monomer VNARs tested have at least a 500 fold lower binding affinity for TNFα compared with the TNF 43 VNAR.

TABLE 1

| TNF VNAR SPR binding data | | | | |
|---|---|---|---|---|
| Binding molecule | $K_a$ (M$^{-1}$ S$^{-1}$) | $K_d$ (S$^{-1}$) | KD [BIAcore T200] | KD [Octet ForteBio] |
| D1 | 1.2E+03 | 2.06E−02 | 50 nM | 1.9 nM |
| C4 | 2.8E+05 | 3.3E−02 | 70 nM | 6.4 nM |
| TNF30 VHH | 5E+04 | 1.6E−07 | 16 nM | N/A |
| TNF43 VNAR | Very Weak affinity- No binding data obtained. Highest conc tested 500 nM | | | >1000 nM |
| BB10 | Negative control- No binding data obtained | | | >1000 nM |
| D1-D1 | 5E+05 | 3.16E−04 | n/a | 0.6 nM |
| D1-C4 | 1.8E+05 | 1.07E−04 | 5 nM | 0.17 nM |
| D1-B4 | 2.7E+05 | 5E−04 | n/a | 15.9 nM |
| TNF30-TNF30 | 3E+04 | 3E−05 | n/a | 0.4 nM |
| D1-BA11-D1 | 1.9E+06 | 2E−04 | 4 nM | 0.1 nM |
| D1-BA11-C4 | 2E+05 | 1.6E−04 | 0.6 nM | 0.13 nM |
| D1-BA11-B4 | 1.7E+06 | 6E−03 | n/a | 0.33 nM |
| TNF30-BA11-TNF30 | 9E+04 | 1.5E−05 | 0.4 nM | 0.38 nM |

In Vitro Neutralisation Assay

To determine the neutralisation capacity and ND$_{50}$ for the VNAR domains, mouse fibrosarcoma cell line L929 [ATCC, CCL-1] was grown in Dulbecco modified eagle medium [GIBCO] supplemented with 10% heat inactivated fetal bovine serum [GIBCO] and 1 μg/ml actinomycin 0 [R & D systems]. For each VNAR clone 5,000 cells per well were incubated in a 96 well plate in duplicate for 24 h at 37° C. with 5% $CO_2$ and humidity. LD$_{50}$ [1× at 0.25 ng/ml] and 10× LD$_{50}$ [2.5 ng/ml] of rhTNFα was added to wells containing either VNAR proteins serially diluted or cells alone. Plates were then incubated for 24 h at 37° C. with 5% $CO_2$ and humidity. Cytotoxicity or cell survival was measured by adding 50 μl of 1:20 dilution WST-1 cell proliferation reagent [Roche], and incubated for 4-8 h at 37° C. with 5% $CO_2$ and humidity. Absorbance was read at 450-560 nm.

TNFα in the presence of 1 μg/ml actinomycin D causes cytotoxicity in L929 fibrosarcoma cells, with an LD$_{50}$ between 0.25-0.3 ng/ml. We demonstrated that our VNAR protein domains at nanomolar concentrations were capable of neutralising up to ten times the LD$_{50}$ of rhTNFα[FIG. 3]. In this experiment the VNARs were joined at their C terminal end by peptide linkers to the IgG Fc domains so as to form bivalent molecules for comparison to the control anti-TNFα antibody MAB210.

When measured as single domains in the neutralization assay the D1 and C4 VNARs did not appear as efficacious as the TNF30 VHH nanobody (FIG. 2). This appears to correlate with single site binding affinity. However when combined as a mixture (FIG. 3) or in bivalent or bispecific formats (Figures xxxx) they unexpectedly demonstrated improved properties over dimeric TNF30 VHH nanobody.

Paracellular Flux Assay

Human epithelial colorectal adenocarcinoma cells (Caco-2) were cultured in DMEM supplemented with 10 (% v/v) heat inactivated FBS and 1% (v/v) Penicillin-Streptomycin (10,000 units/ml and 10,000 µg/ml respectively). Cells were grown to 90% confluence in T75 flasks before seeding on 24 wells, 0.4 µm semipermeable tissue culture transwell inserts (Corning Inc.). Viable cells number was determined by suspending 10 µl cell suspension in 90 µl of 0.4% trypan blue exclusion dye (Beckman Coulter), and carefully transferring the mixture onto a haemocytometer with a cover slip attached.

Following viable cell number determination, $1\times10^5$ cells were seeded per transwell inserts in a final DMEM volume of 100 µl, while 600 µl DMEM without cells was transferred into the outer containing wells. Transwell plates were incubated at 37° C. with 5% (v/v) $CO_2$, and spent DMEM+10% (v/v) FBS replaced every 48 h. Cell proliferation was monitored under a phase contrast microscope (40× magnification objective) until cells attain 100% confluence, usually between 5-7 days post-seeding. Caco-2 cells were grown for a further 21 days allowing differentiation, with spent medium changed every 48 h until differentiation.

Designated insert wells containing polarised cells (apical side) in 100 µl DMEM with 10% (v/v) HI-FBS were treated with 10 ng/ml hTNFα, IFNγ, LPS with or without anti-TNFα VNAR proteins. Treated cells were incubated for 18 h at 37° C. with 5% (v/v) $CO_2$. Following incubation for 18 h with cytokines ±anti-TNFα VNARs, phase contrast images of treated cells were captured followed by the addition of 5 µl of 10 mg/ml Fluorescein isothiocyanate-labelled dextran, molecular weight (3-5 kDa) to apical side (insert wells) of Caco-2 monolayer. Medium from the basolateral side of the transwell chamber was collected 24 h after addition of FITC-dextran.

Fluorescence intensity was measured using a Synergy HT (BioTek®) microplate reader at 485 nm excitation and 520 nm emission wavelengths.

Epithelial Resistance Dysfunction Assay

Human epithelial colorectal adenocarcinoma cells (Caco-2) were cultured in DMEM supplemented with 10 (% v/v) heat inactivated FBS and 1% (v/v) Penicillin-Streptomycin (10,000 units/ml and 10,000 µg/ml respectively). Cells were grown to 90% confluence in T75 flasks before seeding on 12 or 24 wells, 0.4 µm semipermeable tissue culture transwell inserts (Corning Inc.). The protocol described previously was followed until cells achieved full differentiation.

Designated insert wells containing polarised cells (apical side) in 200 µl DMEM with 10% (v/v) HI-FBS were treated with 10 ng/ml hTNFα, and IFNγ with or without anti-TNFα VNAR proteins. Treated cells were incubated for 24 h at 37° C. with 5% (v/v) $CO_2$, and humidity. Following incubation for 24 h with cytokines ±anti-TNFα VNARs, transepithelial electrical resistance (TEER) was measured in the apical chamber using Millicell® ERS-2 Epithelial (Volt/Ohm) meter and MERSSTX01 probe (Merck Millipore). Measured resistance values were normalised to the surface area under treatment.

It is important to note that 12 well tissue culture transwell inserts were seeded with $5\times10^6$ cells/well containing 500 µl DMEM with outer well (basolateral side) containing 1.5 ml DMEM. Also during TEER measurement, DMEM volume in the insert and outer wells were increased to 500 µl and 1.5 ml respectively to allow volt-ohm meter electrodes to fully submerge in the medium without touching the base of the wells.

B. ICOSL Binding VNARS

The isolation and characterization of ICOSL binding VNARS 2D4 and CC3 are disclosed in WO2014/173975 and WO2014/173959.

2. Formation of multivalent and multispecific VNARs.

A TNF Binding Domains

FIG. 3 indicated that the combination of the D1-Fc and C4-Fc molecules showed increased neutralisation capability in the bivalent form. Therefore VNARs D1 and C4 and other combinations were prepared as bivalent or bispecific fusions to demonstrate that when combined together as fusions the same improvement in neutralisation capacity is seen.

Construction of Dimers and Trimers

FIG. 4 provides a diagram of the format of bivalent and bispecific constructs

Two or three separate PCR reactions were set up to amplify the N-terminal, middle terminal [in the case of a trimer], and C-terminal VNAR domains using the oligonucleotide combinations listed below, and each oligonucleotide habouring a specific/unique cloning site, and/or 6× his-tag and c-myc tag for ease of purification and detection respectively.

Dimer Construction PCR Oligos:

N-terminal fragment oligonucleotide pair:

XbaI_FW1 TNF_#127:
SEQ ID 15
GCTAGGCTCTAGAAATAATTTTGTTTAACTTTAAGAAGGAGATATACCAT
GGCTCGAGTGGACCAAACACC

GS_BamHI_Rev_#130:
SEQ ID 16
CGCGCCGGATCCGCCACCTCCGCTACCGCCACCTCCGCTACCGCCACCTC
CGCTACCGCCACCTCCATTCACAGTCACGACAGTGCC

C-terminal oligonucleotide pair:

GS_BamHI_For_#132:
SEQ ID 17
GGTGGCGGatccGGCGCGCACTCCGCTCGAGTGGACCAAACACCGC

EcoRI_stop_myc_#129:
SEQ ID 18
GTCCGGAATTCTCACAGATCCTCTTCTGAGAT-
GAGTTTTTGTTCTGCGGCCCC Trimer construction PCR oligonucleotides: Here we utilized an in-house designed DNA cassette habouring BA11 gene as the middle fragment flanked by Xba1/BamH1 and APA1/EcoR1 cloning sites on its N- and C-terminals respectively. Oligonucleotide pairs listed above can be utilised in the PCR amplification steps, as well as oligonucleotides habouring both Xba1 and BssH11 site in the N-terminal forward oligonucleotide, thus allowing sub-cloning the trimer gene into an in-house eukaryotic expression vector, pEEE2A. Otherwise all clonings are carried out in pET28b (+) expression vector.

XbaI/BssH11-FW1NAR_#197 cassette+:
SEQ ID 19
AATTCCCCTCTAGAAGGCGCGCACTCCGCTCGAGTGGACCAAACACCG A PCR reaction of 2 µl VNAR DNA (50-100 ng), 2 µl forward and reverse oligonucleotide primers (final concentration 1 µM), 5 µl of 10X Taq polymerase buffer, 0.25 µl of Taq polymerase (final concentration 25 U/ml), 0.5 µl dNTPs (final concentration 0.1 mM), and 38.25 µl H$_2$O with a final reaction volume of 50 µl. A PCR program was started with 5 min at 98° C. This was followed by a 30 cycle of 94° C. for 30 seconds, 56° C. for 30 seconds and 72° C. for 1 min. A final extension at 72° C. for 5 min. Amplicons were checked by agarose gel electrophoresis, and purified using QIAquick PCR purification kit. Eluted DNA digested with appropriate restriction endonuclease.

Expression of Dimers and Trimers in *E. coli* SHuffle® T7 Express Cells

The VNAR regions cloned into the expression vector pET28b (+) via the Xbal and EcoRI restriction enzyme sites, and resulting purified plasmid containing VNAR gene was transformed into electrocompetent *E. coli* SHuffle® T7 Express cells [NEB], and selected on TYE agar plates containing 50 µg/ml kanamycin. The anti-hTNFαVNAR-D1, C4 and B4 fusion proteins were expressed in the cytoplasm of SHuffle cells upon induction with IPTG at 30° C.

Single colony of transformed *E. coli* SHuffle® T7 Express cells was grown in 5 ml 2×TY-Kanamycin medium until OD600 0.4-0.6 usually achieved between 4-6 h incubation at 37° C., 250 rpm. This log phase culture was used to inoculate 50 ml TB medium containing kanamycin and PO$_4$ salts, incubated overnight at 30° C., 250 rpm until they attain OD$_{600}$ 6.0-10.0. Cells were centrifuged at 4000 rpm, 30° C. for 15 min, then resuspended in fresh TB-kanamycin-P04 salt medium and allowed to recover for 1-2 h at 30° C., 250 rpm. Cytoplasmic protein expression was induced using a final IPTG concentration of 1 mM, cells incubated at 30° C., 200 rpm for 12-16 h post-induction. Cells were harvested by centrifugation at 6000 rpm, 25° C. for 10 min, and cell pellet wet weight determined. Cell pellet was resuspended in 5 ml/gram of wet cell paste BugBuster™ protein extraction reagent plus Benzonase® (Novagen, UK), and cell suspension was placed on a shaking platform at 10-15 rpm, room temperature for 20 min. Cell suspension was centrifuged at 6000 rpm, 4° C. for 20 min, and soluble protein collected in the supernatant was ready for affinity purification via polyhistidine tag using immobilised metal affinity chromatography (IMAC) resin (nickel-nitrilotriacetic acid, Ni-NTA or Ni-Sepharose). VNAR fusion protein was eluted with 300-500 mM imidazole, pH 8.0 and eluate dialysed against PBS (1 L PBS/1 ml eluted protein), pH 7.4 overnight and then PBS replaced for a further 3-4 h dialysis. Protein quality was assessed via SDS-PAGE and quantified using the Ultraspec 6300 pro uv/visible spectrophotometer (Amersham Biosciences, GE Healthcare).

For eukaryotic cell expression, domains cloned into the BA11 trimer cassette were digested using BssHII and EcoR1 enzymes, and subcloned into pEEE2A eukaryotic expression vector utilising a CMV promoter, and transformed into an *E. coli* strain for plasmid propagation. Isolated and purified plasmid vector containing the VNAR trimer gene was co-incubated with linear polyethylenimine [PEI] for 20 minutes at room temperature. The mixture of plasmid DNA: PEI was transferred unto a cell culture flask containing HEK293 cells with cell growth density of 90% confluence. Transfected HEK293 cells were incubated at 37° C., 5% v/v CO$_2$ for 5-7 days. Cell culture supernatant was harvested, and expressed protein purified using IMAC resin, and dialysed against PBS.

Binding and TNF Neutralization Data

FIG. 5 shows ELISA binding of dimeric and bispecific constructs to TNFα.

The initial ELISA data indicated that the bispecfic D1-C4 construct had increased avidity (combined binding affinity) compared to the TNF30 nanobody dimeric construct.

A number of these were later measured for binding to immobilized TNF in surface plasmon resonance.

TABLE 1 indicates that of the dimeric molecules measured, the D1-C4 bispecific molecule showed superior binding affinity (avidity) compared to the TNF30 bivalent nanonbody construct.

FIG. 6 shows TNF neutralization data for a number of bivalent or bispecific VNAR fusions, compared to the bivalent TNF nanobody. When the binding molecules were tested for TNF neutralisation in the L929 assay, the D1-C4 dimer was equivalent to or superior to the TNF30 nanobody dimeric construct. In this experiment the D1-D1 dimer was inferior to the D1-B4 dimer.

TABLE 1 Shows SPR binding data for the trimeric constructs tested. This indicates that the introduction of the additional domain, acting as a spacer between the TNFα binding domains, appears significantly to improve the relative affinity (avidity) of the molecules for TNFα.

When measured in the TNFα neutralisation assay, the D1-BA11-C4 trimeric construct was equivalent to adalimumab and superior to the TNF30 nanobody construct. In this assay the bivalent molecule comprising the D1 domains was equivalent in efficacy to the TNF30 nanobody construct.

FIG. 7 shows the results of an experiment to measure the ability of the various VNAR formats to neutralize TNFα function.

TABLE 2 summarizes the neutralisation data. When the spacer domain is included both the D1-BA11-D1 and D1-BA11-C4 show a ten-fold or better improvement in neutralisation ability, with the D1-BA11-C4 showing approximately equivalent efficacy to adalimumab and MAB210. The TNF30-BA11-TNF30 also shows an improvement over the TNF30-TNF30 dimeric form but not as markedly. The GlySer linker length of D1-C4 construct (SEQ ID NO 27 & 28) was extended from a (Gly4Ser)2 to a (Gly4Ser)3 with a consequent improvement in hTNF-alpha neutralizing potency.

The data from these experiments are shown in table 2. Further comparative data is given in table 3.

TABLE 2

| Binding Molecule | TNF Neutralisation data using 0.3 ng/ml (LD80) of hTNF-alpha (unless otherwise stated) |
|---|---|
| | ND$_{50}$ (nM) [≥n = 3 ± SEM; except otherwise stated] |
| TNF43 [Horn Shark VNAR] | 7100 nM (Publication: Camacho-Villegas, Tanya, et al. MAbs 5(1): 2013; U.S. Pat. No. 8,496,933. 30 Jul. 2013) |
| TNF43 [Horn Shark VNAR] | No neutralisation seen in vitro at concentrations up to 500 nM (also see FIG. 15 at 100 nM) |
| D1 | 30 ± 3.5 |
| C4 | 100 ± 0.1 |

TABLE 2-continued

TNF Neutralisation data using 0.3 ng/ml (LD80)
of hTNF-alpha (unless otherwise stated)

| Binding Molecule | $ND_{50}$ (nM) [≥n = 3 ± SEM; except otherwise stated] |
|---|---|
| TNF30 [VHH] | 9.2 ± 2.1 |
| D1-Fc | 0.9 ± 0.14 |
| C4-Fc | 0.52 ± 0.2 |
| TNF30-Fc | 0.7 ± 0.07 |
| D1-D1 | 7.0 ± 2.4 |
| D1-C4 | 0.76 ± 0.06 |
| D1-C4 $(Gly_4Ser)_3$ | 0.08 ± 0.02*** (n = 2 with 3 replicates each) |
| D1-B4 | 8.0 ± 25 |
| TNF30- TNF30 | 0.8 ± 0.27 |
| Adalimumab | 0.03 ± 0.009 |
| D1-BA11-D1 | 0.38 ± 0.03 |
| D1-BA11-C4 | 0.02 ± 0.09 |
| TNF30-BA11- TNF30 | 0.3 ± 0.14 |
| D1-Fc-C4 (Quad-X ™) | 0.002 ± 0.0011 |
| D1-C4-Fc (Quad-Y ™) | 0.005 ± 0.0005 (n = 2 ± SD) |
| C4-D1-Fc (Quad-Y ™) | 0.012 ± 0.0016 (n = 2 ± SD) |

A. Binding (B) and Neutralisation (N) data obtained by the inventors

| | Human (Bind/Neutralise) B/N | Dog (B/N) | Cynomolgus (B/N) | Rat (B/N) | Mouse (B/N) | Rabbit (B/N) | Pig (B/N) | Human TNF-β (B/N) |
|---|---|---|---|---|---|---|---|---|
| Lead anti-hTNF-α VNARs (D1 and C4) | +++/+++ | +++/+++ | +++/+++ | −/− | −/− | −/− | −/− | −/− |
| Nanobody Lead (VHH) TNF 30 | +++/+++ | +++/+++ | +++/+++ | −/− | −/− | −/− | +/+ | ++/− |
| Adalimumab (Humira) | +++/+++ | +++/+++ | +++/+++ | −/− | ++/++ | −/− | −/− | −/− |

Note:
+++denotes strong binding/neutralisation activity, ++ moderate; + very weak activity and − denotes no binding/neutralisation activity observed.

B. Cross-reactivity data of clinically available anti-hTNF-alpha biologics as reported in the literature [Assessment Report for Cimzia, European Medicines Agency (2009). Doc. Ref.: EMEA/664021/2009; Assessment Report for Simponi. European Medicines Agency (2009). Doc Ref.: EMEA/446762/2009; Assessment Report for Enbrel. European Medicines Agency (2008). Procedure No. EMEA/H/C/262/11/94; Scientific Discussion on Remicade, European Medicines Agency (2005) (ema.europa.eu/docs/en_GB/document_library/EPAR-_Scientific_Discussion/human/000240/WC500050885.pdf). Last assessed on Sep. 21, 2017; Scientific Discussion on Humira, European Medicines Agency (2004). (ema.europa.eu/docs/en_GB/document_library/EPAR-_Scientific_Discussion/human/000481/WC500050867.pdf). Last assessed on Sep. 21, 2017]

TABLE 3

Cross-reactivity profile of anti-hTNF-alpha VNAR lead construct compared to commercially available anti-hTNF-alpha mAbs and pre-clinical VHH TNF30

| | Human (Bind/Neutralise) B/N | Dog (B/N) | Cynomolgus (B/N) | Rat (B/N) | Mouse (B/N) | Rabbit (B/N) | Pig (B/N) | Human TNF-β (B/N) |
|---|---|---|---|---|---|---|---|---|
| Adalimumab (Humira) | +/+ | +/+ | +/+ | −/− | +/+ | −/− | −/− | −/− |
| Infliximab (Remicade) | +/+ | −/− | −/− | −/− | −/− | −/− | −/− | −/− |
| Etanercept (Enbrel) | +/+ | −/− | +/+ | | +/+ | | | +/+ |

TABLE 3-continued

Cross-reactivity profile of anti-hTNF-alpha VNAR lead construct compared to commercially available anti-hTNF-alpha mAbs and pre-clinical VHH TNF30

| | Human (Bind/Neutralise) B/N | Dog (B/N) | Cynomolgus (B/N) | Rat (B/N) | Mouse (B/N) | Rabbit (B/N) | Pig (B/N) | Human TNF-β (B/N) |
|---|---|---|---|---|---|---|---|---|
| Certolizumab (Cimzia) | +/+ | −/− | +/+ | | | | | |
| Golimumab (Simponi) | +/+ | +/+ | +/+ | −/− | −/− | +/+ | | −/− |

Note:
+/− denotes yes or no binding/neutralisation respectively.

Functional Activity

BACKGROUND

Human epithelial colorectal adenocarcinoma cells (Caco-2) develop morphological characteristics of normal enterocytes when grown on suitable platform (e.g., plastic dishes, nitrocellulose filters). More so collagen coated polycarbonate or polyester membrane have been demonstrated to be suitable for Caco-2 monolayers as an intestinal epithelial transport model systems (Wang, F., et al. *Am. J. Path.* 166.2 (2005): 409-419.; Hidalgo, I. J., et al *Gastroenterology* 1989. 96: 736-49.).

A principle function of epithelial membrane is the maintenance of a barrier to hydrophilic solutes such as Inulin and Dextran. This barrier is compromised in certain diseases involving the intestinal epithelium, which include but not limited to infectious, immune-mediated and idiopathic diseases (Clayburgh, D. R., et al *Lab Invest.* 2004. 84(3): 282-291; Wang, F., et al. *Am. J. Path.* 2005. 166(2): 409-419). Intestinal barrier dysfunctions, measured as increases in paracellular permeability and reduction of intestinal epithelial resistance are closely associated with inflammatory bowel diseases (IBD), such as Crohn's disease (Irvine E. J. and Marshall J. K., *Gastroenterology* 2000. 119.6: 1740-1744.; Wyatt et al., *The Lancet* 1993. 341(8858): 1437-1439.). Also there are evidence supporting the reduction of epithelial tight junction proteins in IBD, consequently contributing to the loss of solutes resulting in leak flux diarrhea (Schulzke J.D. et al., *Ann N Y Acad Sci.* 2009 1165:294-300; Schmitz H. et al., *J. Cell Sci* 1999. 112(1): 137-146). Finally Interferon-γ (IFN-γ), TNFα and Lipopolysaccharide (LPS) have been shown to synergistically induce intestinal epithelial barrier dysfunction in human epithelial cell lines (Wang et al., *J. Cell Science* 1999. 112(1): 137-146; Schuerer-Maly C. C et al., *Immunology* 1994. 81(1): 85).

Anti-TNFα treatment have been shown to repair the intestinal barrier dysfunction in Crohn's disease (Suenaert P. et al., *Am J Gastroenterol* 2002. 97(8): 2000-2004) thus we examined our anti-TNF VNAR domains to demonstrate these would repair these dysfunctions induced in-vitro. We hypothesized that bi-specific/multivalent VNAR domains would be more effective in the prevention of these dysfunctions when compared to VNAR monomers.

FITC-Dextran Paracellular Flux Across Polarised Monolayer of Caco-2 Cells

Human epithelial colorectal adenocarcinoma cells (Caco-2) were cultured in DMEM supplemented with 10 (% v/v) heat inactivated FBS and 1% (v/v) Penicillin-Streptomycin (10,000 units/ml and 10,000 μg/ml respectively). Cells were grown to 90% confluence in T75 flasks before seeding on 24 wells, 0.4 μm semipermeable tissue culture transwell inserts (Corning Inc.). Viable cells number was determined by suspending 10 μl cell suspension in 90 μl of 0.4% trypan blue exclusion dye (Beckman Coulter), and carefully transferring the mixture onto a haemocytometer with a cover slip attached.

Following viable cell number determination, $1\times10^5$ cells were seeded per transwell inserts in a final DMEM volume of 100 μl, while 600 μl DMEM without cells was transferred into the outer containing wells. Transwell plates were incubated at 37° C. with 5% (v/v) $CO_2$, and humidity, and spent DMEM+10% (v/v) FBS replaced every 48 h. Cell proliferation was monitored under a phase contrast microscope (40× magnification objective) until cells attain 100% confluence, usually between 5-7 days post-seeding. Caco-2 cells are grown for a further 21 days allowing differentiation, with spent medium changed every 48 h until differentiation.

Designated insert wells containing polarised cells (apical side) in 100 μl DMEM with 10% (v/v) HI-FBS were treated with 10 ng/ml hTNFα, IFN-γ and LPS with or without anti-TNFα VNAR proteins. Treated cells were incubated for 18 h at 37° C. with 5% (v/v) $CO_2$, and humidity. Following incubation for 18 h with cytokines ±anti-TNFα VNARs, phase contrast images of treated cells were captured followed by the addition of 5 μl of 10 mg/ml Fluorescein isothiocyanate-labelled dextran, molecular weight (3-5 kDa) to apical side (insert wells) of Caco-2 monolayer. Medium from the basolateral side of the transwell chamber was collected 24 h after addition of FITC-dextran.

Fluorescence intensity was measured using a Synergy HT (BioTek®) microplate reader at 485 nm excitation and 520 nm emission wavelengths.

FIG. 8 shows the permeability data from an experiment measuring paracellular flux across polarised monolayer of Caco-2 cells comparing several of the TNF VNAR multidomain binding molecules. This experiment shows that the various bivalent and bispecifc forms show improved function over the monomer forms as a lower concentration of dimer or trimer delivered an increased level of protection of challenged cells.

Epithelial Resistance Dysfunction Assay in Polarised Caco-2 Cell Monolayer

Human epithelial colorectal adenocarcinoma cells (Caco-2) were cultured in DMEM supplemented with 10 (% v/v) heat inactivated FBS and 1% (v/v) Penicillin-Streptomycin (10,000 units/ml and 10,000 μg/ml respectively). Cells were grown to 90% confluence in T75 flasks before seeding on 12 or 24 wells, 0.4 μm semipermeable tissue culture transwell inserts (Corning Inc.). The protocol described previously in section 0 was followed until cells achieved full differentiation.

Designated insert wells containing polarised cells (apical side) in 200 μl DMEM with 10% (v/v) HI-FBS were treated with 10 ng/ml hTNFα, and IFN-γ with or without anti-TNFα VNAR proteins. Treated cells were incubated for 24 h at 37° C. with 5% (v/v) $CO_2$, and humidity. Following incubation for 24 h with cytokines ±anti-TNFα VNARs, transepithelial electrical resistance (TEER) was measured in the apical chamber using Millicell® ERS-2 Epithelial (Volt/Ohm) meter and MERSSTX01 probes (Merck Millipore). Measured resistance values were normalised to the surface area under treatment. It is important to note that 12 well tissue culture transwell inserts were seeded with $5 \times 10^6$ cells/well containing 500 µl DMEM with outer well (basolateral side) containing 1.5 ml DMEM. Also during TEER measurement, DMEM volume in the insert and outer wells were increased to 500 µl and 1.5 ml respectively to allow volt-ohm meter electrodes to fully submerge in the medium without touching the base of the wells.

FIG. 9 shows an assay measuring epithelial resistance in polarized Caco-2 cells. This experiment shows that the various bivalent and bispecifc forms show improved function over the monomer forms.

B ICOSL Binding Domains

Construction of Multivalent Forms and Enhanced Efficacy Data.

2D4 and CC3 Fc Fusions

FIG. 10 shows formats for multivalent and multispecific VNARs of the invention incorporating ICOSL VNARs (and human IgG Fc, which provides additional improved functional characteristics.

Method

Selected VNAR monomeric domains were PCR amplified and subcloned into a eukaryotic expression vector. This cloning was onto the 5' terminal end of a Human IgG1 Fc encoding DNA fragment (this Human IgG1 Fc fragment also encoded a full length Human IgG1 hinge sequence with the 5 prime most Cys residue which normally disulphide bridges to the light chain mutated to a Serine).

Whilst subject to PCR amplification oligonucleotides were used to introduce amino acid residues inserting a linker sequence between the carboxyl terminal end of the VNAR domain and the N terminal residue of the Human IgG1 hinge region as well as restriction endonuclease sites compatible with mammalian vector expression system. The linker sequences introduced by this process were either GGGGSGGGGRT whereby the nucleic acid sequence encoding the underlined RT amino acid residues introduces a BsiW1 restriction endonuclease site or GGGGSGGGADQ in which codon usage of the underlined GADQ amino acid residues introduces a Bcl1 site. Both of these sites are compatible with cloning sites in different versions of the Fc eukaryotic expression vector. At the 5' end of all amplicons a unique BssHll site is introduced which is compatible with eukaryotic vector construction.

DNA sequences to introduce linker VNAR domain fusions to the carboxyl terminal end of the Fc were designed and synthesis of these intermediate fragments was carried out by GeneArt (Invitrogen). The N-terminus of these fragments utilized a naturally-occurring BsrGI site within the human IgG1-derived CH3 region, and an EcoR1 site in the vector. These constructs introduced a linker with amino acid sequence TAAAATAAAATAAAATAAAA between the carboxyl terminal end of the Fc domain and the amino terminal end of the VNAR domain. Codon usage at the underlined triple alanine region of the linker allows for the introduction of a Not/restriction site which can be utilised in subsequent cloning work to assemble further bispecific VNAR constructs.

Post PEI-mediated transfection and transient expression in suspension HEK 293 cells using serum free media, expression levels of NAR Fc fusion proteins were determined by ELISA. Protein A affinity chromatography to purify the VNAR Fc proteins was performed after an initial 0.2 µm filtration clarification step to remove cell debris. A second chromatographic step to polish affinity purified protein was performed using ion exchange or size exclusion chromatography with buffer exchange as appropriate between steps. Proteins were concentrated using Amicon ultra filtration units and final protein concentrations determined by UV spectroscopy. Analytical SEC and SDS PAGE was used to determine integrity of final purified proteins.

ICOSL Neutralization Assay

Ligand-receptor neutralisation assays were conducted as follows: CHO cells expressing human ICOS receptor were grown to confluency in DMEM/F12+5% FBS media in 96-well cell culture plates (Greiner, Bio-One). A total of 20 µl at 1 µg/ml of rmB7-H2/Fc (158-B7, R&D Systems) was preincubated for 1 h with 40 µl of serially diluted anti-ICOSL-VNAR-Fc in DMEM/F12+2% FBS and then added to the cells. Following 1 h incubation at 16° C., cells were gently washed three times with DMEM/F12+2% FBS and incubated for 40 min at 16° C. with goat anti-human Fc-HRP (SIGMA) diluted 1:10,000 in the same media. Cells were washed and developed with TMB substrate.

Figure 1:
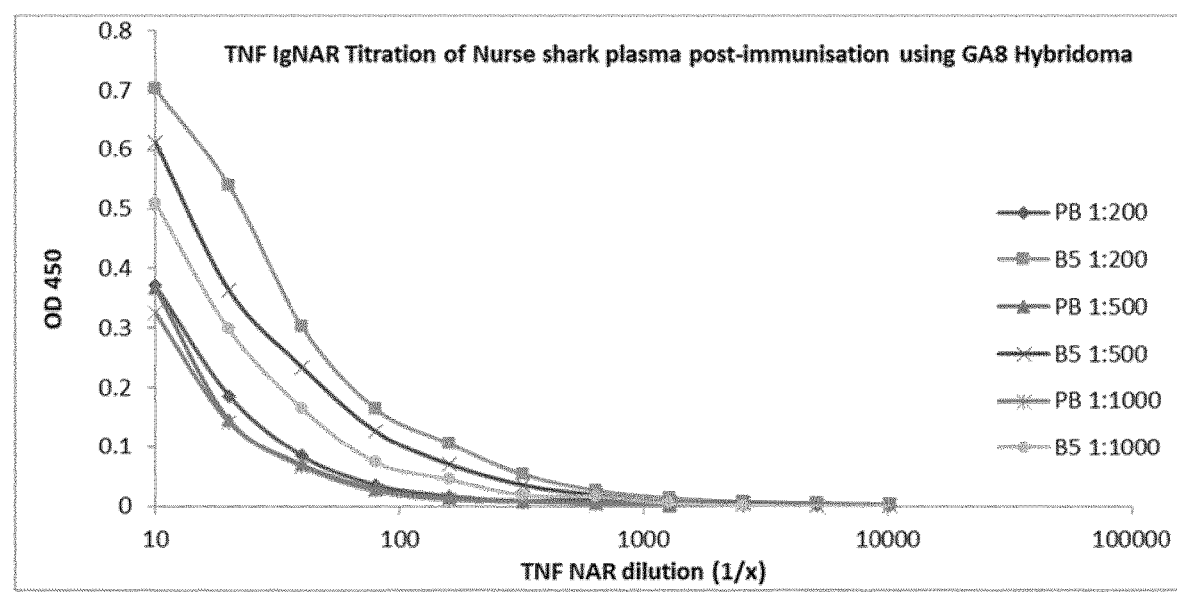
Figure 2:
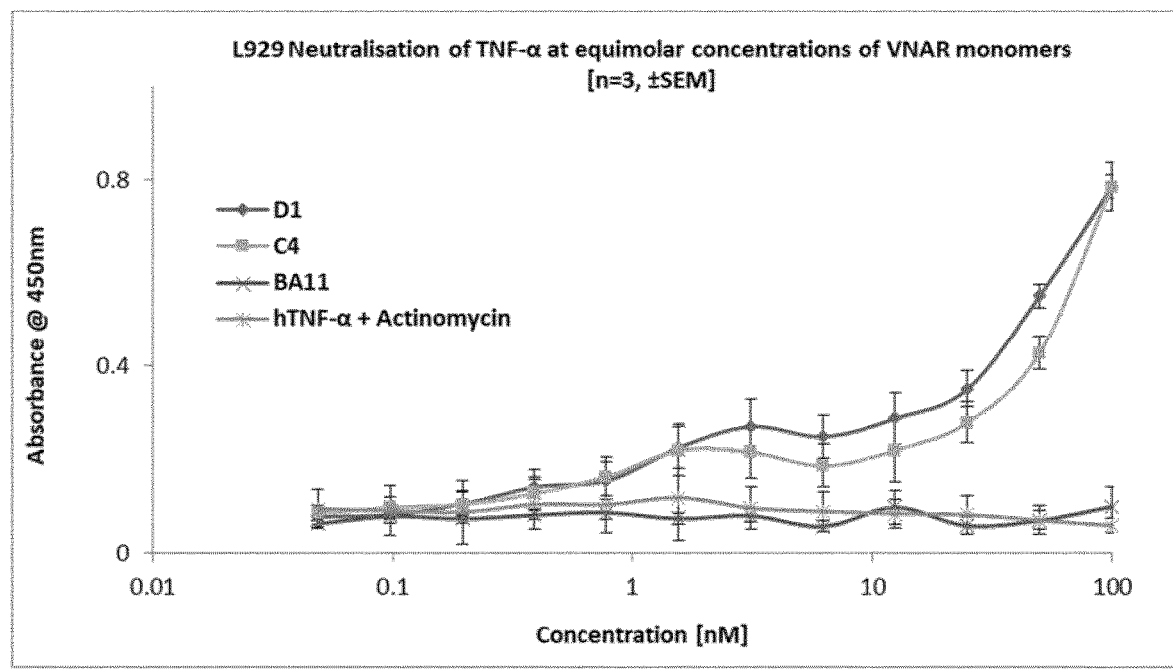
Figure 3:
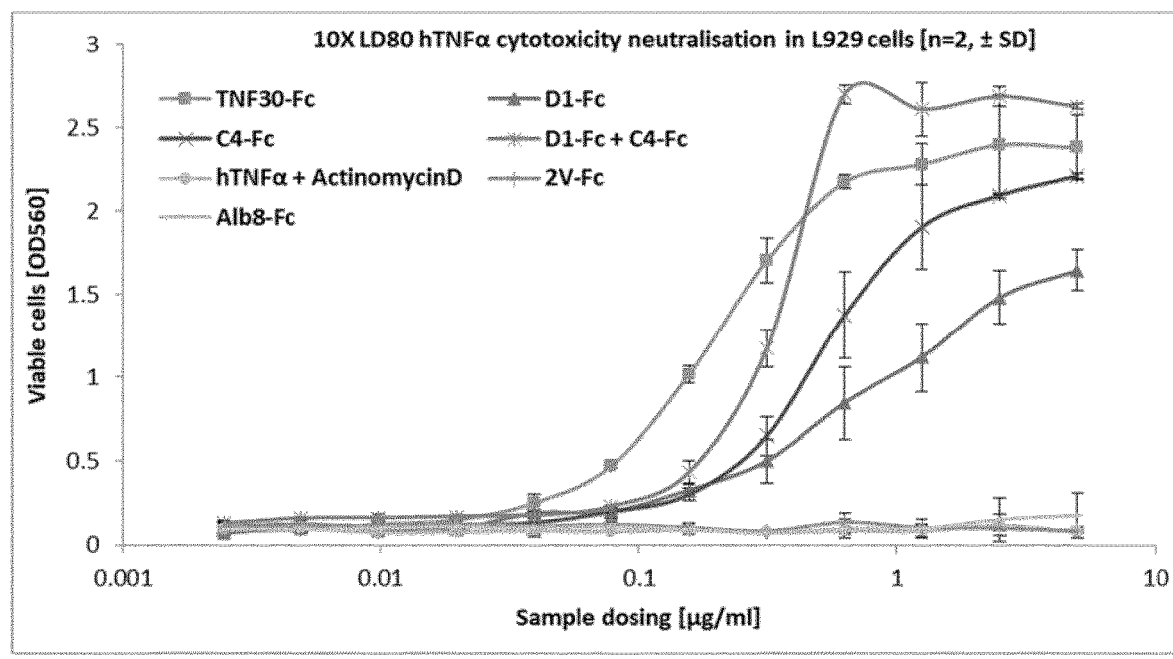
Figure 4:
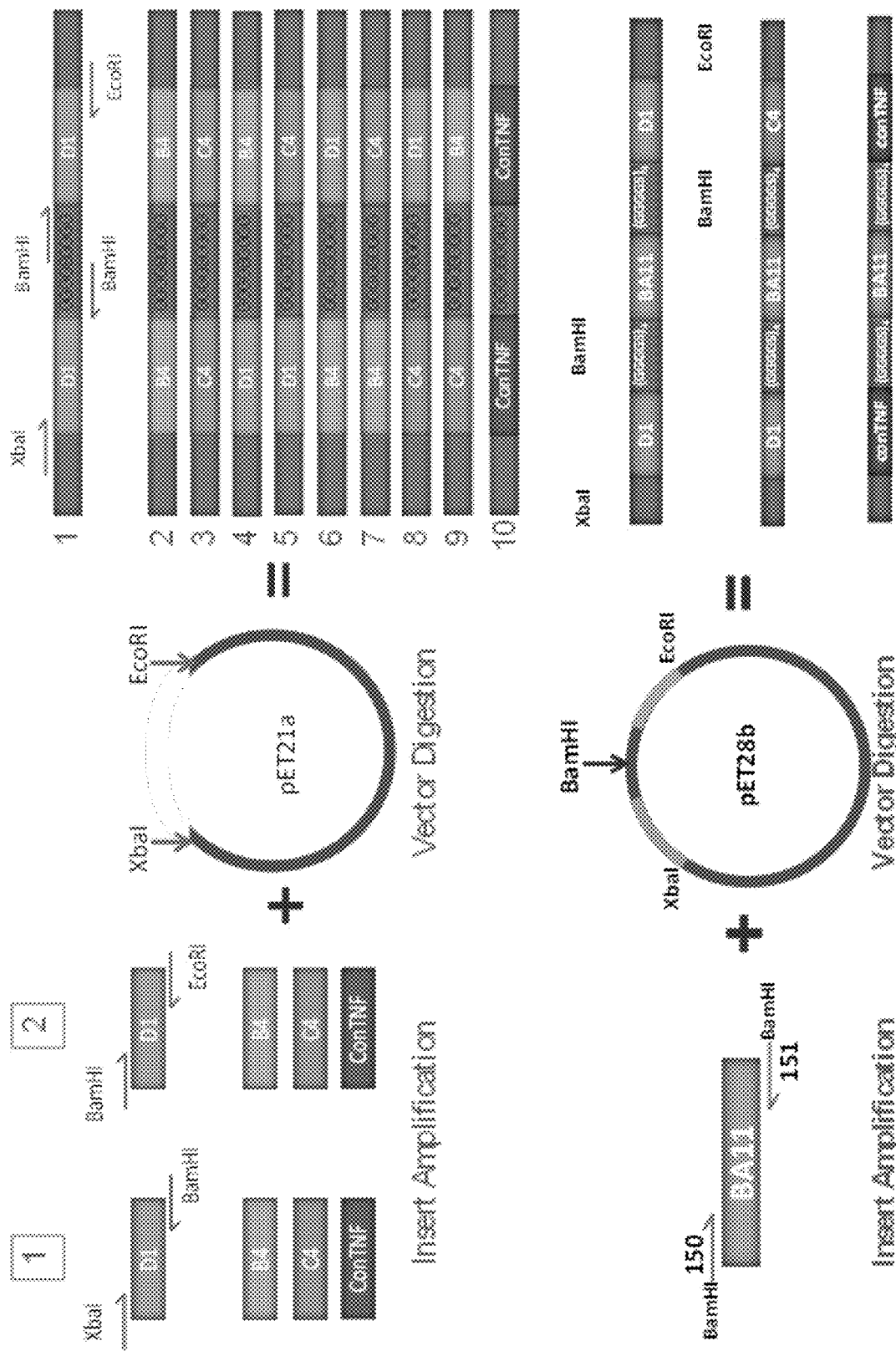
Figure 5:
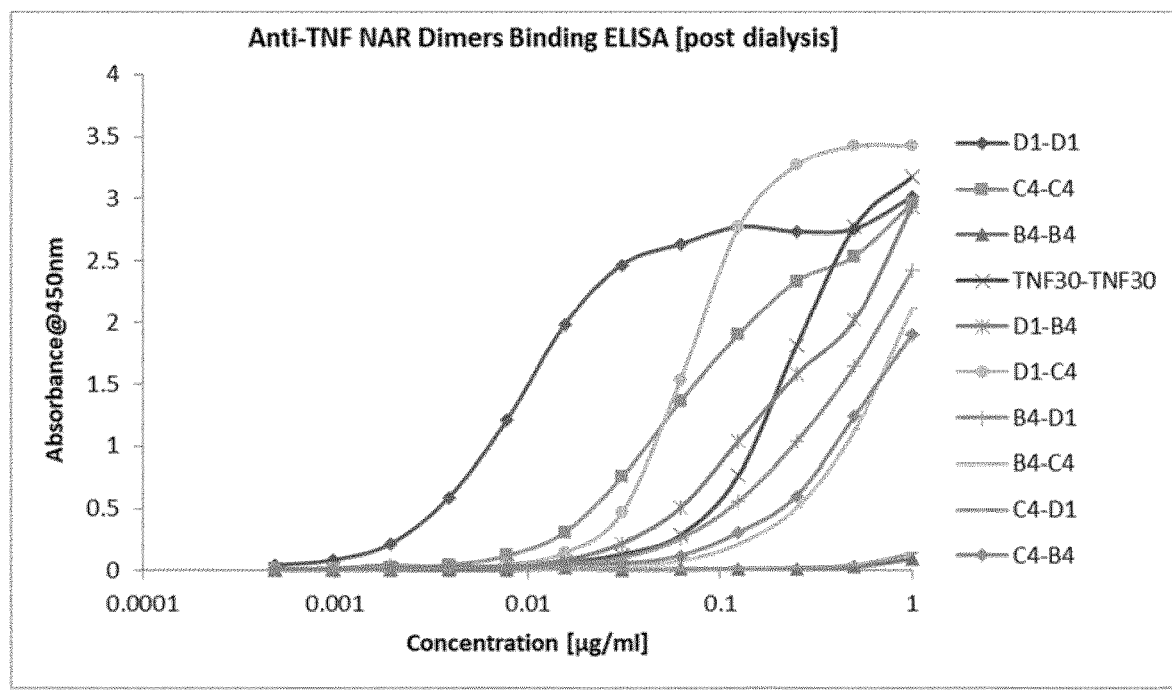
Figure 7:
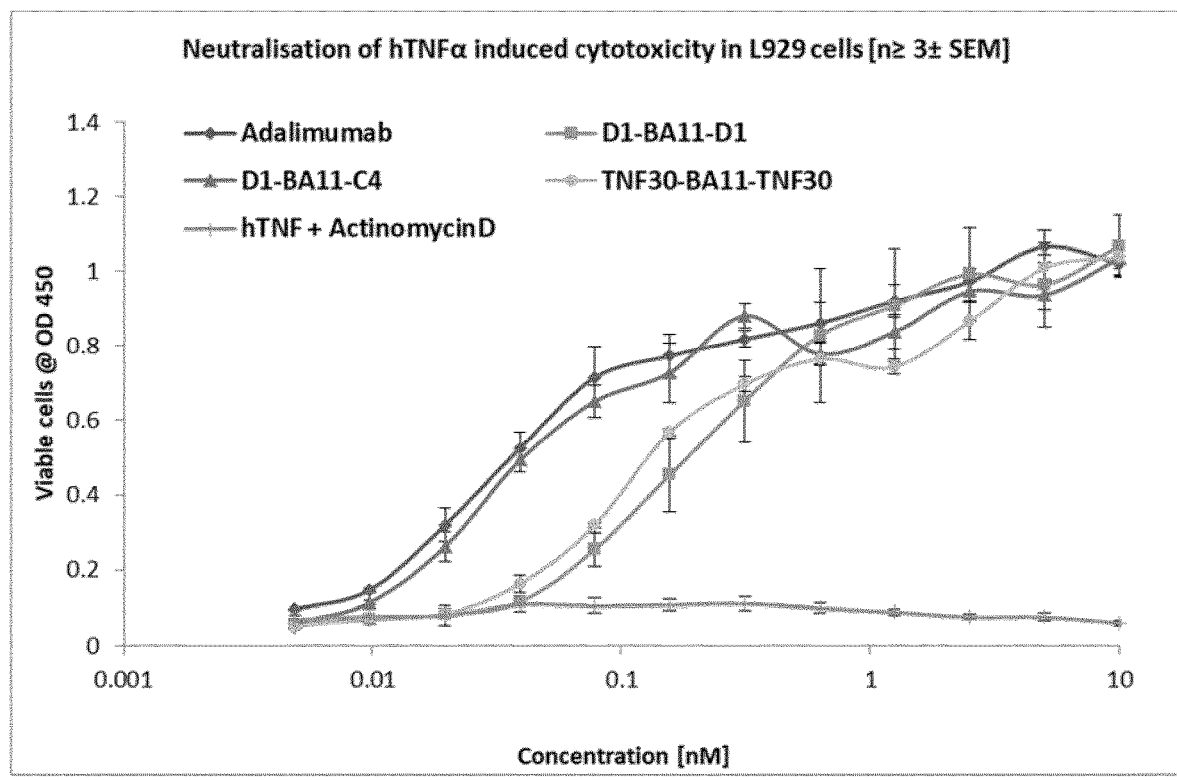
Figure 8:
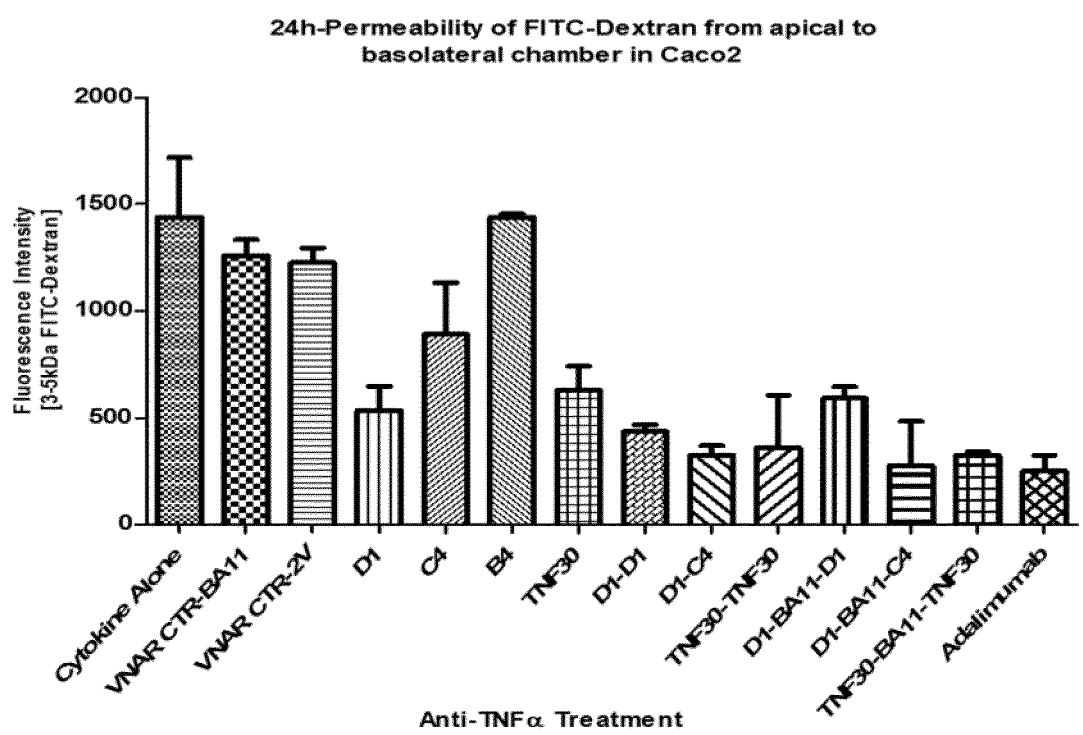
Figure 9:
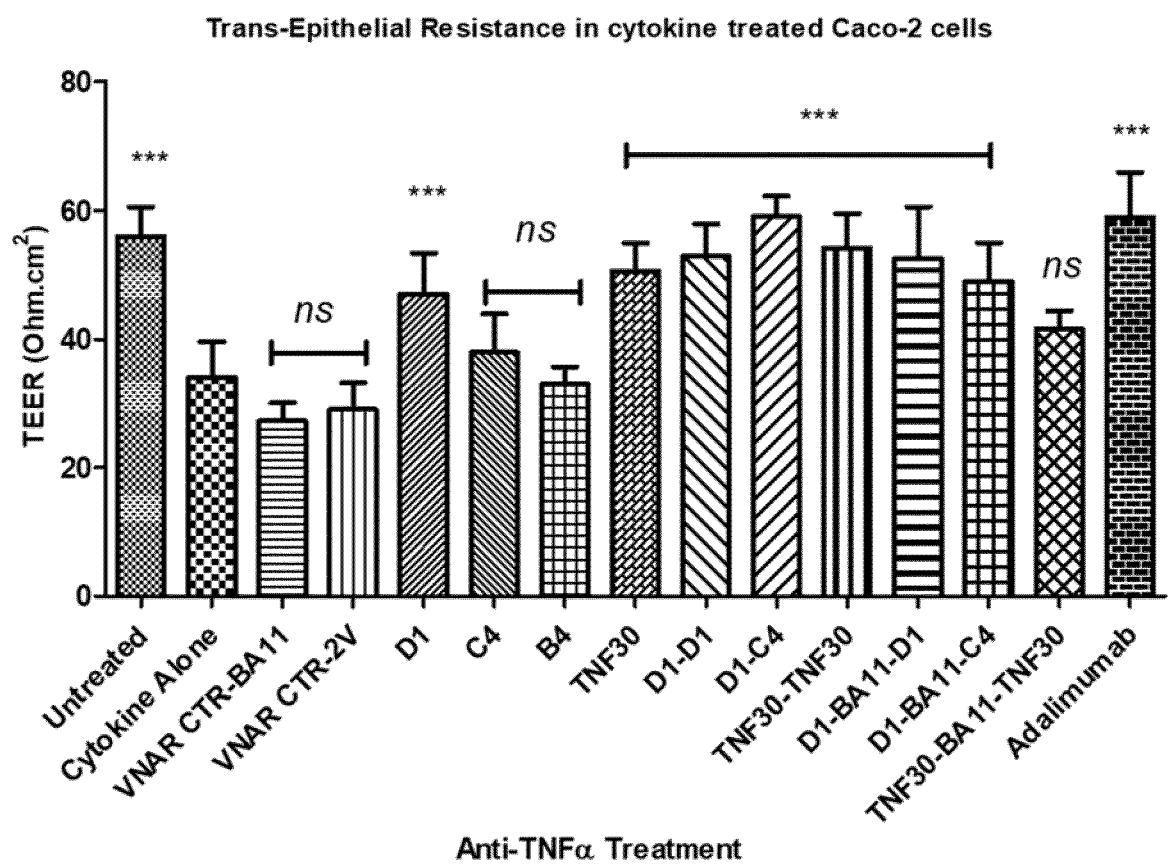
Figure 10:
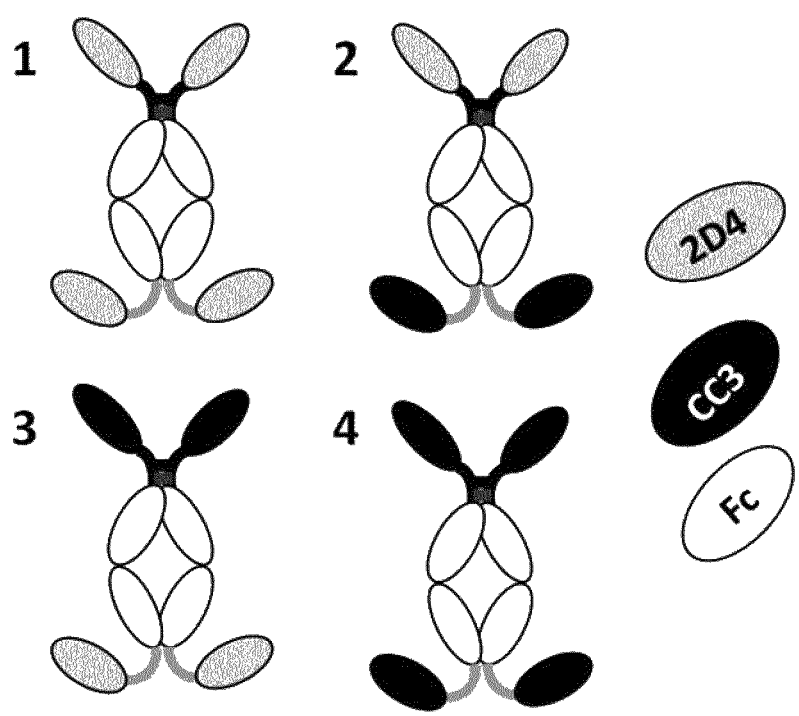
Figure 11:
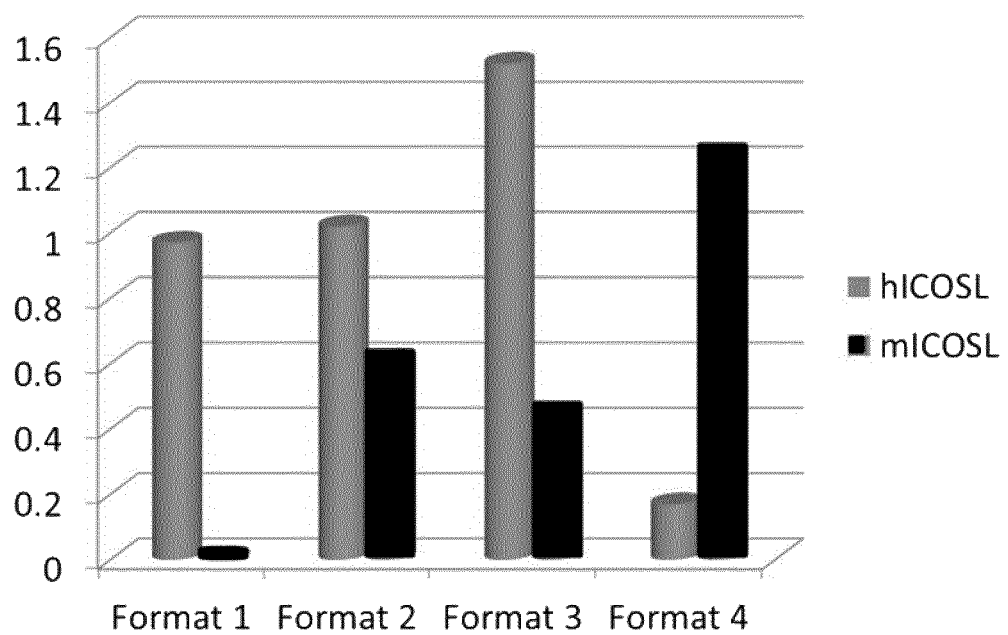
FIG. 11 shows ELISA binding data, indicating that the ICOSL VNARS bind to their cognate antigens in these formats
Figure 12:
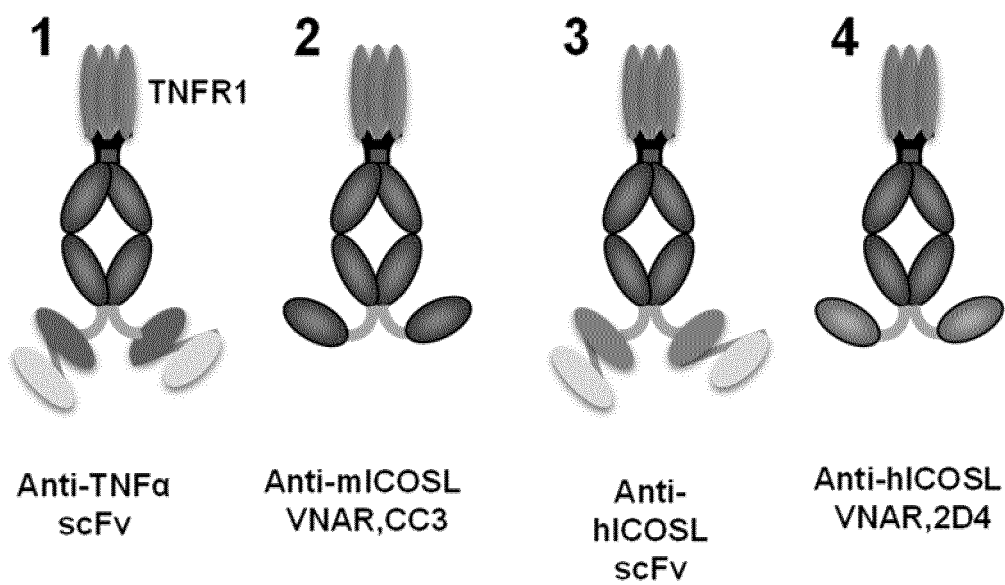
FIG. 12 shows formats for multivalent and multispecific VNARs of the invention incorporating the TNF R1 domain, ICOSL VNARs and human IgG Fc, which provides additional improved functional characteristics.
Figure 13:
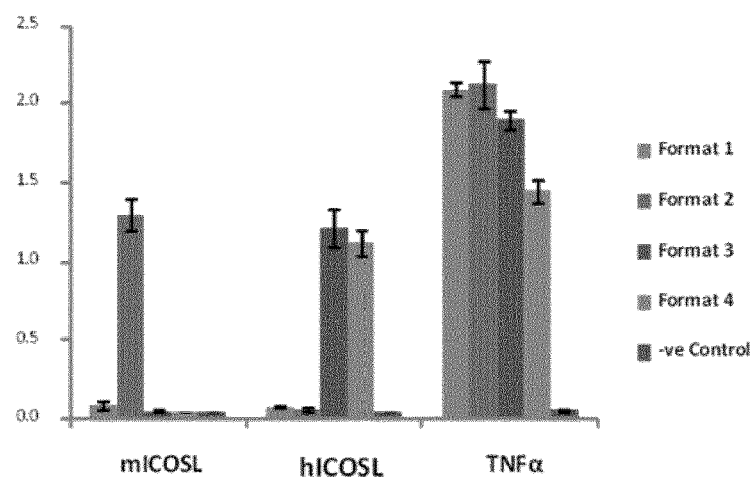
FIG. 13 shows efficacy data for multivalent and multispecific VNARs of the invention incorporating the TNF R1 domain, ICOSL VNARs and human IgG Fc, which provides additional improved functional characteristics.
Figure 13:
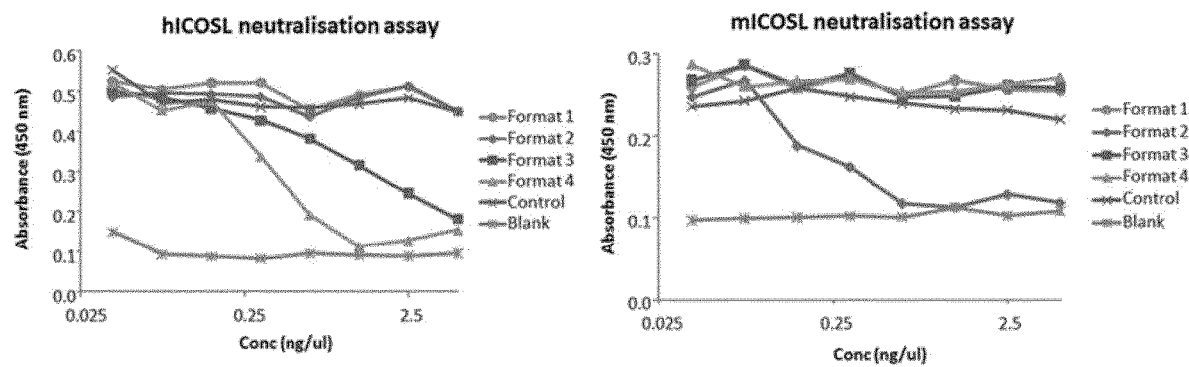
Figure 14:
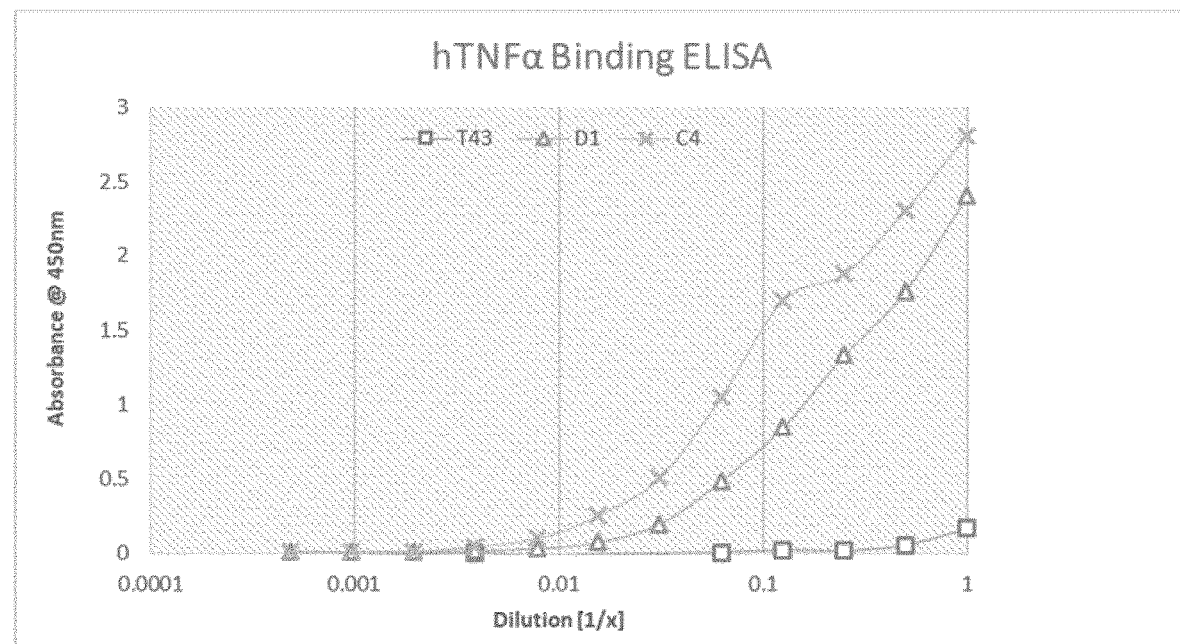
Figure 15:
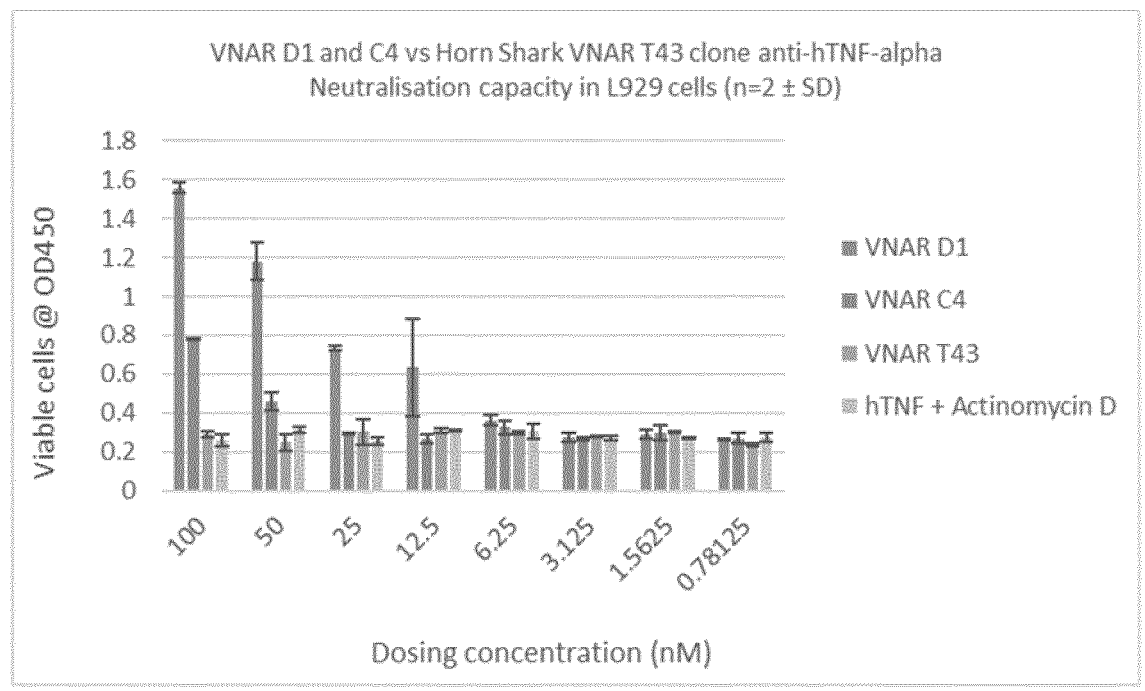
Figure 16:
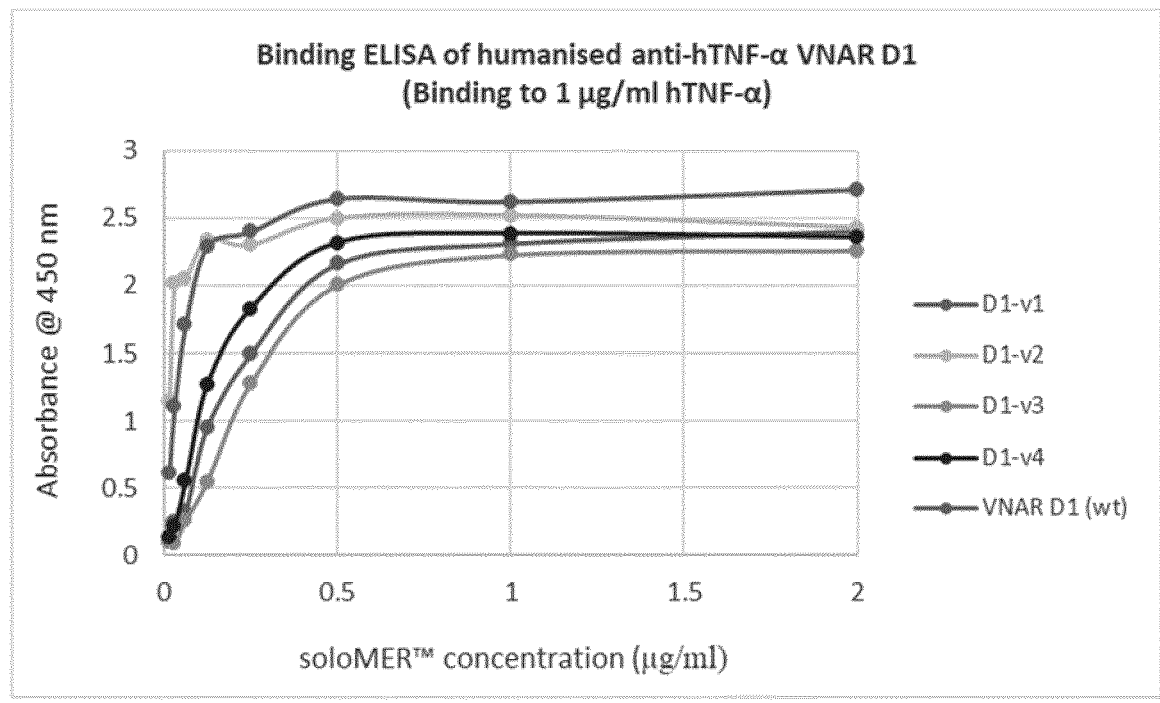
Figure 17:
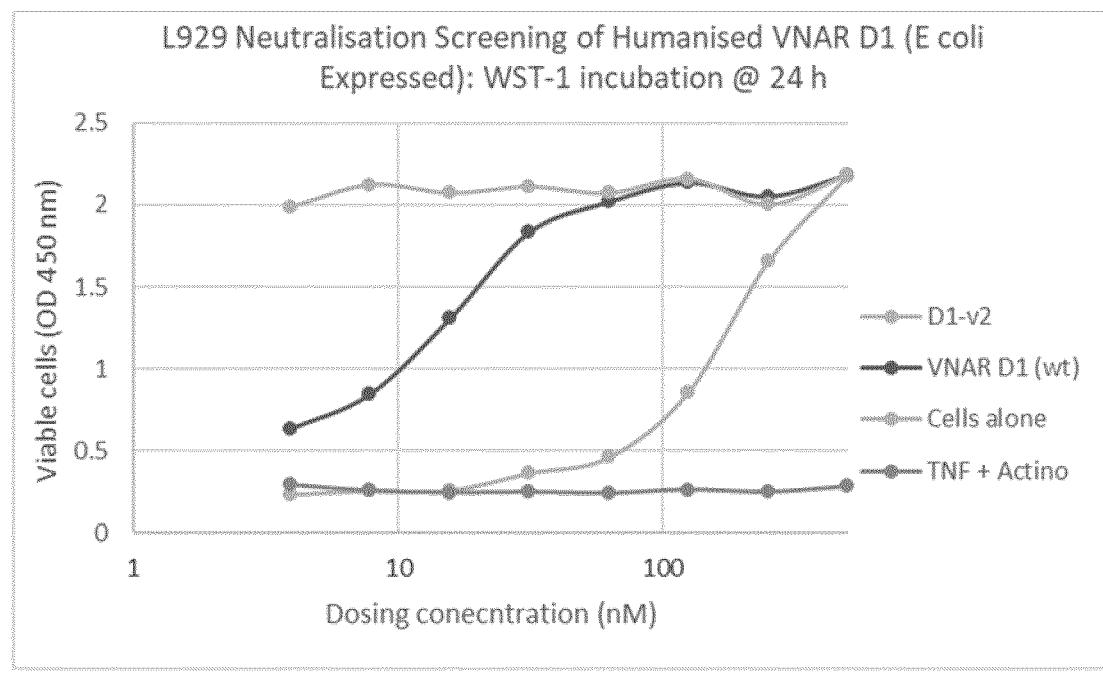
Figure 18:
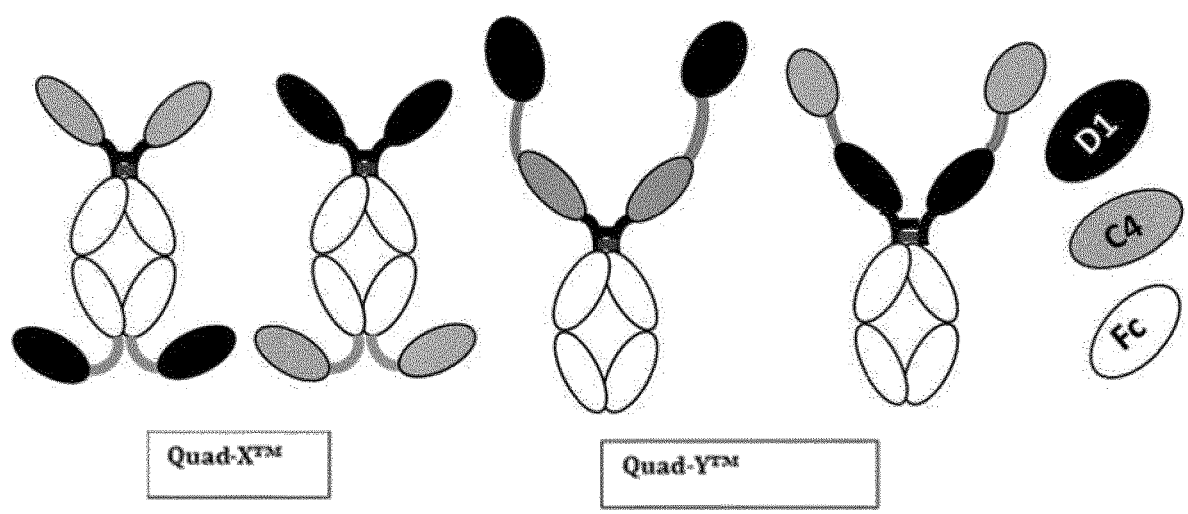
Figure 19:
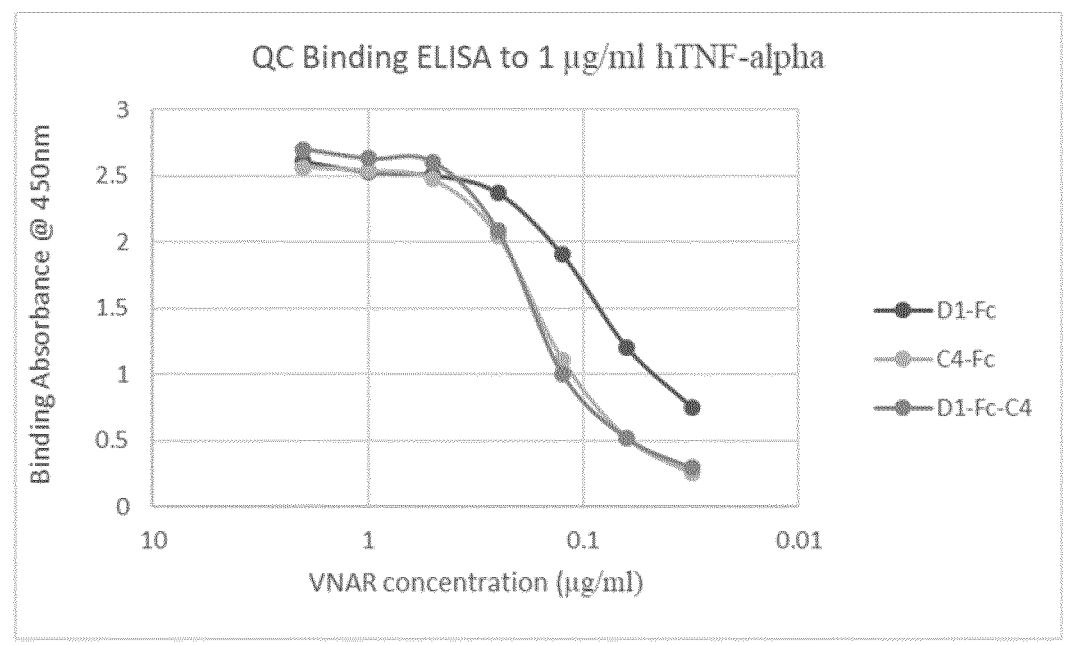
Figure 20:
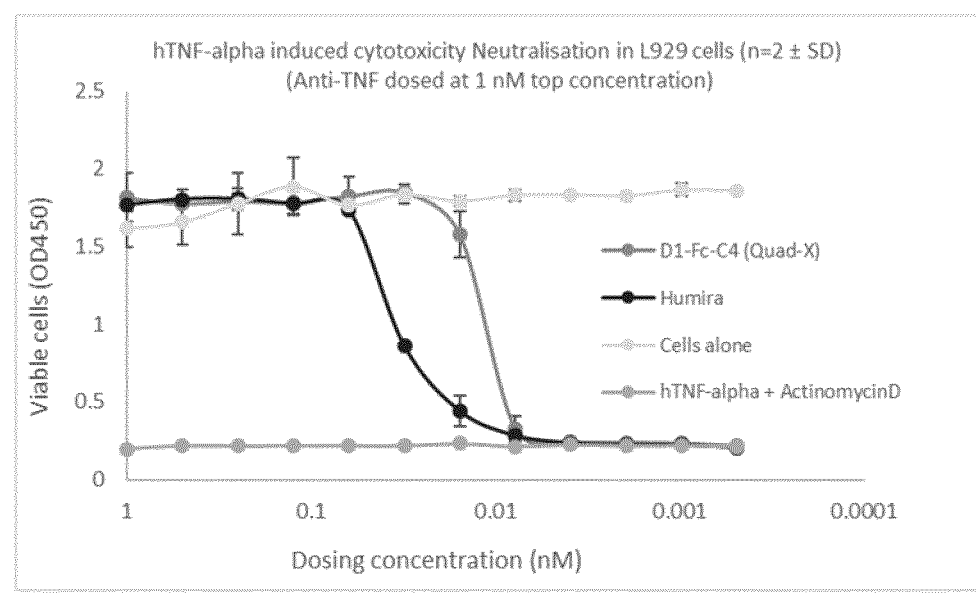
Figure 21:
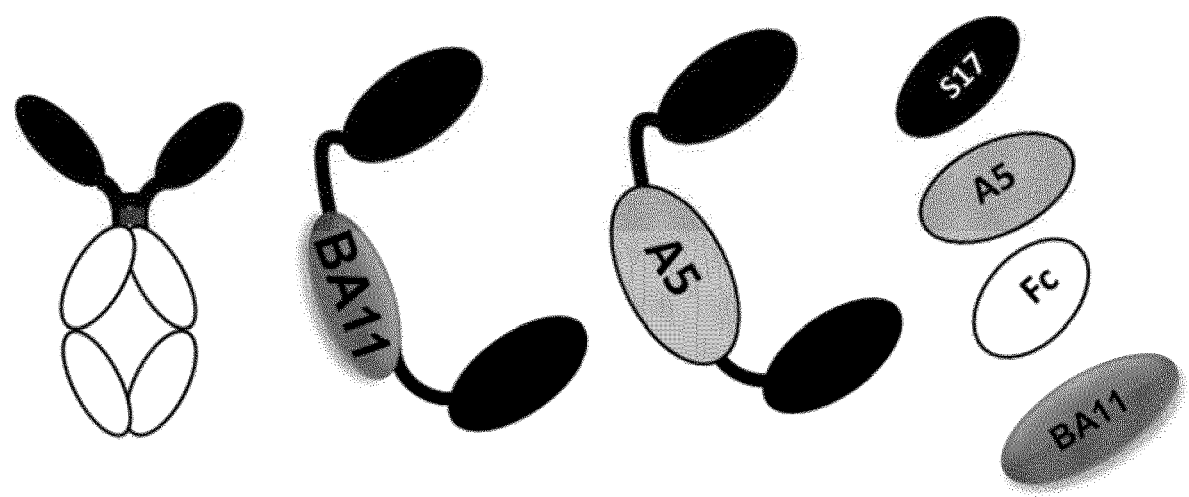
Figure 22:
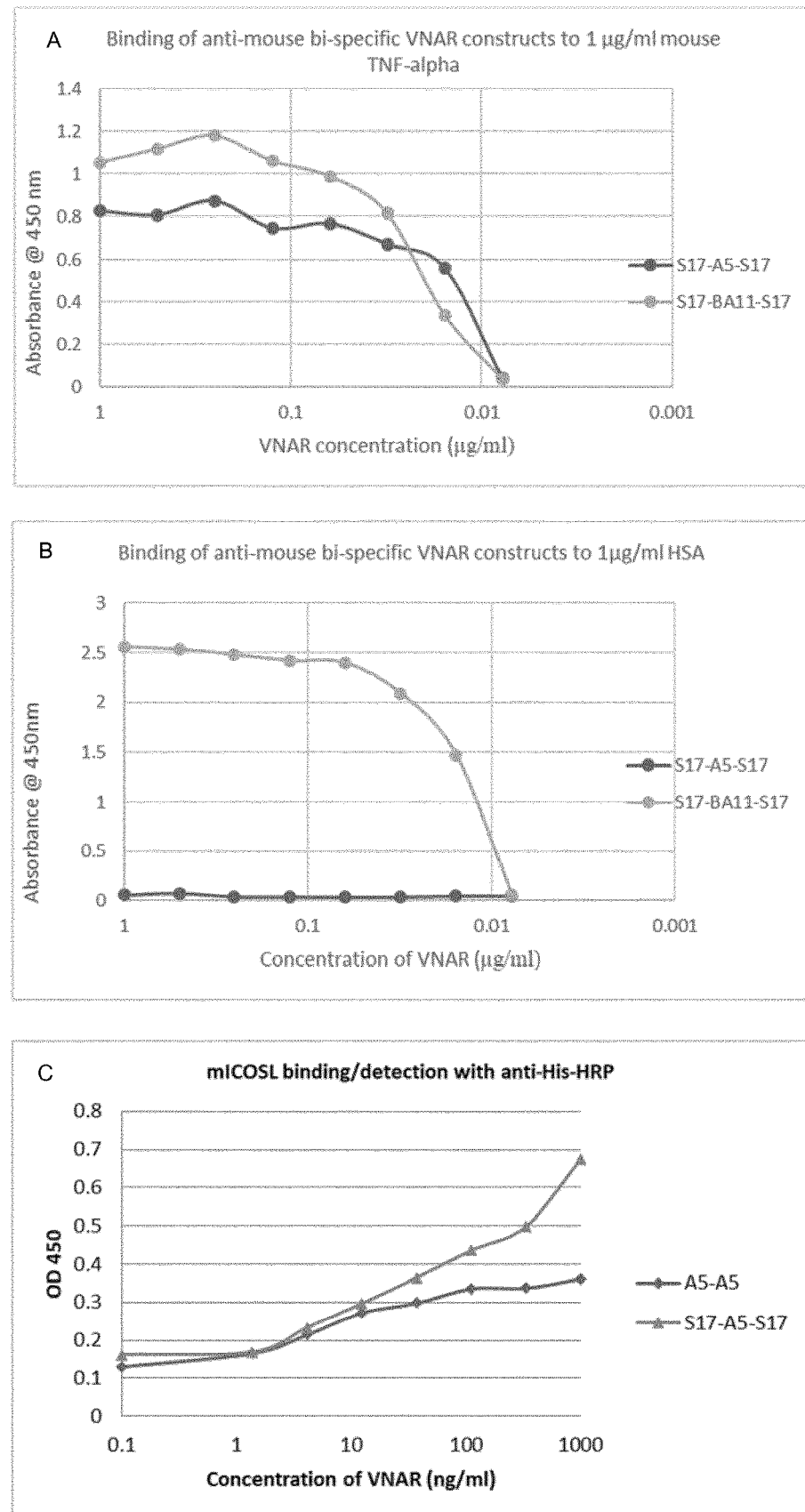
Figure 23:
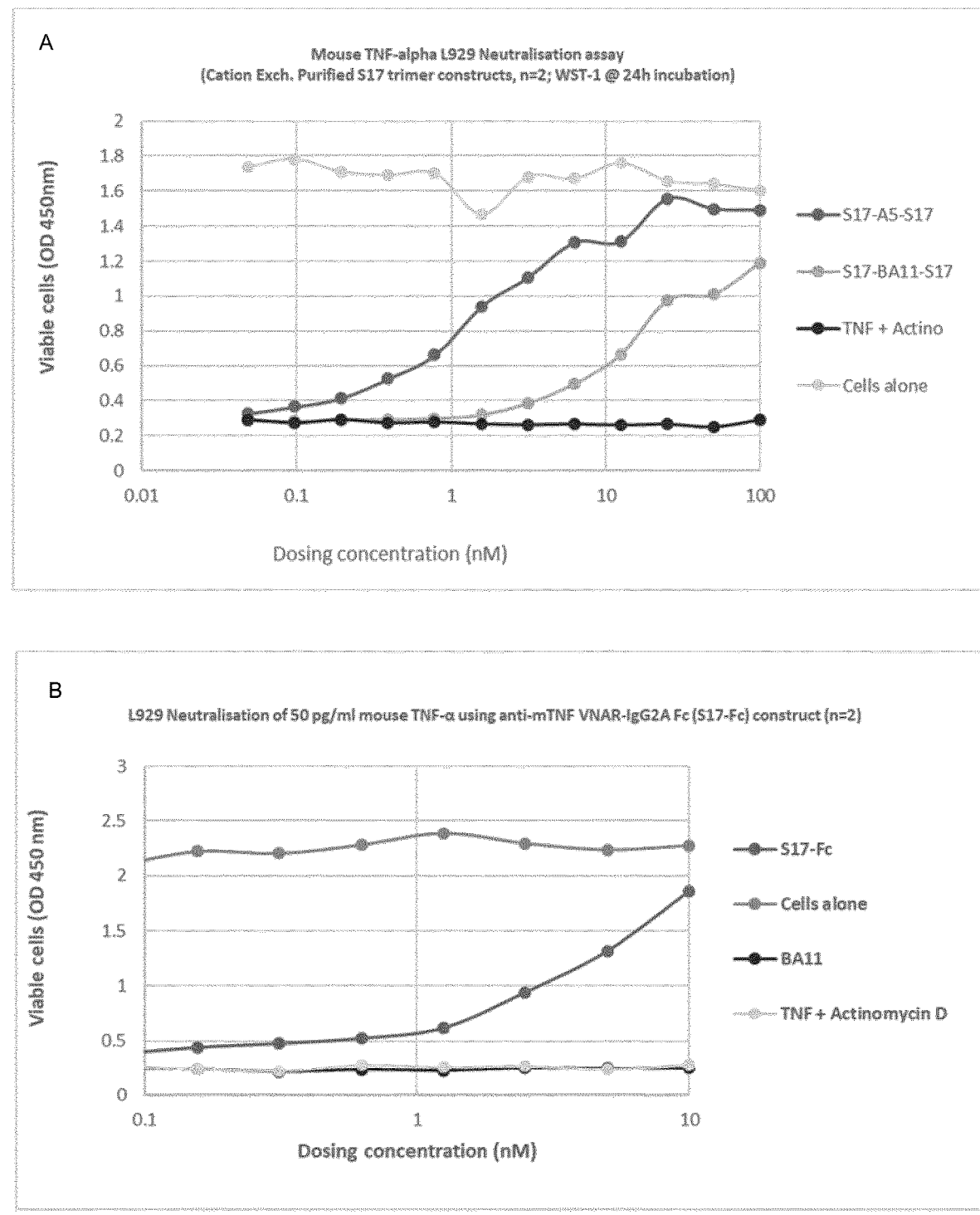
Figure 24:
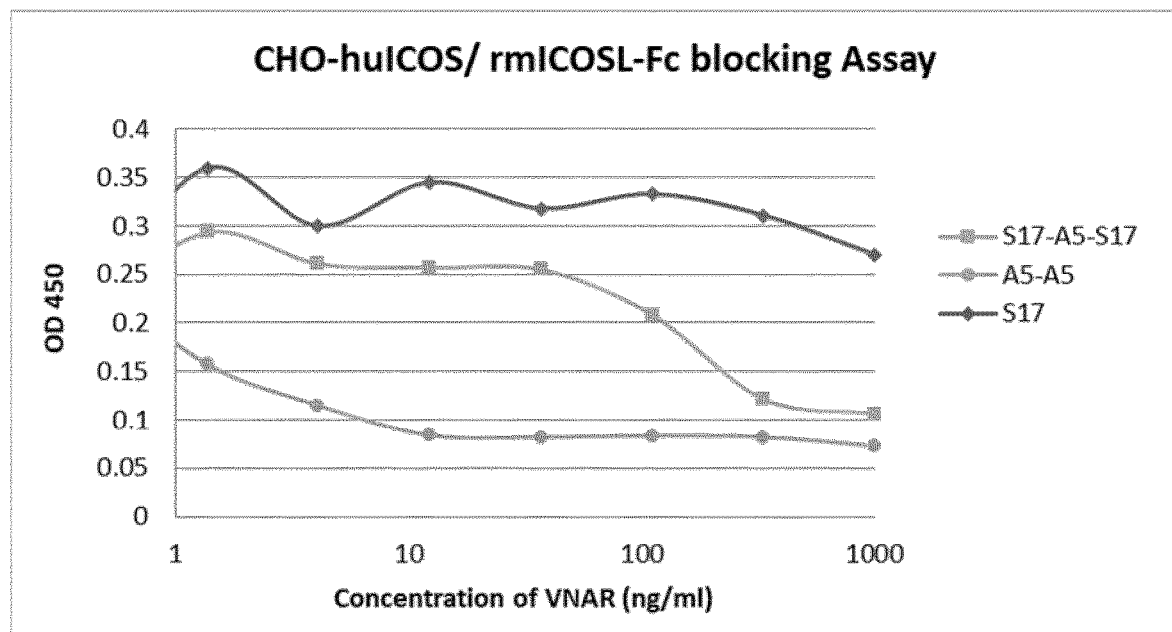
Figure 25:
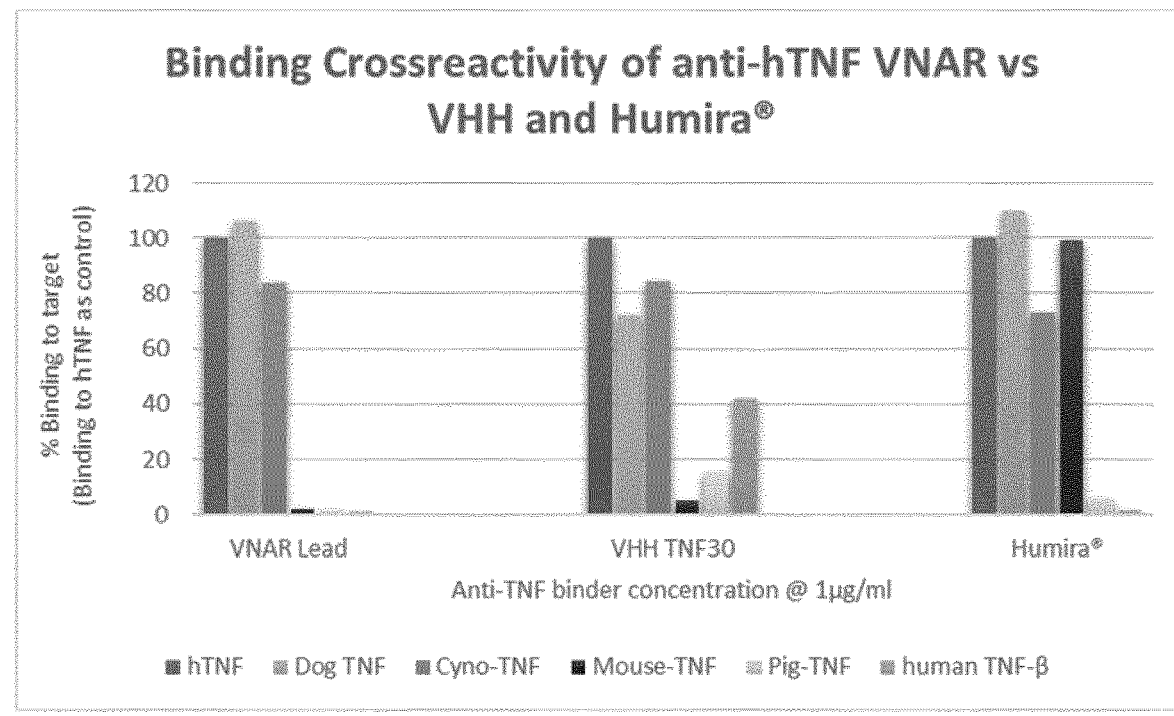
Figure 26:
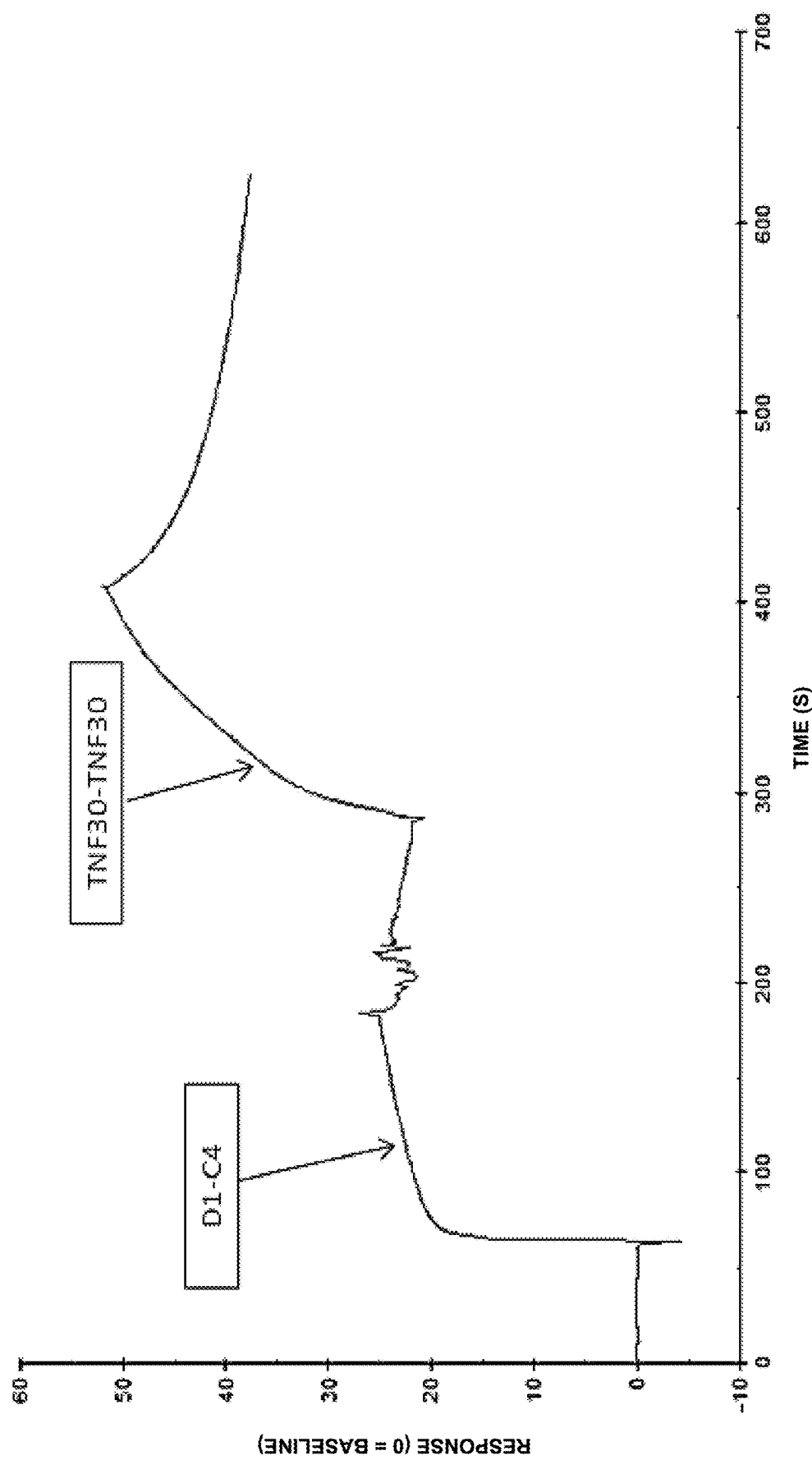
Figure 27:
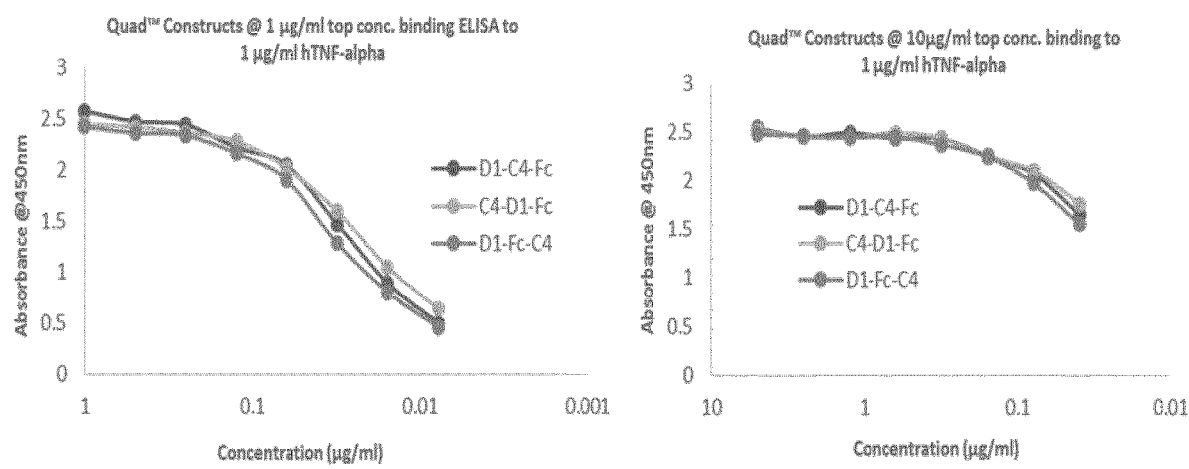
Figure 28:
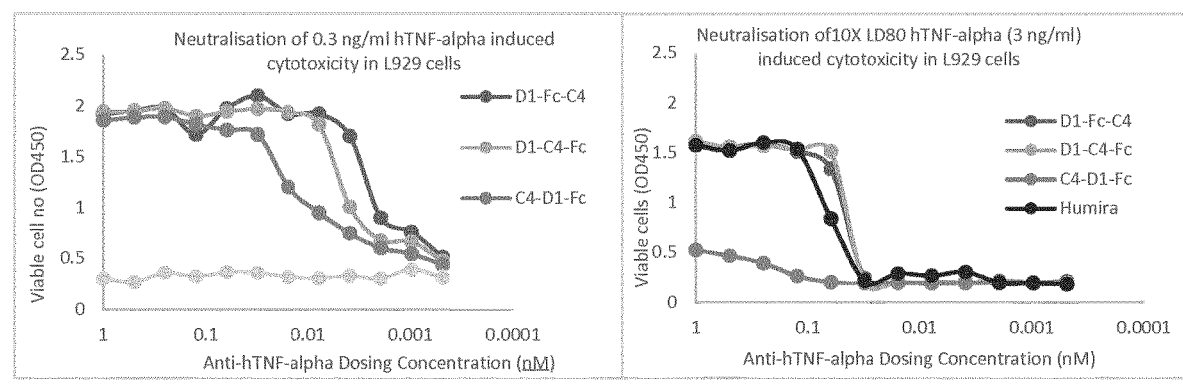
Figure 29:
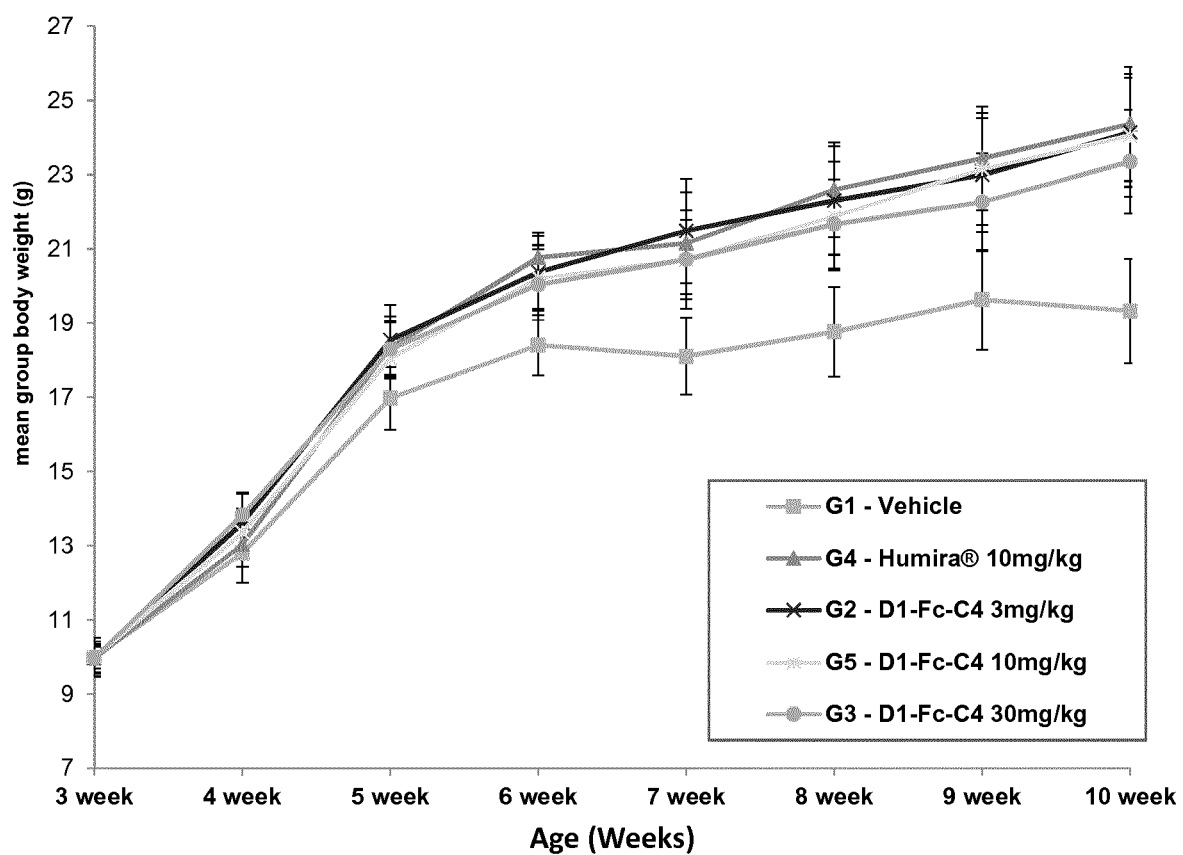

The data shows that the fusions are able to bind to TNF via TNFR1, and to mICOSL and hICOSL via the VNAR domains. The constructs are able to inhibit binding of m or hICOSL to their cognate CHO-expressed receptors These data demonstrate that VNARs combined into multivalent formats are capable of binding to their targets and the molecules are able to show improved properties over the monomer VNARs In Vivo Pre-Clinical Studies Background of the Study The Tg197 murine model of rheumatoid arthritis is a transgenic mouse line carrying and expressing wild type and 3'-modified human tumour necrosis factor (hTNF-α) transgenes. These transgenic mice develop chronic polyarthritis with 100% incidence at 4-7 weeks of age, dependent on the over expression of bioactive human TNF-α (Keffer et al. 1991, EMBO J., Vol. 10, pp. 4025-4031). The exemplification of the therapeutic efficacy of the first anti-TNF-α therapeutic antibody, Remicade® and other anti-TNF-alpha biologics were established using the Tg197 mouse model (Shealy et al., 2002, Arthritis Research & Therapy, 4(5), p.R7; Shealy et al., 2010, MAbs (Vol. 2, No. 4, pp. 428-439). Taylor & Francis).

The aim of the study was to evaluate the therapeutic efficacy of anti-TNF-α D1-Fc-C4 (Quad-X™) in comparison to Humira® in preventing arthritic symptoms in the Tg197 transgenic mouse model of arthritis.

Methods

A total of 40 mice were allocated to each of the 5 test groups, G1-G5 (Table 4). For the purpose of this study, transgenic mice were allocated to groups consisting of 8 mice each that received the test compounds or vehicle buffer (Phosphate buffered saline, PBS, pH 7.4), twice weekly subcutaneously starting at the third week of age, prior to the establishment of arthritis, and continuing over 7 weeks, until the 10th week of age. One additional group of transgenic mice (2 male and 2 female) untreated animals were used as 3-week old control mice for histopathological status, and were sacrificed prior to the first dose administration.

Mice were allocated into groups prior to performing the first arthritis scoring. Age and gender balanced study consisted of 8 ((4♂ and 4♀) heterozygous Tg197 for groups G1-G5 mice that were pooled from different litters of synchronized mating upon weaning. The assignment of the mice to the different experimental groups was performed in a fashion that ensured equal distribution of body weight among the different groups at the start of the study. In vivo arthritis scores was evaluated as described in Table 5.

At the 10th week of age, all animals were sacrificed and the blood (serum isolated and stored at −80° C.) and the two ankle joints of each animal were collected. Ankle joints of all experimental animals were dissected, calcified and further processed to perform histopathological evaluation of arthritis. Ankle histopathology was assessed by microscopic examination according to the histopathology scoring systems described in Table 6, and only representative images were included in the results section.

TABLE 4

Experimental groups

| Group No.[1] | Test article | Dose (mg/kg) | Dose frequency (weeks)[2] | Duration of administration (weeks) | Dose volume (ml/kg) | Route of administration | Animal number | Age at sacrifice (weeks)[3] |
|---|---|---|---|---|---|---|---|---|
| G1 | Vehicle | 0 | 2/wk | 7 | 10 | s.c. | 8(4♂/4♀) | 10 |
| G4 | Humira ® | 10 | 2/wk | 7 | 10 | s.c. | 8(4♂/4♀) | 10 |
| G2 | Test article (D1-Fc-C4) | 3 | 2/wk | 7 | 10 | s.c. | 8(4♂/4♀) | 10 |
| G5 | Test article (D1-Fc-C4) | 10 | 2/wk | 7 | 10 | s.c. | 8(4♂/4♀) | 10 |
| G3 | Test article (D1-Fc-C4) | 30 | 2/wk | 7 | 10 | s.c. | 8(4♂/4♀) | 10 |
| 3-wk old control mice | — | — | — | — | — | — | 4(2♂/2♀) | 3 |

[1]The study was performed in a blinded fashion resulting in the random order of groups described in the table above.

[2]Administration was initiated at the age of 3 weeks.

[3]All mice of groups 1-5 were sacrificed 48 hours after the last dose administration. 3-week old control animals were sacrificed at the study initiation just before the first dose administration.

TABLE 5

Evaluation of in vivo arthritis score

| ARTHRITIS SCORE[1] | CHARACTERISTICS |
|---|---|
| 0/no disease | no arthritis (normal appearance, mouse can support its weight clinging to an inverted or tilted surface such as a wire grid or a cage lid for a period of time, whole body flexibility/evasiveness normal, grip strength maximum) |
| 0.5/mild disease | onset of arthritis (mild joint swelling, all other parameters as above) |
| 1/mild to moderate disease | mild to moderate (joint distortion by swelling, inflamed paw, all other parameters as above) |
| 1.5/moderate disease | moderate arthritis (joint-paw swelling, distortion + last finger inward deformation, brief support clinging to an inverted or tilted surface such as a wire grid or a cage lid, whole body flexibility reduced, reduced grip strength) |
| 2/moderate to severe disease | moderate to severe arthritis (severe joint, paw and finger swelling, joint - leg deformation, no support clinging to an inverted or tilted surface such as a wire grid or a cage lid, no whole-body flexibility, no grip strength, climbing/feeding affected, starts shaking when trying to move, but manages to move forward) |
| 2.5/severe disease | severe arthritis (as above 2+ finger deformation in front paws, mouse movement impaired, shaking not willing to move) |
| 3/very severe disease | very severe arthritis (ankylosis detected on flexion and severely impaired movement, mouse moribund, not shaking anymore, cannot turn/flip around readily when tilted to the side). |

[1]The addition of an extra 0.25 on the scoring of some assessments signifies a tendency towards the next more severe phenotype, i.e. when one, but not all the criteria from the next scale of severity are present. For example, "1.75" means "1.5" with severe swelling but no joint deformation and some strength on flexion.

In vivo arthritis scores with group average scores are depicted as graph in the results section.

TABLE 6

Cumulative histopathological criteria for scoring arthritic phenotype in the ankle joints

| SCORE[1] | DISEASE | CRITERIA |
|---|---|---|
| 0 | Normal | no detectable pathology |
| 1 | Mild | hyperplasia of the synovial membrane and presence of polymorphonuclear infiltrates. Mild tendonitis may be present. |
| 2 | Moderate | pannus and fibrous tissue formation and focal subchondrial bone erosion |
| 3 | Moderate-Severe | cartilage destruction and bone erosion |
| 4 | Severe | extensive cartilage destruction and bone erosion. Bone outline structure is lost |

(Adapted from: Pettit, A. R., et al., 2001, The American journal of pathology, 159(5), pp. 1689-1699; Mould, A. W., et al., 2003, Arthritis & Rheumatology, 48(9), pp. 2660-2669)
[1]Half marks are given when some but not all of the features from the next higher score are present. Hence, a score of "2.5" means pannus and fibrous tissue formation and focal subchondrial bone erosion (score 2), with more bone erosion spread outside and around subchondrial foci, but not as broad and with cartilage destruction, as to justify a score "3".

Histopathological scores with group average scores are depicted as bar graph in the results section and tables in the appendix. Illustrative histopathology images at 25× magnification are also presented in the appendix.

Results

The evaluation of the efficacy of the anti-hTNF-α D1-Fc-C4 (Quad-X™) and Humira® on the Tg197 arthritis model was performed following a prophylactic administration scheme, i.e. starting treatment at the 3rd week of age of the mice when they exhibited mild evidence of in vivo arthritis pathology and early histopathological lesions. By the 10th week of age, the in vivo arthritic score in the vehicle treated control group G1 increased dramatically compared to the 3-week old untreated animals, while at the same age the histopathological lesions observed in the animals of G1 were statistically more severe than that seen in the 3-week control mice group.

Efficacy evaluation of the therapeutic effect of the test article D1-Fc-C4 anti-hTNFα in the in vivo and histopathological as well as body weight arthritis symptoms The 3, 10 and 30 mg/kg dose regimens of D1-Fc-C4 test article afforded statistical significant robust inhibition of the Tg197 in vivo and histopathological arthritic pathology compared to the vehicle treated mice in G1. More specifically, after 14 doses administered twice weekly for a period of 7 weeks, the dose regimens resulted in:

~88 inhibition of the in vivo and ~86% inhibition of arthritis histopathology score following the 3 mg/kg D1-Fc-D4 test article treatment of animals in G2

~88% significant inhibition of the in vivo and ~83% inhibition of arthritis histopathology score following the 10 mg/kg D1-Fc-C4 test article treatment of animals in G5

~88% significant inhibition of the in vivo and ~86% inhibition of arthritis histopathology score following the 30 mg/kg D1-Fc-C4 test article treatment of animals in G3

Similar findings were observed in mean body weight curves of the D1-Fc-C4 test article treated mice which appeared to gain more body weight in all dose levels compared to the vehicle treated mice in G1 although statistical significance was achieved only in the 3 mg/kg and in the 10 mg/kg dose regimens.

D1-Fc-C4 test article dose response efficacy evaluation

Treatment with the 3, 10 and 30 mg/Kg doses of D1-Fc-D4 test article did not exhibit a dose-dependent response efficact as shown by the in vivo arthritic evaluations and body weight scores as well as from the histopathological evaluations in which all doses acted similarly and their therapeutic effects were statistically undifferentiated.

Efficacy evaluation of the therapeutic effect of Humira® in the in vivo and histopathological as well as body weight arthritis symptoms The 10 mg/kg dose regimen of Humira® afforded robust statistical significant inhibition of the Tg197 in vivo and histological arthritic pathology compared to the vehicle treated mice in G1. More specifically, after 14 doses administered twice weekly for a period of 7 weeks, we observed:

~82% inhibition of the in vivo and −86% inhibition of the arthritis histopathology score following the 10 mg/kg Humira® treatment of animals in G4

Similar findings were observed in mean body weight curve of the Humira® treated mice which appeared to gain more body weight compared to the vehicle treated mice in G1.

Dose response comparison between D1-Fc-C4 test article and Humira®

The comparative examination of the inhibitory effects between D1-Fc-C4 test article and Humira® across the 10 mg/kg dose revealed that they were statistically undifferentiated in all parameters evaluated, including body weights, in vivo arthritic scores and histopathological evaluations.

Histopathological comparison of the effect of DI-Fc-C4 test article and Humira® to the 3-week old control animals The inhibitory effects of the 3, 10 and 30 mg/Kg of the D1-Fc-C4 test article as well as the 10 mg/Kg Humira resulted in lower histopathology lesions at week 10 and statistically differentiated from the 3-week old control untreated animals.

TABLE 7

Mean group body weights

| Mean group body weight[1] (g) | Week 3 | Week 4 | Week 5 | Week 6 | Week 7 | Week 8 | Week 9 | Week 10 |
|---|---|---|---|---|---|---|---|---|
| 3-week old control mice | 9.8 ± 0.2 | — | — | — | — | — | — | — |
| G1-Vehicle | 10.0 ± 0.5 | 12.8 ± 0.8 | 17.0 ± 0.8 | 18.4 ± 0.8 | 18.1 ± 1.0 | 18.8 ± 1.2 | 19.6 ± 1.3 | 19.3 ± 1.4 |

TABLE 7-continued

Mean group body weights

| Mean group body weight[1] (g) | Week 3 | Week 4 | Week 5 | Week 6 | Week 7 | Week 8 | Week 9 | Week 10 |
|---|---|---|---|---|---|---|---|---|
| G4-Humira® 10 mg/kg | 10.0 ± 0.3 | 13.0 ± 0.6 | 18.3 ± 0.8 | 20.8 ± 0.7 | 21.2 ± 1.4 | 22.6 ± 1.3 | 23.4 ± 1.4 | 24.4 ± 1.5 |
| G2-D1-Fc-C4 3 mg/kg | 10.0 ± 0.4 | 13.6 ± 0.8 | 18.5 ± 0.9 | 20.4 ± 1.0 | 21.5 ± 1.4 | 22.3 ± 1.5 | 23.0 ± 1.5 | 24.1 ± 1.5 |
| G5-D1-Fc-C4 10 mg/kg | 10.0 ± 0.3 | 13.4 ± 0.7 | 18.1 ± 1.0 | 20.2 ± 0.9 | 20.7 ± 1.3 | 21.9 ± 1.5 | 23.2 ± 1.5 | 24.1 ± 1.7 |
| G3-D1-Fc-C4 30 mg/kg | 10.0 ± 0.4 | 13.8 ± 0.6 | 18.3 ± 0.7 | 20.0 ± 1.0 | 20.7 ± 1.1 | 21.7 ± 1.2 | 22.3 ± 1.3 | 23.4 ± 1.4 |

[1]Data are presented as mean ± SEM

TABLE 8

Mean group in vivo arthritis scores

| Mean group in vivo arthritic scores[1] | Week 3 | Week 4 | Week 5 | Week 6 | Week 7 | Week 8 | Week 9 | Week 10 |
|---|---|---|---|---|---|---|---|---|
| 3-week old control mice | 0.13 ± 0.05 | — | — | — | — | — | — | — |
| G1-Vehicle | 0.14 ± 0.03 | 0.34 ± 0.03 | 0.58 ± 0.04 | 0.84 ± 0.05 | 0.94 ± 0.04 | 0.98 ± 0.04 | 1.20 ± 0.06 | 1.36 ± 0.07 |
| G4-Humira® 10 mg/kg | 0.17 ± 0.04 | 0.28 ± 0.04 | 0.23 ± 0.05 | 0.19 ± 0.04 | 0.33 ± 0.04 | 0.25 ± 0.05 | 0.28 ± 0.04 | 0.25 ± 0.05 |
| G2-D1-Fc-C4 3 mg/kg | 0.13 ± 0.04 | 0.20 ± 0.03 | 0.17 ± 0.04 | 0.17 ± 0.04 | 0.19 ± 0.04 | 0.17 ± 0.03 | 0.16 ± 0.03 | 0.17 ± 0.04 |
| G5-D1-Fc-C4 10 mg/kg | 0.19 ± 0.04 | 0.20 ± 0.04 | 0.17 ± 0.03 | 0.28 ± 0.03 | 0.25 ± 0.03 | 0.27 ± 0.03 | 0.25 ± 0.02 | 0.17 ± 0.04 |
| G3-D1-Fc-C4 30 mg/kg | 0.09 ± 0.03 | 0.17 ± 0.04 | 0.17 ± 0.04 | 0.19 ± 0.05 | 0.22 ± 0.04 | 0.22 ± 0.04 | 0.20 ± 0.03 | 0.17 ± 0.04 |

[1]Data are presented as mean ± SEM

TABLE 9

Mean group arthritis histopathology scores

| Mean group histopathology scores[1] | Week 3 | Week 10 |
|---|---|---|
| 3-week old control mice | 1.22 ± 0.10 | — |
| G1- Vehicle | — | 2.94 ± 0.12 |
| G4- Humira® 10 mg/kg | — | 0.42 ± 0.07 |
| G2- D1-Fc-C4 3 mg/kg | — | 0.41 ± 0.03 |
| G5- D1-Fc-C4 10 mg/kg | — | 0.50 ± 0.05 |
| G3- D1-Fc-C4 30 mg/kg | — | 0.42 ± 0.07 |

In addition, a second exemplification of the in vitro potency enhancement using the VNAR S17 Quad-X™ construct targeting mouse TNF-alpha was conducted.

Figure 30:
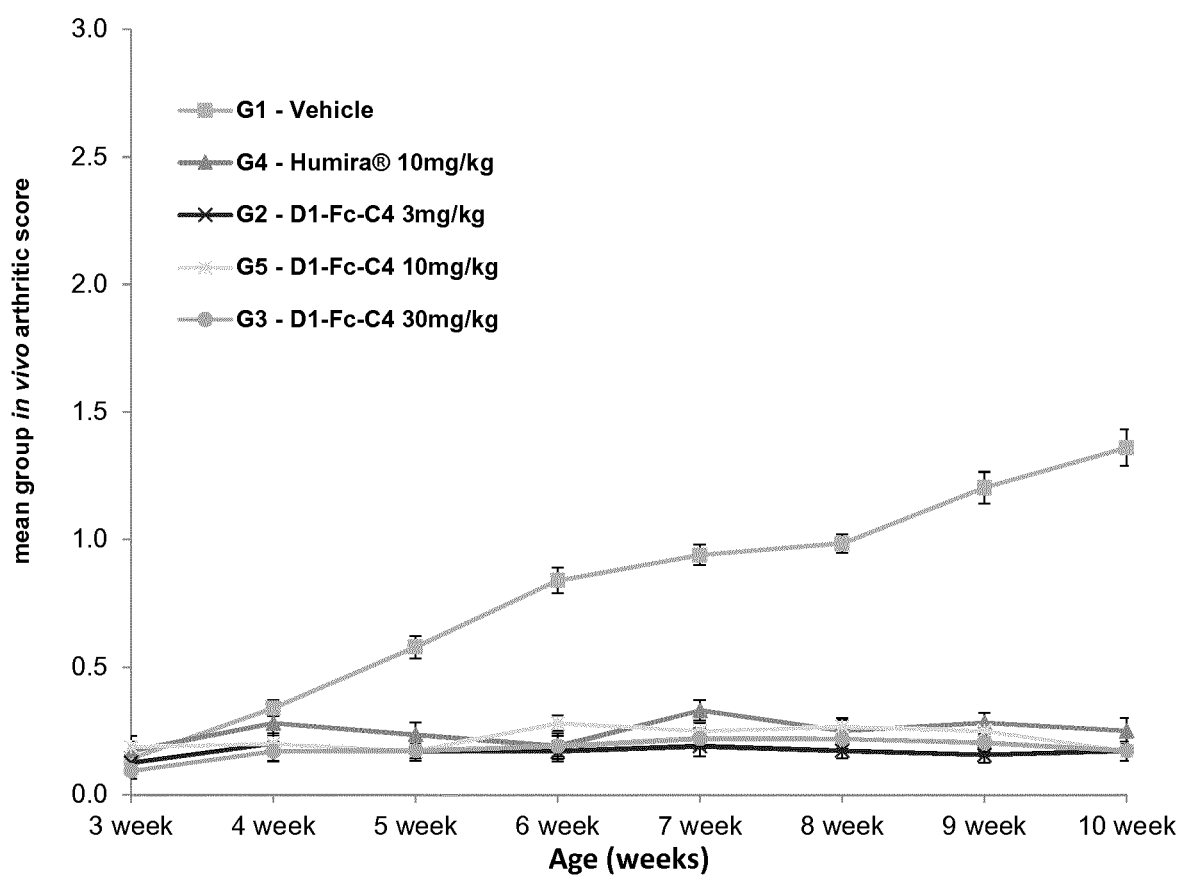

VNAR S17 is a specific anti-mouse TNF-alpha with no binding or neutralizing activity against human TNF-alpha. VNAR S17-Fc is a potent neutralizer of mouse TNF-alpha with in vitro potency (ND50) of approximately 8 nM. When designed as a Quad-X™ construct (S17-Fc-S17), in vitro neutralizing potency improved by ≈40-fold to 0.2 nM (FIG. 30).

Figure 31:
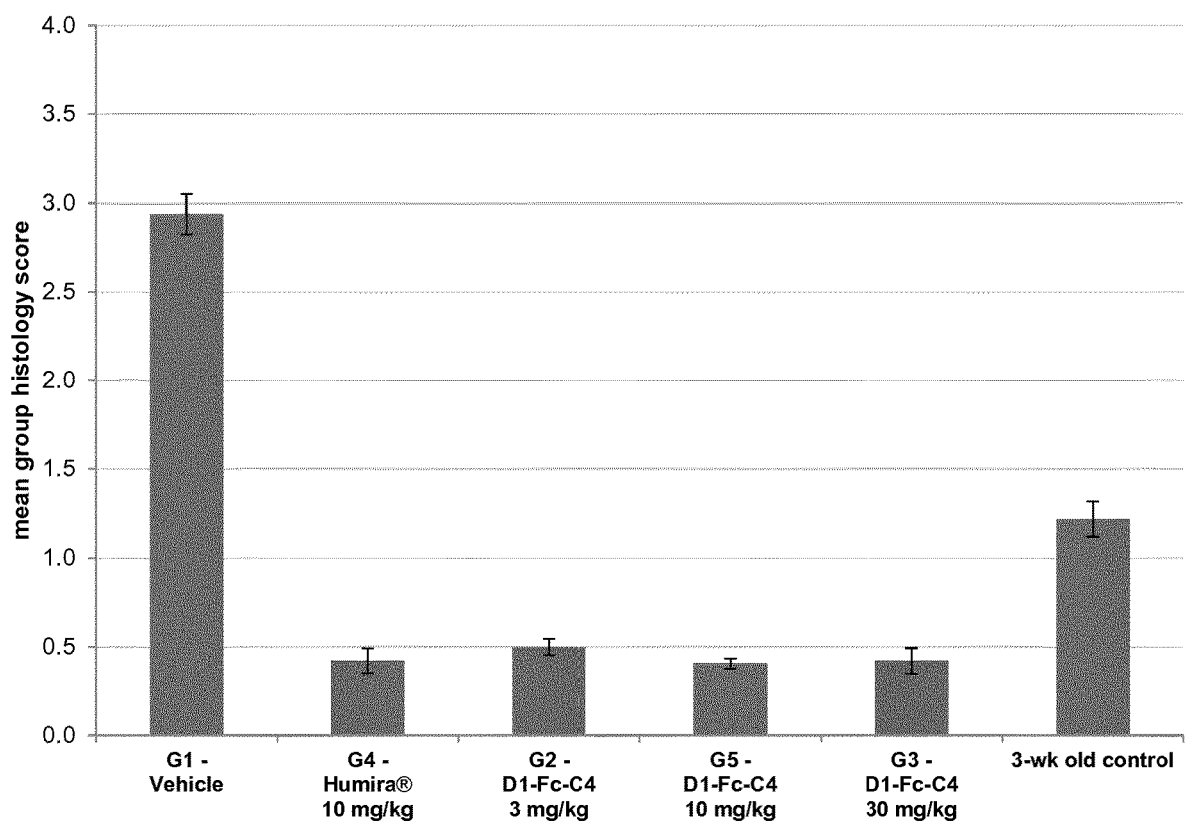
Figure 32:
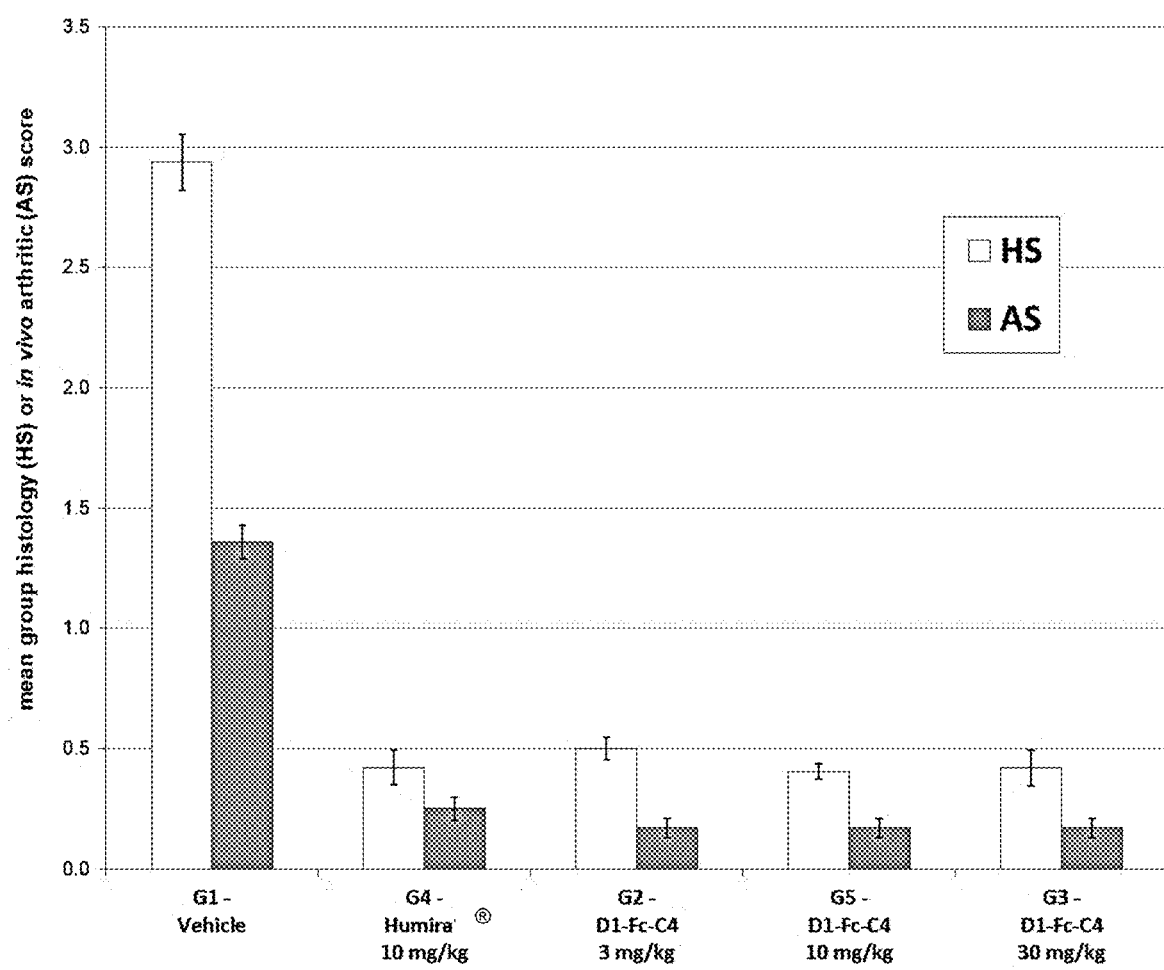

Furthermore, it has been demonstrated that the S17 Quad-X™ and D1-C4 Quad-X™ constructs recognize distinct species of TNF-alpha (FIG. 31).

Discussion and Conclusion

The results of this study show that the reference Humira® and D1-Fc-C4 (Quad-X™) and D1-BA11-C4 anti-hTNF-α articles inhibited the arthritic phenotype observed in Tg197 animals thus resulting in increased body weight and reduced in vivo and histopathological arthritic pathology as compared to the vehicle treated animals.

Figure 33:
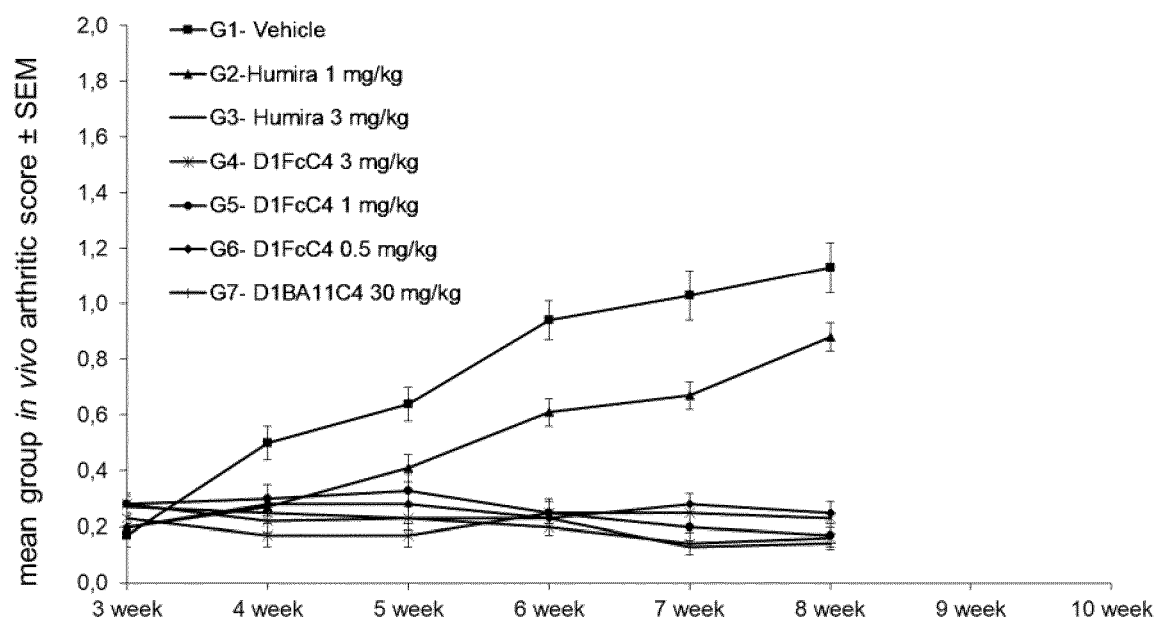
Figure 35:
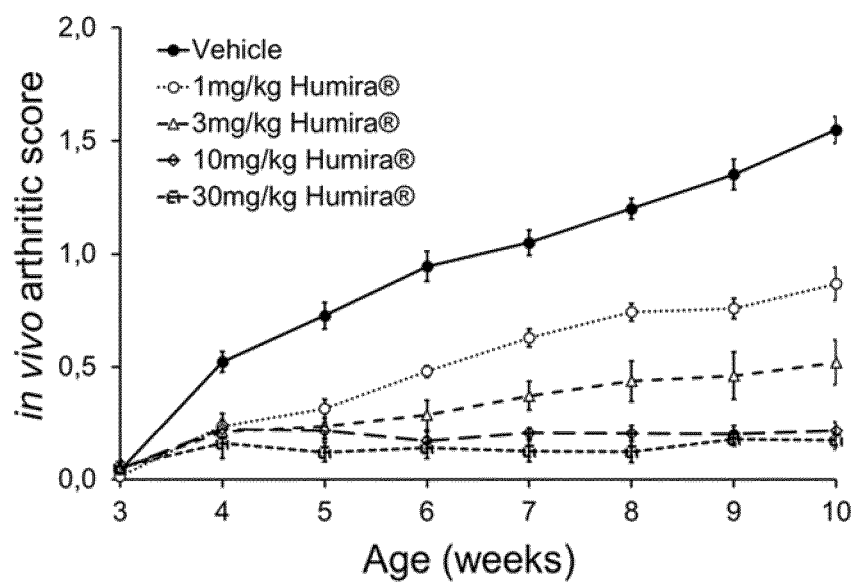
Figure 35:
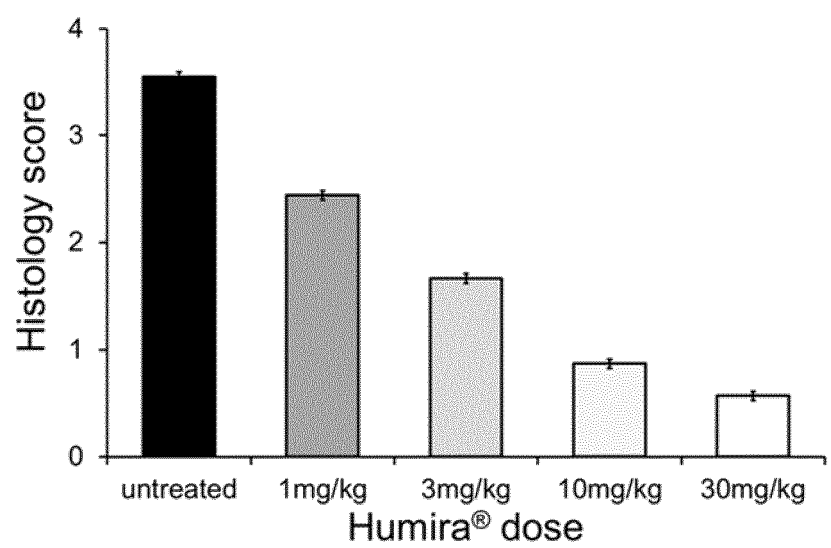

The therapeutic effect of the reference Humira® was evaluated at 10 mg/kg dose (FIG. 29-32) and resulted in statistically significant inhibition of the in vivo arthritic and ankle histopathological evaluations when compared to the vehicle treated mice. In FIG. 33, 1 mg/kg Humira® show significant disease breakthrough at 8 weeks. In a previous Tg197 mice model study using a dosing regimen of 1 mg/kg, 3 mg/kg, 10 mg/kg and 30 mg/kg Humira®, it was shown that there was significant disease breakthrough in the group of mice treated with either 1 mg/kg (FIG. 33) or 3 mg/kg Humira® (FIG. 35). These groups of mice had time-dependent disease progression similar to the untreated group, and in vivo arthritic (AS) and histopathology scores (HS) significantly higher than the groups treated with either 10 mg/kg or 30 mg/kg Humira® (FIG. 33).

The D1-Fc-C4 (Quad-X™) test articles did not exhibit a dose-dependent response as all evaluated doses, i.e. 0.5, 1, 3 mg/kg, 10 mg/kg and 30 mg/kg demonstrated similar and statistically undifferentiated therapeutic effects with complete control of the disease. Furthermore, in vivo arthritic and histopathological evaluations revealed that the therapeutic effect of the 3 mg/kg dose of D1-Fc-C4 test article was statistically comparable to that of 10 mg/kg Humira®. We also did not observe any sign of disease breakthrough in the 3 mg/kg D1-Fc-C4 treated mice at 10 weeks of age, neither did we observe any with 0.5 and 1 mg/kg D1-Fc-C4 at 8 weeks of age.

Figure 34:
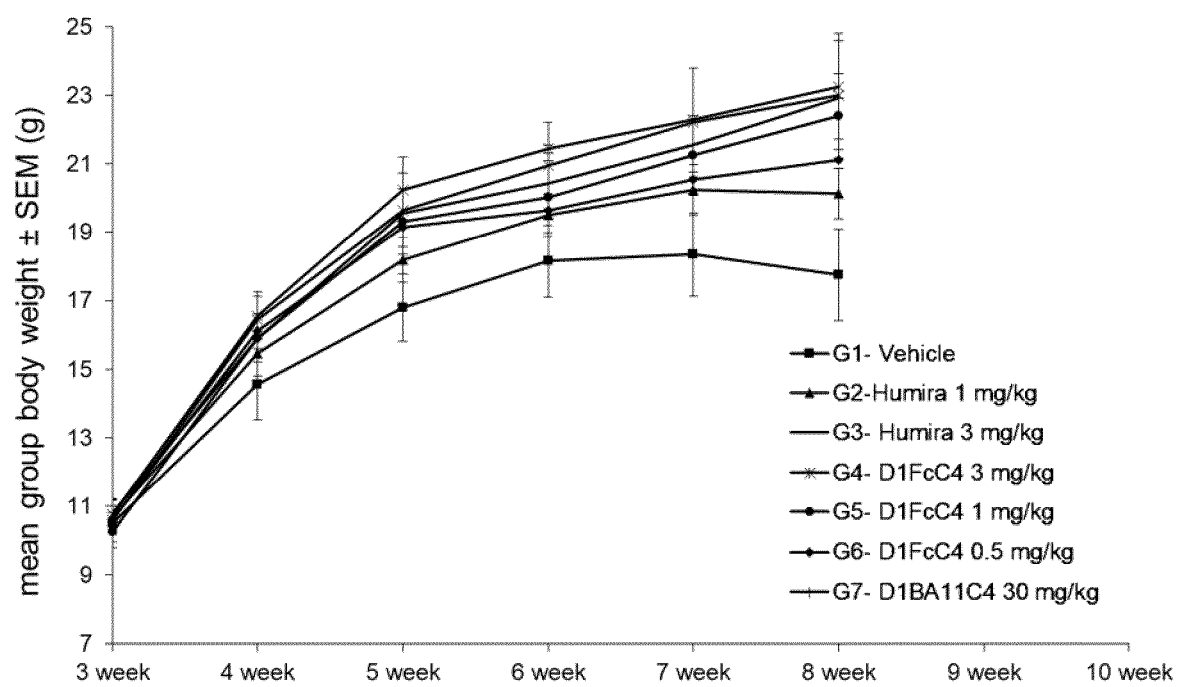

We have therefore further exemplified that the D1-Fc-C4 anti-hTNF-α domain is more potent than the standard therapy, Humira® in neutralising the effects of TNF-alpha both in vitro (L929 and Caco2 data—FIGS. 2, 3, 6 to 8, 20, 23 and 28) and in vivo (FIGS. 29-35). We have also demonstrated the in vivo efficacy of a non-Fc based tandem multivalent VNAR, D1-BA11-C4 (FIGS. 33 and 34).

Figure 36:
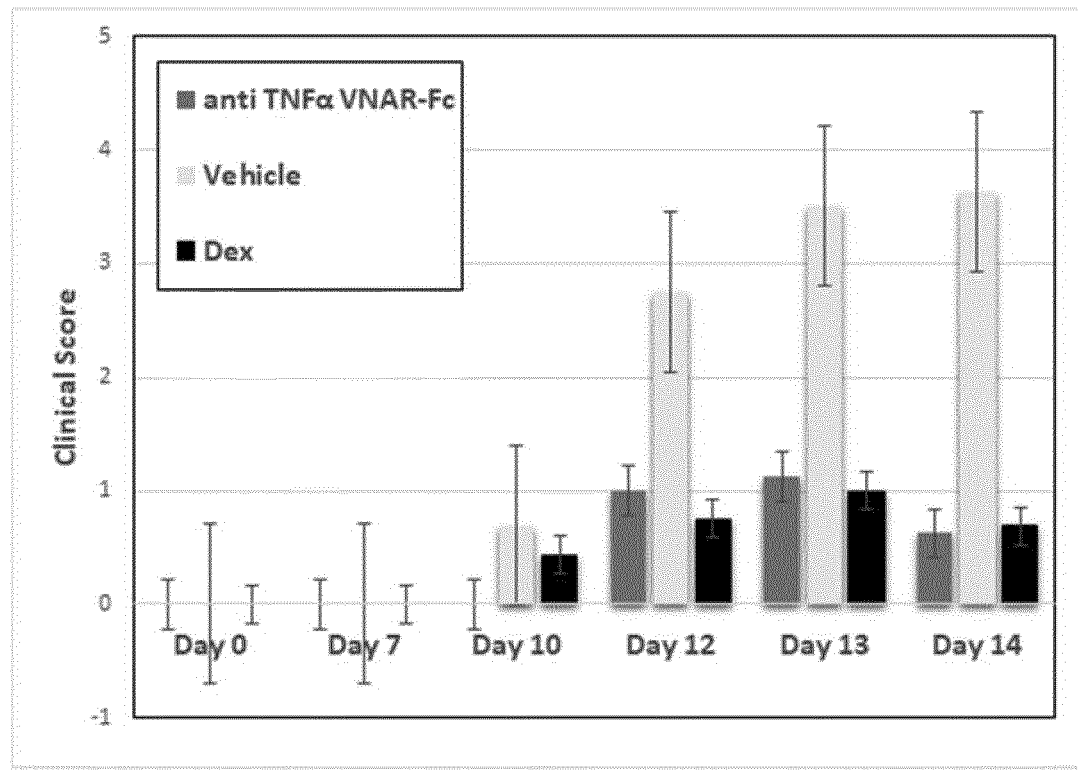
Figure 37A:
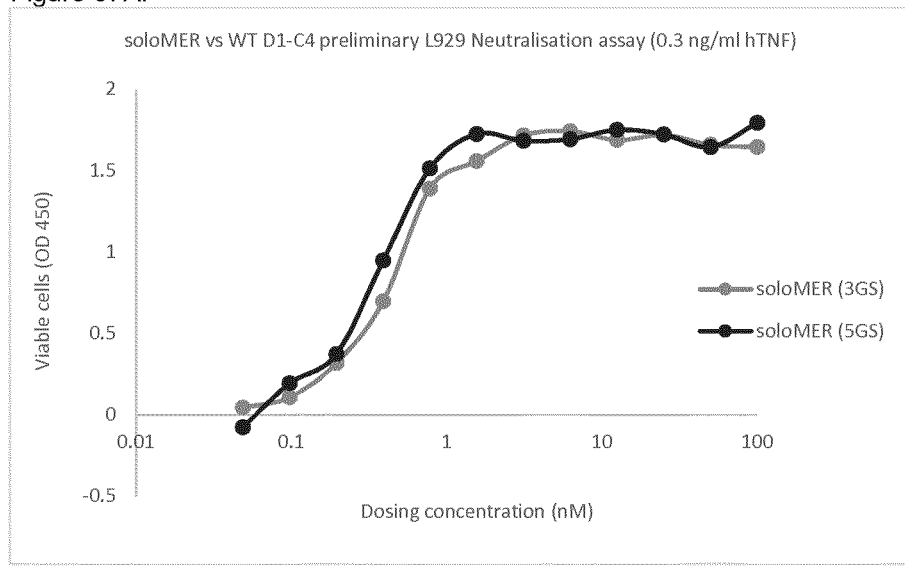
Figure 37B:
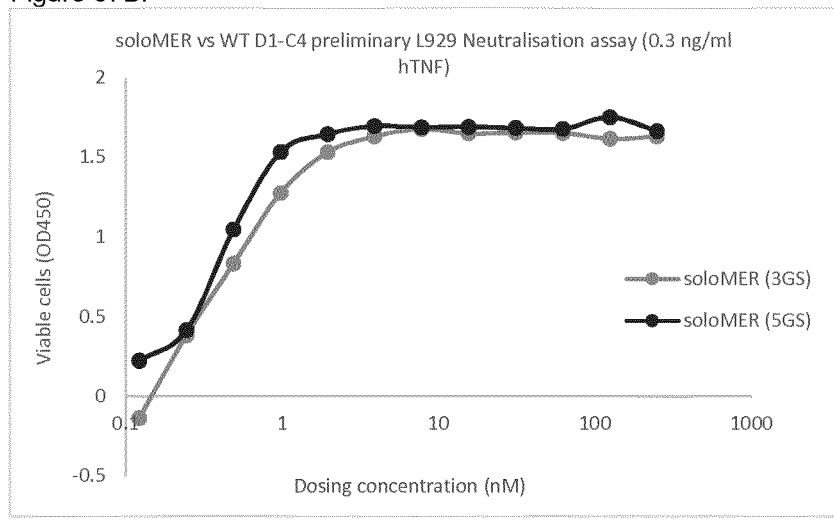
Figure 38:
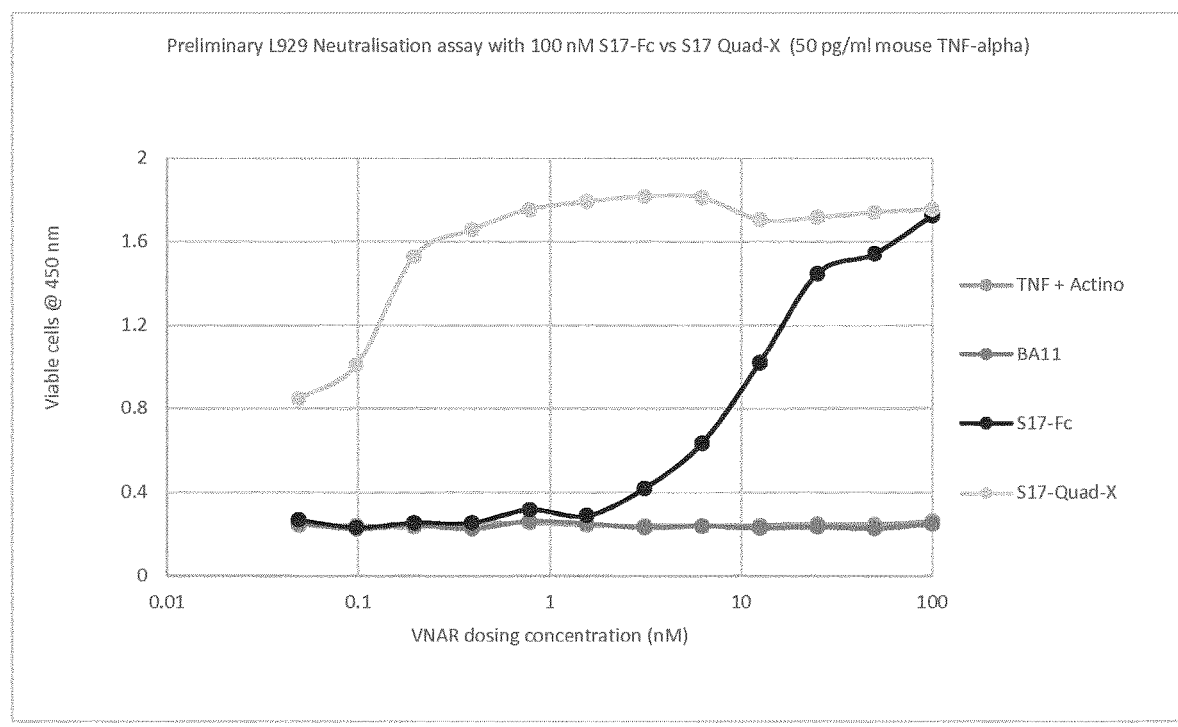
Figure 39A:
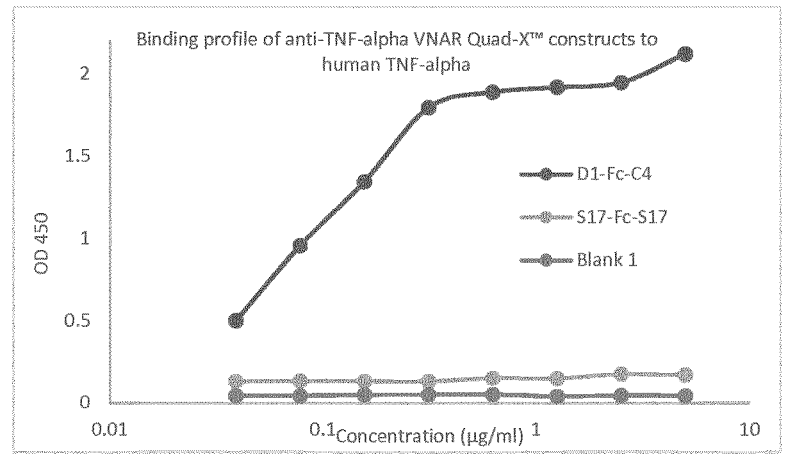
Figure 39B:
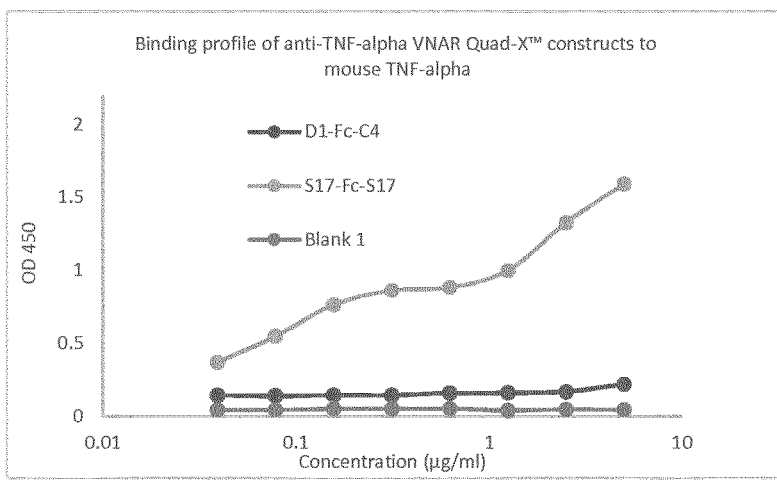
Figure 39C:
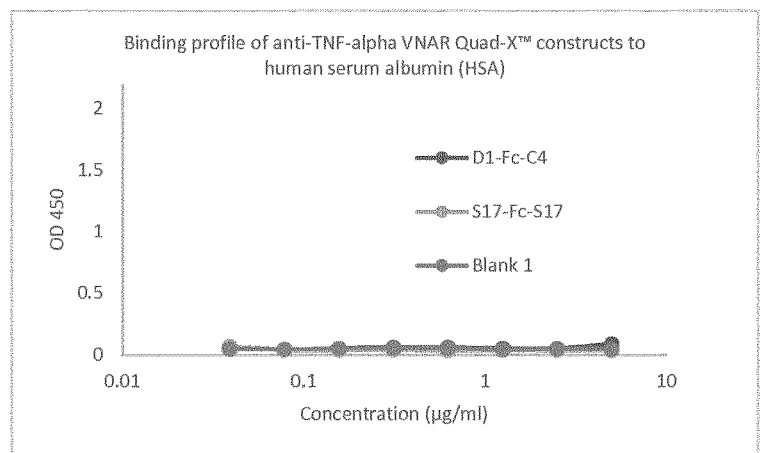

Finally we were able to show that an anti-TNF VNAR (D1-Fc) was also able to control and treat Uveitis (with a similar potency to Dexamethasone) in a rat model of inflammatory eye disease if administered systemically in an Fc alone format (FIG. 36).

The invention claimed is:

1. A multi-domain specific binding molecule comprising at least two VNAR domains which bind to the same or different epitopes of at least one specific antigen, and a spacer sequence located between the at least two VNAR domains, wherein the spacer sequence has independent functionality which is exhibited in the binding molecule and wherein the spacer sequence is derived from an immunoglobulin Fc region, wherein each of the at least two VNAR domains has the structure FW1-CDR1-FW2-HV2-FW3a-HV4-FW3b-CDR3-FW4 in the N- to C-terminal direction,
   wherein at least one of the VNAR domains is a TNF-alpha specific VNAR binding domain comprising the following CDRs and hyper-variable regions (HV):
   CDR1: HCATSS (SEQ ID NO: 68) or NCGLSS (SEQ ID NO: 69) or NCALSS (SEQ ID NO: 70);
   HV2: TNEESISKG (SEQ ID NO: 71);
   HV4: SGSKS (SEQ ID NO: 72) or EGSKS (SEQ ID NO: 73);
   CDR3: ECQYGLAEYDV (SEQ ID NO: 1) or SWWTQNWRCSNSDV (SEQ ID NO: 6) or YIP-CIDELVYMISGGTSGPIHDV (SEQ ID NO: 11).

2. The multi-domain specific binding molecule of claim 1, wherein at least one of the VNAR domains in the multi-domain specific binding molecule exhibits higher binding affinity for its target compared to the monomeric VNAR.

3. The multi-domain specific binding molecule of claim 1, wherein the at least two VNAR domains bind to the same or different epitopes of one specific antigen.

4. The multi-domain specific binding molecule of claim 3, wherein the at least two VNAR domains bind to different epitopes of one specific antigen.

5. The multi-domain specific binding molecule of claim 1, wherein the at least two VNAR domains each bind to a different specific antigen.

6. The multi-domain specific binding molecule of claim 1, wherein the spacer sequence is derived from a human immunoglobulin Fc region.

7. The multi-domain specific binding molecule of claim 1, wherein the VNAR binding domain comprises the amino acid sequence of SEQ ID NO: 2, 7, or 12.

8. The multi-domain specific binding molecule of claim 1, wherein the VNAR domain is humanized or de-immunized.

9. The multi-domain specific binding molecule of claim 1, wherein at least one of the VNAR domains has an amino acid sequence selected from the group consisting of SEQ ID NO: 2, 7 and 12.

10. The multi-domain specific binding molecule of claim 8, wherein at least two of the VNAR domains have an amino acid sequence selected from the group consisting of SEQ ID NOS: 2, 7 and 12.

11. The multi-domain specific binding molecule of claim 6, wherein at least two of the VNAR domains have an amino acid sequence selected from the group consisting of SEQ ID NOS: 2, 7 and 12.

12. The multi-domain specific binding molecule as claimed in claim 1 modified at one or more amino acid sequence positions to reduce potential immunogenicity when administered to a human.

13. An isolated nucleic acid comprising a polynucleotide sequence that encodes a multi-domain specific binding molecule according to claim 1.

14. A method for preparing a binding molecule, comprising cultivating or maintaining a host cell comprising the polynucleotide of claim 12 under conditions such that said host cell produces the binding molecule, optionally further comprising isolating the binding molecule.

15. A pharmaceutical composition comprising the multi-domain specific binding molecule of claim 1 and optionally at least one pharmaceutically acceptable carrier.

16. A method for treating a condition mediated by TNFα, the method comprising the administering of a therapeutically effective amount of a composition of claim 15 that specifically binds to TNFα.

\* \* \* \* \*